(12) United States Patent
Deville et al.

(10) Patent No.: US 11,191,547 B2
(45) Date of Patent: Dec. 7, 2021

(54) LEFT ATRIAL APPENDAGE CLIPPING DEVICE AND METHODS FOR CLIPPING THE LAA

(71) Applicant: Syntheon 2.0, LLC, Miami, FL (US)

(72) Inventors: Derek Dee Deville, Coral Gables, FL (US); Matthew A. Palmer, Miami, FL (US); Richard Cartledge, Boca Raton, FL (US); Thomas O. Bales, Jr., Miami, FL (US); M. Sean McBrayer, Coral Gables, FL (US); Eric Petersen, Homestead, FL (US); Tyler Bond, Miami, FL (US); William T. Bales, Miami, FL (US); Michael Walter Kirk, Miami, FL (US)

(73) Assignee: Syntheon 2.0, LLC, Miami, FL (US)

(*) Notice: Subject to any disclaimer, the term of this patent is extended or adjusted under 35 U.S.C. 154(b) by 211 days.

(21) Appl. No.: 16/256,561

(22) Filed: Jan. 24, 2019

(65) Prior Publication Data

US 2019/0231356 A1 Aug. 1, 2019

Related U.S. Application Data

(60) Provisional application No. 62/622,751, filed on Jan. 26, 2018, provisional application No. 62/650,766, (Continued)

(51) Int. Cl.
*A61B 17/122* (2006.01)
*A61B 17/128* (2006.01)
*A61B 17/00* (2006.01)

(52) U.S. Cl.
CPC ...... *A61B 17/1227* (2013.01); *A61B 17/1285* (2013.01); *A61B 2017/00243* (2013.01)

(58) Field of Classification Search
CPC ...... A61B 2017/00243; A61B 17/0057; A61B 17/12122; A61B 17/1285; A61B 17/122; (Continued)

(56) References Cited

U.S. PATENT DOCUMENTS

| 2,876,778 A | 3/1959 | Kees, Jr. |
| 4,552,128 A | 11/1985 | Haber |

(Continued)

OTHER PUBLICATIONS

International Search Report for Application No. PCT/US19/15140 dated Apr. 25, 2019.

*Primary Examiner* — Katherine M Shi
(74) *Attorney, Agent, or Firm* — Gregory L. Mayback; Dickinson Wright PLLC

(57) ABSTRACT

An external LAA exclusion clip comprises a clipping assembly comprising first and second opposing clip struts each of the clip struts having a tissue-contacting surface and first and second bias surfaces, a bias assembly connecting the first clip strut to the second clip strut to align the first and second clip struts in a strut plane passing through the tissue-contacting surface. The bias assembly comprises at least one first bias spring connected to the first bias surface of the first clip strut and to the first bias surface of the second clip strut and at least one second bias spring connected to the second bias surface of the first clip strut and the second bias surface of the second clip strut. The first bias spring and the second bias spring are configured to permit movement of the first and second clip struts in the strut plane.

50 Claims, 50 Drawing Sheets

Related U.S. Application Data filed on Mar. 30, 2018, provisional application No. 62/727,850, filed on Sep. 6, 2018, provisional application No. 62/743,708, filed on Oct. 10, 2018.

(58) Field of Classification Search
CPC ...... A61B 17/1227; A61B 2017/00575; A61B 2017/00632; A61B 17/00234; A61B 17/12013; A61B 2017/00867; F16B 2/10; F16B 2/12; F16B 2/22; F16B 2/20; F16B 2/243; F16B 2/04; F16B 2/02
See application file for complete search history.

(56) References Cited

U.S. PATENT DOCUMENTS

| | | |
|---|---|---|
| 5,074,869 A | 12/1991 | Daicoff |
| 5,217,473 A | 6/1993 | Inbae |
| 5,445,167 A | 8/1995 | Yoon et al. |
| 6,096,052 A | 8/2000 | Callister et al. |
| 6,394,998 B1 | 5/2002 | Wallace et al. |
| 6,488,689 B1 | 12/2002 | Kaplan et al. |
| 6,849,075 B2 | 2/2005 | Bertolero et al. |
| 7,226,448 B2 | 6/2007 | Bertolero et al. |
| 7,399,300 B2 | 7/2008 | Bertolero et al. |
| 7,542,807 B2 | 6/2009 | Bertolero et al. |
| 7,591,818 B2 | 9/2009 | Bertolero et al. |
| 7,645,285 B2 | 1/2010 | Cosgrove et al. |
| 7,749,157 B2 | 7/2010 | Bertolero |
| 7,819,867 B2 | 10/2010 | Bertolero et al. |
| 7,951,069 B2 | 5/2011 | Bertolero |
| 7,957,820 B2 | 6/2011 | Bertolero et al. |
| 7,998,138 B2 | 8/2011 | McAuley |
| 8,007,504 B2 | 8/2011 | Zenati et al. |
| 8,096,990 B2 | 1/2012 | Swanson et al. |
| 8,419,729 B2 | 4/2013 | Ibrahim et al. |
| 8,454,593 B2 | 6/2013 | Bertolero et al. |
| 8,460,282 B2 | 6/2013 | McAuley |
| 8,465,507 B2 | 6/2013 | Cosgrove et al. |
| 8,535,307 B2 | 9/2013 | Bertolero et al. |
| 8,535,343 B2 | 9/2013 | van der Burg et al. |
| 8,545,498 B2 | 10/2013 | Bertolero et al. |
| 8,603,108 B2 | 12/2013 | Roue et al. |
| 8,636,754 B2 | 1/2014 | Hughett, Sr. et al. |
| 8,636,764 B2 | 1/2014 | Miles et al. |
| 8,647,361 B2 | 2/2014 | Borillo et al. |
| 8,663,245 B2 | 3/2014 | Francischelli et al. |
| 8,663,268 B2 | 3/2014 | Quinn et al. |
| 8,663,273 B2 | 3/2014 | Khairkhahan et al. |
| 8,715,302 B2 | 5/2014 | Ibrahim et al. |
| 8,715,318 B2 | 5/2014 | Miles et al. |
| 8,764,793 B2 | 7/2014 | Lee |
| 8,784,469 B2 | 7/2014 | Kassab |
| 8,795,328 B2 | 8/2014 | Miles et al. |
| 8,814,778 B2 | 8/2014 | Kiser et al. |
| 8,828,051 B2 | 9/2014 | Javois et al. |
| 8,834,519 B2 | 9/2014 | van der Burg et al. |
| 8,852,218 B2 | 10/2014 | Hughett, Sr. et al. |
| 8,932,308 B2 | 1/2015 | Ibrahim et al. |
| 9,011,551 B2 | 4/2015 | Oral et al. |
| 9,017,349 B2 | 4/2015 | Privitera et al. |
| 9,119,607 B2 | 5/2015 | Amin |
| 9,060,799 B2 | 6/2015 | Santilli |
| 9,089,414 B2 | 7/2015 | Zimmerman et al. |
| 9,101,364 B2 | 8/2015 | Ibrahim et al. |
| 9,119,627 B2 | 9/2015 | Cosgrove et al. |
| 9,138,213 B2 | 9/2015 | Amin et al. |
| 9,161,758 B2 | 10/2015 | Figulla et al. |
| 9,168,043 B2 | 10/2015 | van der Burg et al. |
| 9,179,920 B2 | 11/2015 | Ren |
| 9,186,152 B2 | 11/2015 | Campbell et al. |
| 9,211,124 B2 | 12/2015 | Campbell et al. |
| 9,393,023 B2 | 7/2016 | Privitera et al. |
| 9,427,277 B2 | 8/2016 | Swanson et al. |
| 9,456,822 B2 | 10/2016 | Krishnan |
| 9,510,811 B2 | 12/2016 | Akpinar |
| 9,510,904 B2 | 12/2016 | Krishnan |
| 9,554,804 B2 | 1/2017 | Erzberger et al. |
| 9,566,073 B2 | 2/2017 | Kassab et al. |
| 9,572,584 B2 | 2/2017 | Miles et al. |
| 9,592,058 B2 | 3/2017 | Erzberger et al. |
| 9,597,086 B2 | 3/2017 | Larsen et al. |
| 9,649,115 B2 | 5/2017 | Edmiston et al. |
| 9,656,063 B2 | 5/2017 | Kelley et al. |
| 9,693,781 B2 | 7/2017 | Miles et al. |
| 9,724,105 B2 | 8/2017 | Kaplan et al. |
| 9,737,309 B1 | 8/2017 | Ad |
| 9,763,666 B2 | 9/2017 | Wu et al. |
| 9,770,232 B2 | 9/2017 | Amin et al. |
| 9,795,387 B2 | 10/2017 | Miles et al. |
| 9,808,253 B2 | 11/2017 | Li et al. |
| 9,826,980 B2 | 11/2017 | Figulla et al. |
| 9,839,431 B2 | 12/2017 | Meyer et al. |
| 9,849,011 B2 | 12/2017 | Zimmerman et al. |
| 9,861,371 B2 | 1/2018 | Martin et al. |
| 9,888,925 B2 | 2/2018 | Bertolero et al. |
| 10,314,585 B2 | 6/2019 | Williamson, IV et al. |
| 10,631,874 B2 | 4/2020 | Martin et al. |
| 2004/0030335 A1 | 2/2004 | Zenati et al. |
| 2005/0149068 A1 | 7/2005 | Williams et al. |
| 2005/0149069 A1 | 7/2005 | Bertolero et al. |
| 2005/0165429 A1 | 7/2005 | Douglas et al. |
| 2005/0177182 A1 | 8/2005 | van der Burg et al. |
| 2005/0273129 A1 | 12/2005 | Michels et al. |
| 2005/0277959 A1 | 12/2005 | Cosgrove et al. |
| 2006/0020271 A1 | 1/2006 | Stewart et al. |
| 2007/0060951 A1 | 3/2007 | Shannon |
| 2007/0129737 A1 | 6/2007 | Goldfarb et al. |
| 2008/0125795 A1 | 5/2008 | Kaplan et al. |
| 2008/0208324 A1 | 8/2008 | Glithero et al. |
| 2009/0012545 A1 | 1/2009 | Williamson, IV et al. |
| 2009/0099596 A1 | 4/2009 | McGuckin, Jr. et al. |
| 2009/0112249 A1 | 4/2009 | Miles et al. |
| 2009/0209986 A1 | 8/2009 | Stewart et al. |
| 2009/0228038 A1 | 9/2009 | Amin |
| 2009/0306685 A1 | 12/2009 | Fill |
| 2010/0114152 A1 | 5/2010 | Shukla |
| 2010/0179570 A1 | 7/2010 | Privitera et al. |
| 2010/0204716 A1 | 8/2010 | Stewart et al. |
| 2010/0228279 A1 | 9/2010 | Miles et al. |
| 2011/0009853 A1 | 1/2011 | Bertolero et al. |
| 2011/0046437 A1 | 2/2011 | Kassab et al. |
| 2011/0046622 A1 | 2/2011 | McAuley |
| 2011/0054515 A1 | 3/2011 | Bridgeman et al. |
| 2011/0082495 A1 | 4/2011 | Ruiz |
| 2011/0178539 A1 | 7/2011 | Holmes, Jr. et al. |
| 2011/0208233 A1 | 8/2011 | McGuckin, Jr. et al. |
| 2011/0218566 A1 | 9/2011 | van der Burg et al. |
| 2011/0230903 A1 | 9/2011 | Bertolero |
| 2011/0301595 A1 | 12/2011 | McAuley |
| 2012/0035622 A1 | 2/2012 | Kiser et al. |
| 2012/0035631 A1 | 2/2012 | Hughett, Sr. et al. |
| 2012/0035643 A1 | 2/2012 | Khairkhahan et al. |
| 2012/0059394 A1 | 3/2012 | Brenner et al. |
| 2012/0059400 A1 | 3/2012 | Williamson, IV et al. |
| 2012/0071918 A1 | 3/2012 | Amin et al. |
| 2012/0123445 A1 | 5/2012 | Hughett, Sr. et al. |
| 2012/0157916 A1 | 6/2012 | Quinn et al. |
| 2012/0172927 A1 | 7/2012 | Campbell et al. |
| 2012/0232585 A1 | 9/2012 | Roue et al. |
| 2012/0239083 A1 | 9/2012 | Kreidler |
| 2012/0271337 A1 | 10/2012 | Figulla et al. |
| 2012/0271343 A1 | 10/2012 | Borillo et al. |
| 2012/0283585 A1 | 11/2012 | Werneth et al. |
| 2012/0283773 A1 | 11/2012 | Van Tassel et al. |
| 2012/0296160 A1 | 11/2012 | Hill et al. |
| 2012/0323262 A1 | 12/2012 | Ibrahim et al. |
| 2012/0323267 A1 | 12/2012 | Ren |
| 2013/0006343 A1 | 1/2013 | Kassab |
| 2013/0018413 A1 | 1/2013 | Oral et al. |
| 2013/0018414 A1 | 1/2013 | Widomski et al. |
| 2013/0041404 A1 | 2/2013 | Amin et al. |
| 2013/0046254 A1 | 2/2013 | Venkatraman et al. |
| 2013/0110154 A1 | 5/2013 | van der Burg et al. |
| 2013/0131649 A1 | 5/2013 | Hughett, Sr. et al. |

(56) References Cited

U.S. PATENT DOCUMENTS

| | | |
|---|---|---|
| 2013/0190799 A1 | 7/2013 | Clark |
| 2013/0237908 A1 | 9/2013 | Clark |
| 2013/0237996 A1 | 9/2013 | Bertolero et al. |
| 2013/0245369 A1 | 9/2013 | Dal Molin |
| 2013/0338686 A1 | 12/2013 | Ruiz |
| 2014/0005714 A1 | 1/2014 | Quick et al. |
| 2014/0012254 A1 | 1/2014 | Bertolero et al. |
| 2014/0018831 A1 | 1/2014 | Kassab et al. |
| 2014/0018841 A1 | 1/2014 | Peiffer et al. |
| 2014/0039488 A1 | 2/2014 | Bertolero et al. |
| 2014/0039543 A1 | 2/2014 | Willems et al. |
| 2014/0046360 A1 | 2/2014 | van der Burg et al. |
| 2014/0100596 A1 | 4/2014 | Rudman et al. |
| 2014/0142597 A1 | 5/2014 | Winkler et al. |
| 2014/0142617 A1 | 5/2014 | Larsen et al. |
| 2014/0148842 A1 | 5/2014 | Khairkhahan et al. |
| 2014/0172004 A1 | 6/2014 | De Canniere |
| 2014/0172005 A1 | 6/2014 | De Cannier |
| 2014/0188159 A1 | 7/2014 | Steege |
| 2014/0207169 A1 | 7/2014 | Miles et al. |
| 2014/0221993 A1 | 8/2014 | Bertolero et al. |
| 2014/0257365 A1 | 9/2014 | McGuckin, Jr. |
| 2014/0277074 A1 | 9/2014 | Kaplan et al. |
| 2015/0088173 A1 | 3/2015 | Guzman Sanchez et al. |
| 2015/0119884 A1 | 4/2015 | Fung et al. |
| 2015/0173767 A1 | 6/2015 | Monti et al. |
| 2015/0182225 A1 | 7/2015 | Morejohn et al. |
| 2015/0190135 A1 | 7/2015 | Ibrahim et al. |
| 2015/0223813 A1 | 8/2015 | Williamson, IV et al. |
| 2015/0223820 A1 | 8/2015 | Olson et al. |
| 2015/0230909 A1 | 8/2015 | Zaver et al. |
| 2015/0250482 A1 | 9/2015 | Slaughter et al. |
| 2015/0320426 A1 | 11/2015 | Cosgrove et al. |
| 2015/0327979 A1 | 11/2015 | Quinn et al. |
| 2015/0374380 A1 | 12/2015 | Miller et al. |
| 2016/0008001 A1 | 1/2016 | Winkler et al. |
| 2016/0022273 A1 | 1/2016 | Kassab |
| 2016/0058539 A1 | 3/2016 | VanTassel et al. |
| 2016/0066922 A1 | 3/2016 | Bridgeman et al. |
| 2016/0066974 A1 | 3/2016 | Coulombe |
| 2016/0074043 A1 | 3/2016 | Friedman et al. |
| 2016/0089151 A1 | 3/2016 | Siegel et al. |
| 2016/0095603 A1 | 4/2016 | McGuckin, Jr. et al. |
| 2016/0100844 A1 | 4/2016 | Li et al. |
| 2016/0106432 A1 | 4/2016 | Mesallum |
| 2016/0166242 A1 | 6/2016 | Krishnan |
| 2016/0192911 A1 | 7/2016 | Kassab et al. |
| 2016/0192912 A1 | 7/2016 | Kassab et al. |
| 2016/0235412 A1 | 8/2016 | Liddicoat et al. |
| 2016/0249932 A1 | 9/2016 | Rogers et al. |
| 2016/0278749 A1 | 9/2016 | Javois et al. |
| 2016/0278750 A1 | 9/2016 | Akpinar |
| 2016/0278781 A1 | 9/2016 | Fung et al. |
| 2016/0287261 A1 | 10/2016 | Li et al. |
| 2016/0310147 A1 | 10/2016 | Squire et al. |
| 2016/0317135 A1 | 11/2016 | Glimsdale et al. |
| 2016/0317235 A1 | 11/2016 | Privitera et al. |
| 2016/0331382 A1 | 11/2016 | Center et al. |
| 2016/0339210 A9 | 11/2016 | Kassab et al. |
| 2016/0374657 A1 | 12/2016 | Kreidler |
| 2017/0007262 A1 | 1/2017 | Amplatz et al. |
| 2017/0027552 A1 | 2/2017 | Turkington et al. |
| 2017/0035433 A1 | 2/2017 | Forbes |
| 2017/0035434 A1 | 2/2017 | Forbes |
| 2017/0035435 A1 | 2/2017 | Amin et al. |
| 2017/0035436 A1 | 2/2017 | Morita |
| 2017/0042549 A1 | 2/2017 | Kaplan et al. |
| 2017/0042550 A1 | 2/2017 | Chakraborty et al. |
| 2017/0065262 A9 | 3/2017 | Kassab |
| 2017/0065280 A1 | 3/2017 | Micher et al. |
| 2017/0065283 A9 | 3/2017 | Kassab et al. |
| 2017/0095238 A1 | 4/2017 | Rudman et al. |
| 2017/0095256 A1 | 4/2017 | Lindgren et al. |
| 2017/0095257 A1 | 4/2017 | Miller et al. |
| 2017/0100112 A1 | 4/2017 | van der Burg et al. |
| 2017/0100183 A1 | 4/2017 | Iaizzo et al. |
| 2017/0119400 A1 | 5/2017 | Amplatz et al. |
| 2017/0156840 A1 | 6/2017 | Edmiston et al. |
| 2017/0196568 A1 | 7/2017 | Gross et al. |
| 2017/0215888 A1 | 8/2017 | Miles et al. |
| 2017/0215889 A1 | 8/2017 | Edmiston et al. |
| 2017/0224350 A1 | 8/2017 | Shimizu et al. |
| 2017/0224355 A1 | 8/2017 | Bowman et al. |
| 2017/0231639 A1 | 8/2017 | Miller |
| 2017/0245861 A1 | 8/2017 | Clark, III et al. |
| 2017/0245866 A1 | 8/2017 | Kiser et al. |
| 2017/0258475 A1 | 9/2017 | Mellmann et al. |
| 2017/0273690 A1 | 9/2017 | Miles et al. |
| 2017/0281193 A1 | 10/2017 | Asirvatham et al. |
| 2017/0290592 A1 | 10/2017 | Miller et al. |
| 2017/0290594 A1 | 10/2017 | Chakraborty et al. |
| 2017/0290595 A1 | 10/2017 | Miles et al. |
| 2017/0325820 A1 | 11/2017 | Miles et al. |
| 2017/0325824 A1 | 11/2017 | Li et al. |
| 2017/0340329 A1 | 11/2017 | Groothuis et al. |
| 2017/0340334 A1 | 11/2017 | Miles et al. |
| 2017/0340335 A1 | 11/2017 | Ad |
| 2017/0340336 A1 | 11/2017 | Osypka |
| 2017/0354421 A1 | 12/2017 | Maguire et al. |
| 2018/0000485 A1 | 1/2018 | Ad |
| 2018/0000487 A1 | 1/2018 | Miles et al. |
| 2018/0000490 A1 | 1/2018 | Kaplan et al. |
| 2018/0008412 A1 | 1/2018 | Callas et al. |
| 2019/0105104 A1 | 4/2019 | Bertolero et al. |
| 2020/0100789 A1 | 4/2020 | Bertolero et al. |
| 2020/0222056 A1 | 7/2020 | Martin et al. |

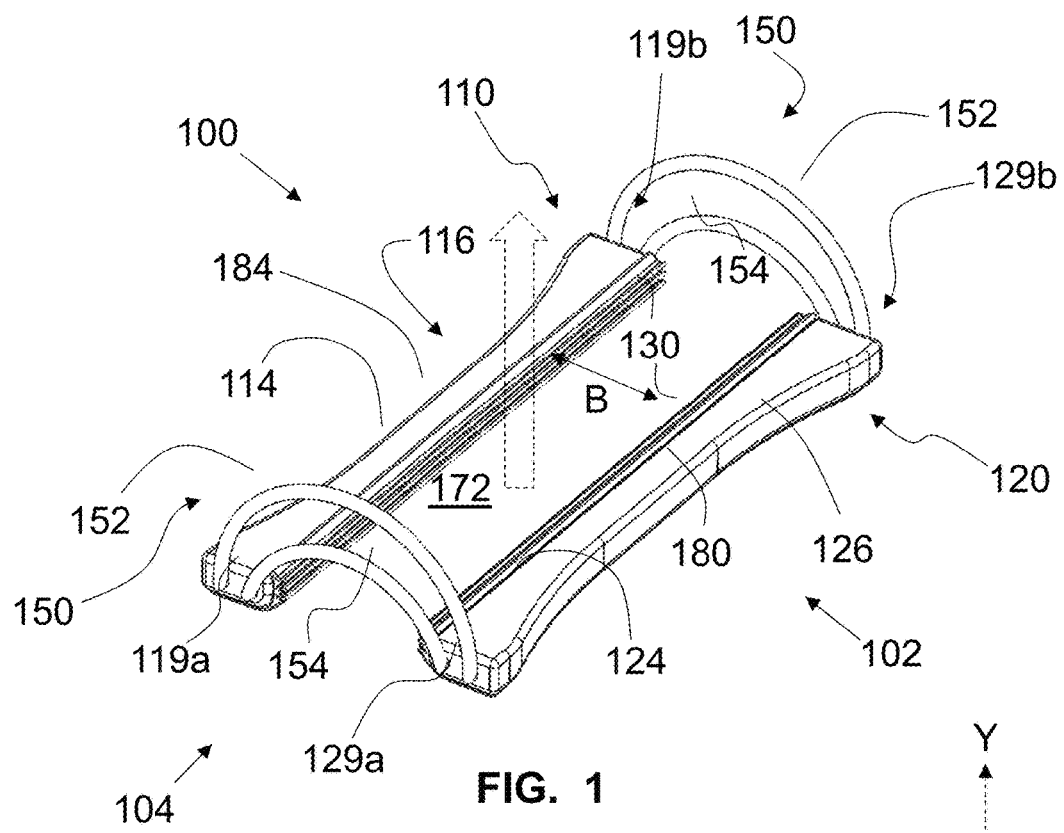
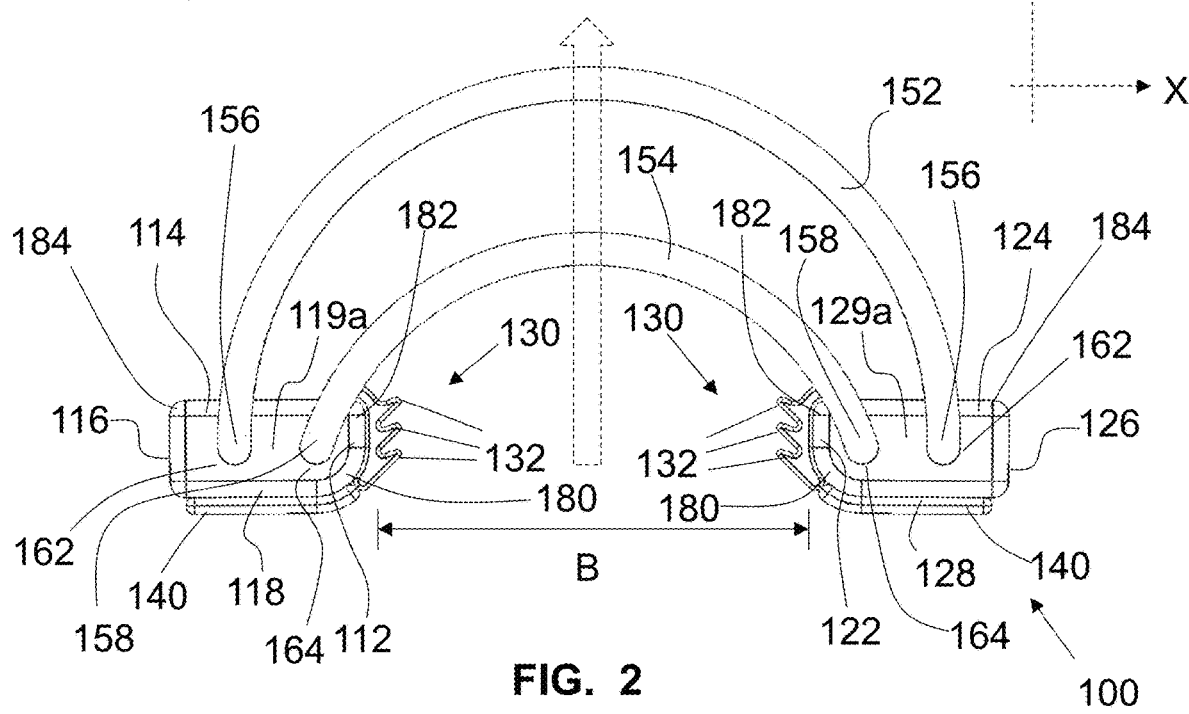
FIG. 1
FIG. 2

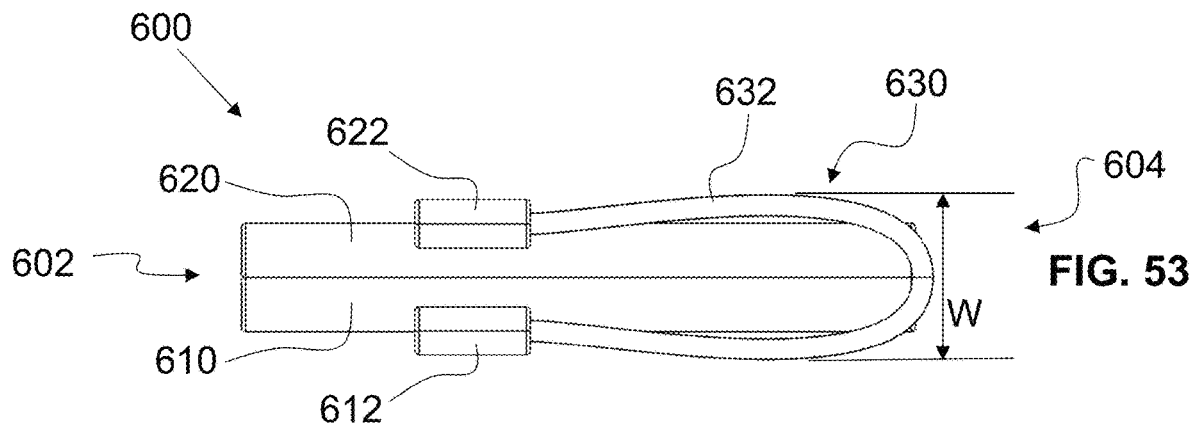
FIG. 53
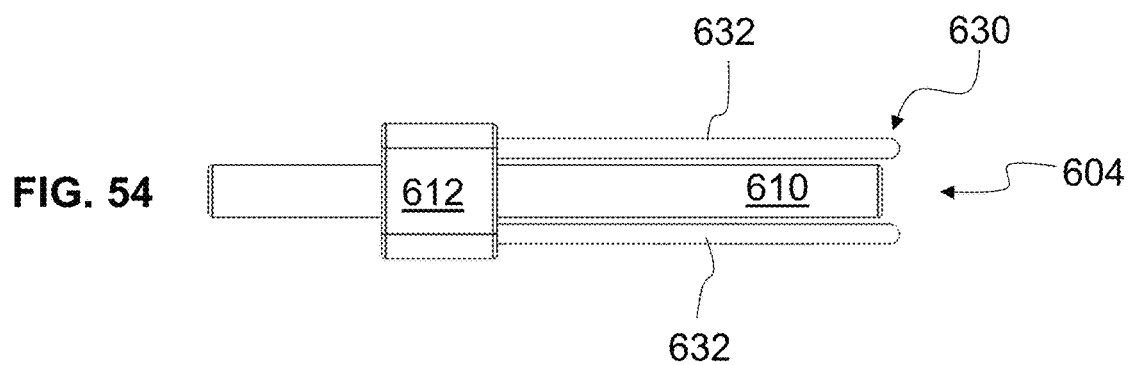
FIG. 54
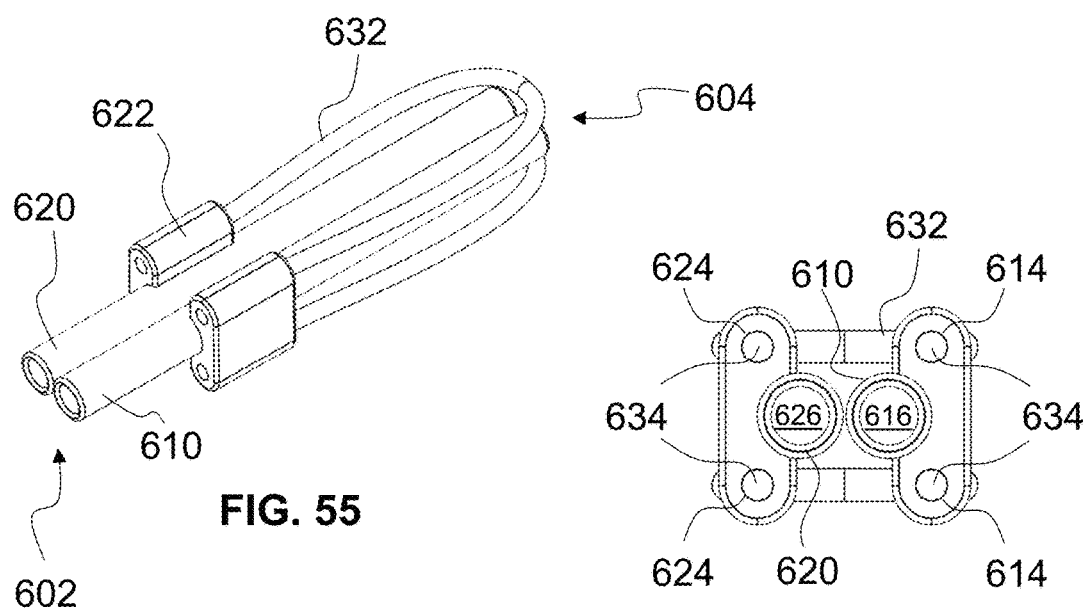
FIG. 55
FIG. 56

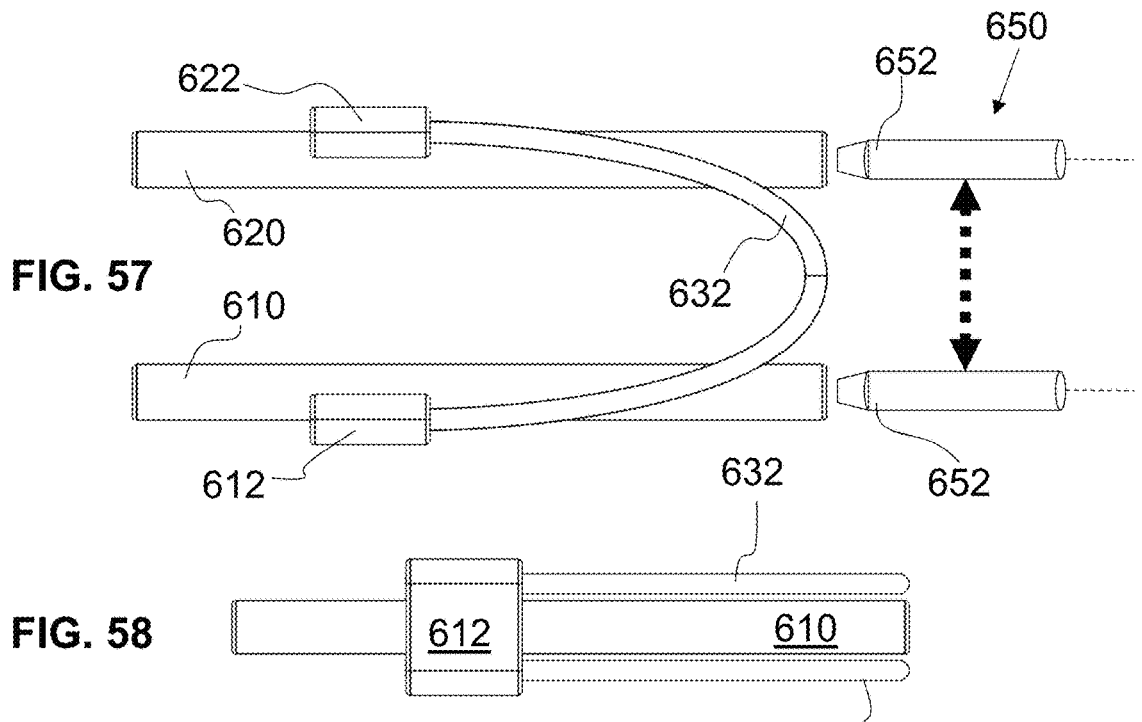
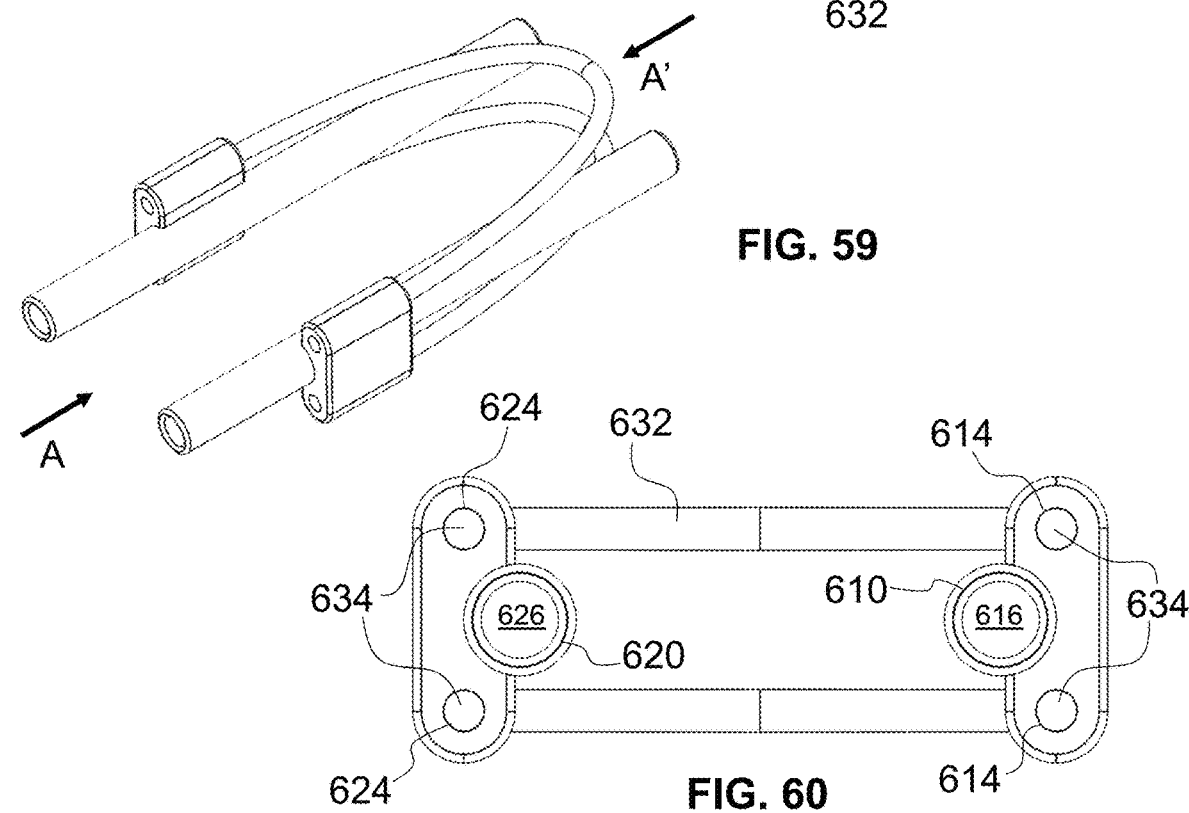

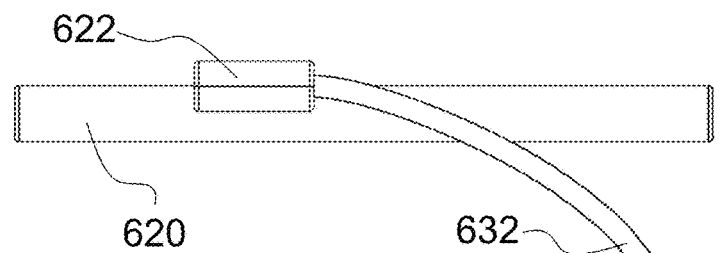
FIG. 61
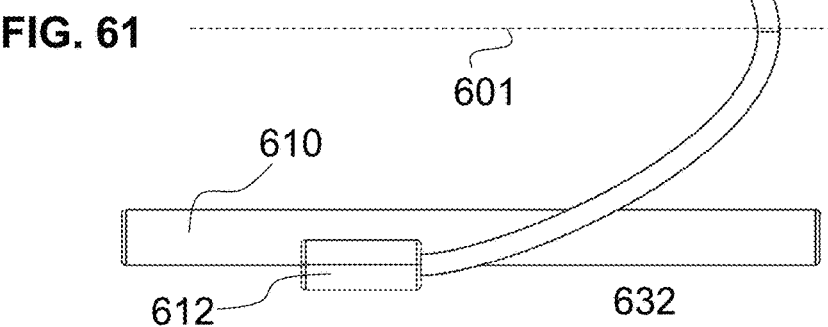
FIG. 62
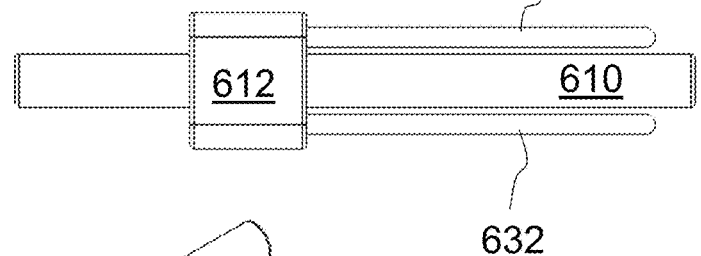
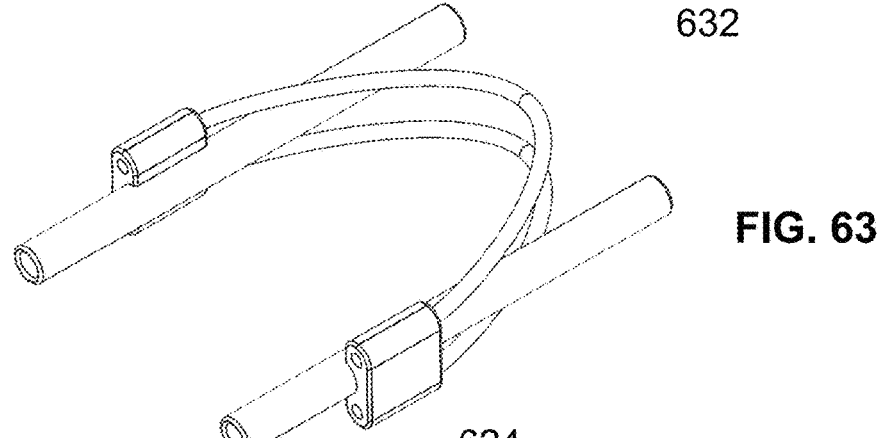
FIG. 63
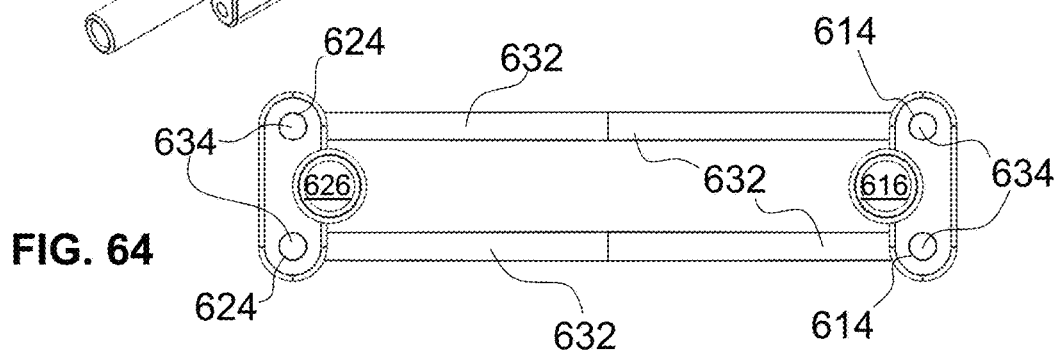
FIG. 64

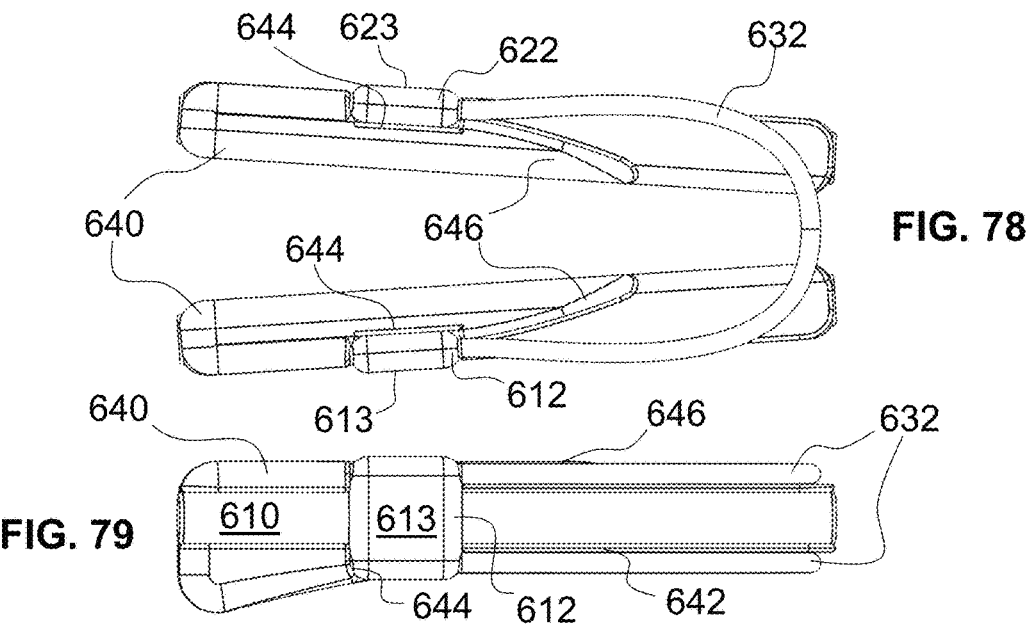
FIG. 78
FIG. 79
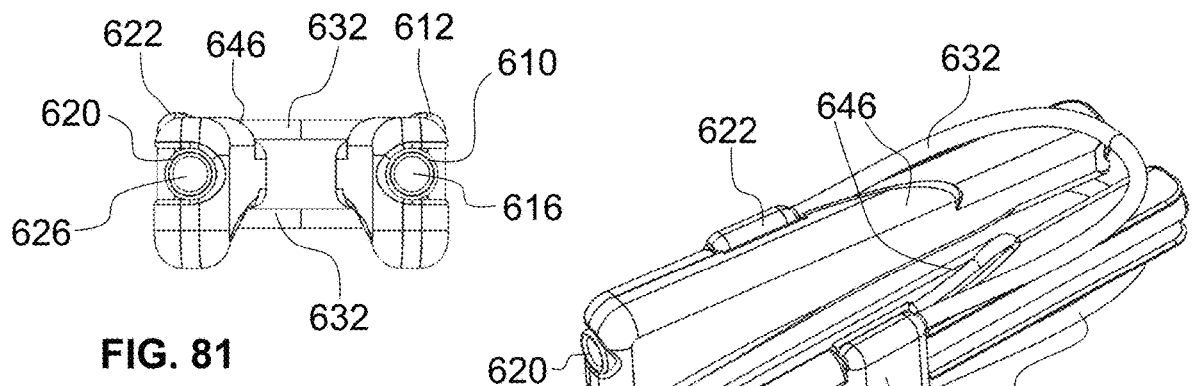
FIG. 81
FIG. 80
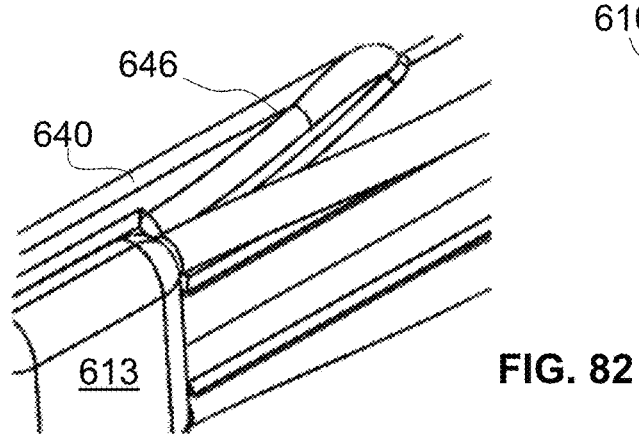
FIG. 82

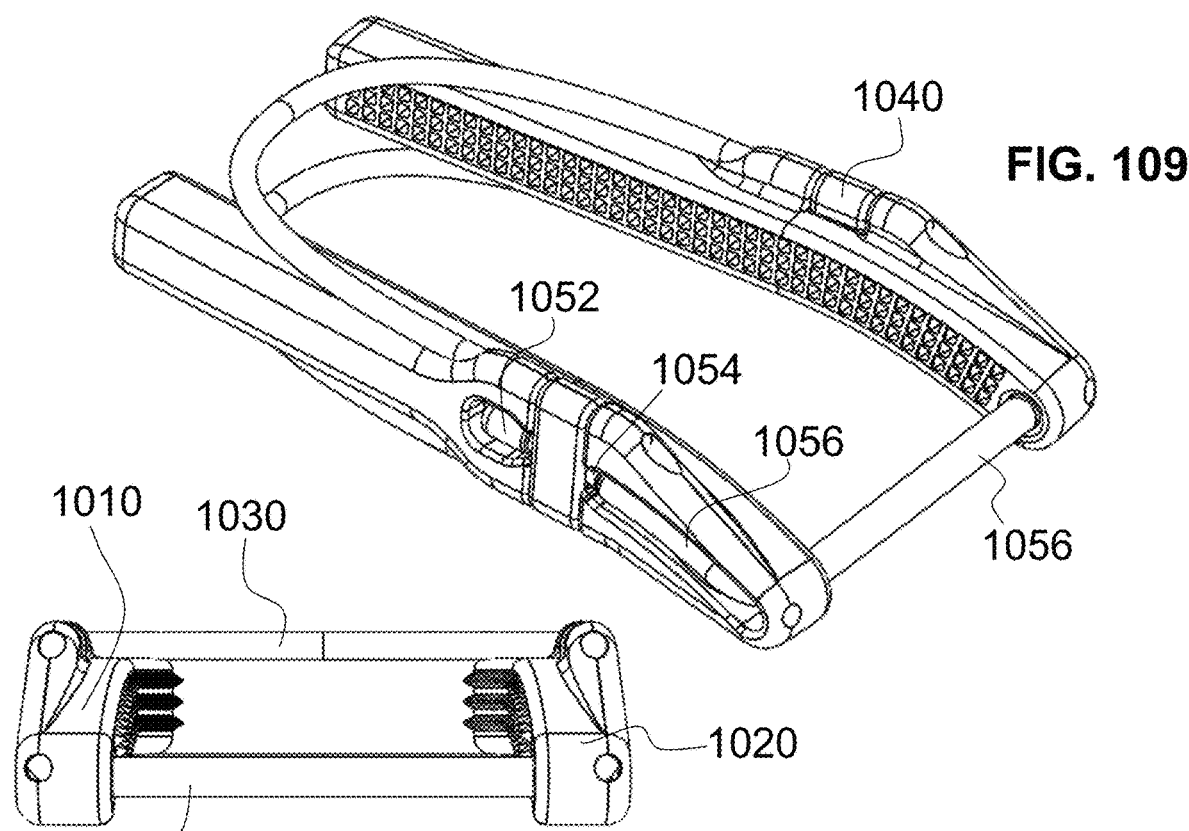
FIG. 109
FIG. 110
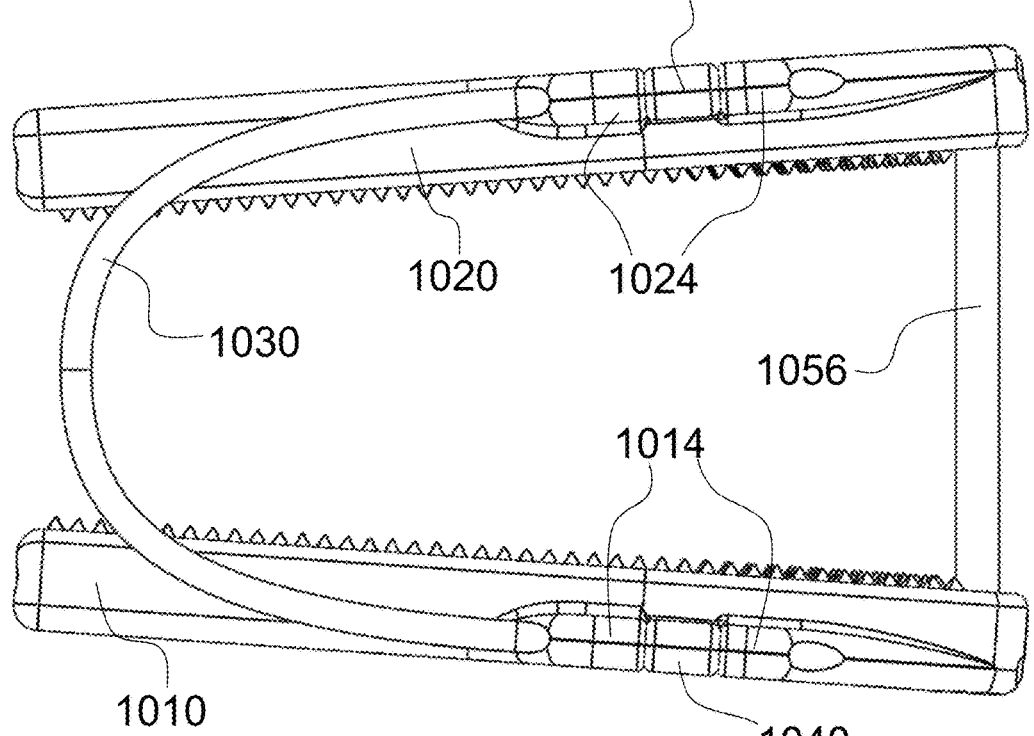
FIG. 111

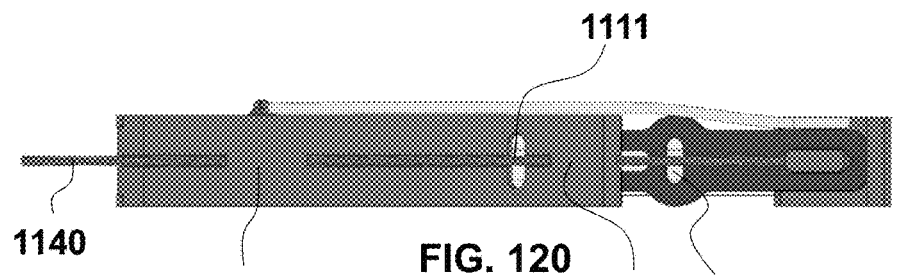
FIG. 120
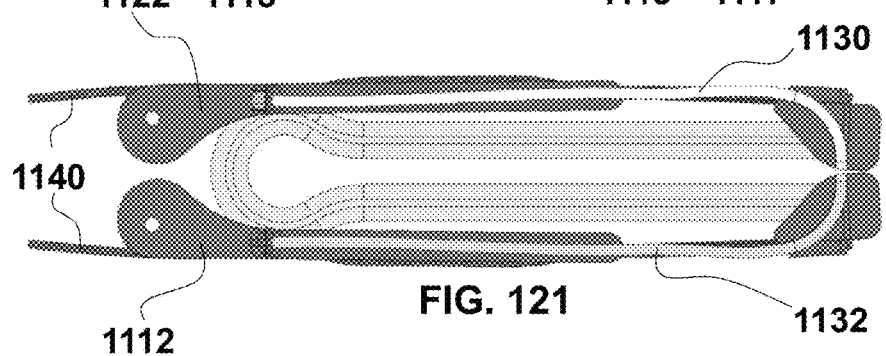
FIG. 121
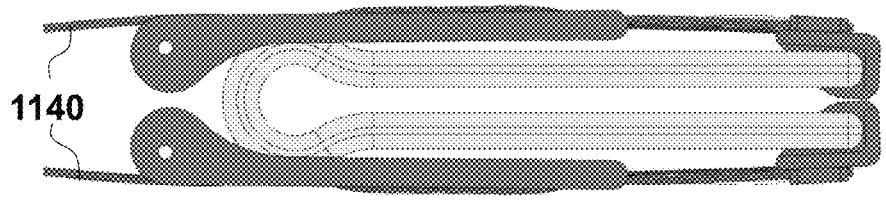
FIG. 122
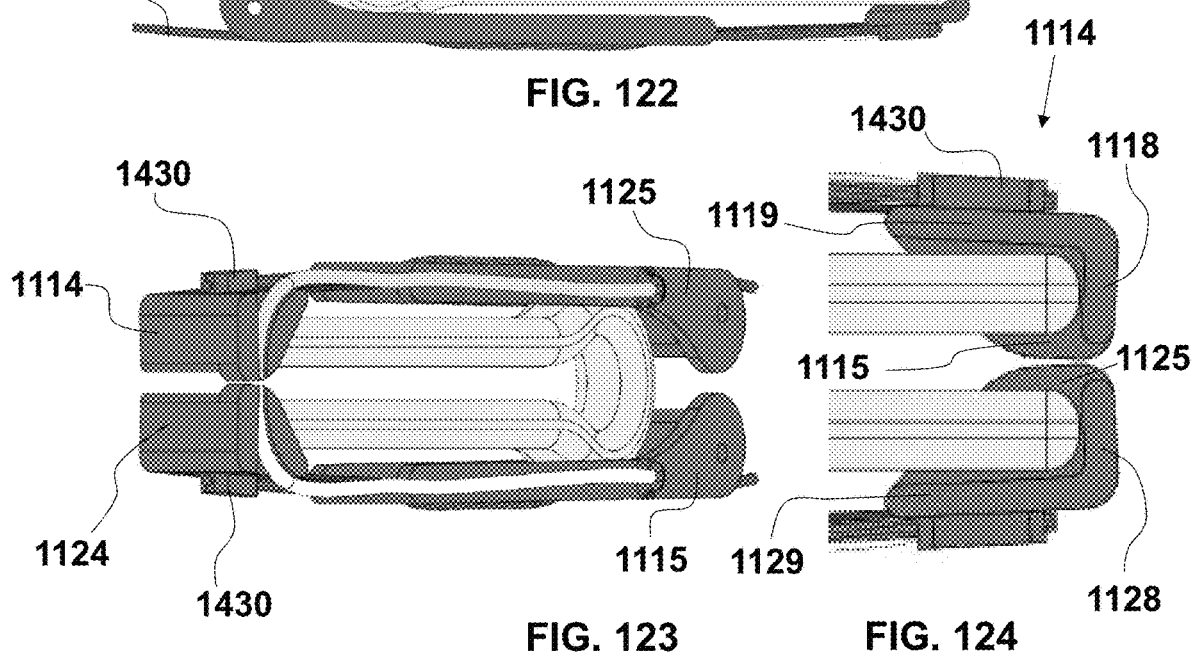
FIG. 123
FIG. 124

LEFT ATRIAL APPENDAGE CLIPPING DEVICE AND METHODS FOR CLIPPING THE LAA

CROSS-REFERENCE TO RELATED APPLICATIONS

This application claims the priority, under 35 U.S.C. § 119, of U.S. Provisional Patent Application No. 62/622,751, filed Jan. 26, 2018, Application No. 62/650,766, filed Mar. 30, 2018, Application No. 62/727,850, filed Sep. 6, 2018, and Application No. 62/743,708, filed Oct. 10, 2018; the prior applications are herewith incorporated by reference herein in their entireties.

STATEMENT REGARDING FEDERALLY SPONSORED RESEARCH OR DEVELOPMENT

Not applicable.

FIELD OF THE INVENTION

The present systems, apparatuses, and methods lie generally in the field of surgical approaches to externally occluding the fluid passageway of a hollow tissue structure. Specifically, the present disclosure relates to devices, systems, and methods that externally clip the left atrial appendage ("LAA") of the heart to exclude the LAA from the left atrium of the heart, to effectively closing off the fluid passageway between the LAA and the left atrium.

BACKGROUND OF THE INVENTION

Presently, in the United States, the most common type of cardiac arrhythmia is atrial fibrillation (AF), which is characterized as the chaotic and rapid electrical activity of the upper chambers of the heart. There are several causes and risk factors leading to the development of atrial fibrillation, including hypertension, acute and chronic rheumatic heart disease, and hyperthyroidism. Because of this abnormal heart rhythm, contraction of the atrial fibers is asynchronous (not in harmony or unison), such that atrial pumping could cease altogether. Therefore, one of the most dangerous conditions occurring during atrial fibrillation is the disruption or stasis of the blood flow in the atria, which can lead to thrombus (blood clot) formation, placing the afflicted person at a high risk of a heart attack or an embolic stroke. The great majority of blood clots resulting from atrial fibrillation originate in the LAA, due to the LAA's anatomical position and physiological characteristics. The LAA is a pedunculated and finger-shaped, sack-like cavity connected to the lateral wall of the left atrium between the mitral valve and the root of the left pulmonary vein. Thus, the LAA is a prime location for the detrimental pooling and accumulation of stagnant blood when the heart is not contracting to squeeze blood into the ventricles at a normal and coordinated pace. As a result, clots can easily form and accumulate in the LAA, build upon themselves, and propagate out from the LAA and into the atrium. Accordingly, because the LAA is predisposed for thrombus formation, the containment or elimination of clots formed in the LAA of atrial fibrillation patients would greatly reduce the incidence of stroke in those patients.

Pharmacological therapies, such as blood thinners, anticoagulants, and antiplatelet medications are well-known and routinely used to reduce the risk of blood clot formation. However, these medications are associated oftentimes with both harmful and distressing side effects and complications, including excessive bleeding, headaches, dizziness, fatigue, and contraindications, making patient compliance and tolerance very difficult. Thus, there is a compelling interest in developing alternatives that increase efficacy, limit any dangerous and chronic side effects, and improve a patient's quality of life.

Accordingly, another approach to reducing or entirely eliminating the risk of clot formation in the LAA is through an open chest, thoracotomy, thoracoscopy, or percutaneous surgical intervention that effectively shuts off or substantially restricts blood flow between the LAA and left atrium. The exact role of the LAA as a part of the cardiovascular system is not entirely clear. It is thought that the LAA is perhaps suited to act as a kind of decompression chamber during left ventricle systole and during other periods when left atrial pressure is high. However, it does not appear that the LAA performs a necessary function and is considered physiologically insignificant to the anatomy and function of the heart. Therefore, surgically cutting off fluid communication to the LAA, or obliterating (i.e., removing) the LAA from the heart entirely, are promising and feasible approaches to drastically reducing the risk of clot formation in the LAA.

Each of the existing surgical approaches has its associated benefits and disadvantages. For example, the complete removal of the LAA eliminates all danger of future clot formation therein. However, there remains the risk of, during the procedure, dislodging and releasing an already-existing blood clot into the bloodstream. In addition, removal of the LAA creates a substantial wound on the heart that must be carefully controlled, expertly clamped, and sutured shut with absolute precision to avoid significant bleeding. Furthermore, removal of the LAA is clearly a dramatic anatomical change and, therefore, should be considered with caution as the hemodynamic and hormonal roles of the LAA are still a subject of ongoing study and understanding.

Other surgical approaches aim to seal or block off, or occlude, the fluid passageway between the LAA and the left atrium without removing any of the anatomy. For example, a surgeon may surgically stitch or staple the LAA (e.g., via direct intra-atrial suture or external ligation) to effectively close the passageway, thereby reducing the LAA to just a blind pouch isolated from the left atrium. In a further example, a biocompatible barrier device may be implanted from within the left atrium at the entrance to the LAA and anchored within the passageway using a percutaneous delivery device (such as a vascular catheter). An example of such a device is the WATCHMAN™ Left Atrial Appendage Closure Device sold by Boston Scientific Corporation. Although some of these procedures can be conducted using minimally invasive techniques (e.g., thoracotomy, thoracoscopy), there remains considerable risk because the heart tissue is either pierced or an intrusion is made into the heart's interior. Furthermore, the effectiveness of these procedures depends upon the exact placement of the staples, sutures, implant, or other occlusion device, thus requiring the surgeon's ultraprecision. In addition, any foreign device left in the chamber of the heart has the future potential of being a thrombosis-generating site as some biocompatible materials could eventually break down and/or promote clot formation. Accordingly, there is a great desire for developing different surgical approaches for occluding or isolating the LAA that do not require an actual breach of the heart tissue.

One example of such a procedure is the permanent surgical application of an exclusion clip to the exterior surface of the LAA. Specifically, an exclusion clip is positioned about and around the base of the LAA to apply a sufficient pinching or clamping pressure that effectively closes the interior fluid passageway between the LAA and the atrium, without ever penetrating the heart. Therefore, the potential for uncontrolled bleeding or other trauma occurring to the heart is drastically reduced. Also, because no element of the exclusion clip is introduced into the cardiovascular system, there is minimal risk of inadvertently creating a site that promotes formation of clots in the future. Still yet, there are several inherent limitations in the existing exclusion clip designs and in the systems, procedures, and delivery devices presently used for applying the exclusion clips.

By way of background, the currently existing exclusion clips employed to isolate the LAA are generally formed from a pair of elongated and opposing clamping members urged together by one or more spring members. Prior to application of the exclusion clip to the LAA, a delivery device engages the exclusion clip and imparts a force counteracting the spring-biased closing force of the spring member or members in order to separate the clamping members from each other and create an interior space therebetween. During application, the LAA is positioned within the interior space of the exclusion clip to be received between the opposing clamping members. Once the surgeon determines that the exclusion clip is in a desirable position with respect to the LAA, the clip's delivery device relieves the counteracting force imparted to the spring member or members and disengages from the exclusion clip. As a result, the clamping members return to their inwardly spring-biased state to snugly surround the LAA in a grip-like manner and produce a clamping action against the exterior surface of the LAA. An example of such a device is the ATRICLIP® Left Atrial Appendage Exclusion System that is sold by AtriCure, Inc.

Presently, exclusion clips are designed to be either open-ended or closed-loop. The closed-loop exclusion clips are generally comprised of a pair of parallel and opposing clamping members connected on both ends by spring members to form a loop. By contrast, open-ended exclusion clips include a pair of opposing clamping members connected to one another at just a single end by a spring or spring-biased hinge-like member that urges the clamping members to pivot towards one another to generate the necessary clamping action.

Accordingly, to ensure the effectiveness and safety of the exclusion clip approach to isolating the LAA, the exclusion clip must be positioned accurately with respect to the LAA and the remainder of the heart, and with sufficient pressure, to adequately and permanently close off the blood flow into and out from the LAA, while at the same time not severing or otherwise damaging the LAA or any other surrounding structure. Therefore, the surgeon must skillfully control the placement of the exclusion clip and determine that the clip is sufficiently closed and securely in place, which is not an insignificant feat. Once the exclusion clip seats on the LAA, the interposed tissue will desiccate and otherwise shrink and change, thereby requiring a different and greater amount of clamping force to keep the LAA sealed properly.

A further limitation of existing exclusion clip designs (in particular, the closed-loop design) is that the distance of the interior opening between the opposing clamping members is restricted by the spring-biasing force imposed by the spring member or members, wherein the spring-biasing force is dependent upon the degree to which the spring member or members are able to flex. As a result, a surgeon might struggle to apply the exclusion clip when a patient's LAA is of a relatively large size.

Open-ended LAA exclusion clips are sometimes preferred over closed-ended clips because they only require lateral access to the LAA and, therefore, can be positioned when there is limited access to the heart and with less-invasive procedures. A drawback of open-ended clips, however, is that it is often difficult for the surgeon to determine when the clip has been positioned completely across the entire width of the LAA. Because a lateral approach is used to place the clip, the far end of the LAA is usually not visible to the surgeon. This requires the surgeon to estimate the position of the distal end of the clip and release the clip when the surgeon believes that the clip spans entirely across the LAA. If the surgeon's estimation is incorrect and an open-ended clip is positioned only partially across the LAA when it is released into the clamped configuration, only partial exclusion of the LAA is achieved. Such an implantation will likely lead to complications, requiring further surgery to correct the partial exclusion.

There is, therefore, a need in the art for an applicator device for open-ended LAA exclusion clips that provides the surgeon with a positive indication that the clip has been positioned completely across the LAA before it is released into the clamped implanted configuration.

Further, as described above, the LAA must be suitably oriented and held in a stable position to bring the LAA into the interior space of the exclusion clip during its application. Accordingly, an instrument separate from the clip delivery device, such as a surgical grasper, is typically used to manipulate the LAA into position. In fact, in all occlusion, exclusion, and obliteration procedures of the LAA, it is necessary to use a separate instrument solely dedicated to orienting the LAA into the correct position. As a result, in an exclusion clip procedure, the surgeon must simultaneously operate the clip delivery device and the stabilization instrument (or directly stabilize the heart), thereby occupying both of the surgeon's hands. This limits the surgeon's mobility and freedom, which can also lead to fatigue. Importantly, if not performed carefully, just a slight misstep in the simple manipulation of the LAA may tear or perforate the LAA, potentially causing an immediate danger of life-threatening hemorrhaging. Therefore, there is a need in the art for an exclusion clip and delivery device system that simplifies and improves the precision of the interaction between the exclusion clip and the LAA, and minimizes or eliminates the need for and/or involvement of a separate grasping or nudging device with the LAA.

Additionally, there is a need in the art for an exclusion clip whose shape, material characteristics, tolerances, and surface area features improve the surface-to-surface interaction between the clip's clamping members and both the LAA and the left atrium once the clip is in place, as well as strengthen the grip of the exclusion clip about the LAA without causing any damage to the tissue, not only during the surgical procedure, but also over the lifetime of the implanted clip.

Thus, a need exists to overcome the problems with the prior art systems, designs, and processes as discussed above.

SUMMARY OF THE INVENTION

The systems, apparatuses, and methods that are described provide devices, systems, and methods that clip the exterior surface of the left atrial appendage to fluidically disconnect the interior of the LAA from the left atrium that overcome the hereinafore-mentioned disadvantages of the heretofore-known devices and methods of this general type. More specifically, the systems, apparatuses, and methods described provide an LAA exclusion clip having structural features that, during the surgical application of the exclusion clip, act in such a way, and, in some instances, act in concert with the method of application, to, themselves, according to principles of physics, naturally and instinctually motivate, encourage, and/or bring forward the LAA into the opening at the clip's interior, these features being referred to herein as "self-motivating." Such a self-motivating exclusion clip beneficially minimizes or obviates the need for a stabilization instrument separate from the clip delivery device for manipulating the LAA with respect to the exclusion clip, resulting in a one-handed and no-touch procedure.

The systems, apparatuses, and methods described further provide a closed-loop exclusion clip that gives the surgeon greater precision and control over the degree of clamping pressure that is applied and is free of the conventional restrictions resulting from employing spring members to connect the terminating ends of the clip's opposing clamping members.

The systems, apparatuses, and methods described further provide tissue-crossing sensors for jaw-based surgical instruments that give the surgeon greater precision and control over placement of a distal end of a jaw when that distal end is obscured or blocked by the surgical environment. The sensor of the surgical instrument facilitates placement and deployment of an exclusion device, such as an LAA exclusion clip. The exclusion clip applicator and system generates a positive visual and/or audible indication when the clip is placed completely across the anatomical structure to be occluded prior to releasing the clip into its clamped configuration.

In one embodiment, the delivery device comprises a shaft having a proximal end and a distal end, a handle housing one or more controls connected to the proximal end of the shaft, and an applicator head connected to the distal end of the shaft. The applicator head comprises two opposing jaws adapted to receive an open ended exclusion clip. The jaws pivot between a closed and an open position by a pivot assembly located at or near the proximal end of the applicator head attached to the shaft. The pivoting action of the jaws is controlled by one or more of the controls on the handle. At the tip of each of the jaws there is a holding or cup member. The cup members are adapted to come into contact, or into very close proximity, with each other when the jaws are closed. The jaws are configured to allow sufficient space to mount an exclusion clip between them when in the closed position. To allow the jaws to closely conform to the clip, and the cup members to be in close proximity upon closing of the jaws, the middle part of each of the jaws may comprise a flexible, spring-like member.

In a "passive" embodiment of the delivery device, the applicator head is outfitted with two different types of fiber optic wire. The first type is "collector-type" fiber optic wire. This type of fiber optic wire is designed to collect ambient light that strikes the wire along its entire length and guide the light so that it exits through the two ends of the wire. The second type of fiber optic wire used in the passive embodiment is transmitter-type fiber optic wire. This type of fiber optic wire is designed to collect light at one of its ends and transmit it so that it is output at the opposite end.

In the passive embodiment of the delivery device, a first of the opposing jaws of the applicator head is outfitted with a length of collector-type fiber optic wire disposed so that as much of the length of the wire as possible is exposed to ambient light during use of the device. This positioning can be achieved by wrapping or coiling the wire around the jaw or by gluing or otherwise attaching the wire to the surface of the jaw. One or both ends of this collector-type wire is received and captured by the cup member disposed at the tip of the first jaw. The cup is configured so that the captured end or ends of the collector-type wire are positioned directly facing the cup member of the second opposing jaw. The role of the collector-type wire is to capture as much ambient light as possible and route it for output at the tip of the first opposing jaw and directed towards the second opposing jaw.

The second opposing jaw in the passive embodiment is equipped with transmitter-type fiber optic wire. One end of the wire is retained by the cup member on the second opposing jaw. This end of the transmitter-type wire is positioned so that, when the opposing jaws are in the closed position, the end is in very close proximity to an end of the collector-type wire in the first opposing jaw. The opposite end of the transmitter-type wire is routed along the second opposing jaw to a location where it can be retained but remain visible to the user of the device. To enhance visibility of light being emitted by the opposite end of this wire, a lens, prism, or other optical enhancing device can be fitted at the termination point. Alternatively, the opposite end of the transmitter-type wire can be terminated at an electronic light sensor (such as a photocell, phototransistor or photodiode) which, upon sensing illumination, triggers an electronic audible or visual indicator, such as an LED or a horn.

A second "active" exemplary embodiment of the delivery device employs only transmitter-type fiber optic wire on both opposing jaws. The wire in the first opposing jaw extends between the cup member at the tip and an active source of light (such as an LED, laser, or infrared emitter). The configuration of the wire in the second opposing jaw is the same as in the passive embodiment. This exemplary embodiment does not rely on ambient light collected by the wire on the first jaw, but rather on actively generated light. The active embodiment can alternatively include additional variations and improvements. For example, the type of light generated and transmitted by the fiber optic wires can be of a frequency or color selected to maximize transmissivity through body fluids, such as blood, to ensure accurate indications should blood contaminate the ends of the fiber optic wires. The frequency of light can be chosen so that it is at a wavelength other than that generated by the traditional light sources used in thoracoscopic procedures, in order to avoid false positive indications. In addition, the generated light can be encoded with a known pulsed frequency to ensure that the light received at the second opposing jaw is, indeed, the generated light and not ambient light. Such an exemplary configuration uses an electronic sensor that avoids false indications by only triggering an indication when the light received at the sensor is of the expected pulsed frequency.

The applicator device can be used with open-ended exclusion clips having a number of different designs, whether known in the art or indicated herein. The exclusion clip is placed between the two opposing jaws with the open end of the clip facing distally in the direction of the tips of the jaws. Each of the parallel clamping members of the exclusion clip is fastened releasably to the jaw immediately adjacent to it. In this fashion, when control on the device's handle is actuated to separate the opposing jaws, the exclusion clip is forced open. When control is actuated to permit the opposing jaws to close, the spring in the exclusion clip urges the jaws to close around the clip as the clip closes.

The exclusion clip is fastened releasably to the jaws in a number of different ways. One exemplary embodiment utilizes sutures that extend from clamping members on the clip and wrap around release cables disposed on each of the opposing jaws. When an operator is satisfied that the clip is correctly positioned, release cables are pulled and removed from the applicator head, thus releasing the exclusion clip from the device. Once the release cables have been pulled, the clip is permanently applied. In an alternative exemplary embodiment, the fiber optic wires can serve the same function as the release cables. That is, the sutures are wrapped around the fiber optic wires and, when the clip is correctly positioned, the fiber optic wires are pulled out, thus releasing the clip.

In operation, regardless of whether the active or passive device is being used, the surgeon commences application of the clip by opening the jaws and clip by actuating an appropriate control on the handle. The open end of the clip is then positioned across the LAA using a lateral approach. When the surgeon believes the clip is inserted sufficiently to completely span the LAA when closed, the handle control is actuated to permit the clip to close, clamping the LAA. If the surgeon correctly estimated the insertion distance of the clip, the tips of the opposing jaws will come into very close proximity to each other with no structures (such as the LAA) between them. Such an orientation permits the light generated at the first opposing jaw to be collected by the fiber optic cable in the second opposing jaw, and the audible or visible indicator is triggered at the opposite end of the wire in the second jaw. Upon receiving such feedback, the surgeon is informed that adequate placement is likely and can release the clip from the applicator head, thus permanently applying the clip across the LAA. If, on the other hand, no visible or audible indication is received by the surgeon upon releasing the handle control and closing the clip and jaws around the LAA, this would indicate to the surgeon that something, possibly the LAA or another structure, is obstructing the light from reaching the second opposing jaw. The surgeon can then reopen the clip and attempt to correctly position the clip until the audible or visual indication is received.

Although the above-described exemplary embodiments rely on light transmitted through a fiber optic network, those skilled in the art will recognize that similar embodiments can be implemented using mediums other than light. For example, radio frequency waves, hall-effect sensors, ultrasonic waves, conductivity sensors, capacitance sensors, and the like may serve as alternative sensing measures.

The systems, devices, and methods herein described are also not limited to applicators or exclusion devices. Any device in which a jaw assembly must clear a structure before being actuated can also benefit from the disclosed sensor. Such devices include, without limitation, stapling devices, grasper or clamp devices, electrocautery or ultrasonic sealers, and the like.

In alternative exemplary embodiments, the fiber optic network need not be exclusively disposed on the opposing jaws. The fiber optic network can be completely or partially embedded within the clip itself. In such exemplary embodiments, the fiber optic network can be adapted to easily detach from the clip for removal upon withdrawal of the applicator device.

Although the embodiments of the invention shown in the figures have the ends of the fiber optic wires aligned with the ends of the fastener and on a plane above the fastener, in alternative exemplary embodiments, the fiber optic wire ends can be aligned inside, or extend beyond, the ends of the fastener. Similarly, in alternative embodiments, the fiber optic wire ends can be located above, below, or through the middle of the fastener. Any combination of these relative positionings can also be used.

In some exemplary embodiments, the holding members as cup members can have structural features guiding them to align upon closing of the jaws. The flexible members in the jaws allow the cup members to contact each other, or very closely approximate each other, even when tissue clamped in the fastener holds the fastener partially open.

As previously discussed, the indicator light can be positioned anywhere it would be visible to the operator of the device. This includes, without limitation, the handle, the jaw, the shaft, or combinations thereof in which multiple indicators are used. The indicator itself can be visible (such as a light), an audible indicator (such as a horn or beeper), or tactile.

Some exemplary embodiments of the described systems, devices, and methods can be equipped with a lockout mechanism that prevents release of the fastener until a positive indication of proper placement is received.

In some exemplary embodiments, the ends of the fiber optic wires can include features, such as a cup and dome, to exclude fluids when the features come in contact with each other.

The limitations of known devices are overcome with the exemplary applicator for an open-ended exclusion clip that provides the surgeon with a positive indication that the distal end of the clip is completely across the anatomical structure to be occluded prior to releasing the clip into its clamped configuration and thus ensure complete exclusion upon clamping.

With the foregoing and other objects in view, there is provided, an external left atrial appendage (LAA) exclusion clip, comprising a clipping assembly comprising first and second opposing clip struts each of the clip struts having a tissue-contacting surface and first and second bias surfaces, a bias assembly connecting the first clip strut to the second clip strut to align the first and second clip struts in a strut plane passing through the tissue-contacting surface, the bias assembly comprising at least one first bias spring connected to the first bias surface of the first clip strut and to the first bias surface of the second clip strut and at least one second bias spring connected to the second bias surface of the first clip strut and the second bias surface of the second clip strut, and the at least one first bias spring and the at least one second bias spring being configured to permit movement of the first and second clip struts in the strut plane.

In accordance with another feature, the first clip strut has a first proximal end and a first distal end, the second clip strut has a second proximal end and a second distal end, the at least one first bias spring is connected to an intermediate position at the first bias surface of the first clip strut between the first proximal end and the first distal end and an intermediate position at the first bias surface of the second clip strut between the second proximal end and the second distal end, and the at least one second bias spring is connected to an intermediate position at the second bias surface of the first clip strut between the first proximal end and the first distal end and an intermediate position at the second bias surface of the second clip strut between the second proximal end and the second distal end.

In accordance with a further feature, the first bias surface of the first clip strut is a first upper side, the second bias surface of the first clip strut is a first lower side, the first bias surface of the second clip strut is a second upper side, the second bias surface of the second clip strut is a second lower side, the tissue-contacting surface of the first clip strut comprises a first LAA contacting surface having a first longitudinal centerline, the tissue-contacting surface of the second clip strut comprises a second LAA contacting surface having a second longitudinal centerline, and the strut plane passes through the first and second longitudinal centerlines.

In accordance with an added feature, the clip is sized to fit into a laparoscopic port having an interior diameter and the clipping assembly and the bias assembly together have a maximum outer width that is no greater than the interior diameter of the port.

In accordance with an additional feature, the first and second clip struts have a maximum longitudinal length, the at least one first bias spring has a longitudinal length shorter than the maximum longitudinal length, and the at least one second bias spring has a longitudinal length shorter than the maximum longitudinal length.

In accordance with yet another feature, the clip is sized to fit into a laparoscopic port having an interior diameter, the clipping assembly and the bias assembly together have a maximum outer width that is no greater than the interior diameter of the port, the first and second clip struts have a maximum longitudinal length, the at least one first bias spring has a longitudinal length shorter than the maximum longitudinal length and the at least one second bias spring has a longitudinal length shorter than the maximum longitudinal length.

In accordance with yet a further feature, the bias assembly is configured to permit yaw movement of the first and second clip struts in the strut plane.

In accordance with yet an added feature, the bias assembly is configured to permit yaw movement of the first clip strut in the strut plane independent of yaw movement of the second clip strut in the strut plane.

In accordance with yet an additional feature, the first bias surface of the first clip strut is a first upper side, the first bias surface of the second clip strut is a second upper side, the first upper side and the second upper side together define an outer upper boundary, and the first bias spring remains within the outer upper boundary.

In accordance with again another feature, the second bias surface of the first clip strut is a first lower side, the second bias surface of the second clip strut is a second lower side, the first lower side and the second lower side together define an outer lower boundary, and the second bias spring remains within the outer lower boundary.

In accordance with again a further feature, the first clip strut has a first longitudinal axis, the second clip strut has a second longitudinal axis and the at least one first bias spring and the at least one second bias spring balance forces such that the first and second clip struts undergo substantially no rotation about the respective first and second longitudinal axes when the first and second struts move in the strut plane.

In accordance with again an added feature, the first clip strut has a first longitudinal axis, the second clip strut has a second longitudinal axis, the at least one first bias spring and the at least one second bias spring balance forces such that the first and second clip struts have substantially no torque when the first and second struts move in the strut plane.

In accordance with again an additional feature, the first clip strut has a first proximal end and the second clip strut has a second proximal end, and which further comprises a delivery device removably connected to the first and second proximal ends and configured to move the first and second clip struts in the strut plane.

In accordance with still another feature, the first clip strut has a first proximal end and the second clip strut has a second proximal end, and which further comprises a delivery device removably connected to the first and second proximal ends and configured to move the first and second clip struts independently in the strut plane.

In accordance with still a further feature, the first clip strut has a first proximal end with a first proximal opening, the second clip strut has a second proximal end with a second proximal opening, and which further comprises a delivery device removably connected to the first and second proximal ends through the first and second proximal openings, the delivery device configured to move the first and second clip struts in the strut plane.

In accordance with a concomitant feature, the first clip strut has a first proximal end with a first proximal opening, the second clip strut has a second proximal end with a second proximal opening, and which further comprises a delivery device removably connected only to the first and second proximal ends through the first and second proximal openings, the delivery device configured to move the first and second clip struts in the strut plane.

With the foregoing and other objects in view, there is provided, an externally implantable, left atrial appendage (LAA) exclusion clip comprising a clipping assembly comprising a first clip strut having a first LAA contacting surface, a first rotation axis, a first end, and a second end opposite the first end, a second clip strut having a second LAA contacting surface, a second rotation axis substantially parallel to the first rotation axis, a first end, and a second end opposite the first end of the second clip strut, a bias assembly connecting the first clip strut to the second clip strut and comprising at least one first bias spring connected to the first end of the first clip strut and to the first end of the second clip strut and at least one second bias spring connected to the second end of the first clip strut and to the second end of the second clip strut, and the connections of the at least one first bias spring and the at least one second bias spring being configured to permit rotation of the first clip strut about the first rotation axis and the second clip strut about the second rotation axis.

In accordance with another feature, the first LAA contacting surface has a first given roughness, the first clip strut comprises a first reduced-friction surface adjacent the first LAA contacting surface, the first reduced-friction surface having a surface roughness substantially smoother than the first given roughness, the second LAA contacting surface has a second given roughness, and the second clip strut comprises a second reduced-friction surface adjacent the second LAA contacting surface, the second reduced-friction surface having a surface roughness substantially smoother than the second given roughness.

In accordance with a further feature, the first reduced-friction surface and the second reduced-friction surface are substantially smooth.

In accordance with an added feature, the first reduced-friction surface and the second reduced-friction surface comprise a hydrophilic coating.

In accordance with an additional feature, the first given roughness is a texture.

In accordance with yet another feature, the second given roughness is a texture.

In accordance with yet a further feature, at least one of the first and second LAA contacting surfaces has a given roughness and at least one of the first and second clip struts comprise a reduced-friction surface adjacent the at least one of the first and second LAA contacting surfaces having the given roughness, the reduced-friction surface being substantially smooth.

In accordance with yet an added feature, the reduced-friction surface comprises a hydrophilic coating.

In accordance with yet an additional feature, the first clip strut comprises a first motivator surface adjacent the first LAA contacting surface, the first motivator surface having a self-motivator and the second clip strut comprises a second motivator surface adjacent the second LAA contacting surface, the second motivator surface having a self-motivator.

In accordance with again another feature, the connections of the at least one first bias spring and the at least one second bias spring are configured to permit rotation of the first clip strut about the first rotation axis and the second clip strut about the second rotation axis such that the first motivator surface faces the second motivator surface in a first orientation and the first LAA contacting surface faces the second LAA contacting surface in a second orientation.

In accordance with again a further feature, the second orientation is at an angle to the first orientation.

In accordance with again an added feature, the connections of the at least one first bias spring and the at least one second bias spring are configured to permit rotation of the first clip strut about the first rotation axis and the second clip strut about the second rotation axis such that the first LAA contacting surface is parallel to the second LAA contacting surface in a first orientation and the first LAA contacting surface is parallel to the second LAA contacting surface in a second orientation at an angle to the first orientation.

In accordance with again an additional feature, the angle is substantially ninety degrees.

In accordance with still another feature, the first LAA contacting surface has a given shape and the second LAA contacting surface has a shape that is a mirror image of the given shape.

In accordance with a concomitant feature, the first and second clip struts, the at least one first bias spring, and the at least one second bias spring define an opening sized to receive therein an LAA and the bias assembly is configured to bias rotation of the first and second clip struts to contact the LAA with the first and second LAA contacting surfaces on opposing sides thereof with an inwardly directed force sufficient to substantially exclude blood flow from inside the LAA.

Although the systems, apparatuses, and methods are illustrated and described herein as embodied in devices, systems, and methods that clip about the exterior surface of the LAA to effectively close off the interior of the LAA from the left atrium, it is, nevertheless, not intended to be limited to the details shown because various modifications and structural changes may be made therein without departing from the spirit of the invention and within the scope and range of equivalents of the claims. Additionally, well-known elements of exemplary embodiments will not be described in detail or will be omitted so as not to obscure the relevant details of the systems, apparatuses, and methods.

Additional advantages and other features characteristic of the systems, apparatuses, and methods will be set forth in the detailed description that follows and may be apparent from the detailed description or may be learned by practice of exemplary embodiments. Still other advantages of the systems, apparatuses, and methods may be realized by any of the instrumentalities, methods, or combinations particularly pointed out in the claims.

Other features that are considered as characteristic for the systems, apparatuses, and methods are set forth in the appended claims. As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one of ordinary skill in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the systems, apparatuses, and methods of the invention that are regarded as novel, it is believed that the systems, apparatuses, and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the systems, apparatuses, and methods. Advantages of embodiments of the systems, apparatuses, and methods will be apparent from the following detailed description of the exemplary embodiments thereof, which description should be considered in conjunction with the accompanying drawings in which:

FIG. 1 is a perspective view of an exemplary embodiment of a left atrial appendage surgical implant clip in an extended, open orientation;

FIG. 2 is an enlarged, elevational view of a distal end of the clip of FIG. 1;

FIG. 53 is a top or bottom plan view of an exemplary embodiment of another left atrial appendage surgical implant clip in a closed orientation;

FIG. 54 is a side elevational view of the clip of FIG. 53;

FIG. 55 is a perspective view of the clip of FIG. 53;

FIG. 56 is an enlarged, open end elevational view of the clip of FIG. 53;

FIG. 57 is a top or bottom plan view of the clip of FIG. 53 in an intermediate expanded orientation with an exploded, fragmentary, diagrammatical illustration of clip-contacting ends of an exemplary embodiment of a clip delivery device;

FIG. 58 is a side elevational view of the clip of FIG. 57;

FIG. 59 is a perspective view of the clip of FIG. 57;

FIG. 60 is an enlarged, open end elevational view of the clip of FIG. 57;

FIG. 61 is a top or bottom plan view of the clip of FIG. 53 in an expanded orientation;

FIG. 62 is a side elevational view of the clip of FIG. 61;

FIG. 63 is a perspective view of the clip of FIG. 61;

FIG. 64 is an enlarged, open end elevational view of the clip of FIG. 61;

FIG. 78 is a top plan view of the clip of FIG. 53 in a distal-side-open, intermediate expanded orientation and with an exemplary embodiment of a clip strut cover;

FIG. 79 is a side elevational view of the clip and cover of FIG. 78;

FIG. 80 is a perspective view of the clip and cover of FIG. 78;

FIG. 81 is an open end elevational view of the clip and cover of FIG. 78;

FIG. 82 is a fragmentary, enlarged portion of the clip and cover of FIG. 80;

FIG. 109 is a perspective view of the clip of FIG. 108 in a fully open orientation and with the convertible band extended between the struts;

FIG. 110 is a distal end elevational view of the clip of FIG. 109;

FIG. 111 is a top plan view of the clip of FIG. 109;

FIG. 119 is a perspective view of the end effector jaws and clip of FIG. 118 viewed from a side of a distal end thereof;

FIG. 120 is a right side elevational view of the end effector jaws and clip of FIG. 118;

FIG. 121 is a top plan view of the end effector jaws and clip of FIG. 118;

FIG. 122 is a bottom plan view of the end effector jaws and clip of FIG. 118;

FIG. 123 is a perspective view of the end effector jaws and clip of FIG. 118 from above a distal end thereof;

FIG. 124 is a fragmentary, enlarged bottom plan view of a distal portion of the end effector jaws and clip of FIG. 118;

Figure 125:
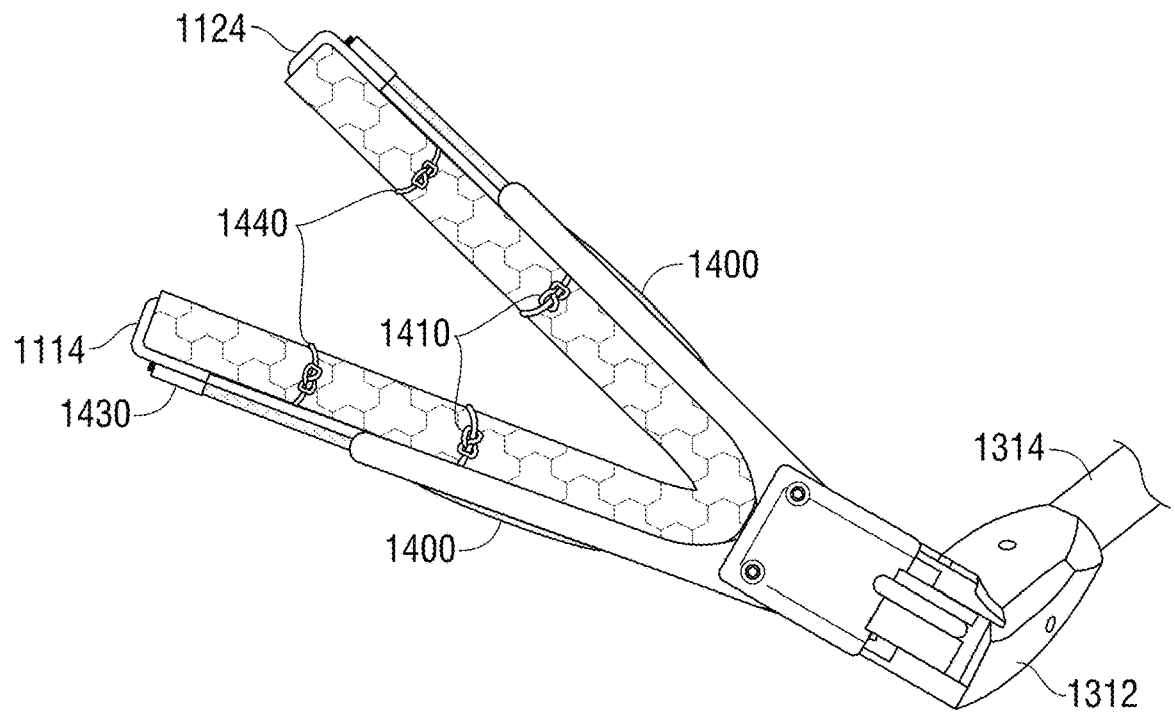
Figure 126:
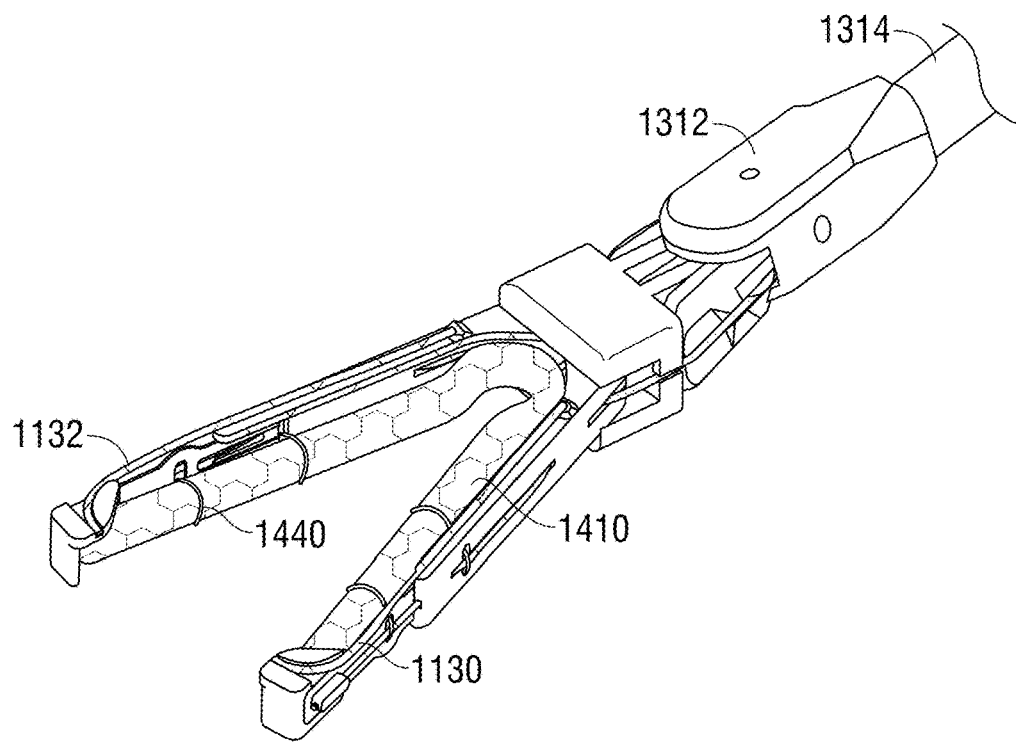
Figure 127:
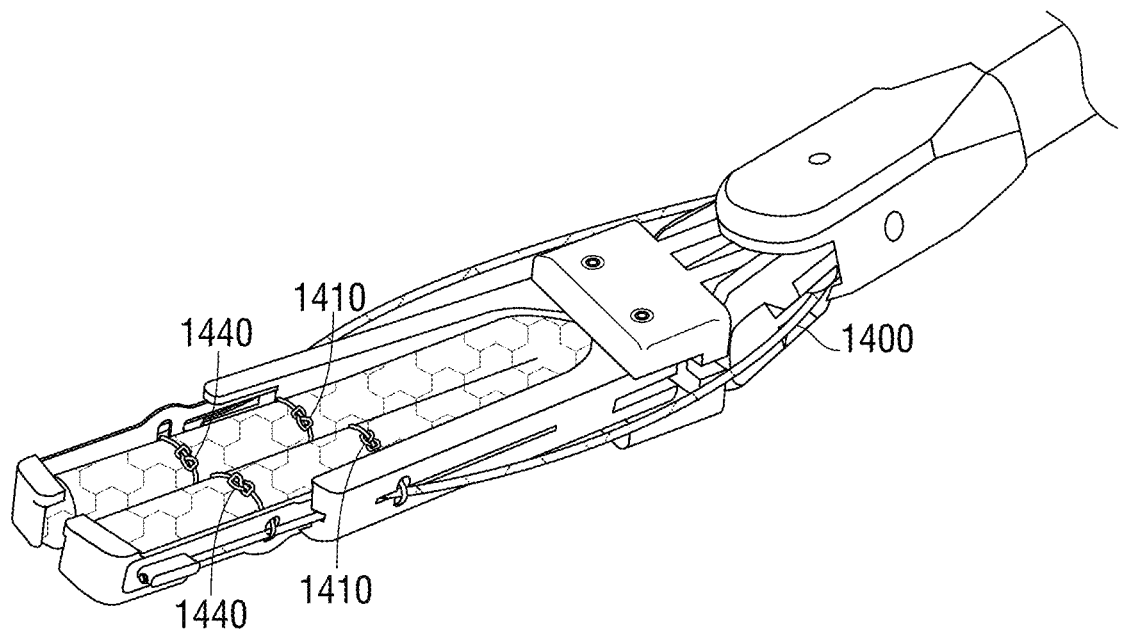
Figure 128:
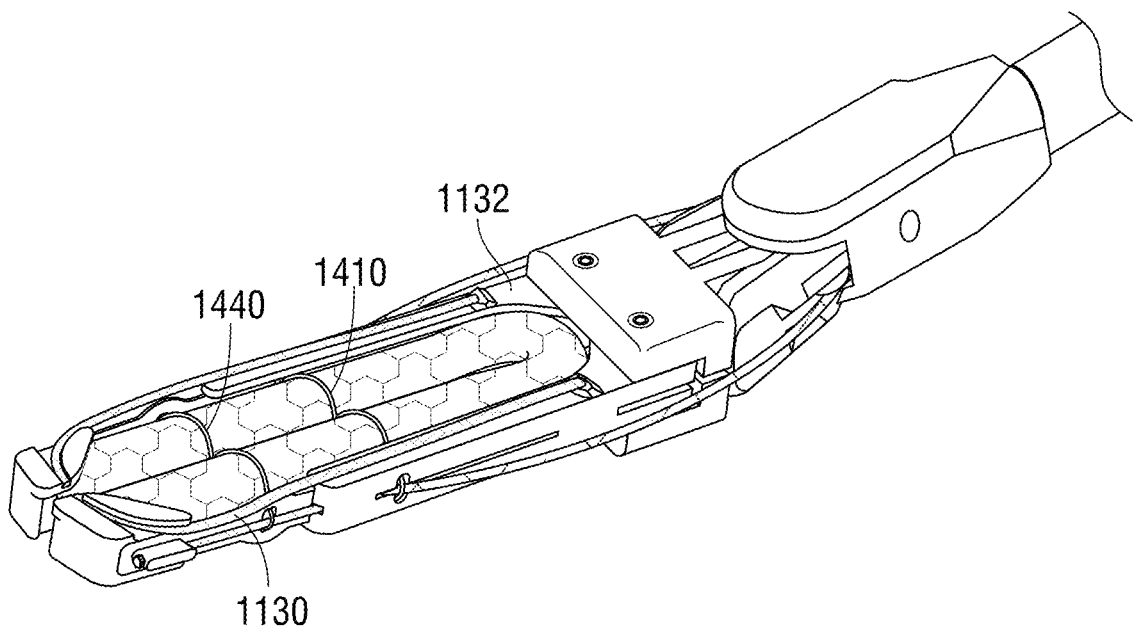

FIG. 125 is a fragmentary, perspective view of an exemplary embodiment of an end effector with a shaft, a clevis, and jaws having a closed-end sensor for installing a tissue-occlusion clip with the jaws in an open orientation, with the sensor in a jaw-open sensing state, with the clip having a protective fabric sleeve in an open orientation loaded within the jaws, with the clevis articulated at an articulation joint to a distal end of a shaft, and with a handle not illustrated;

FIG. 126 is a perspective view of the end effector, clip, clevis, and shaft of FIG. 125 viewed from above a distal end thereof;

FIG. 127 is a bottom perspective view of the end effector, clip, and clevis of FIG. 125 with the jaws in a closed orientation, with the clip in a tissue-occluding state, and with the sensor in a jaw-closed sensing state; and FIG. 128 is a top perspective view of the end effector, clip, clevis, and shaft of FIG. 125 viewed from above a left side thereof.

DETAILED DESCRIPTION OF THE EMBODIMENTS

As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one skilled in the art to variously employ the systems, apparatuses, and methods in virtually any appropriately detailed structure. Further, the terms and phrases used herein are not intended to be limiting, but rather, to provide an understandable description of the systems, apparatuses, and methods. While the specification concludes with claims defining the features of the systems, apparatuses, and methods that are regarded as novel, it is believed that the systems, apparatuses, and methods will be better understood from a consideration of the following description in conjunction with the drawing figures, in which like reference numerals are carried forward.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Alternate embodiments may be devised without departing from the spirit or the scope of the invention. Additionally, well-known elements of exemplary embodiments of the systems, apparatuses, and methods will not be described in detail or will be omitted so as not to obscure the relevant details of the systems, apparatuses, and methods.

Before the systems, apparatuses, and methods are disclosed and described, it is to be understood that the terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact (e.g., directly coupled). However, "coupled" may also mean that two or more elements are not in direct contact with each other, but yet still cooperate or interact with each other (e.g., indirectly coupled).

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, top/bottom, and proximal/distal. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

It will be appreciated that embodiments of the systems, apparatuses, and methods described herein may be comprised of one or more conventional processors and unique stored program instructions that control the one or more processors to implement, in conjunction with certain non-processor circuits and other elements, some, most, or all of the functions of the devices, systems, and methods described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs) or field-programmable gate arrays (FPGA), in which each function or some combinations of certain of the functions are implemented as custom logic. Of course, a combination of these approaches could also be used. Thus, methods and means for these functions have been described herein.

The terms "program," "software," "software application," and the like as used herein, are defined as a sequence of instructions designed for execution on a computer system or programmable device. A "program," "software," "application," "computer program," or "software application" may include a subroutine, a function, a procedure, an object method, an object implementation, an executable application, an applet, a servlet, a source code, an object code, any computer language logic, a shared library/dynamic load library and/or other sequence of instructions designed for execution on a computer system.

Herein various embodiments of the systems, apparatuses, and methods are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments. Referring now to the figures of the drawings in detail and first, particularly to FIGS. 1 to 12, there is depicted a first exemplary embodiment of an externally implantable and spring-biased left atrial appendage exclusion clip 100. The exclusion clip 100 comprises a clipping assembly 102 and a biasing assembly 104. The clipping assembly 102 is comprised of two opposing clip struts, referenced herein as a first clip strut 110 and a second clip strut 120. Each of the first and second clip struts 110, 120 in this exemplary embodiment is substantially in the form of a six-sided rectangular column, the particulars of the shape will be discussed in further detail below. Also in the exemplary embodiment, the first and second clip struts 110, 120 are mirror images of one another. The body of each clip strut 110, 120 is comprised of any suitable biocompatible material, such as titanium, stainless steel, chromium-cobalt alloy, nickel-titanium alloy, ceramic, polyetheretherketone, liquid-crystal polymer, polymethylmethacrylate, and epoxy. In addition, each clip strut body 110, 120 is formed to not present or have any sharp edges or corners in the clip 100 that could potentially cause tissue damage within the body. Accordingly, in an exemplary embodiment thereof, each of the edges and corners of the clip strut body is rounded, curved, and/or beveled to create a substantially smooth exterior. Regarding the interior of each clip strut body, it may be formed as hollow, partially hollow, or completely solid.

As mentioned above, each of the first and second clip struts 110, 120 has six sides. Specifically, each clip strut 110, 120 comprises a first side 112, 122, a second side 114, 124, a third side 116, 126, a fourth side 118, 128, and two opposing ends 119a-b, 129a-b. To orientate a viewer as to the relative positions of these enumerated sides, an x-y axis has been applied to the various views of embodiments of the inventive exclusion clip in the several figures, and directions, such as inward, outward, upward, and downward, are used with respect to these figures for illustrative and explanatory purposes only. Concentrating initially on the configuration of the exclusion clip 100 that is depicted in FIGS. 1 to 4, FIGS. 1 to 4 depict the exclusion clip 100 in an expanded state in which a diameter of the interior opening of the exclusion clip 100 in the clip's 100 freestanding state has been extended to create a wider or enlarged interior opening 172 (diameter B). In this expanded configuration, the first side 112, 122 of each clip strut 110, 120 faces inward (along the x-axis) towards the interior opening 172 such that the first sides 112, 122 are situated face-to-face and substantially directly opposite one another. The second side 114, 124 of each clip strut 110, 120 is situated at a substantially 90-degree angle with respect to the first side 112, 122 of a respective one of the clip struts 110, 120, and faces in the upward direction along the y-axis. Further, the fourth side 118, 128 of each clip strut 110, 120 is also positioned at a substantially 90-degree angle with respect to the first side 112, 122 of a respective one of the clip struts 110, 120, but faces in the opposite direction of the first side 112, 122, namely, in the downward direction along the y-axis. The third side 116, 126 of each clip strut 110, 120 forms a common edge with a respective second side 114, 124, forms a common edge with a respective fourth side 118, 128, and is situated opposite the respective first side 112, 122 such that it faces along the x-axis in a direction that points outward away from the interior opening 172 of the exclusion clip 100. Lastly, each pair of ends 119a-b, 129a-b of each clip strut 110, 120 comprises the two opposing ends thereof, wherein each end 119a-b, 129a-b faces in a direction that is perpendicular to both the x and y axes (i.e., along a z-axis).

Figure 3:
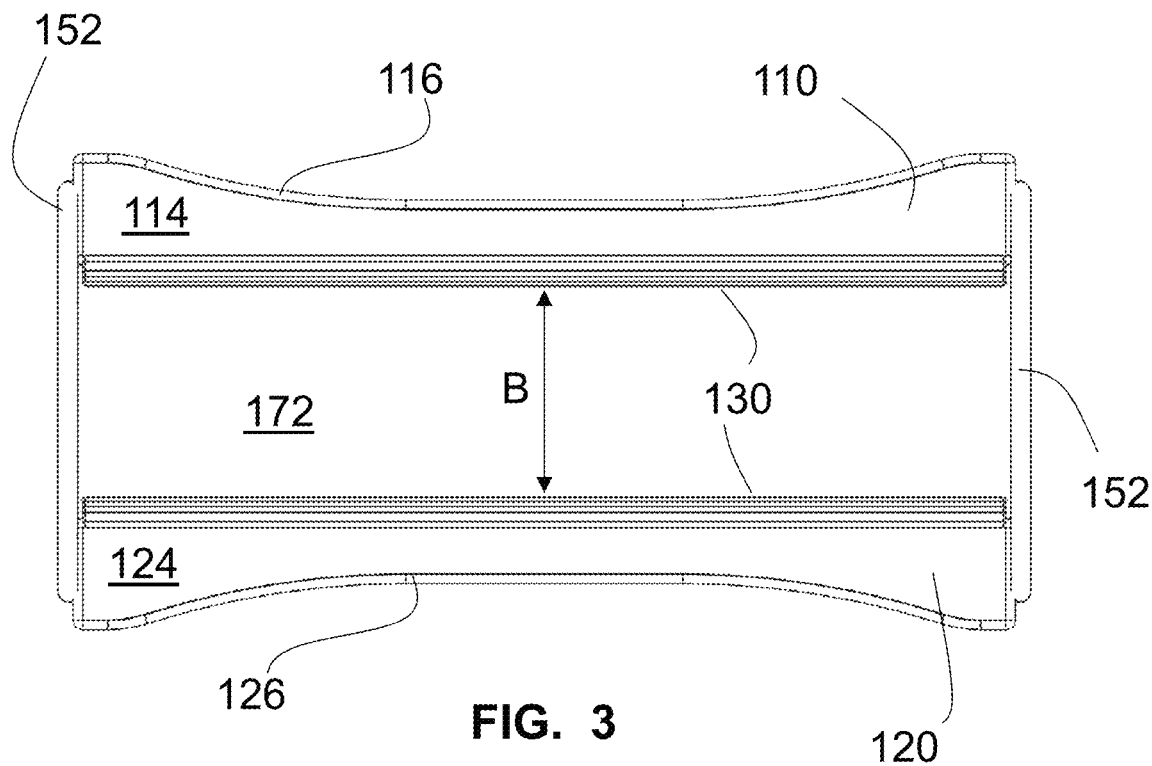
FIG. 3 is a top plan view of the clip of FIG. 1.
Figure 4:
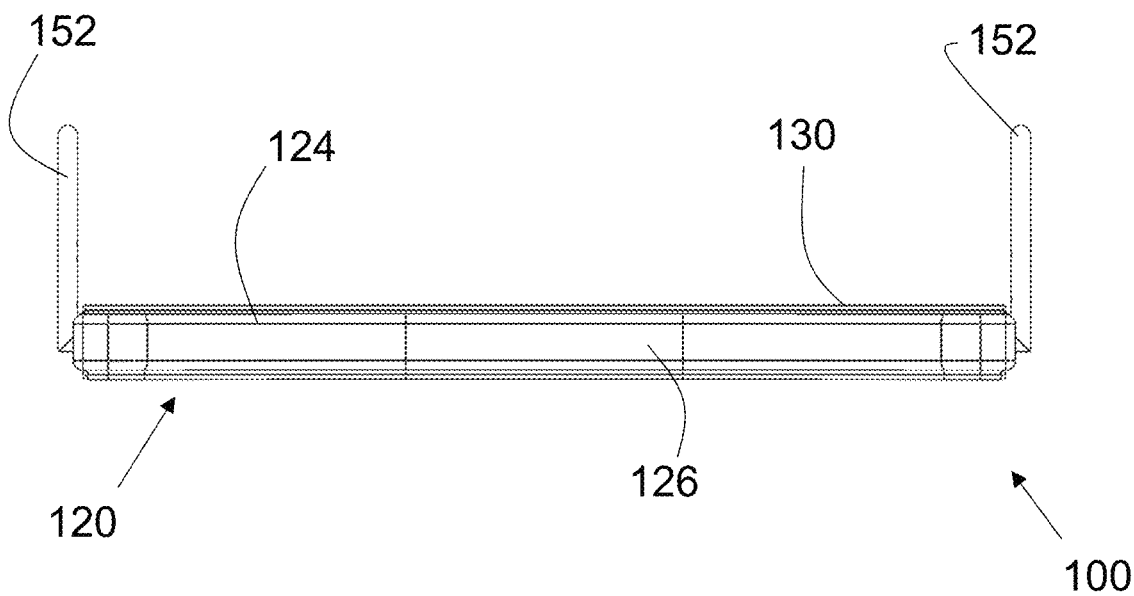
FIG. 4 is a side elevational view of the clip of FIG. 1.

As is best shown in FIG. 2, in this exemplary embodiment, the first side 112, 122 of each clip strut 110, 120 defines a substantially flat rectangular surface with a slightly rounded upper edge 182 leading into the neighboring second side 114, 124 and a more aggressively-rounded lower edge 180 leading into the neighboring fourth side 118, 128. By contrast, the third side 116, 126 of each clip strut 110, 120 is not a substantially flat rectangular surface. Rather, as best shown in FIG. 3, the third side 116, 126 exhibits a bend or curve that arches in the inward direction (i.e., towards the interior opening 172 of clip 100) along the x-axis to form a concave surface, wherein the degree or the sharpness of the bend or curve increases when approaching the center of the third side 116, 126. Therefore, the first side 112, 122 may be characterized as a "flat side" of the clip strut 110, 120, and the third side 116, 126 may be characterized as the "concave side" of the clip strut 110, 120. Certain advantages of the concave shape of the third sides 116, 126 are described in detail further below.

Figure 5:
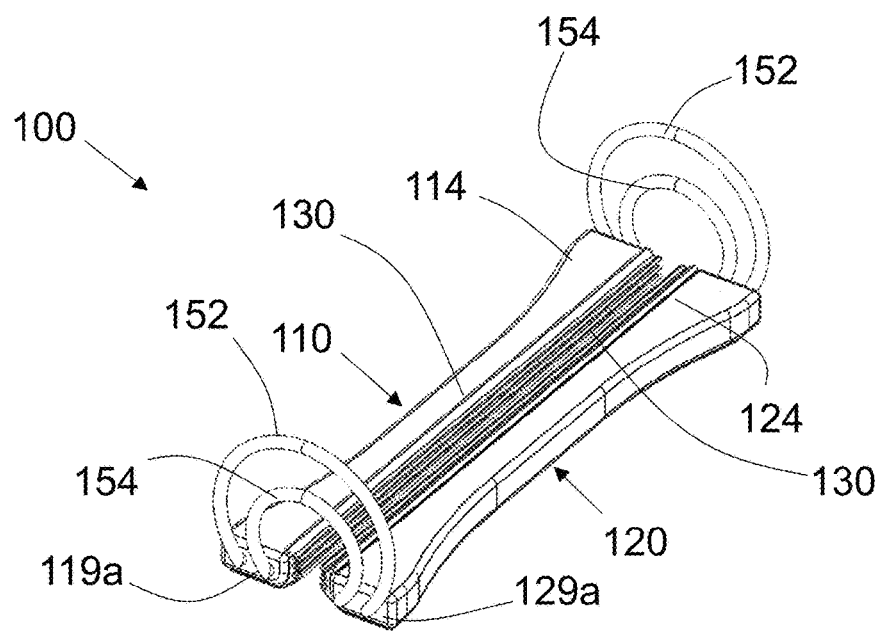
FIG. 5 is a perspective view of the clip of FIG. 1 in an intermediate, contracted pre-implantation orientation.
Figure 6:
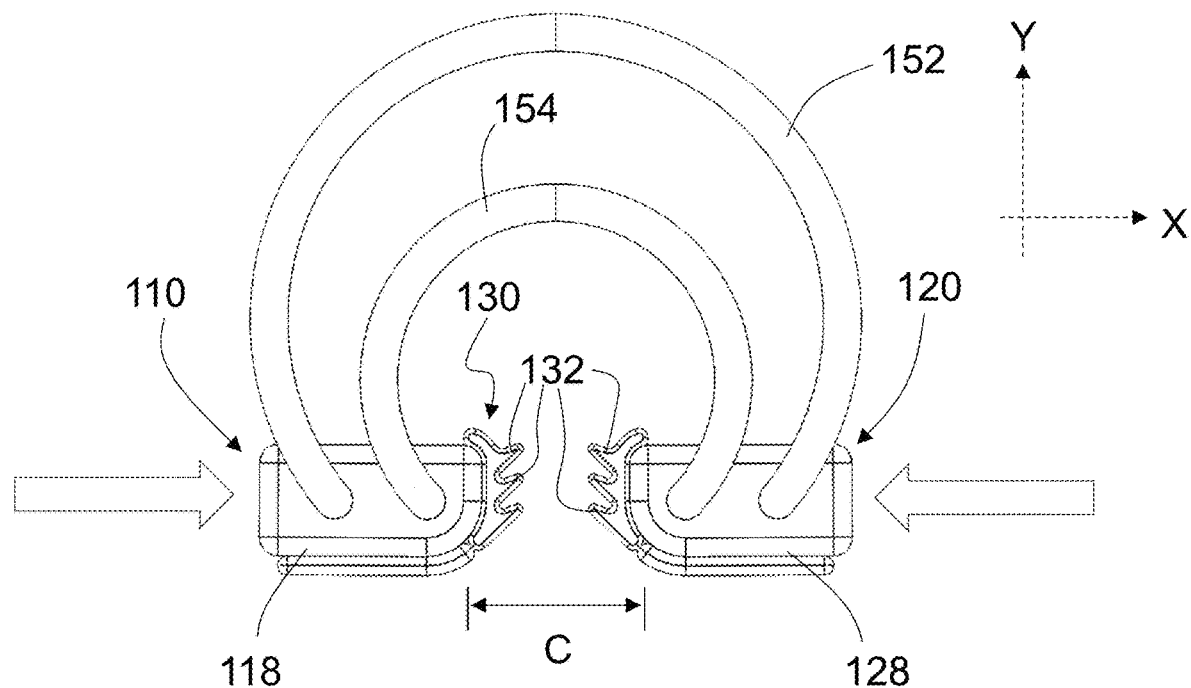
FIG. 6 is an enlarged, elevational view of a distal end of the clip of FIG. 5.
Figure 7:
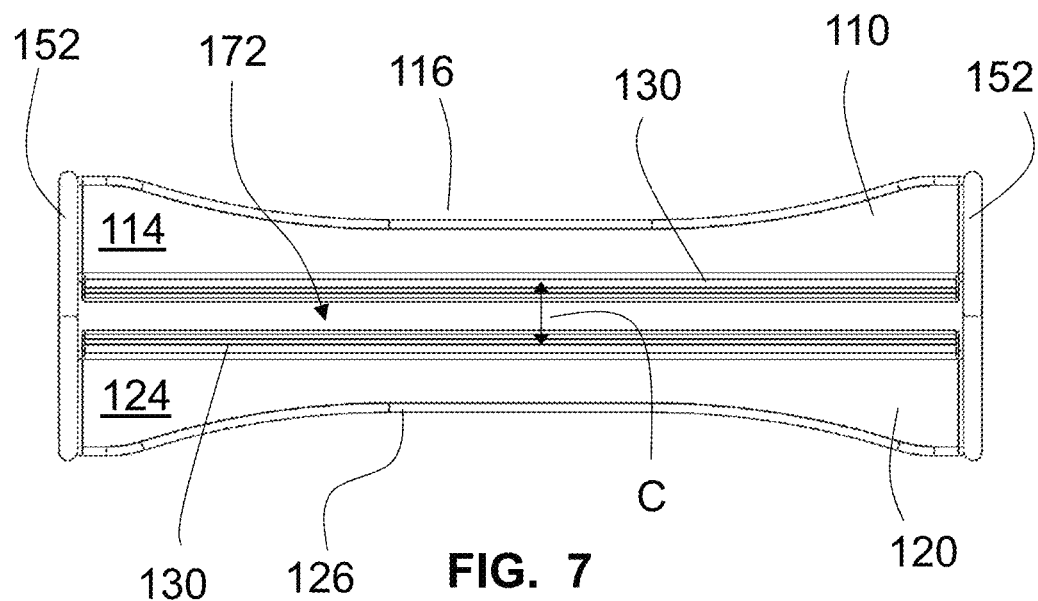
FIG. 7 is a top plan view of the clip of FIG. 5.

With respect to the biasing assembly 104 of the exclusion clip 100, it acts to connect the clip struts 110, 120 to one another in a bridge-like manner to form a complete clip assembly 100 for capturing the LAA, and orients the relative positions of the first and second clip struts 110, 120 with respect to one another. Specifically, the biasing assembly 104 continuously exerts a spring-biasing force on the first and second clip struts 110, 120, urging either one of the clip struts 110, 120 towards the other clip strut 110, 120, or urging both of the clip struts 110, 120 together, in the inward direction along the x-axis throughout the process of implanting the exclusion clip 100, from the initial capture of the LAA in the clip's expanded capture state (as shown in FIGS. 1 to 4), to a continued, but still reversible, installation in the clip's intermediate capture state (as shown in FIGS. 5 to 7), and to the final capture of the LAA in the clip's implanted and closed state (as depicted in the progression from the formation in FIG. 8 to the formation in FIGS. 9 to 12) in which the exclusion clip 100 has been released from a non-illustrated clip delivery device to provide a last creeping and tightening movement of the LAA into its final position into the clip's interior opening 172.

In the exemplary embodiment depicted in FIGS. 1 to 12, the biasing assembly 104 is comprised of oppositely-situated spring members 150, wherein each spring member 150 is positioned at one of the two ends 119, 129 of the exclusion clip 100. As shown in the exemplary embodiment, each spring member 150 comprises a set of springs, including an outer (or upper) spring 152 and an inner (or lower) spring 154. However, in an alternative exemplary embodiment, each spring member 150 comprises only a single spring. Each of the springs 152, 154 is substantially semi-circular or "horseshoe" in shape, whereby the inner spring 154 has a smaller radius of curvature than that of the outer spring 152 (as used here, the term "radius" broadly refers to a curvature path that is both circular and non-circular, i.e., not in a perfect circle). Each spring member 150 is attached to a pair of neighboring clip strut ends (either pair 119a, 129a or pair 119b, 129b), located at one of the two far ends of the exclusion clip 100, thereby connecting the clip struts 110, 120 together to construct a boundary defined by the exclusion clip 100. Specifically, each of the two ends 158 of one inner spring 154 is rotationally connected to a respective one of the clip strut ends 119a, 129a at an attachment point 164 in a longitudinally fixed manner so that the spring 154 does not become dislodged. The attachment point 164 is at a location of the clip strut end 119a, 129a that is nearer to the first side 112, 122 of the corresponding clip strut 110, 120 than the third side 116, 126. Similarly, each of the two ends 156 of the outer spring 152 is rotationally connected to a respective one of the clip strut ends 119a, 129a at an attachment point 162 also in a longitudinally fixed manner. Relative to the attachment point 164, the attachment point 162 is nearer to the third side 116, 126 of the corresponding clip strut 110, 120 than to the first side 112, 122. Accordingly, when anchored to the two clip struts 110, 120 in this fashion, the outer and inner springs 152, 154 are positioned together in a substantially concentric manner and extend from the clip struts 110, 120 in an upwards direction along the y-axis. Likewise, at the other opposite far end of the exclusion clip 100, outer and inner springs 152, 154 of the second spring member 150 are, in an identical manner, fixedly connected to the neighboring pair of clip strut ends 119b, 129b rotationally and longitudinally in a concentric fashion. These dual attachment points 162, 164 at each clip strut end 119a-b, 129a-b add a considerable amount of stability to the biasing assembly 104 and to the overall clip structure.

Due to the inward-facing turns of the outer and inner springs 152, 154, the spring members 150, in this exemplary configuration, inherently and continuously exert a spring-biasing force that urges the first and second clip struts 110, 120 towards each other. The amount of spring-biasing force that is exerted by the spring members 150 at any given time is, according to Hooke's Law, dependent upon the internal spring constant k of each spring 152, 154 and the distance each of the springs 152, 154 is stretched with respect to its equilibrium point. It is noted that if the material of the spring 152, 154 is superelastic, such as in the case where the material is a nickel-titanium (Ni—Ti) alloy (e.g., nitinol), the spring force does not obey Hooke's Law and, instead, the force is approximately constant rather than increasing linearly with displacement. In such a case, when reference is made herein to a spring constant, that is to be replaced with the particular characteristic of the material.

Each of the outer and inner springs 152, 154 is comprised of a suitable biocompatible material having the desired spring constant k, wherein each of the springs 152, 154 may be comprised of an identical material. Alternatively, different materials may comprise the various springs 152, 154 if it is beneficial that the springs 152, 154 have differences in their respective material properties. Examples of such materials include, but are not limited to, chrome-cobalt alloy, stainless steel, titanium alloy, and superelastic alloys such as Ni—Ti. Additionally, if it is beneficial to have variable stiffnesses between the outer springs 152 and the inner springs 154, the outer springs 152 may be composed and shaped differently from the inner springs 154.

Figure 8:
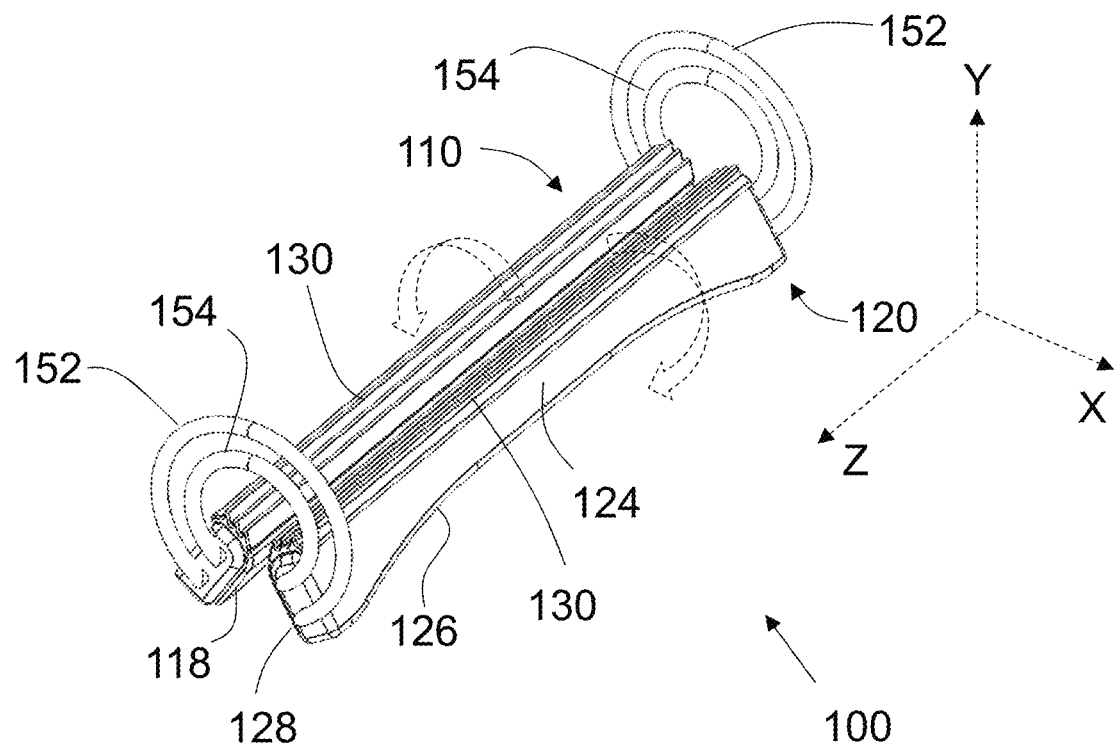
FIG. 8 is a perspective view of the clip of FIG. 1 in an intermediate, contracted and partially rotated pre-implantation orientation.

Further, as mentioned above, there exists a degree of rotational freedom at each of the connections between the upper and lower springs 152, 154 and the clip struts 110, 120 at the attachment points 162, 164. This degree of rotation permits each of the clip struts 110, 120 to rotate with respect to the spring members 150 in an upward direction along the y-axis such that, when, for example, a substantially downward moving pressure is externally applied to an outer portion of the clip struts 110, 120 (e.g., at outer edges 184 of the second sides 114, 124) or a substantially upward moving pressure is externally applied to an inner portion of the clip struts 110, 120 (e.g., at edges 180), this torque force causes each clip strut 110, 120 to rotate or pivot with respect to the spring members 150 in a clockwise or a counterclockwise direction (about the z-axis as illustrated in FIG. 8) as dictated by the curvature of the outer and the inner springs 152, 154, causing a striking transformation in the configuration of the exclusion clip 100 as depicted in the transition of FIG. 5 to FIG. 8 to FIG. 9. As explained in greater detail below, this rotation or pivoting ability of the clip struts 110, 120 assists in manipulating the LAA further into the clip interior 172 and enhances a gripping force exerted by the exclusion clip 100 when it is applied to the LAA.

Accordingly, the connection between each end 156, 158 of the springs 152, 154 and its respective clip strut 110, 120 may comprise any suitable rotatable connection that retains the spring members 150 while also providing the clip struts 110, 120 with the desired degree of rotation with respect to the spring members 150. For example, in one exemplary embodiment, each attachment point 162, 164 comprises a hole, groove, or channel (not shown) that has been bored to a partial distance or depth into the respective clip strut end 119a-b, 129a-b in the longitudinal direction of the clip struts 110, 120 (which could be a blind hole) and matingly receives a portion of its respective spring end 156, 158. The spring ends 156, 158 and/or the holes, grooves, or channels of the clip strut ends 119a-b, 129a-b that receive the spring ends 156, 158 may be shaped or configured in such a manner that the interaction between the hole, groove, or channel and the spring end 156, 158 that is inserted therein creates a torsion effect. In one exemplary embodiment, each attachment point 162, 164 may be comprised of an elongated hole that extends a partial distance into the clip strut body and is larger in diameter than the diameter of the springs 152, 154 and terminates at an interior floor in which the spring ends 156, 158 become fixed. For example, the interior floor may comprise a secondary hole (which hole also could be blind) having a diameter that is slightly smaller than the diameter of the respective one of the spring ends 156, 158, such that the spring end 156, 158 is fixed by a press fit into the secondary hole. In another example, the interior floor of the hole may open up into an enlarged secondary aperture or window for receiving the respective spring end 156, 158, wherein the spring end 156, 158 is configured to have a crimped or bent distal end such that the distal end becomes cooperatively lodged or hooked into the secondary aperture or window upon insertion of the spring end 156, 158 into the body of the respective clip strut 110, 120 (examples of which are described in further detail below). Alternatively, friction between the secondary aperture or window and the distal end of the spring end 156, 158 as the spring end 156, 158 is inserted into the hole may actively force or deform the distal end into a crimped or bent configuration to fix the spring end 156, 158 into a fixed position (an example of which is described in further detail below).

With the configuration of the exclusion clip 100 as described, an exemplary embodiment of a procedure for implanting the clip 100 to isolate the LAA from the left atrium of the heart to effectively close off the interior fluid passageway between the LAA and the left atrium is described. In a freestanding or resting state of the exclusion clip 100, the first and second clip struts 110, 120 are positioned in close proximity to one another, or in surface-to-surface contact with each other, due to the spring-biasing force exerted by the biasing assembly 104, as depicted in FIGS. 9 to 12. Accordingly, in this freestanding or resting state, there is a relatively minimal interior opening 172 between the opposing clip struts 110, 120, a width thereof depicted by arrow A. Therefore, to safely engage the LAA and to surround its full girth during the implantation of the exclusion clip 100, the clip struts 110, 120 are separated from each other in a controlled manner to widen the interior opening 172 between the clip struts 110, 120 and place the exclusion clip 100 into an expanded state (as depicted in FIGS. 1 to 4). Accordingly, a clip delivery device (not presently shown) is used to engage the freestanding exclusion clip 100 prior to its placement within the patient's body and throughout the implantation process to securely transport the clip 100 to the surgical site of the LAA and to alter the relative positions of the clip struts 110, 120 during the implantation process. Thus, an exemplary clip delivery device that is compatible for use with the exclusion clip 100 is configured to temporarily engage and retain the clip 100 into an appropriate position during the implantation process, as well as disengage from the clip 100 once the implantation process is completed. Furthermore, the clip delivery device is configured to impose a counter-force to the spring-biasing force of the biasing assembly 104 to precisely control placement of the clip struts 110, 120 relative to one another, and to control the amount of compressive force that is exerted by the exclusion clip 100 on the LAA during the implantation process. In one exemplary embodiment of such a suitable clip delivery device, the main components thereof comprise a control handle, an elongated shaft, and a LAA clip-application head. In use, the control handle is oriented in a proximal direction (i.e., in the direction of the surgeon) to be manipulated by the surgeon. Further, the shaft forms an intermediate connection between the control handle and the clip-application head, such that the control handle is situated at the proximal end of the shaft and the clip-application head is situated at the distal end of the shaft (the distal end being the farthest away from the surgeon). The clip-application head is configured to selectively engage and retain both of the first and second clip struts 110, 120 and, by applying an adjustable counter-force to the spring-biasing force of the clip's biasing assembly 104, controllably separate the clip struts 110, 120 into the expanded state depicted, for example, in FIG. 1 to create an extended interior opening 172 of the clip 100, a width thereof being defined by arrow B. In this capacity, the clip-application head may be configured to displace just one of the clip struts 110, 120 in a direction that is opposite from the other of the clip struts 110, 120, or the clip-application head may be configured to displace both of the first and second clip struts 110, 120 in mutually opposite directions to effect the desired separation. The control handle, the shaft, and the clip-application head are operatively connected such that the operation of the clip-application head to cause the movement of the clip strut(s) 110, 120 is actuated by the surgeon using one or more controls present at the control handle. Accordingly, as a first step in the implantation procedure, the exclusion clip 100 is removably engaged with the clip-application head (using, for example, a series of cords (e.g., surgical sutures) to bind the clip 100 to the clip-application head) and, prior to advancing the exclusion clip 100 into the patient's thoracic cavity, the clip 100 is readied for its application to the LAA by placing the clip 100 into the expanded state depicted in FIGS. 1 to 4 to widen the clip's interior opening 172 to the desired enlarged diameter B.

Next, using the clip delivery device, the surgeon delivers the exclusion clip 100 (in its expanded state) into the thoracic cavity and to the location of the LAA. At this juncture, it is important to note that a variety of surgical methods for gaining access to the LAA may be employed and the instant exemplary exclusion procedure is not intended to be limited to any specific technique for accessing the LAA. For example, the LAA may be accessed by way of a conventional open-chest or open-heart procedure in which the surgeon makes a large incision in the middle of the chest and breastbone to have direct access to the heart. Alternatively, a left thoracotomy may be performed to create a small incision in the intercostal space between two adjacent ribs such that the clip delivery device is inserted through the chest wall. In a further alternative, a thoracoscopic procedure may be conducted to create several smaller incisions (referred to as "ports) in the chest wall to allow for the insertion of multiple instruments (e.g., a camera), including the clip delivery device. Once the exclusion clip 100 is within an appropriate range of the LAA, the surgeon carefully advances the LAA into the central opening 172 of the expanded clip 100 (in the direction of the dashed arrows in FIGS. 1 and 2), such that the base portion of the LAA is situated between the first sides 112, 122 of the first and second clip struts 110, 120, and the fourth sides 118, 128 of the first and second clip struts 110, 120 have come to rest, as best as possible, in surface-to-surface contact with the topography of the heart's outer surface on either side of the LAA (or a part on a surface of the fourth sides 118, 128, such as a pad, is in surface-to-surface contact with the heart). At this stage, the initial capture of the LAA is complete.

It should be appreciated that, in the case of accessing the LAA through lesser invasive surgical approaches (e.g., thoracotomy or thoracoscopy) in which small incisions are made, alternative exemplary embodiments of the clip delivery device may be configured to permit delivering the exclusion clip 100 to the site of the LAA while the clip 100 is in its unexpanded form in order to ease manipulation of the clip 100 through the small incision(s). In such embodiments, the exclusion clip 100 is placed into its expanded state after the clip has advanced into the thoracic cavity.

Figure 9:
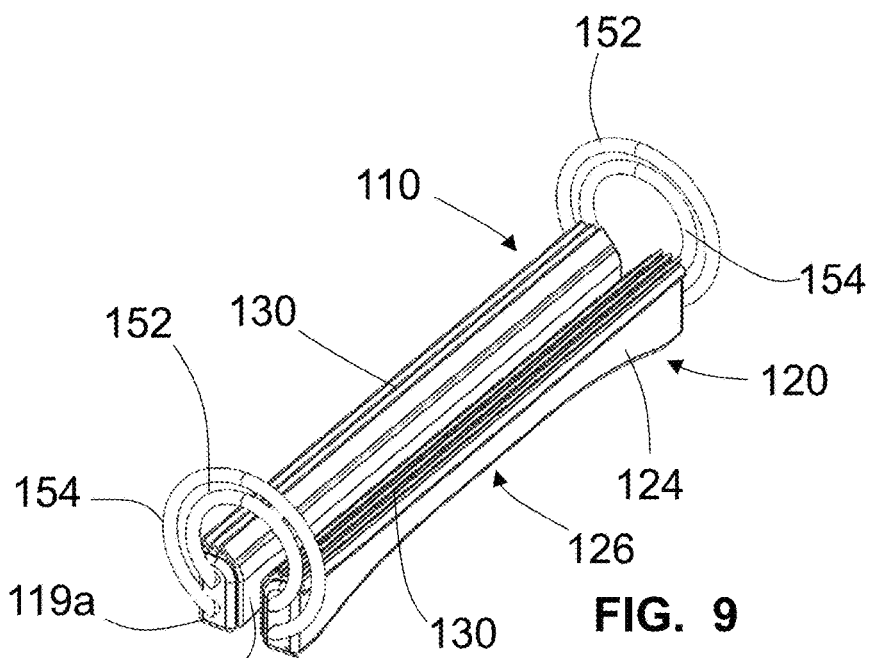
FIG. 9 is a perspective view of the clip of FIG. 1 in a contracted and fully rotated implantation orientation.
Figure 10:
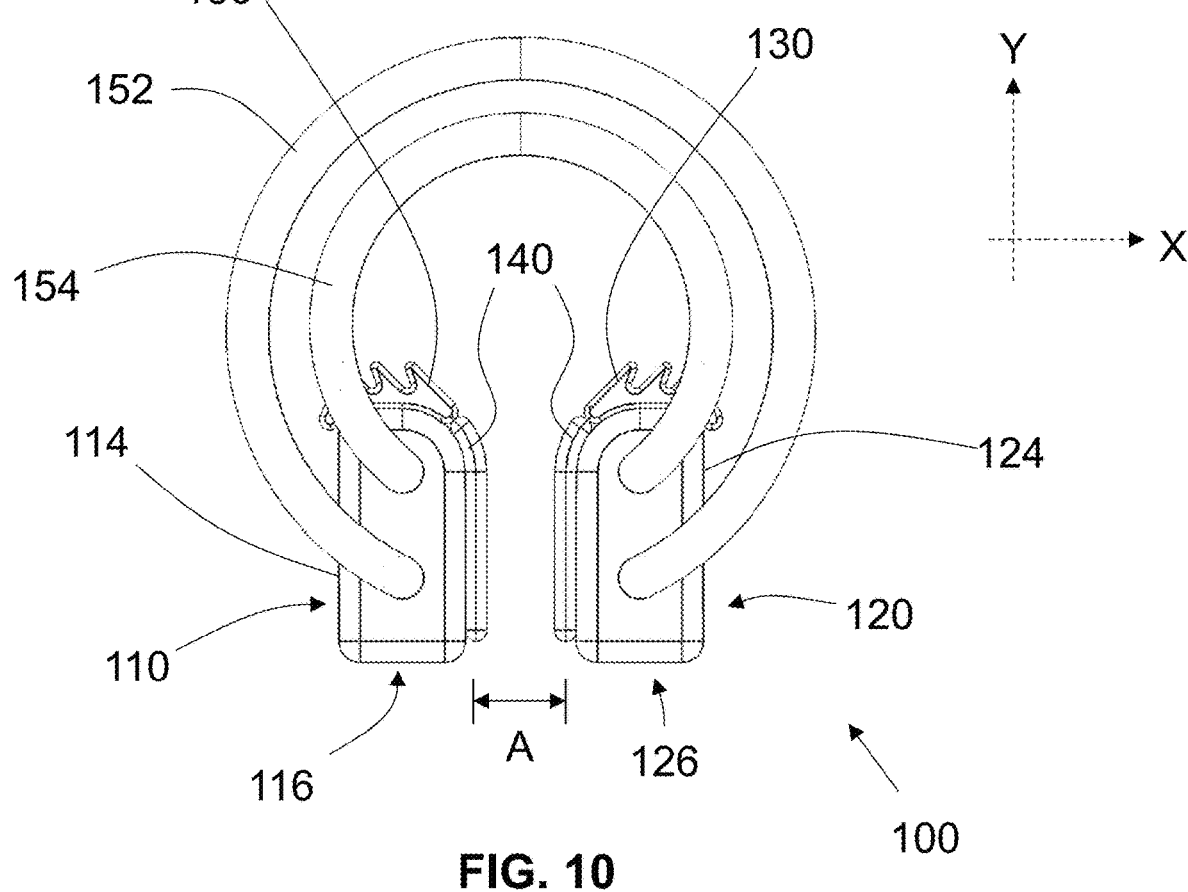
FIG. 10 is an enlarged, elevational view of a distal end of the clip of FIG. 9.
Figure 11:
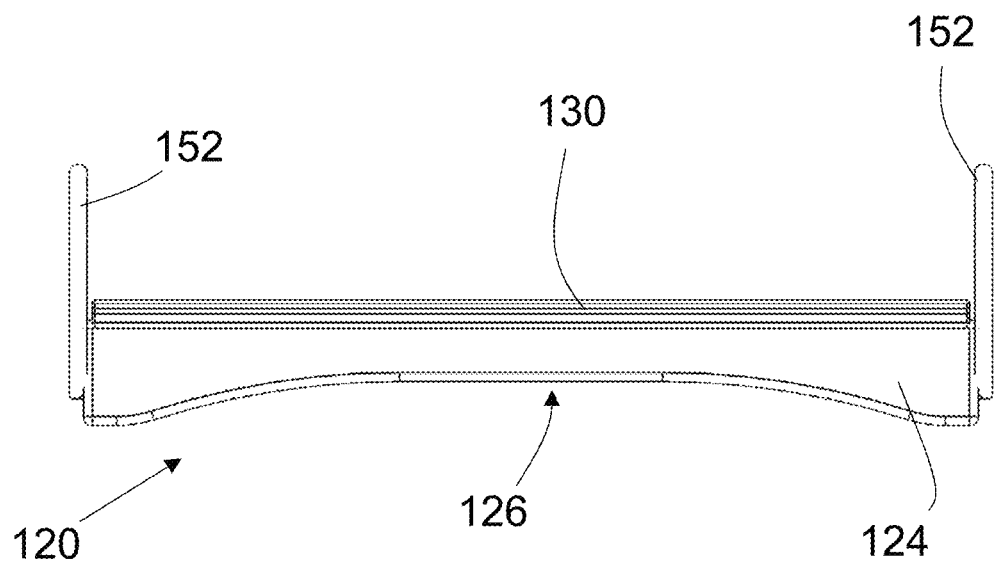
FIG. 11 is a side elevational view of the clip of FIG. 9.
Figure 12:
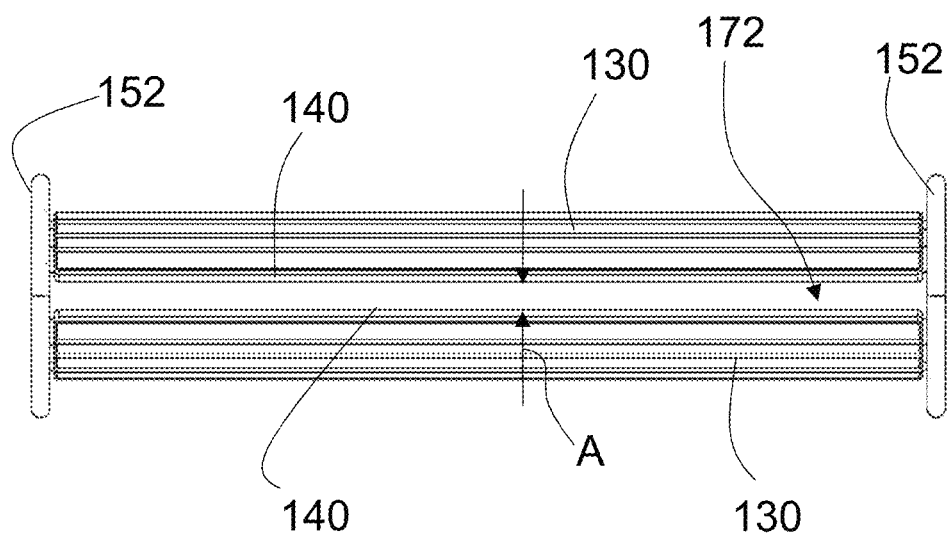
FIG. 12 is a top plan view of the clip of FIG. 9.

In the next step, the surgeon actuates the clip delivery device to controllably close the exclusion clip 100 about the base portion of the LAA to such a degree that the clamping force exerted by the first sides 112, 122 of the clip struts 110, 120 against the LAA is sufficient to effectively suppress the blood flow entering and exiting the interior of the LAA, referred to herein as "LAA exclusion." FIGS. 5 to 7 illustrate the configuration of the exclusion clip 100 while it is in this intermediate capture state. As best shown in FIG. 6, the first and second clip struts 110, 120 are now situated closer to one another, resulting in the interior opening 172 having a reduced diameter, illustrated by arrow C. With respect to the instant exemplary embodiment, two potential mechanisms, one referred to herein as "passive" and one referred to herein "active," are envisioned for bringing about this closure of the exclusion clip 100. The "passive" mechanism comprises the surgeon actuating a control of the clip delivery device to relieve or ease, at a controlled pace, the amount of counter-force that, as described above, is exerted by the clip-application head in opposition to the spring-biasing force of the spring members 150 to place the clip 100 into its expanded state. Relieving the counter-force permits one or both of the clip struts 110, 120 to return towards its (or their) inherent, resting spring-biased condition, thus allowing one or both clip struts 110, 120 to move towards the opposing clip strut 110, 120 in the inward direction of the dashed arrows depicted in FIG. 6 (i.e., along the x-axis), which, as described in further detail below, creates a momentum that, subsequently, causes one or both of the clip struts 110, 120 to rotate into the final implantation position (e.g., as shown in FIGS. 9 and 10). With respect to the "active" mechanism, this approach not only comprises the surgeon causing the release of the counter-force, but it also comprises further actuating the clip-application head to apply some direct pressure to one or both of the clip struts 110, 120 (and/or one or both of the spring members 150) to provide an additional force to one or both of the clip struts 110, 120, for example, in the direction of the dashed arrows in FIG. 6.

At this stage in the implantation process, the exclusion clip 100 is now in a position in which the surgeon can determine if the current, intermediate position is optimal and effective to close the blood flow into and out of the interior of the LAA. If the surgeon does not prefer the current position of the exclusion clip 100, the surgeon can actuate the clip delivery device to controllably disengage the clip 100 from the LAA by returning the clip 100 to an expanded or slightly-expanded state and, thereafter, re-engage and close the clip 100 about the LAA at a different position, or with a different amount of clamping force, from the initial attempt. Using the clip delivery device, this process may be repeated as many times as necessary to achieve a satisfactory placement.

When the surgeon has determined that the exclusion clip 100 is in a desirable LAA-exclusion position, the surgeon actuates the clip delivery device to place the exclusion clip 100 into a final implanted state, which state is depicted in FIGS. 9 to 12. This final implanted state effects a creeping and tightening movement that brings the LAA further and securely into the interior opening 127 of the exclusion clip 100, thereby reinforcing the long-term strength and stability of the clip's grip on the LAA for the duration of the life of the permanent clip implant. As depicted in FIG. 8, this final implanted state of the exclusion clip 100 is characterized by a substantially 90-degree rotation of each of the first and second clip struts 110, 120 with respect to each of spring members 150. As shown in FIGS. 9 to 12, this transformed configuration results in the first sides 112, 122 of each clip strut 110, 120 facing in the upward direction along the y-axis, the second sides 114, 124 of each clip strut 110, 120 facing in the outward direction along the x-axis, the third sides 116, 126 of each clip strut 110, 120 facing in the downward direction along the y-axis such that each of the third sides 116, 126 now comprise the surface of the clip 100 that is resting against the heart topography that surrounds the base portion of the LAA, and the fourth sides 118, 128 of each clip strut 110, 120 facing one another in the inward direction along the x-axis such that each of the fourth sides 118, 128 is tightly pressed into surface-to-surface contact with the outside surface of the LAA. In this configuration, the fourth sides 118, 128 are separated by a distance A, wherein the distance A is dictated by the spring-biasing force of the spring members 150 and the thickness of the LAA.

As mentioned above, to produce the 90-degree rotation, a torque force must be applied to each clip strut 110, 120 to cause the angular displacement of the clip struts 110, 120 with respect to the spring members 150. With respect to the instant exemplary embodiment, multiple sources of this torque force are envisioned. In one example, as mentioned above, the surgeon's actuation of the clip delivery device to ease the amount of counter-force being exerted by the clip-application head allows the inherit spring-biasing force of the spring members 150 to become the dominant force action, thereby causing the spring members 150 to coil inward to the maximum extent possible, wherein the resulting surface-to-surface interaction between the interior areas of the first sides 112, 122, 180 of the clip struts 110, 120 and the interposed LAA automatically forces the clip struts 110, 120 to rotate in the clockwise or counterclockwise direction (see the dashed arrows in FIG. 8) as dictated by the curvature of the spring members 150. In an alternative exemplary configuration, a more active approach is used, in which the surgeon actuates the clip-application head to forcibly turn each of the clip struts 110, 120 ninety degrees in the desired direction by directly contacting each clip strut 110, 120 and/or each spring member 150 with the clip-application head. Accordingly, the clip delivery device (including the clip-application head) is configured to adapt to the expanded, intermediate capture, and final implantation conditions of the exclusion clip 100 such that it can force or follow the relative positions of the clip struts 110, 120 throughout the entire implantation process. Furthermore, it is important to note that, irrespective of the mechanism used to rotate the clip struts 110, 120, it is necessary that the spring members 150 contract to some degree during the 90-degree rotation to ensure that the optimal gap (i.e., distance A) between the first and second clip struts 110, 120 remains substantially constant, which gap effectively retains and occludes the LAA captured therebetween.

Accordingly, the 90-degree rotation of the clip struts 110, 120 creates a girding-type motion in which the LAA is further "swept-up" into the interior opening 172 of the exclusion clip 100, resulting in a tighter and more stable grip that eliminates any residual pouch, or void space, of the LAA created at the junction between the left atrium and base portion of the LAA during the intermediate capture stage of the implantation process. In fact, this 90-degree "roll" of the clip struts 110, 120 effectively positions the exclusion clip 100 one or more millimeters downward along the LAA than otherwise would be possible. The elimination of any void space at the junction is significant to ensuring that no blood clots are formed therein.

Despite this being the final implantation stage, the surgeon may continue to adjust the position of the exclusion clip 100 by reversing the closure of the clip 100, returning the clip 100 to its expanded state, and repeating the closure and rotation steps described above. In other words, after the clip delivery device has positioned the struts 110, 120 to oppose one another in the final implantation state, the surgeon still has the ability to reverse the exclusion clip implantation process entirely. Once the surgeon is satisfied with the placement, the clip-application head of the clip delivery device is permanently disengaged from the exclusion clip 100. For example, if one or more sutures were used to temporarily attach the exclusion clip 100 to the clip-application head, the sutures would be severed at this stage.

In addition to the girding effect, a further benefit of the 90-degree rotation of the clip struts 110, 120 is the resulting placement of the third sides 116, 126 of the clips struts 110, 120. As described above (and depicted in FIGS. 9 to 11), at the end of the rotation and during the remainder of the life of the clip implant, the third sides 116, 126 comprise a portion of the exclusion clip 100 that rests against the non-planar and irregular topography of the heart that surrounds the base portion of the LAA. Accordingly, it is the "concave side" of the clip 100 that will permanently rest against the surface of the heart when implanted. In contrast to a flat surface, the concave shape more accurately conforms to the natural curvature of the heart, allowing the clip 100 to comfortably settle into a well-seated, non-obstructive, and protected position with respect to the heart's curved surface. Furthermore, if the clip 100 was to have straight faces rather than the concave faces described and shown, when placed against the non-planar surface of the left atrium, a distance between the atrial surface and the clip surface would be greater at the far ends of the clip 100, possibly resulting in a condition known as "dog ears," in which there are small pockets of LAA remaining in communication with the atrium. Such pockets present possible sites for the growth of blood clots that may result in emboli. Thus, the curved shape of the third sides 116, 126 advantageously eliminates this condition.

Another significant feature of the exclusion clip 100 according to the exemplary embodiment of FIGS. 1 to 12 pertains to the fourth sides 118, 128 of the clip struts 110, 120. As described above, the fourth sides 118, 128 are the surfaces of the exclusion clip 100 that are in permanent surface-to-surface contact with the LAA once the clip 100 is fully implanted. Therefore, to promote a healthy and enduring interaction between the exclusion clip 100 and the LAA, a LAA-contacting surface 140 may be applied to, or integrally formed with, all or a portion of the surface of one or both of the fourth sides 118, 128. In an exemplary gripping configuration, the LAA-contacting surface 140 provides a contact surface that is gentle and non-abrading but is also not overtly slick such that the gripping force of the exclusion clip 100 on the LAA is not weakened over time. Therefore, in such a gripping configuration, the LAA-contacting surface 140 is comprised of any suitable bio-compatible material that is relatively non-slippery. For example, the LAA-contacting surface 140 may be comprised of a cushiony padding material, such as a woven polyester, silicone rubber, PTFE, expanded PTFE, urethane, or other elastic material that increases the traction against the LAA to resist the exclusion clip 100 from slipping and becoming dislodged from the LAA. In another gripping example, the LAA-contacting surface 140 of one or both of the fourth sides 118, 128 comprises a slightly raised surface texture that is not harmful to the LAA tissue when placed in contact therewith.

The above explanation provides a description of an exemplary clip strut body of the clipping assembly 102 of the exclusion clip 100. However, various betterments to the clipping assembly 102 may be applied to, or integrally formed with, the clip strut body to improve aspects of the clip's function. For example, in the exemplary embodiment disclosed in FIGS. 1 to 12, a "self-motivator" or traction element 130 is applied to a portion of, or, as depicted, to substantially the entire surface of each of the first sides 112, 122 of the clip struts 110, 120. As described in detail above, the first sides 112, 122 of the clip struts 110, 120 are the surfaces of the exclusion clip 100 that initially capture and manipulate the LAA into the interior opening 127 between the clip struts 110, 120 during application of the clip 100. The self-motivator or traction element 130 is comprised of any structural component that acts in concert or cooperation with the external movements of the surgeon and/or clip delivery device during application of the exclusion clip 100, or with the pulsatile motion of the LAA (or, more generally, the heart), or with both, to naturally encourage the LAA to delicately advance into the interior opening 172 of the clip 100 and, thereafter, inhibit the LAA from escaping back out from the clip 100. Therefore, unlike prior art devices and methods, the self-motivator or traction element 130 utilizes a component, or components, of the exclusion clip device itself to manipulate the LAA into the desired position with little to no use of a separate instrument (e.g., a surgical grasper). Several exemplary embodiments of a self-motivator 130 or traction element operating according to these principles are described below. In an alternative exemplary embodiment, the element 130 is a coating of a slippery material, such as a hydrophilic coating. With a slippery coating, the opposing surfaces of the exclusion clip 100 can, for example, be easily slid over the LAA during application of the clip.

Depicted in the exemplary embodiment of FIGS. 1 to 12 is a self-motivator or traction element 130 that comprises one or more elastomeric fingers 132 (or appendages) that extend in the direction of the interior opening 127 of the exclusion clip 100. To be more precise, as best shown in FIG. 2, when the exclusion clip 100 is in its expanded state, the fingers 132 are oriented at a positive angle (i.e., θ>0°) with respect to the x-axis and, therefore, are oriented in the same direction in which the LAA is received into the interior 127 of the clip 100 (see the dashed arrow in FIG. 2). As a result, as the LAA is being received between the first and second clip struts 110, 120 of the exclusion clip 100, the fingers 132 come into contact with the LAA and combine with the pulsatile movement of the LAA and/or the back-and-forth movements of the clip delivery device caused by the surgeon to naturally ratchet the LAA into the clip 100 in the direction of the dashed arrow in FIG. 2, while also prohibiting movement of the LAA back out from the clip 100 in the direction opposite the dashed arrow. Significantly, in the exemplary embodiment of FIGS. 1 to 12, the self-motivator or traction element 130 extends onto the edges 180, 182 of each of the first sides 112, 122 in order to maintain the underlying rounded edges discussed above.

In another exemplary embodiment, the self-motivator or traction element 130 may be in the form of a plurality of tiny non-illustrated feet structures configured to react with a forward-moving impulse when subjected to vibrational forces, similar to the way in which the HEXBUG® toys operate. These feet may be nano or micro in scale and may be applied along the entire, or just a portion of, the surfaces of the first sides 112, 122 of the exclusion clip 100. When coming into contact with the LAA during the implantation process, the pulsatile motion of the LAA may be sufficient to cause the necessary vibration to the clip 100. Alternatively, it may be necessary to transmit an external vibrational force to the exclusion clip 100 in order to fully activate the feet to cause internal LAA motivation. In such an exemplary embodiment, the clip delivery device is equipped internally with a small motor that creates the vibrations in the clip-application head, which vibrations are then directly transmitted to the clip 100. Once the feet are activated, the surface-to-surface contact occurring between the feet and the LAA while the LAA enters the interior opening 172 of the clip 100 will cause the LAA to be continuously taken up into the clip's interior opening 172 due to the forward impulse momentum of the feet.

In further non-illustrated exemplary embodiments of the exclusion clip 100, the self-motivator or traction element 130 may be comprised of other tiny particles that, when grouped closely together, form a one-way friction material due to the resulting van der Waals force such that, when oriented in the direction in which the LAA is to be received into the clip's interior opening 172 of the exclusion clip 100, the particles encourage or direct the LAA further into the interior opening 172 upon coming into surface-to-surface contact with the LAA during the implantation process. Though comprised of synthetic materials, these particles may be modeled after naturally occurring examples. For instance, the tiny microscopic hairs or fibers (i.e., setae and spatulea) found on the feet pads of geckos exhibits a frictional adhesive character that may be usefully mimicked for the instant purpose. Another naturally-occurring example is the denticles found on sharkskin. Other technologies include nanotube forests (which are comprised of an array of carbon nanotubes) and other tiny one-directional microstructures (e.g., a tilted mountain range of a plurality of triangular or pyramid-shaped structures).

In another non-illustrated exemplary embodiment of the exclusion clip 100, the self-motivator or traction element 130 may be comprised of a series of rollers that, upon coming into surface-to-surface contact with the LAA during the implantation process, creates a conveyer-like driving force that directs the LAA into the clip's interior opening 172, due to the slip torque resulting from the friction between the pulsating LAA and the rollers. The rollers may be placed in a variety of configurations. For example, the rollers may be disposed along a single elongated shaft. In an alternative configuration, the shaft may be segmented into a plurality of shorter shafts placed in a line or placed in parallel lines to create a series of rows. In various exemplary embodiments, the rollers could be free to rotate in any direction, or could be restricted to rotating in only one direction. In the unidirectional embodiment, application of the clip 100 to the LAA is enhanced by the rollers preventing backwards movement of the LAA out of the clip 100. Conversely, in the free rotation embodiment of the rollers, the rollers reduce the risk of applying too much traction to the LAA if the clip 100 needs to be repositioned.

While the exclusion clip 100 according to the exemplary embodiment of FIGS. 1 to 12 has benefits, the shape of the biasing assembly 104 has some requirements. First, to deploy the exclusion clip 100, a compatible clip delivery device must comprise a rigid outer frame that can encircle a sufficient portion of the exclusion clip 100 to exert control over the movement of one or both clip struts 110, 120. Second, due to the inward-turning configuration of the spring members 150, the biasing assembly 104 limits the distance that the clips struts 110, 120 can be separated from one another. Third, the rigid outer frame of the clip delivery device limits the extent to which the exclusion clip 100 can be opened regardless of the degree to which the exclusion clip 100 can, itself, be opened. Fourth, the biasing assembly 104 requires a constantly increasing counter-force in order to separate the clip struts 110, 120 to expand the exclusion clip 100. Fifth, while the clip struts 110, 120 limit two directions of LAA movement when the LAA is captured in the exclusion clip 100, the other two opposing sides of the LAA comprising the far ends where the spring members 150 are located are not contained by, or are not closed on the plane of, the LAA-contacting surfaces of the clip 100, which could detrimentally lead to the far sides of the LAA tissue leaking out of, or not being effectively clamped by, the clip 100 at the location of the spring members 150.

Figure 29:
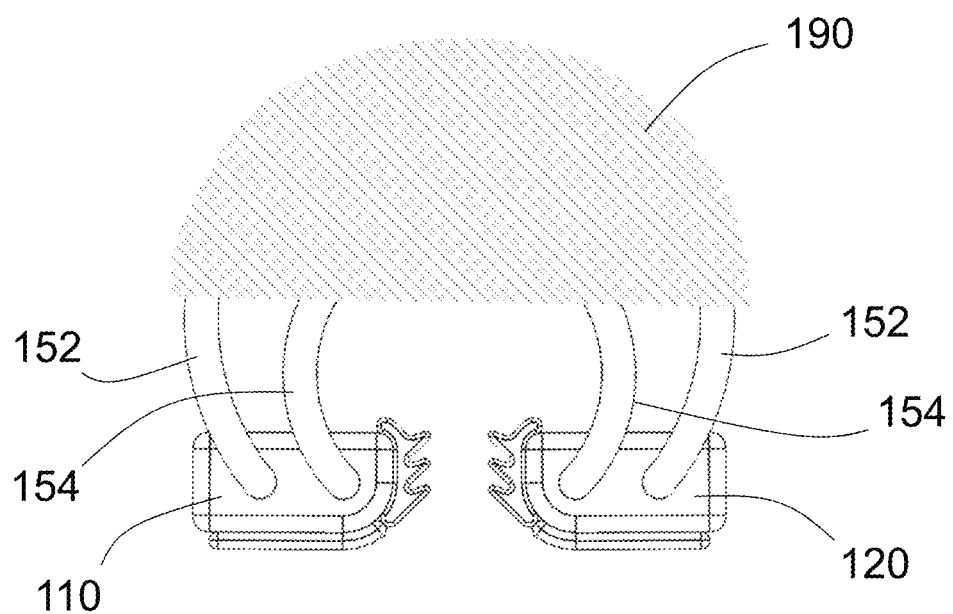
FIG. 29 is an enlarged, elevational view of a distal end of the clip of FIG. 5 with a web.
Figure 30:
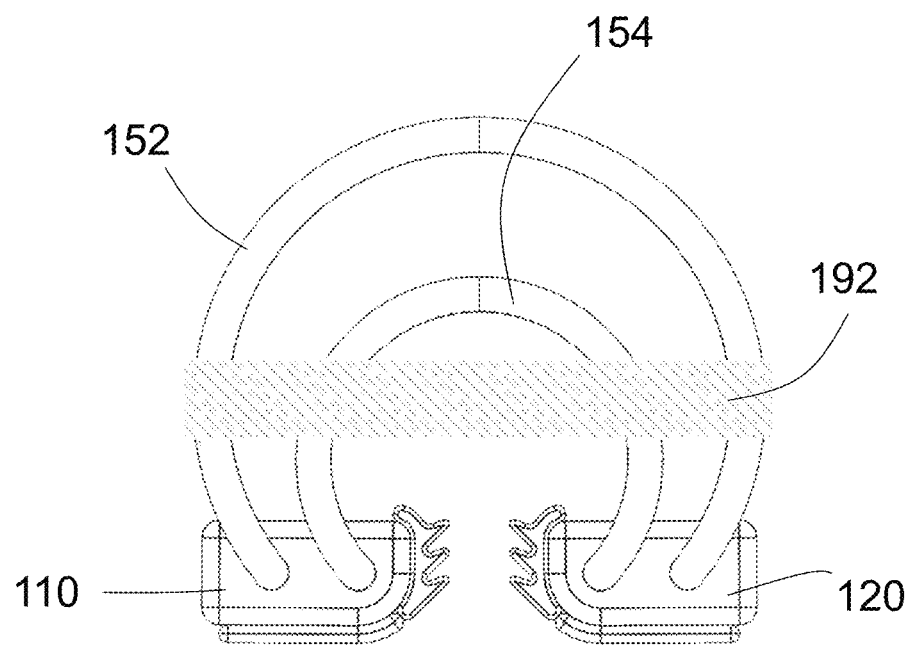
FIG. 30 is an enlarged, elevational view of a distal end of the clip of FIG. 5 with a web portion.

To ameliorate or substantially prevent leakage of the LAA out of from the area of the spring members 150 of the exclusion clip 100, a stretchable barrier structure may be applied to either or both spring member 150 (each of which could have one or two springs 152, 154) to barricade the LAA from leaking outward from the spring member 150 in the longitudinal directions. Depicted in FIGS. 29 and 30 are two exemplary embodiments of a web (which can be stretchable, taut, or have portions with different stretchability) applied to a portion of the body of the spring member 150 such that the web covers a portion of the open span that is created, e.g., by the arc of the springs 152, 154. Accordingly, the web acts to substantially prevent the LAA from exuding outward from the exclusion clip 100 in the area of the spring members 150. In the embodiment shown in FIG. 29, the web is in the form of a boot 190 that is slipped over a top portion of the springs 152, 154 and extends downward along a portion of the body of the springs 152, 154, thereby conforming to the shape of the outer spring 152 when the two springs 152, 154 are substantially coplanar. In another example, FIG. 30 depicts an embodiment of a web that is in the form of a band 192 positioned about an intermediate region of the body of the springs 152, 154. The web in this example is comprised of an elastic material that provides enough resiliency to securely maintain the stretchable web on the spring members 150, while also providing the necessary stretching capacity needed so that the stretchable web does not unduly restrict the spring members 150 from transitioning into their expanded state.

Certain safeguards may also be taken to prevent the exterior surfaces of the spring members 150 from causing trauma to the surrounding body tissue and causing ingrowth of the tissue. For example, the exterior surface of the spring members 150 may be entirely or partially coated with a suitable slickening agent. In another example, the spring members 150 may be entirely or partially encapsulated by a flexible blunting member, such as the stretchable web described above, that is comprised of a material having suitable characteristics. Such materials may include, but are not limited to, silicone, ePTFE, and urethane, etc. In an exemplary embodiment, the flexible blunting member is comprised of an elongated tubular member that securely surrounds one or more of the springs 152, 154. Further, the tubular member may be comprised of a series of circular or annular tubular sections. Alternatively, the tubular member may be comprised of a central lumen surrounded by a plurality of lumens.

Figure 31:
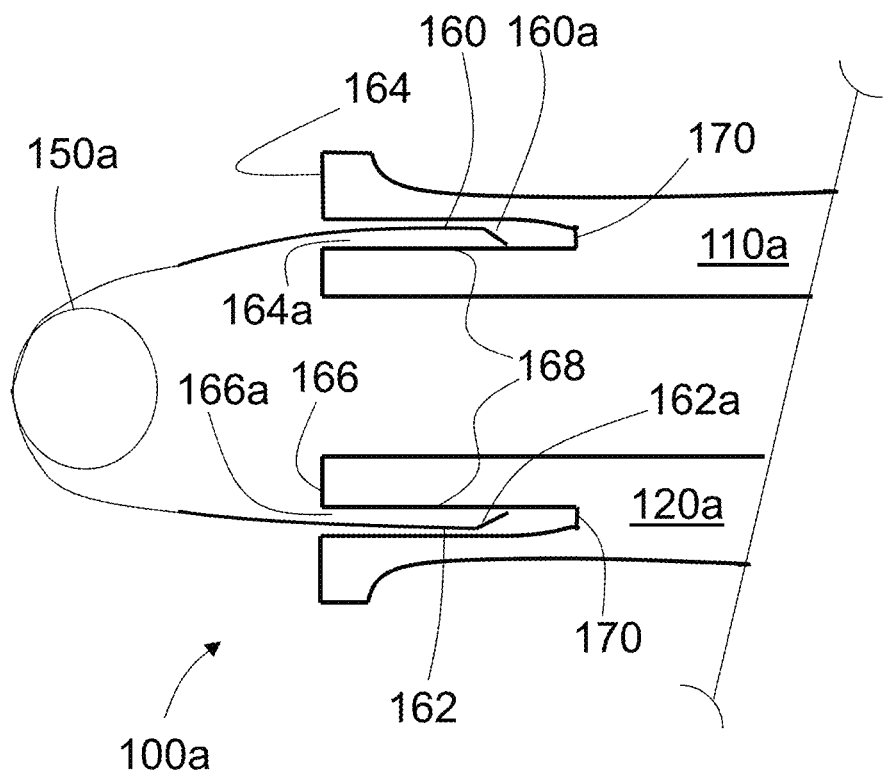
FIG. 31 is a fragmentary, diagrammatic, enlarged, cross-sectional view of a further exemplary embodiment of a left atrial appendage surgical implant clip.
Figure 32:
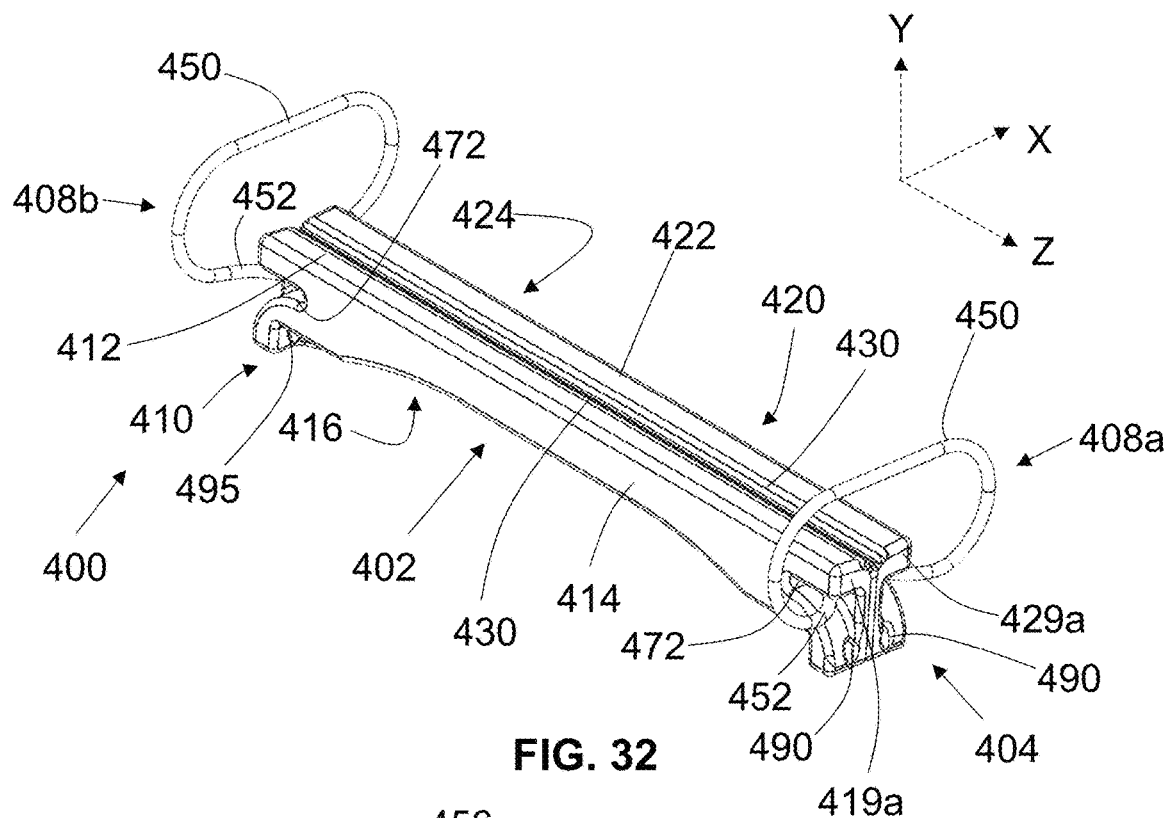
FIG. 32 is a perspective view of still another exemplary embodiment of a left atrial appendage surgical implant clip in a contracted and rotated orientation.

It should be appreciated that, although the depiction in FIGS. 1 to 12 and the corresponding description above of the first exemplary embodiment of the exclusion clip 100 indicates that each of the spring members 150 comprises two concentric "horseshoe-shaped" springs 152, 154, the spring members 150 are not limited to this particular type, shape or configuration, and may be in the form of any spring-like structure that provides the necessary degree of spring-biasing force to the opposing clip struts 110, 120 to bias one or both of the clip struts 110, 120 towards the opposing clip strut 110, 120 with enough force for the exclusion clip 100 to capture the LAA and remain securely implanted. For example, each spring member 150 may be comprised of only a single "horseshoe-shaped" spring. FIGS. 32 to 50 depict further possible exemplary embodiments of a spring-biased exclusion clip and are described in greater detail below. FIG. 31 illustrates a partial view of an exemplary embodiment of a spring-biased exclusion clip 100a in an expanded state (i.e., in the configuration depicted in FIGS. 1 to 4), where just the left side of the exclusion clip 110a is pictured. In this embodiment, the clip 100a comprises first and second clip struts 110a, 120a oppositely situated from one another and connected to each other by a spring member 150a in the manner described above with respect to the embodiment shown in FIGS. 1 to 12 with the exception that each spring member 150a comprises a single nonspecific spring structure terminating at spring ends 160, 162 and, at each end 160, 162, forming a rotatable and longitudinally fixed connection with each clip strut 110a, 120a. More specifically, in a central region of the respective end 164, 166 of each clip strut 110a, 120a is an aperture 164a, 166a opening into a cylindrical channel 168 that extends partially into the clip strut body (substantially along a centerline thereof) and matingly receives therein a respective one of spring ends 160, 162. Further, each channel 168 terminates at a floor 170. To rotationally fix the spring ends 160, 162 with respect to the clip struts 110a, 120a, the spring end 160, 162, as it is being advanced into its respective channel 168, traverses a 90-degree spiral groove or track (not shown) that winds along at least a section of the interior surface of channel 168. T bend or crimp 160a, 162a is formed at the tip of each spring end 160, 162 such that the spring end 160, 162 is oriented to engage the spiral groove. Additionally, the shape of each channel 168 may be further modified such that, for example, the channel 168 has one or more variations in its interior diameter along the length of the channel 168. For example, in the embodiment of FIG. 31, the interior diameter of the channel 168 slightly decreases when approaching the floor 170. Accordingly, as a result of the interaction between the bended or crimped spring end 160, 162 and the interior shape and the spiral groove or track of the channel 168, a balance of forces is achieved by placing the spring-biasing force on the center of the clip struts 110a, 120a, and a torsion effect is created that longitudinally secures each spring member 150a into position and allows for the clip struts 110a, 120a to freely rotate about the spring members 150a into the final implanted state of the clip 100a (i.e., in the configuration shown in FIGS. 9 to 12).

Referring now to FIGS. 13 to 28, there is shown a second exemplary embodiment of an externally implantable, left atrial appendage exclusion clip 200 comprising a clipping assembly 202 and a bias assembly 204. Benefits of the exclusion clip 200 are many. First, to deploy the exclusion clip 200, a rigid outer head having a frame encircling the exclusion clip 200 is not needed. Second, the bias assembly 204 does not limit the distance that the clip struts 210, 220 can be separated from one another, which means that there is no limit to the amount that the exclusion clip 200 can open. Third, the bias assembly 204 provides little or no force on the clip struts 210, 220 when the exclusion clips 200 is opened and closed. Fourth, the clip struts 210, 220 and control cords 252, 262 limit all four possible directions of LAA movement when captured in the exclusion clip 200. The clip 200 can be referred to as being cord-tensioned.

The clipping assembly 102 comprises two opposing clip struts, a distal clip strut 210 and a proximal clip strut 220. In the exemplary embodiment shown in FIGS. 13 to 28, the clip struts 210, 220 are substantially in the form of a rectangular column and are mirror images of one another. Each of the struts 210, 220 have a first side 212, 222 comprising a self-motivator 230, a second side 214, 224, a third side 216, 226, a fourth side 218, 228 comprising a LAA-contacting surface 240, and fifth and sixth opposing ends 219a, 219b, 229a, 229b.

The bias assembly 204 comprises a first or distal strut bias sub-assembly 250 and a second or proximal strut bias sub-assembly 260.

The distal strut bias sub-assembly 250 comprises a distal control cord 252, a first distal end anchor 254, and a distal tension device 256. The distal control cord 252 terminates at the first distal end anchor 254 and begins at a proximal handle of a clip delivery device 300. The terminating end of the distal control cord 252 and the first distal end anchor 254 movably reside within a first anchor hollow 217a defined by the distal clip strut 210. The distal control cord 252 extends from the first anchor hollow 217a through a passage 215a and exits the distal clip strut 210, in this exemplary embodiment, at the fourth side 218 as shown in FIG. 14. The distal control cord 252 can, in an alternative embodiment, exit the distal clip strut 210 at the fifth side 219a, which will be described in further detail below. The distal control cord 252 then extends across the gap 270 formed by the opposing surfaces of the two control struts 210, 220. (The gap 270 as defined herein is not limited to the space between the two opposing self-motivators 230 because the two control struts 210, 220 rotate to also present the fourth sides 218, 228 facing one another later in the implanting process, as shown in FIGS. 24 to 28 and as described in further detail below. Thus, the gap 270 is broadly defined to comprise two opposing sides of an interior 272 of the exclusion clip 200 at any time during the exclusion clip implantation process.) The gap 270 is shown at an extended opening position in FIG. 13. In an exemplary embodiment, this extended opening position can be a maximum extended position. However, the extended opening position shown can also be an intermediate extended position. Because the distance of the gap 270 is controlled by the delivery device 300, the only limitation of the gap distance is the length of the distal and proximal control cords 252, 262 and the length of the extension axle 320, as will be described in further detail below. Thus, the exclusion clip 200 provides the ability to open the clip struts 210, 220 up much further than shown in the figures.

After crossing the gap 270, the distal control cord 252 enters the fourth side 228 of the proximal clip strut 220 and passes through a channel 227 defined by the proximal clip strut 220. In the exemplary embodiment shown, the channel 227 leaves the proximal clip strut 220 at an exit 225 defined by the second side 224 of the proximal clip strut 220. The distal control cord 252 exits the proximal clip strut 220 at the second side 224, at which exit 225 is a cord capture assembly 280, which is described in further detail below with respect to FIG. 19. The distal control cord 252 then enters a proximal base part 310 of the delivery system 300; the proximal base part 310 is shown with dashed lines in FIGS. 13 and 20. The distal control cord 252 extends through or at the proximal base part 310 and is led to a non-illustrated cord control device located in the proximal handle of the delivery device 300. The cord control device controls distal (outbound) and proximal (inbound) movement of the distal control cord 252 with respect to the delivery device 300.

In an alternative, non-illustrated, exemplary embodiment, the channel 227 leaves the proximal clip strut 220 at an exit 225 defined by the fifth end 229a of the proximal clip strut 220. A beneficial difference in exiting at the fifth end 229a is that the distal control cord 252 executes two bends between the first distal end anchor 254 and the proximal base part 310 and the proximal control cord 262 also executes two bends between the second distal end anchor 264 and the proximal base part 310. Thus, the force imparted on both the distal and proximal tension devices 256, 266 is balanced. At the exit 225 on the second side 224 is the cord capture assembly 280. As above, the distal control cord 252 then enters a proximal base part 310 of the delivery system 300. The distal control cord 252 extends through or at the proximal base part 310 and is led to a non-illustrated cord control device located in the proximal handle of the delivery device 300. The cord control device controls distal (outbound) and proximal (inbound) movement of the distal control cord 252 with respect to the delivery device 300.

In another alternative, non-illustrated exemplary embodiment, the channel 227 is coaxial with the proximal strut movement axle 350 and the proximal strut movement axle 350 is hollow. In this configuration, the exit 225 is the open hollow end of the proximal strut movement axle 350 opposite the proximal strut rotation receiver 352. Therefore, the distal control cord 252 leaves the proximal clip strut 220 at the exit 225 and travels entire through the longitudinal extent of the proximal strut movement axle 350, which is removably attached to the fifth end 229a of the proximal clip strut 220. Other features of the distal control cord 252 are explained with respect to other embodiments herein and, therefore, are not repeated here.

Figure 16:
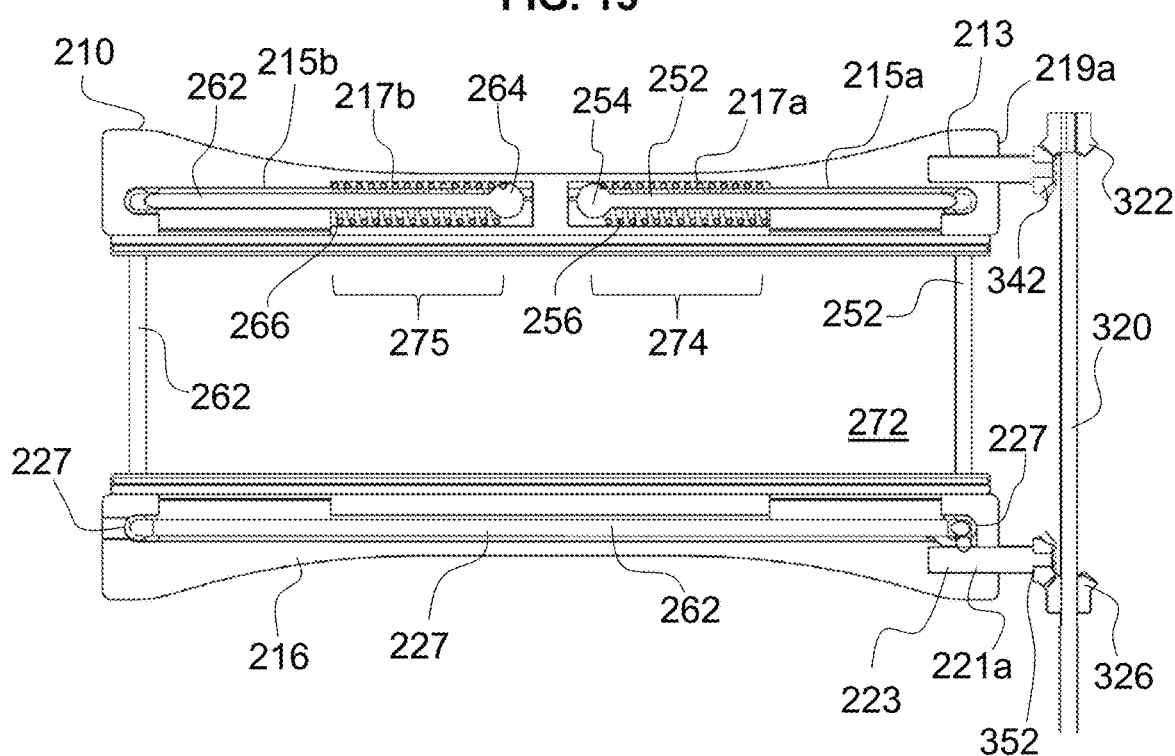
FIG. 16 is a fragmentary, enlarged, horizontal cross-sectional view of the clip and control assembly of FIG. 13.

The distal tension device 256 provides the terminating end of the distal control cord 252 with an ability to not be fixed, at least over a distance 274 defined by the first anchor hollow 217a and the first distal end anchor 254 (see, e.g., FIG. 16). In an exemplary embodiment, the distal tension device 256 is a spring having opposing anchor points, a first anchor point of the spring located at the first distal end anchor 254 and a second anchor point of the spring located at a wall within the anchor hollow 217a of the distal clip strut 210. These anchor points define the distance 274 that the distal tension device 256 provides to the distal control cord 252 when a spring is the distal tension device 256. With the first distal end anchor 254 being a sphere and the distal tension device 256 being a spring, the end of the spring connecting the first distal end anchor 254 is in the form of a circle that self-centers on the sphere. Another exemplary embodiment for the distal tension device, which is substantially constant over a length of travel, includes a "negator" spring, which in an exemplary embodiment is a spring made of a stainless steel, a superelastic alloy or an elastomer spring.

The distal tension device 256 allows movement of the first distal end anchor 254 based upon a pre-defined force limit that is dependent upon the type of bias being used. In other words, if the bias device is a spring, then movement of that spring and the force required will follow Hooke's law. The spring can be unloaded within the anchor hollow 271a or it can be pre-loaded. In the latter case, a given amount of force must be overcome before the distal tension device 256 will allow the first distal end anchor 254 to move further within the anchor hollow 217a. If the force applied to the distal control cord 252 is less than this given amount of force, the first distal end anchor 254 will not move from its pre-loaded position. Once the force applied is greater than the given amount, the first distal end anchor 254 will move up to its travel limit within the anchor hollow 217a. By using a pre-loaded spring, the amount of tension over the range of motion of the tension device would be more constant than if the spring were not preloaded. In the case of a negator spring, the force exerted would be substantially constant over the displacement range of the spring, resulting in a definite amount of compression on the tissue, independent of the thickness of tissue between the clamp elements.

Figure 18:
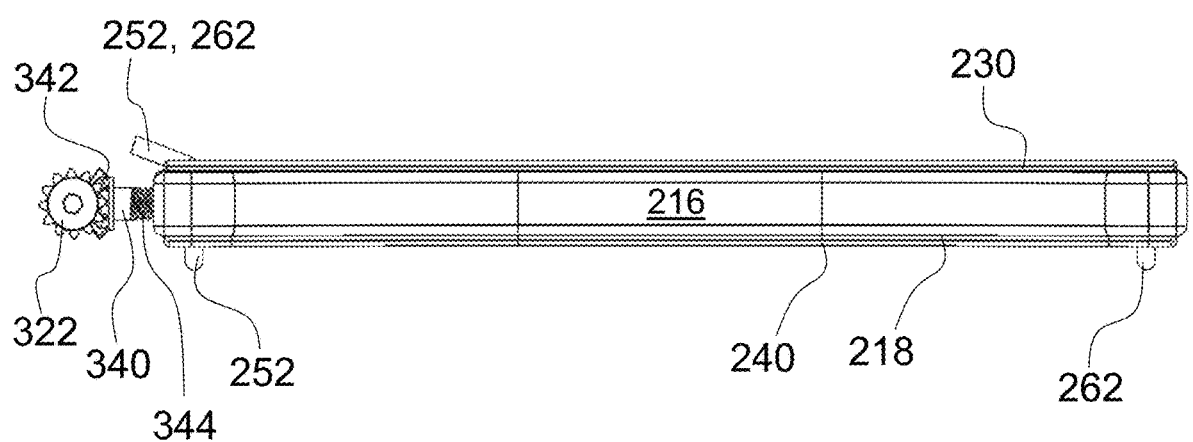
FIG. 18 is a distal side elevational view of the clip and control assembly of FIG. 13.

Like the distal strut bias sub-assembly 250, the proximal strut bias sub-assembly 260 comprises a proximal control cord 262, a second distal end anchor 264, and a proximal tension device 266. The proximal control cord 262 terminates at the second distal end anchor 264 and begins at the proximal handle of the clip delivery device 300. The terminating end of the proximal control cord 262 and the second distal end anchor 264 movably reside within a second anchor hollow 217b defined by the distal clip strut 210 as shown in FIG. 16. The proximal control cord 262 extends from the second anchor hollow 217b through a passage 215b and exits the distal clip strut 210, in this exemplary embodiment, at the fourth side 218 as shown in FIG. 18. The proximal control cord 262 can, in an alternative embodiment, exit the distal clip strut 210 at the fifth side 219a. The proximal control cord 262 then extends across the gap 270 formed by the opposing surfaces of the two control struts 210, 220. After crossing the gap 270, the proximal control cord 262 enters the fourth side 228 of the proximal clip strut 220 and passes through a channel 227 defined by the proximal clip strut 220. The channel 227 enters the body of the proximal clip strut 220 orthogonal to the fourth side 228 and then, in the exemplary embodiment shown, in particular, in FIG. 16, turns parallel to the fourth side 228 to traverses a longitudinal extent of the proximal clip strut 220. In the exemplary embodiment, the channel 227 ends at an exit 223 (see, e.g., FIG. 19) defined by the second side 224 of the proximal clip strut 220. (As above, and not repeated, the exit 223 can be defined by the fifth end 229a.) The proximal control cord 262 exits the proximal clip strut 220 at the second side 224, at which exit 223 is the cord capture assembly 280, which is described in further detail below with respect to FIG. 19. The proximal control cord 262 then enters the proximal base part 310 of the delivery system 300. The proximal control cord 262 extends through, outside, adjacent, or at the proximal base part 310 and is led to the non-illustrated cord control device located in the proximal handle of the delivery device 300. The cord control device controls distal (outbound) and proximal (inbound) movement of the proximal control cord 262 with respect to the delivery device 300.

The proximal tension device 266 provides the terminating end of the proximal control cord 262 with an ability to be movable and not fixed at least over a distance 275 defined by the second anchor hollow 217b and the second distal end anchor 264 (see, e.g., FIG. 16). In an exemplary embodiment, the proximal tension device 266 is a spring having opposing anchor points, a first anchor point of the spring located at the second distal end anchor 264 and a second anchor point of the spring located at a wall within the anchor hollow 217b of the distal clip strut 210. These anchor points define the distance 275 that the proximal tension device 266 provides to the proximal control cord 262 when a spring is the proximal tension device 266. With the second distal end anchor 264 being a sphere and the proximal tension device 266 being a spring, the end of the spring connecting the second distal end anchor 264 is in the form of a circle that self-centers on the sphere. The proximal tension device 266 allows movement of the second distal end anchor 264 based upon a pre-defined force limit that is described above and is not repeated here.

Figure 17:
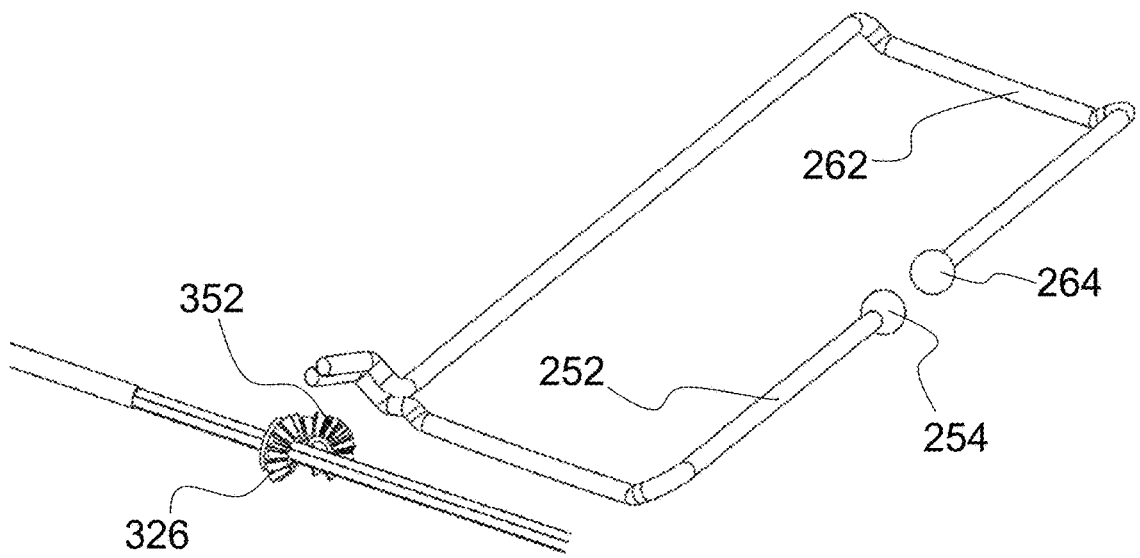
FIG. 17 is a fragmentary perspective view of a portion of a strut bias sub-assembly and a portion of the control assembly of FIG. 13.
Figure 19:
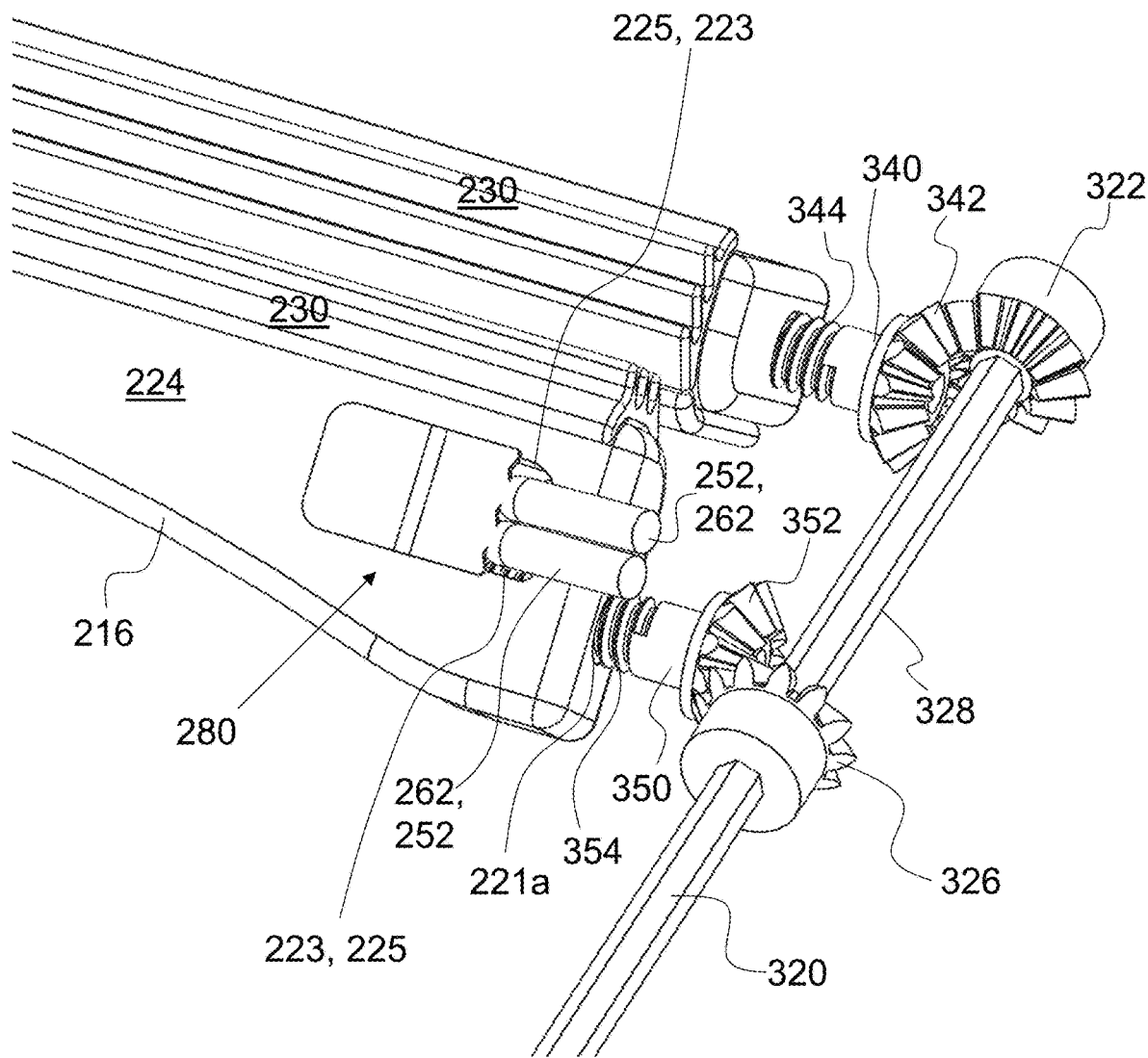
FIG. 19 is a fragmentary, enlarged, perspective view of a portion of the clip and control assembly of FIG. 13 with clip struts in an intermediate, contracted and partially rotated pre-implantation orientation.

FIG. 17 illustrates the distal and proximal control cords 252, 262 in a shape as they pass through the various channels and hollows of the distal and proximal clip struts 210, 220 and how they exit at the exits 223, 225, which in this exemplary embodiment is from the second side 224. The control cords 252, 262 are stacked when they pass through the exits 223, 225 and they can be stacked in either orientation. In other words, the exit 225 for the distal control cord 252 can be located distal of the exit 223 for the proximal control cord 262 or it can be located proximal of the exit 223. The exits 223, 225 are shown in FIG. 19 at the cord capture assembly 280 for the embodiment where the control cords 252, 262 exit the second side 224. The control cords 252, 262 exit the cord capture assembly 280 and operatively connect to the proximal base part 310. In an exemplary embodiment, the proximal base part 310 has one or two control cord paths in which the control cords 252, 262 are directed, these paths being smooth and allowing free slidable movement of the control cords 252, 262 therein. The control cords 252, 262 continue proximally to a handle of the delivery device 300, in which is disposed a cord control assembly that moves the control cords 252, 262 as needed to carry out the implantation procedure of the exclusion clip 200, which control is described in further detail below.

FIGS. 13 through 28 illustrate one exemplary embodiment of a distal portion of the delivery device 300 for the exclusion clip 200. This exemplary distal portion comprises the proximal base part 310, the extension axle 320, a distal base part 330, a distal strut movement axle 340, and a proximal strut movement axle 350.

The proximal base part 310 has a body through which the extension axle 320 passes (the extension axle can also pass adjacent, outside, or at the body of the proximal base part 310). The extension axle 320 is radially fixed to remain in place in one position with respect to the body of the proximal base part 310 but is longitudinally free to extend distally and retract proximally with respect to the body. In an alternative non-illustrated exemplary embodiment, a stabilizing bar extends proximally from the distal base part 330 to and into the proximal base part 310. In one exemplary embodiment, the stabilizing bar is fixed to the distal base part 330 and has a longitudinal extent that enters a hole in the distal face of the proximal base part 310 (which hold could be a through-hole or blind), the hole having a cross-section that is substantially similar to a cross-section of the stabilizing bar. In this manner, forces that act upon the distal base part 330, whether from the environment or transferred from the handle of the delivery device 300, are not solely transmitted into the extent 328 of the extension axle 320 that is located between the proximal and distal base parts 310, 320 when such forces are applied thereto.

A distal strut rotation device 322 is fixed at the distal end of the extension axle 320 and is located within the distal base part 330 (the distal strut rotation device 322 can also be located adjacent, outside, or at the distal base part 330). A distal rotation device anchor 332 connects the extension axle 320 to the distal base part 330 to permit free rotation of the distal strut rotation device 322 with respect to the distal base part 330 while preventing longitudinal movement of the distal strut rotation device 322 with respect to the distal base part 330. The distal rotation device anchor 332 is illustrated diagrammatically with a dashed line. In an exemplary embodiment, the distal strut rotation device 322 is a miter gear, shown, for example, in FIGS. 13 and 14. This miter gear, therefore, rotates within the distal base part 330 but does not move with respect to the distal base part 330 in an axial direction of the extension axle 320. In an exemplary embodiment, the distal rotation device anchor 332 is a blind cylindrical hole having a given circumference and the distal strut rotation device 322 has a boss with an outer shape corresponding to the given circumference. Accordingly, the distal strut rotation device 322 is free to rotate within the hole but cannot move distally further into the hole.

A proximal rotation anchor 312 (diagrammatically indicated with a dashed line within the proximal base part 310) longitudinally fixes a proximal strut rotation device 326 with respect to the axis of the extension axle 320 within the proximal base part 310 (the proximal strut rotation device 326 can also be located adjacent, outside, or at the proximal base part 310) but allows the proximal strut rotation device 326 to rotate freely with any rotation of the extension axle 320. In an exemplary embodiment, the proximal rotation anchor 312 is constructed to allow rotary motion of the proximal strut rotation device 326 but restrain axial motion of the proximal strut rotation device 326 within the proximal base part 310. For example, this anchor 312 can be a thrust bearing assembly in which a hub of the proximal strut rotation device 326 contains a thrust ring that engages an annular recess in the proximal rotation anchor 312. In an exemplary embodiment, the proximal strut rotation device 326 is a miter gear. This miter gear, therefore, rotates within the proximal base part 310 in synchronization with any rotation of the extension axle 320 but does not move along the axis of the extension axle 320 with respect to the proximal base part 310. One exemplary embodiment for the connection of the proximal strut rotation device 326 forms a distal extent 328 of the extension axle 320 having a polygonal cross-section and provides the proximal strut rotation device 326 with a central hollow having a cross-section corresponding in shape to the polygonal cross-section of the extension axle 320, which extent 328 is shown in FIG. 14. Thus, the extension axle 320 can freely move through the proximal strut rotation device 326 along its rotation axis but any rotation of the extension axle 320 results in a corresponding rotation of the proximal strut rotation device 326.

As shown well in FIGS. 15 to 19, rotation of the distal clip strut 210 occurs with the distal strut movement axle 340. The distal strut movement axle 340 has a base that is rotationally fixed to the fifth end 219*a*. Opposite the base of the distal strut movement axle 340 is a distal strut rotation receiver 342 that connects to the distal strut rotation device 322 and rotates correspondingly with rotation of the distal strut rotation device 322. In an exemplary embodiment, the distal strut rotation receiver 342 is a miter gear. Accordingly, rotation of the miter gear of the distal strut rotation device 322 causes a corresponding rotation of the distal clip strut 210 about the axis of the distal strut movement axle 340.

If the distal strut movement axle 340 were fixed permanently to the distal clip strut 210, then the distal clip strut 210 could not be deployed into a patient (at least without extending laterally from the fifth end 219*a*). Therefore, the distal strut movement axle 340 is removably connected to the distal clip strut 210. In a first exemplary embodiment illustrated, for example, in FIGS. 13, 15, 16, and 20, this removable connection is formed by a blind axle hole 213 in which the base of the distal strut movement axle 340 is inserted in a slidable manner. To keep the distal strut movement axle 340 within the blind axle hole 213, a pin passage 211 formed in the distal clip strut 210 receives therein a grenade pin 360. As long as the grenade pin 360 is in the pin passage 211, the distal strut movement axle 340 is fixed within the blind axle hole 213, both rotationally and axially. When the grenade pin 360 is removed, the distal strut movement axle 340 easily slides out of the blind axle hole 213 with a small amount of outwardly directed force applied to the distal strut movement axle 340. To transfer this force at the appropriate time, the distal strut rotation receiver 342 is disposed within the distal base part 330 in a freely rotatable manner but is axially trapped in position with respect to the distal base part 330. Therefore, when the grenade pin 360 is pulled out of the pin passage 211, any force applied to the delivery device 300 that acts to pull the distal strut movement axle 340 outwardly will cause the distal strut movement axle 340 to remove from the blind axle hole 213 and disconnect the distal clip strut 210 from the delivery device 300 (with the exception of the distal control cord 252, which disconnection is described below).

In a second exemplary embodiment illustrated, for example, in FIGS. 18, 19, 21, 23, and 25 to 27, this removable connection is formed by a threaded axle hole 213, 221a in which the threaded base 344, 354 of the distal or proximal strut movement axle 340, 350, respectively, is threadably inserted. When it is desired to remove the distal and proximal strut movement axles 340, 350 from the distal and proximal clip struts 210, 220, appropriate rotation of the distal and proximal strut movement axle 340, 350 with respect to the distal and proximal clip strut 210, 220 respectively occurs. For example, once the control cords 252, 262 have been secured, the clip struts 200, 220 can no longer rotate relative to one another; in that condition, the extension axle 320 is rotated in a direction to unscrew the distal and proximal strut movement axles 340, 350. When the distal and proximal strut movement axles 340, 350 are screwed out from the respective threaded axle hole 213, 221a, simple movement of the delivery device 300 away from the clip struts 210, 220 removes the distal and proximal strut movement axles 340, 350 from the exclusion clip 200 (with the exception of the control cords 252, 262, which disconnection is described below).

As shown well in FIGS. 15 to 19, rotation of the proximal clip strut 220 occurs with the proximal strut movement axle 350. The proximal strut movement axle 350 has a base that is rotationally fixed to the fifth end 229a. Opposite the base of the proximal strut movement axle 350 is a proximal strut rotation receiver 352 that connects to the proximal strut rotation device 326 and rotates correspondingly with rotation of the proximal strut rotation device 326. In an exemplary embodiment, the proximal strut rotation receiver 352 is a miter gear. Accordingly, rotation of the miter gear of the proximal strut rotation device 326 causes a corresponding rotation of the proximal clip strut 220 about the axis of the proximal strut movement axle 350.

If the proximal strut movement axle 350 were fixed permanently to the proximal clip strut 220, then the proximal clip strut 220 could not be deployed into a patient (at least without extending laterally from the fifth end 219a). Therefore, the proximal strut movement axle 350 is removably connected to the proximal clip strut 220. In a first exemplary embodiment illustrated, for example, in FIGS. 13, 15, 16, and 20, this removable connection is formed by a blind axle hole 221a in which the base of the proximal strut movement axle 350 is inserted in a slidable manner. To keep the proximal strut movement axle 350 within the blind axle hole 221a, a pin passage 211 formed in the proximal clip strut 220 receives therein a grenade pin 360. As long as the grenade pin 360 is in the pin passage 211, the proximal strut movement axle 350 is fixed in the blind axle hole 221a both rotationally and axially. When the grenade pin 360 is removed, the proximal strut movement axle 350 easily slides out of the blind axle hole 221a with a small amount of outwardly directed force applied to the proximal strut movement axle 350. To transfer this force at the appropriate time, the proximal strut rotation receiver 352 is disposed within the proximal base part 310 in a freely rotatable manner but is axially trapped in position with respect to the proximal base part 310. Therefore, when the grenade pin 360 is pulled out of the pin passage 211, any force applied to the delivery device 300 that acts to pull the proximal strut movement axle 350 outwardly will cause the proximal strut movement axle 350 to remove from the blind axle hole 221a and disconnect the proximal clip strut 220 from the delivery device 300 (with the exception of the proximal control cord 262, which disconnection is described below).

In a second exemplary embodiment illustrated, for example, in FIGS. 18, 19, 21, 23, and 25 to 27, this removable connection is formed by a threaded axle hole 223 in which the threaded base 344 of the proximal strut movement axle 350 is inserted threadably. The remainder of the proximal strut movement axle 340 is the same as the distal strut movement axle 340 above, therefore, the explanation is not reproduced here.

The cord capture assembly 280 is located at the exits 223, 225 where the distal and proximal control cords 252, 262 leave the proximal clip strut 220. The cord capture assembly 280 has a structure that allows free and unhindered movement of the control cords 252, 262 therethrough when the exclusion clip 200 is in the process of being implanted. When the clip struts 210, 220 are in the implantation position and ready to be implanted, the control cords 252, 262 are secured in place. In an exemplary embodiment that is illustrated in FIGS. 13, 15, 20, and 21, and in particular in FIGS. 19 and 28, the cord capture assembly 280 is a spring-hinged door that is held open while the exclusion clip 200 is in the process of being implanted. When the exclusion clip 200 is ready for permanent implantation, the spring of the door is released, thereby clamping the door onto the control cords 252, 262 and permanently retaining them there in position as well as with the current pre-bias force that has been applied to the distal and proximal tension devices 256, 266.

With the distal and proximal control cords 252, 262 retained in place, a cord cutter 314 at the proximal base part 310 (diagrammatically indicated in FIG. 13 with dashed lines) severs the control cords 252, 262.

As set forth above, the distal and proximal strut movement axles 340, 350 are connected removably to the distal and proximal clip struts 210, 220. In the exemplary embodiment where grenade pins 360 are used, a pin remover 362 is connected to each of the grenade pins 360. The pin remover 362 is diagrammatically illustrated in FIG. 13 with a dot-dashed line. Before, after, or at the same time the cord cutter 314 severs the control cords 252, 262, a control at the handle of the delivery system 300 is actuated and the pin remover 362 acts to pull the grenade pins 360 out from each of the distal and proximal clip struts 210, 220. The grenade pins 360 can be retracted all the way back to the handle separate from the proximal base part 310 or they can be pulled to the proximal base part 310 or into corresponding recesses at the proximal base part 310 for withdrawal from the patient along with withdrawal of the delivery system.

With the configuration as described, the delivery system 300 is able to effect all of the controls for carrying out implantation of the exclusion clip 200, including movement of the distal clip strut 210 with respect to the proximal clip strut 220, rotation of both the distal and proximal clip struts 210, 220, extension and withdrawal of the control cords 252, 262. In this regard, the process for effecting these controls is described with respect to the figures and, in particular, FIGS. 13 and 20 to 24.

Figure 13:
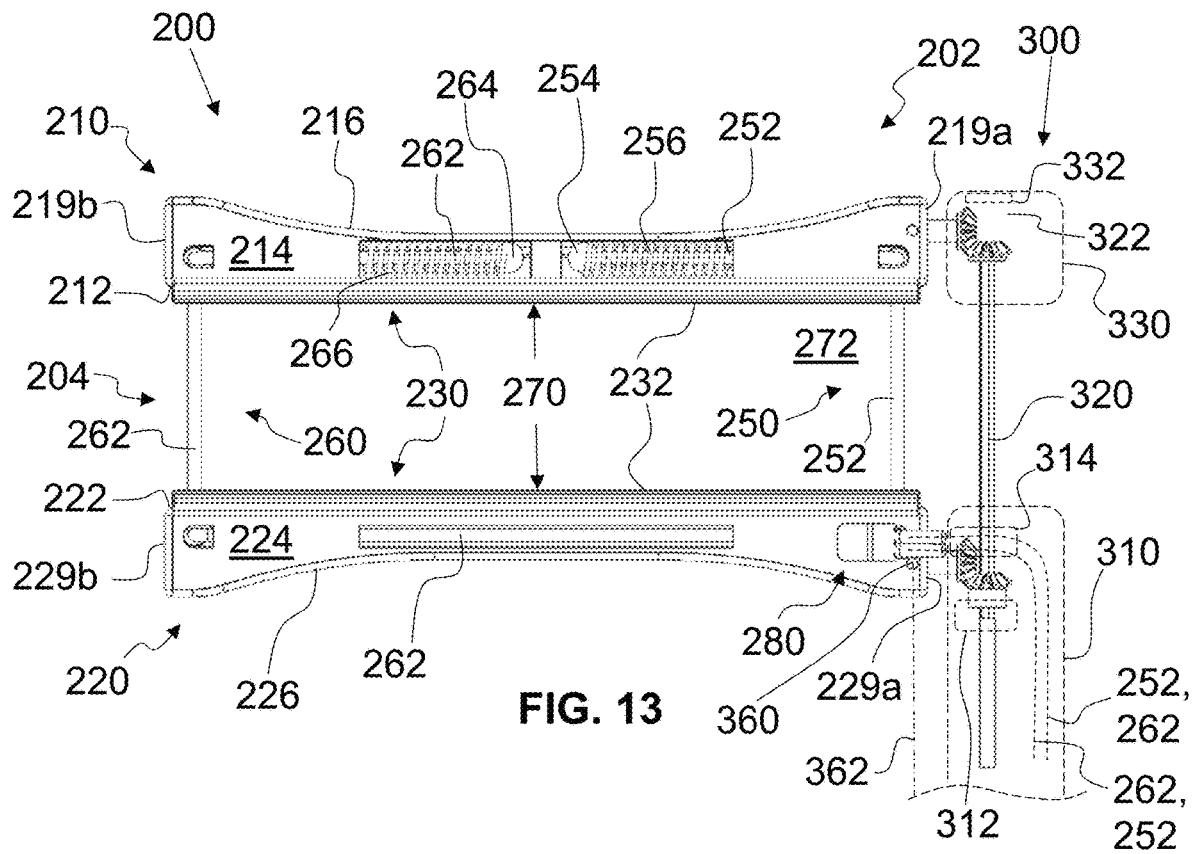
FIG. 13 is a fragmentary, top plan view of another exemplary embodiment of a left atrial appendage surgical implant clip in an extended, open orientation mounted on a distal end of a portion of an implantation control assembly of a control handle.
Figure 14:
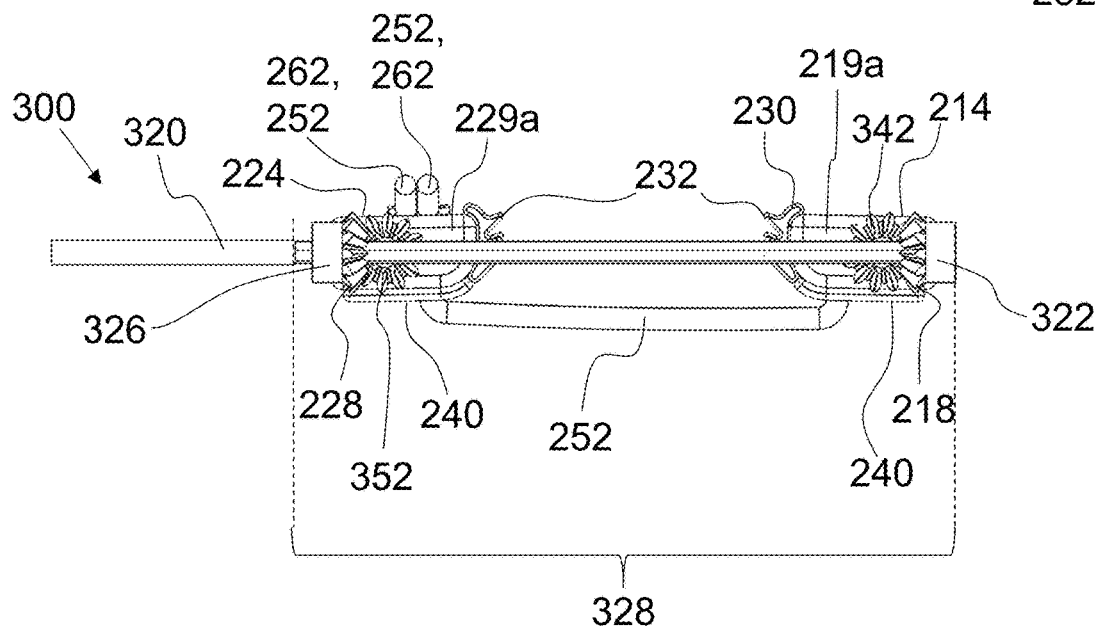
FIG. 14 is a fragmentary, enlarged, right side elevational view of the clip and control assembly of FIG. 13.
Figure 15:
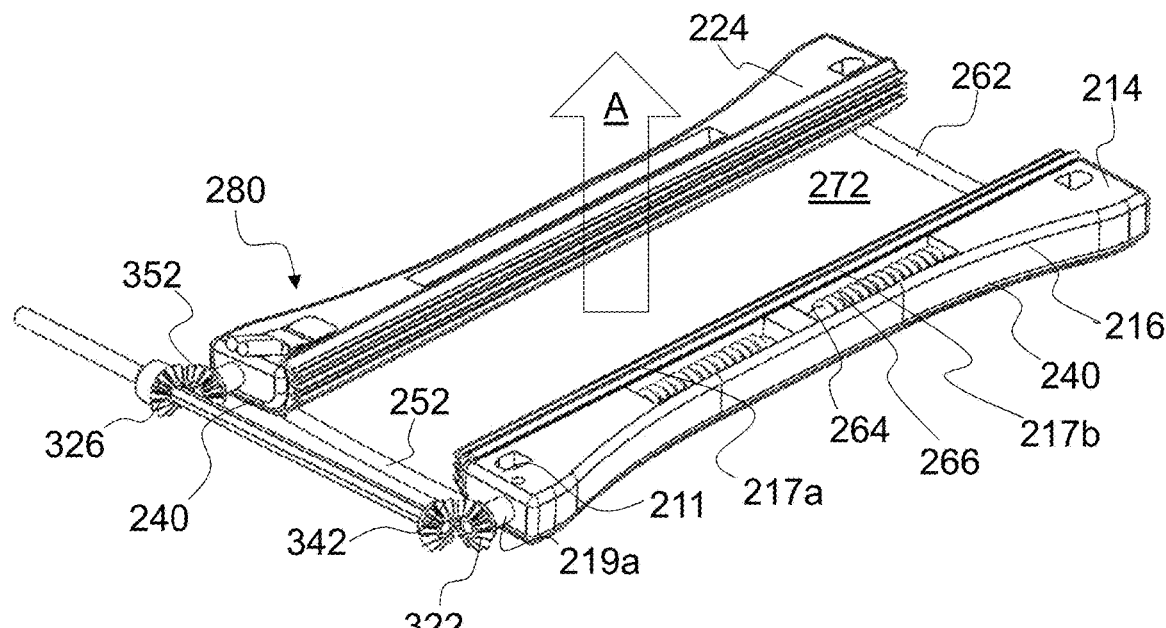
FIG. 15 is a fragmentary, perspective view of the clip and control assembly of FIG. 13.
Figure 20:
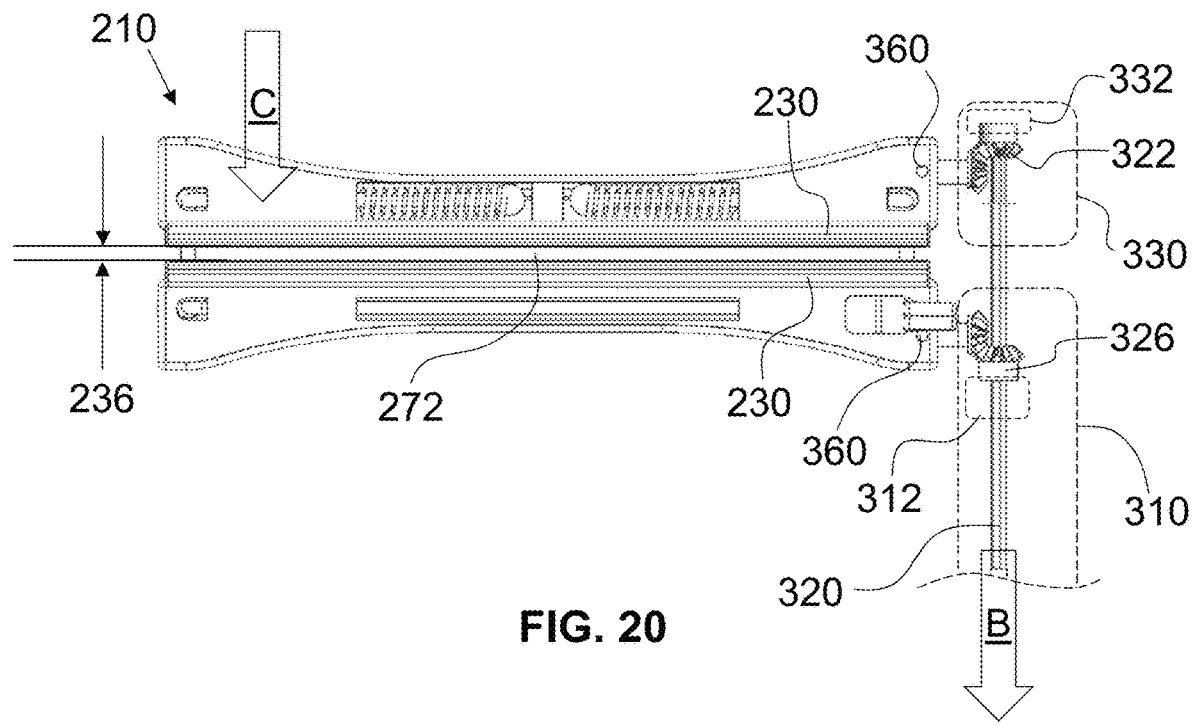
FIG. 20 is a fragmentary, top plan view of the clip and control assembly of FIG. 13 with clip struts in an intermediate, contracted and non-rotated pre-implantation orientation.
Figure 21:
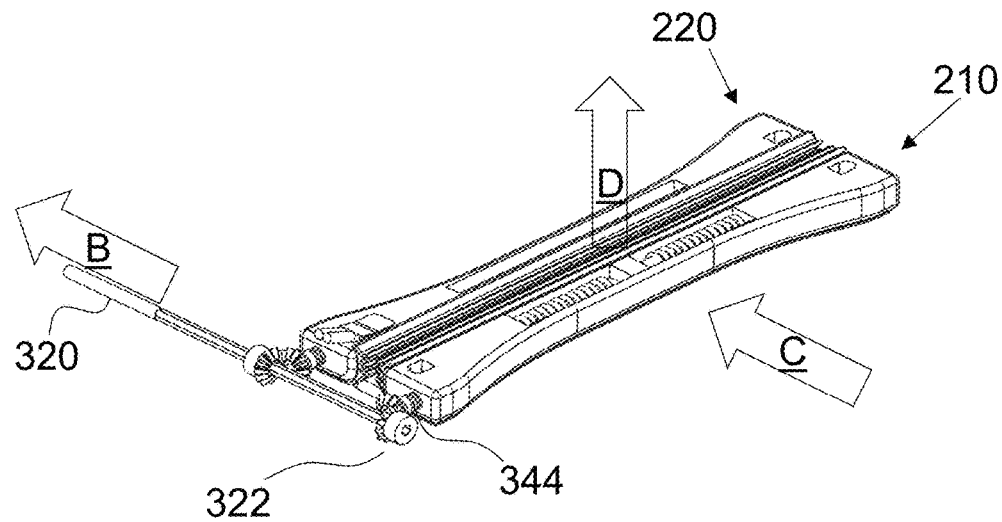
FIG. 21 is a fragmentary, perspective view of the clip and control assembly of FIG. 20.
Figure 22:
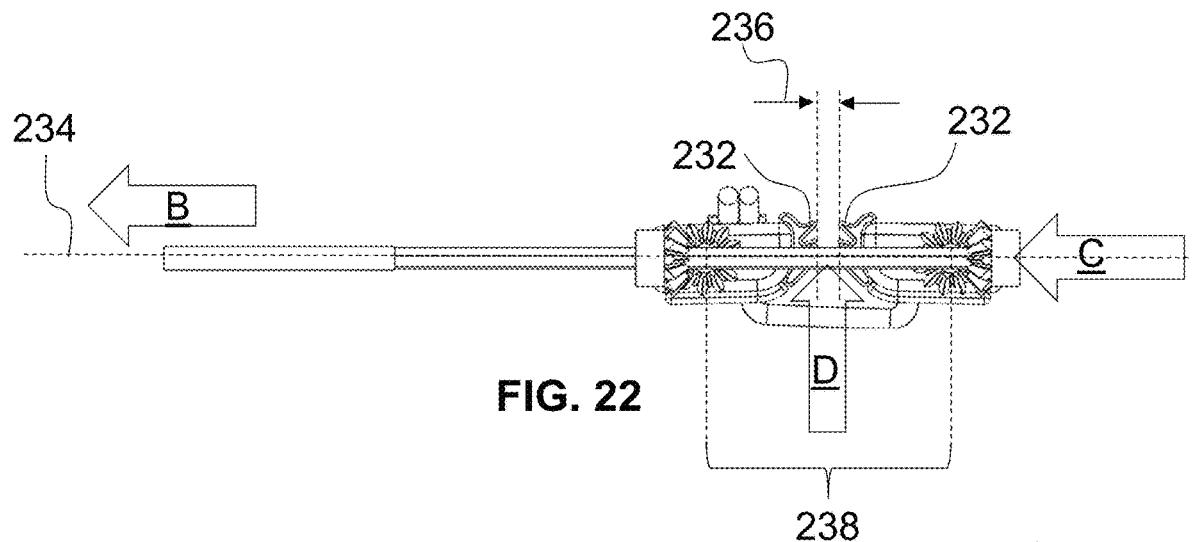
FIG. 22 is a fragmentary, enlarged, right side elevational view of the clip and control assembly of FIG. 20.
Figure 23:
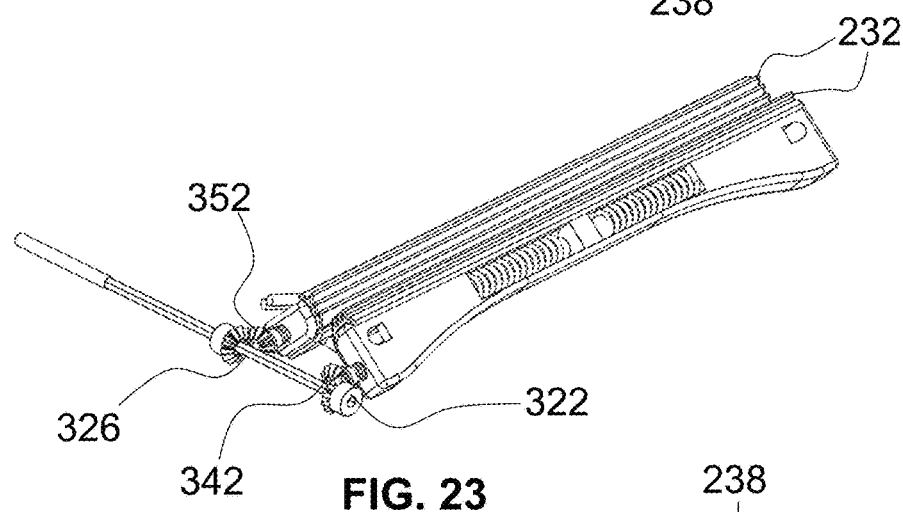
FIG. 23 is a fragmentary, perspective view of the clip and control assembly of FIG. 19 with clip struts in the intermediate, contracted and partially rotated pre-implantation orientation.
Figure 24:
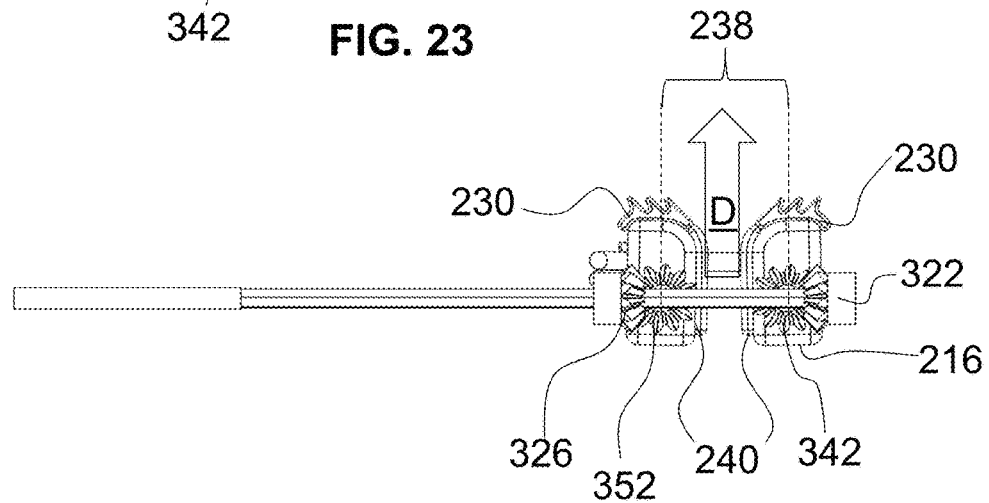
FIG. 24 is a fragmentary, enlarged, right side elevational view of the clip and control assembly of FIG. 13 with clip struts in a contracted and fully rotated implantation orientation.
Figure 25:
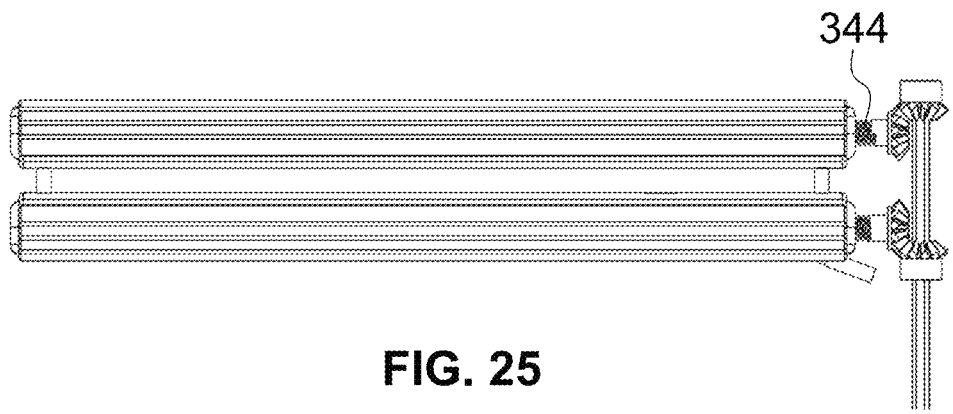
FIG. 25 is a fragmentary, top plan view of the clip and control assembly of FIG. 24.
Figure 26:
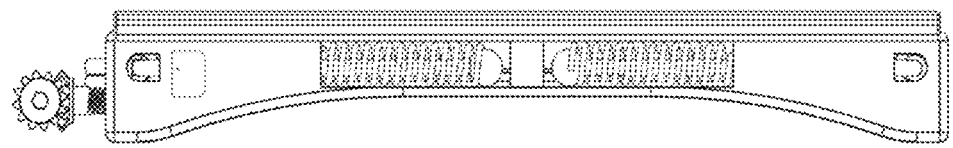
FIG. 26 is a fragmentary, distal elevational view of the clip and control assembly of FIG. 24.
Figure 27:
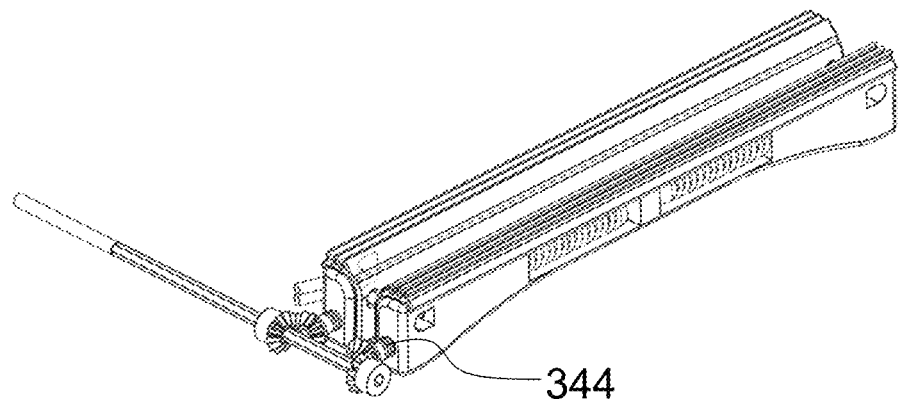
FIG. 27 is a fragmentary, perspective view of the clip and control assembly of FIG. 24.
Figure 28:
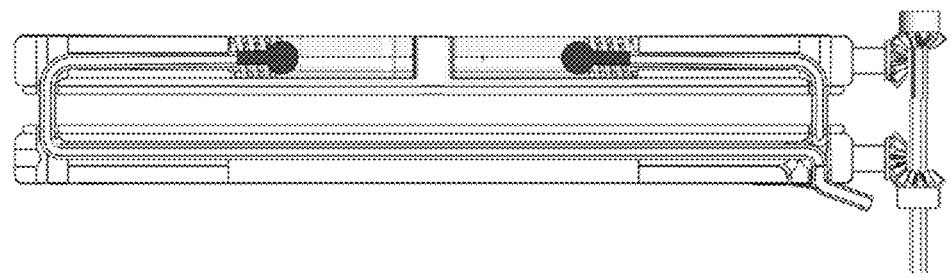
FIG. 28 is a fragmentary, horizontal cross-sectional view of the clip and control assembly of FIG. 24.

In a first step, the exclusion clip 200 is brought to the site of the LAA for LAA exclusion in an open state (also referred to as expanded or extended), which state is shown in FIGS. 13 to 18. The surgeon then places the LAA into the interior 272 of the exclusion clip 200 in the direction of arrow A in FIG. 15 and rests the fourth side 218, as best as possible, against the outer surface of the heart on either side of the LAA. The pulsatile movement of the heart and the LAA practically ensures that the LAA is not able to be positioned for exclusion in a best possible orientation without further motivation of the LAA into an improved position with respect to the interior 272 of the exclusion clip 200. This is why surgeons are required to use separate motivators (e.g., graspers or a blunt (Kittner) dissector) to manipulate the LAA with the surgeon's second hand, thereby requiring the surgeon to use two hands in past procedures. As explained above, this manipulation is not desirable because damage to the fragile LAA can and does occur with disastrous consequences. In a next step, the delivery device 300 is activated to close the exclusion clip 200 about the LAA, in this exemplary embodiment, by moving the distal clip strut 210 towards the proximal clip strut 220. This movement occurs with two simultaneous actions. One action involves movement of the distal clip strut 210 in the proximal direction. In particular and with reference to FIG. 20, the delivery device 300 moves the extension axle 320 in the proximal direction (indicated by arrow B). Because the proximal base part 310, the proximal rotation anchor 312, and the proximal strut rotation device 326 are fixed longitudinally to the delivery device 300, they remain in place as the extension axle 320 moves proximally. The proximal clip strut 220 also remains in place as long as it is attached to the proximal strut movement axle 340. The distal rotation device anchor 332 allows the extension axle 320 and the distal strut rotation device 322 to rotate but proximal movement of the extension axle 320 causes the assembly comprising the distal base part 330, the distal rotation device anchor 332, the distal strut rotation device 322, and the distal strut movement axle 340 to move proximally with corresponding movement of the extension axle 320. This movement, therefore, causes the distal clip strut 210 to move from its extended state (e.g., FIG. 15) to a retracted or closed state, which is illustrated in FIGS. 20 to 22. Movement of the distal clip strut 210 is equal to movement of the extension axle 320 as indicated with arrow C in FIG. 20. As can be seen in these figures, neither the distal clip strut 210 nor the proximal clip strut 220 have rotated. The second simultaneous action involves movement of the distal and proximal control cords 252, 262. Because the control cords 252, 262 lay across the gap 270, as the distal clip strut 210 moves towards the proximal clip strut 220, the control cords 252, 262 would bend or bunch up if not moved. Accordingly, the delivery device 300 gathers slack in the control cords 252, 262 as movement of the distal clip strut 210 occurs. As seen in FIG. 13, the control cords 252, 262 leave the distal clip strut 224 and connect to the proximal base part 310. These control cords 252, 262 extend back to handle of the delivery device 300. Slack removal can occur manually or automatically. In a manual process, when the surgeon causes the delivery device 300 to move the distal clip strut 210 proximally by rotating the extension axle 320, the surgeon can be holding the proximal ends of the control cords 252, 262 and manually pull the control cords 252, 262 as closure of the exclusion clip 200 occurs. Alternatively, in one exemplary embodiment of an automatic mode, rotation of the extension axle 320 can be associated with a transmission that is connected to a spindle connected to proximal ends of the control cords 252, 262 and winding up and letting out the control cords 252, 262 as rotation occurs. The transmission can be geared to match the longitudinal movement of the extension axle 320 with the taking up or letting out of the control cords 252, 262. For example, for a 2 cm proximal movement of the extension axle 320 (i.e., 2 cm proximal movement of the distal clip strut 214), the spindle takes up 2 cm in length of the control cords 252, 262. Likewise, for a 1 cm distal movement of the extension axle 320 (i.e., 1 cm distal movement of the distal clip strut 214), the spindle lets out 1 cm in length of the control cords 252, 262.

The exclusion clip 200 is now in a position in which the surgeon can decide if the current, intermediate implantation position is optimal/desired. If the surgeon does not prefer the current state of LAA exclusion, the surgeon causes the extension axle 320 to extend and part the clip struts 210, 220, to then repeat this LAA exclusion process step. As the surgeon is determining if the current state of LAA exclusion is desirable, the self-motivator 230 of the clip struts 210, 220 automatically activates. The motivator fingers 232 are oriented at an angle to a plane 234 defined by the closing movement of distal and proximal clip strut 210, 220. In particular as shown in FIG. 22, the motivator fingers 232 are oriented at a positive angle with respect to the plane 234, a positive angle being defined as extending from the plane 234 upwards with respect to the view shown in FIG. 22 and in a direction (arrow D) in which the LAA is intended to extend through the interior 272 of the exclusion clip 200. In this configuration, therefore, the motivator fingers 232 act in the manner of a ratchet, permitting movement of the LAA in the direction of arrow D but prohibiting or retarding movement of the LAA in the direction opposite arrow D. What is significant about this configuration is that the motivator fingers 232 automatically act to motivate the LAA further into the interior 272 of the exclusion clip 200 without the surgeon having to use a separate tool. As is known with respect to vibratory part feeders (and toys, such as hexbugs and electric football), vibration of a structure's body can cause directed movement of the entire body. Because the LAA is, essentially, vibrating with a heartbeat, the LAA is naturally and automatically caused by the motivator fingers 232 to enter the interior 272 further and further and, significantly, is prevented from exiting the interior 272 by the positive angle of the motivator fingers 232. This means that LAA exclusion is enhanced by the presence of the self-motivator 230, 232. In addition to the heartbeat, the surgeon can manually vibrate the delivery device 300 to motivate the LAA further into the interior 272 by shaking the hand holding the delivery device 300.

This self-motivating action can be enhanced further by incorporating a vibrator at the handle of the delivery device 300. When the vibrator is activated to vibrate the entire delivery device 300, including the proximal base part 310 and the shaft extending to or part of the proximal base part 310, the exclusion clip 200 vibrates, which vibration causes the motivator fingers to actively motivate the LAA into the interior 272 further and further. An exemplary amplitude of vibration is in proportion to a separation distance between motivator fingers 232 on one of the self-motivators 230. For example, if the multiple fingers 232 on one of the struts 210, 220 have a pitch (separation) of 1 mm, then motion on the order of from approximately 0.1 mm to approximately 2.0 mm would induce lateral displacement of the fingers against the surface of the LAA. If the pitch of the fingers were 0.1 mm, then vibration from approximately 0.01 mm to approximately 0.2 mm would effect such motion.

After the delivery device 300 has positioned the struts 210, 220 to oppose one another in the implantation process to the initial capture state of the LAA shown in FIGS. 20 to 22, the surgeon still has the ability to reverse the exclusion clip implantation process. When the surgeon has determined that the exclusion clip 200 is in a desirable LAA-exclusion position, the surgeon activates the delivery device 300 to rotate the distal and proximal clip struts 210, 220 (see progression from FIG. 22, to FIG. 23, to FIG. 24) to a final implantation position, shown in FIGS. 24 to 28. Rotation of the clip struts 210, 220 is caused by rotation of the extension axle 320. In the exemplary embodiment shown where the distal strut rotation device 322, the proximal strut rotation device 326, the distal strut rotation receiver 342, the proximal strut rotation receiver 352 are all miter gears with the same number of teeth, rotation of the extension axle 320 causes a direct and corresponding rotation of the clip struts 210, 220, the distal clip strut 210 rotating clockwise in the views of FIGS. 21 to 24 and the proximal clip strut 220 rotating counterclockwise in the same views. While the distal and proximal clip struts 210, 220 can simply rotate, if they did without further relative movement of one another, the exclusion distance 236 between the two self-motivators 230 would increase because the self-motivators 230 are at a distance from the rotation axes of the distal and proximal strut movement axles 340, 350. Therefore, to keep the exclusion distance 236 substantially constant as the clip struts 210, 220 rotate (e.g., from the view of FIG. 22 to the view of FIG. 24), the two clip struts 210, 220 move towards one another, which means that the extension axle 320 moves proximally from a separation distance 238 of the strut rotation receivers 342, 352 shown in FIG. 22 to a smaller separation distance 238 shown in FIG. 24. The further movement of the distal clip strut 210 towards the proximal clip strut 220 also shortens the length of the control cords 252, 262. Accordingly, in the strut-rotation step, the spindle in the delivery device 300 takes up any further slack in the control cords 252, 262 to keep them taut.

Rotation of the clip struts 210, 220 into the final implantation position effects a creeping and tightening movement of the LAA further into the interior 272 of the exclusion clip 200. This creeping and tightening movement is beneficial because, by assuring the clip is brought into close apposition against the external wall of the atrium, a minimum amount of unclamped LAA results, thereby resulting in minimization of remaining pouch or "dog ears." Even with the exclusion clip in the final implantation position, the surgeon still has the ability to reverse the exclusion clip implantation process, either partially or completely.

In the final implantation position, shown in FIGS. 24 to 28, the self-motivators 230 no longer rest against the portion of LAA compressed between the clip struts 210, 220. Instead, with the fourth sides 218 of the clip struts 210, 220 facing one another, the LAA-contacting surface 240 is the primary surface of contact with the opposing compressed sides of the interposed LAA. It is desirable to have all surfaces of the exclusion clip 200 contacting the LAA to be atraumatic. Accordingly, the leading edges of the self-motivator 230 adjacent the trailing edges of the LAA-contacting surface 240 have surfaces that provide a smooth transition, in particular, they have the same height and the self-motivators 230 continue the respective curves of the opposing LAA-contacting surfaces 240. Likewise, the edge and/or corner of the third side 216, 226 facing the LAA-contacting surface 240 is curved and/or beveled.

In the final implantation position of the exclusion clip 200, the clip release sequence can begin. First, the control cords 252, 262 are tightened to pre-bias the distal strut bias sub-assembly 250 and the proximal strut bias sub-assembly 260 located within the distal clip strut 210. This pre-biasing can occur manually. For example, in a manual operation, the surgeon can pull the control cords 252, 262 (or lever/s in the handle that is/are connected to the control cords 252, 262) to move the first and second distal end anchors 254, 264. The amount of force applied to the control cords 252, 262 can appear as a bar within a window of the handle, the desired pre-bias force being present when, for example, a first line aligns with a second line. Alternatively, the pre-biasing can occur automatically. For example, an electric motor controlled by a microcontroller can cause the spindle to wind the control cords 252, 262 and measure the force imparted on the control cords 252, 262. Measurement of this force can occur by the motion of a spring scale within the handle or by a switch or an electronic transducer, for example, and when that amount of force is detected, activation of the motor can cease. In the pre-bias state where the distal and proximal strut bias sub-assemblies 250, 260 are in the spring configuration shown, for example, in FIG. 16, the first and second distal end anchors 254, 264 can be pulled to a biased position such as that shown in FIG. 28. In such a position, expansion force by the captured LAA (e.g., due to swelling) can be taken up by additional movement of the first and second distal end anchors 254, 264 and desiccation and/or shrinkage of the capture LAA can be accounted for by expansion of the springs and return movement of the first and second distal end anchors 254, 264.

The configuration of the tension devices 256, 266, therefore, allows the exclusion clip 200 to possess an ability to compensate for changes in forces applied to the clip struts 210, 220 after the exclusion clip 200 has been applied to the LAA, for example, after the LAA tissue has desiccated and/or deformed. More particularly, during implantation, the surgeon secures the exclusion clip 200 on opposing sides of the LAA. Then, the surgeon or the delivery device 300 pulls on the distal and proximal control cords 254, 264 so that the distal and proximal tension devices 256, 266 compress the LAA to a desired extent. The control cords 254, 264 are, then, secured in the cord capture assembly 280 with the tension devices 256, 266 in a compressed state. This, in essence, pre-biases the force applied to the LAA and, if the tissue expands between the clip struts 210, 220, the tension devices 256, 266 act to decrease force on that expanded tissue. Similarly, if the tissue contracts between the clip struts 210, 220, the tension devices 256, 266 act to increase force on the contracted tissue. In these ways the tension devices 256, 266 will accommodate either shrinkage or expansion of the LAA within the limits of their range of displacement.

The control cords 252, 262 are now ready to be fixed so that further movement of the control cords 252, 262 from outside the exclusion clip 200 is prevented. Accordingly, in the next step, the cord cutter 314 severs the control cords 252, 262. Either after or during the cord cutting, the strut movement axles 340, 350 are removed. In the embodiment with grenade pins 360, the pin remover 362 is actuated to remove the grenade pins 360 and the distal and proximal base parts 330, 310 are moved away from the implanted exclusion clip 200. The strut movement axles 340, 350, therefore, pull away and out of the clip struts 210, 220 to leave the exclusion clip 200 implanted on the LAA. Alternatively, in the embodiment where the strut movement axles 340, 350 are threaded into the clip struts 210, 220, the extension axle 320 is rotated to unscrew the strut movement axles 340, 350. With no further connection to the clip struts 210, 220, the distal and proximal base parts 330, 310 fall away from the implanted exclusion clip 200 to leave the exclusion clip 200 implanted on the LAA.

Figure 40:
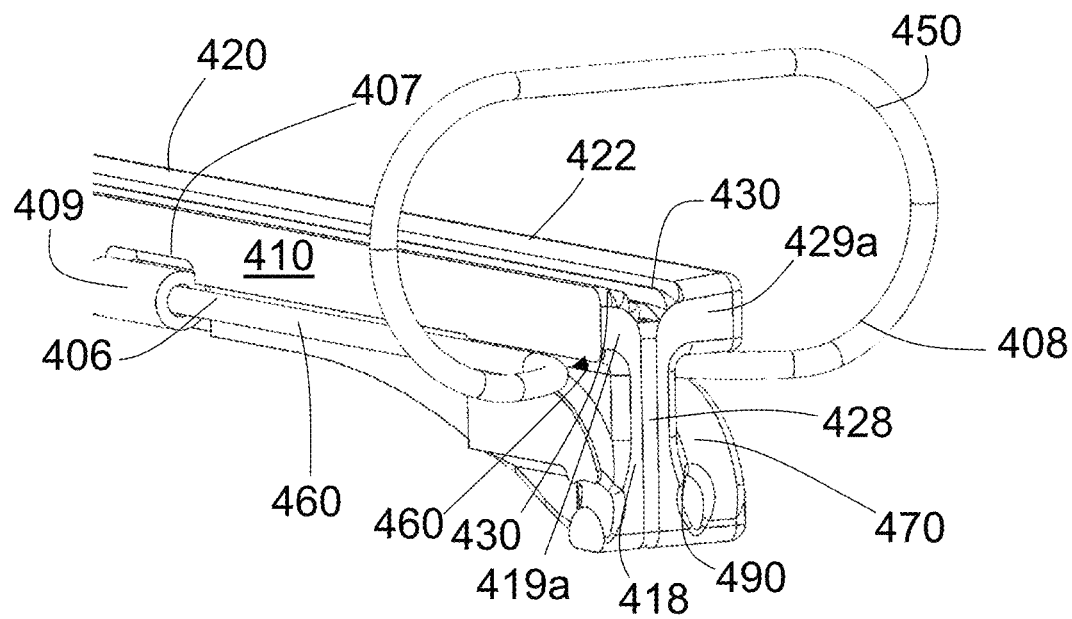
FIG. 40 is a fragmentary, enlarged, perspective and partially longitudinal cross-sectional view of a distal end of the clip of FIG. 32.
Figure 41:
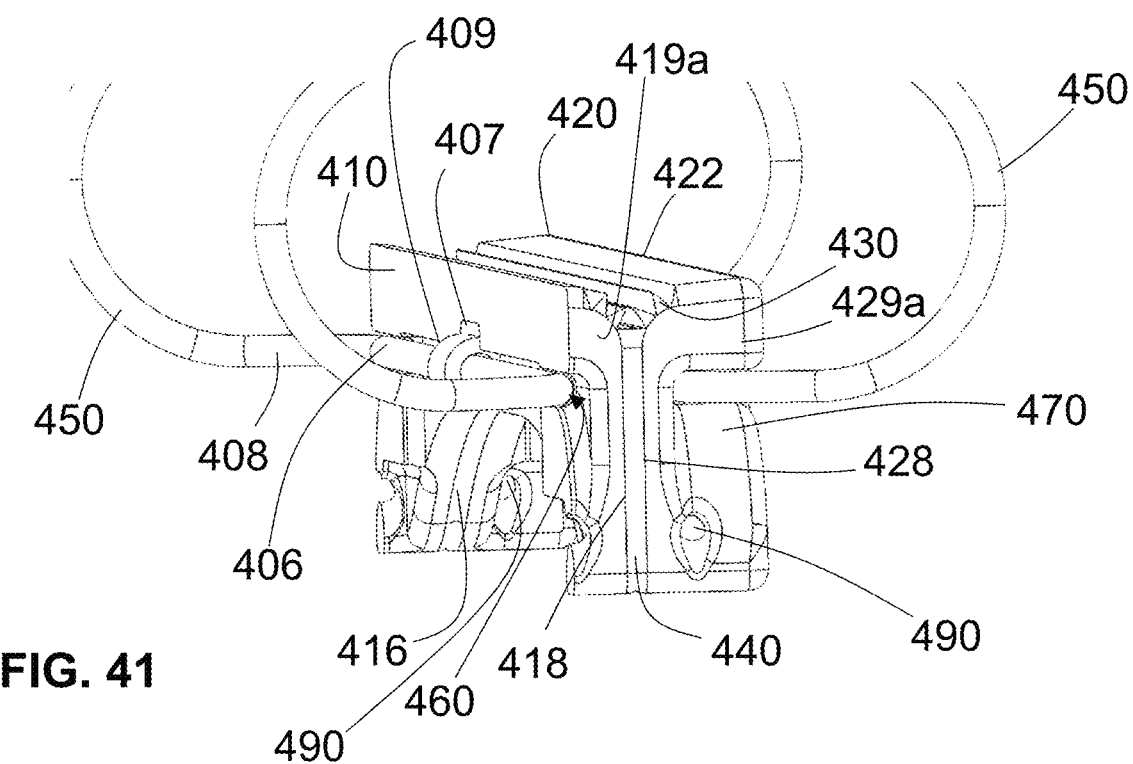
FIG. 41 is a fragmentary, enlarged, perspective and partially longitudinal cross-sectional view of a distal end of the clip of FIG. 32.
Figure 42:
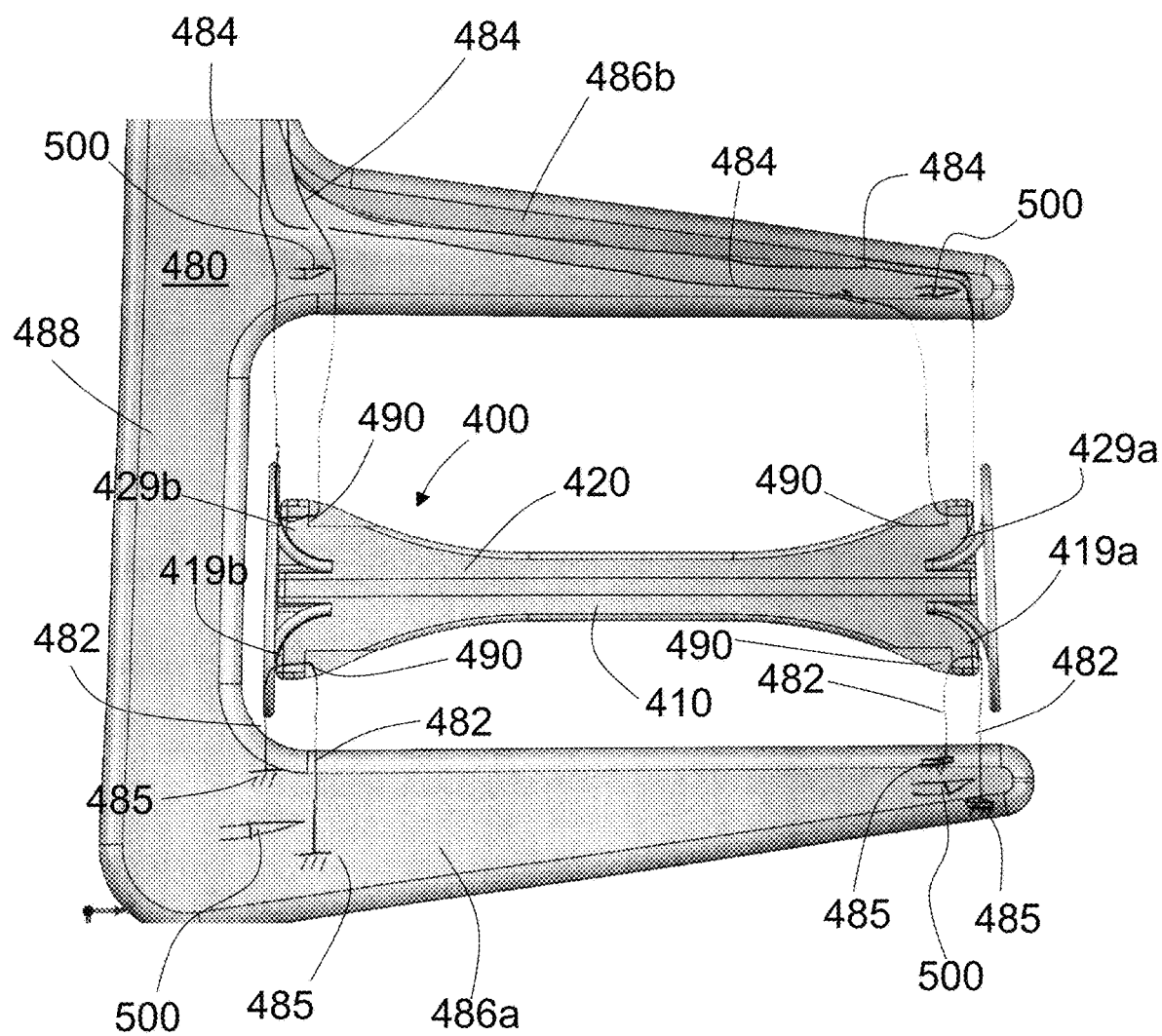
FIG. 42 is a fragmentary, top plan view of the clip of FIG. 32 within an exemplary embodiment of a clip-application head of a clip delivery device.
Figure 43:
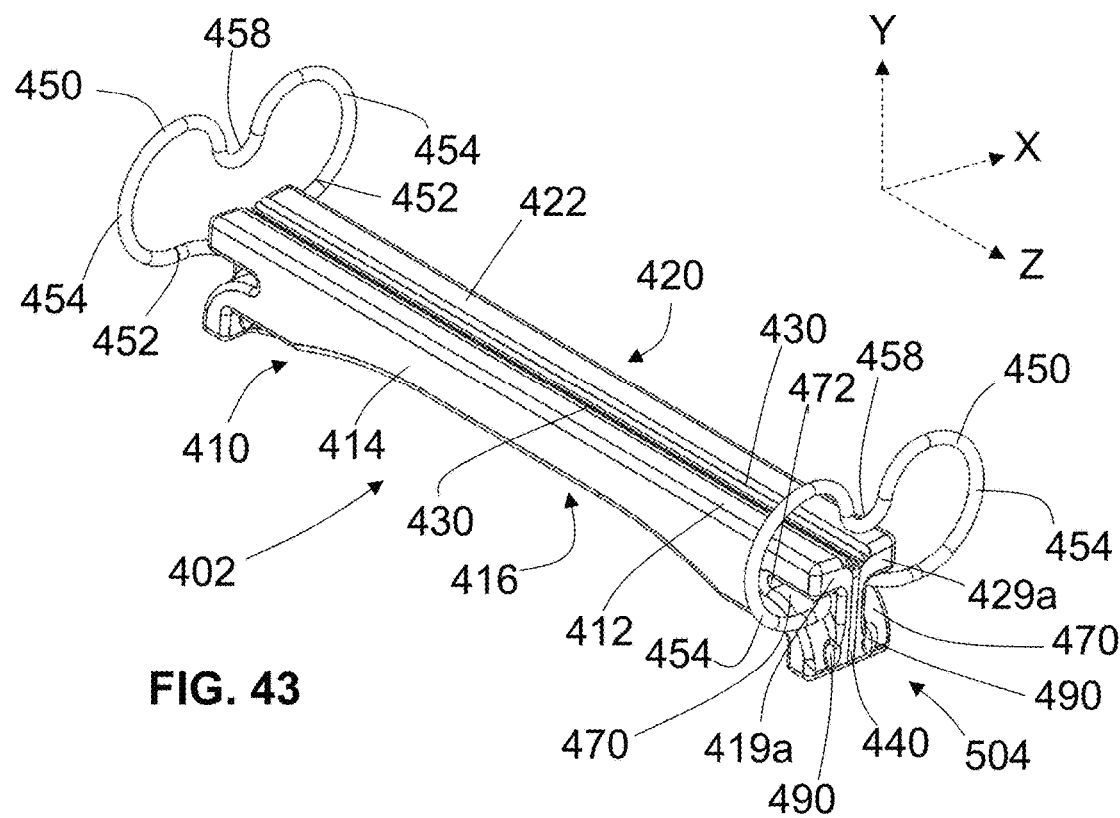
FIG. 43 is a perspective view of yet another exemplary embodiment of a left atrial appendage surgical implant clip in a contracted and rotated orientation.
Figure 44:
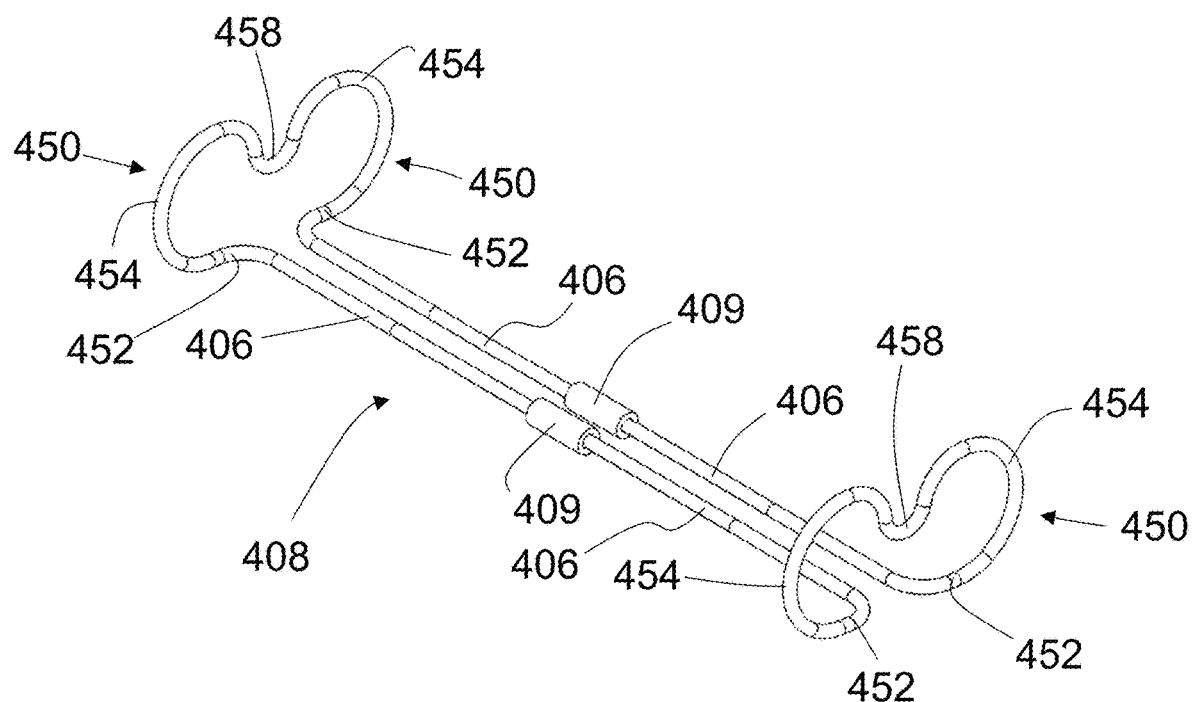
FIG. 44 is a perspective view of a biasing member of the clip of FIG. 43.

Referring now to FIGS. 32 to 42, there is shown a third exemplary embodiment of an externally implantable, left atrial appendage exclusion clip 400 that, similar to the exemplary embodiment of FIGS. 1 to 12, operates according to a spring-biased mechanism. In this embodiment, the exclusion clip 400 comprises a clipping assembly 402 and a biasing assembly 404. Further, the clipping assembly 402 is comprised of two opposing clip struts, which are referred to herein as a first clip strut 410 and a second clip strut 420. In addition, the biasing assembly 404 is comprised of a single closed-circuit biasing member 408 (which is shown in isolation in FIG. 39) that is molded in two parts 408a, 408b (see FIGS. 48 to 51) to form, in general terms, two straight, parallel, coplanar elongated portions 406 that transition into two turn sections 450, each turn section 450 being positioned at a far end of the clip 400 opposite the other turn section and extending in the upward direction (along the y-axis), and substantially perpendicular, from the plane of the elongated portions 406. As is best shown in the underside, isolated, and exposed views presented in FIGS. 37 to 39, each of the elongated portions 406 of the biasing member part 408a, 408b dramatically transitions into its respective turn section 450 at a curved section 452 that deviates outward (along the x-axis) from the elongated portion 406 and begins the ascent in the upward direction (along the y-axis). This curved section 452 leads or twists upward into the oblong "racetrack-shaped" turn sections 450, wherein each turn section 450 is characterized by two inward-facing curved portions 454 interconnected at the apex of the turn section 450 by a flat intermediate portion 456 (although, as will be described below, the intermediate portion 456 has advantages when curved). This orientation and configuration of the turn sections 450, as well as the shape of each turn section 450, creates the pre-loaded spring-biasing force that biases the elongated portions 406 towards each other. Other advantageous aspects of the racetrack shape is that it is a wider opening and a lower height than the springs in the embodiment of FIG. 1, for example. Also, the racetrack shape allows the clip 400 to have a lower load for opening but still have substantially the same clipping force applied to the surfaces of the LAA. The biasing member 408 is comprised of any suitable biocompatible material having a desired spring constant k. Examples of such materials include, but are not limited to, chrome-cobalt alloy, stainless steel, titanium alloy, and superelastic alloys such as Ni—Ti. If beneficial, different materials may comprise different sections of the biasing member 408 such that there exists a variation in stiffness along the length of the biasing member 408. When compared to the "horseshoe-shaped" spring members 150 of the exemplary embodiment of the exclusion clip 100 depicted in FIGS. 1 to 12, the "racetrack-shaped" turn sections 450 of the exemplary embodiments have a lower profile, thereby resulting in a less intrusive clip structure and less open space for the LAA tissue to leak out or escape from. In further comparison, the "racetrack-shaped" turn sections 450 also have a broader span and longer distance, thereby increasing the amount of available flexing capacity when placing the exclusion clip 400 into its expanded state (which is described in detail below), thus permitting the exclusion clip 400 to assume a wider stance with respect to the LAA during the initial capture thereof. Further, due to the ability to have the curved section 452 start and end before the distal-most extent of the distal ends 419, 429 by providing recessed pockets 472, the turn sections 450 can be disposed above the first side 412, 422 of the clip struts 410, 420 and not at a longitudinal distance from the distal ends 419, 429. Briefly, the implantation of the exclusion clip 400 substantially mimics the procedure described above with respect to the exemplary embodiment of FIGS. 1 to 12, in which a user-controlled clip delivery device applies a counter-force to the inherently-provided spring-biasing force of the biasing member 408 to place the exclusion clip 400 into an initial expanded state to enlarge the interior opening of the exclusion clip 400. Using the clip delivery device, the surgeon positions the expanded clip 400 about the LAA to, in conjunction with controllably releasing the applied counter-force, cause the exclusion clip 400 to motivate the LAA into the clip's interior opening, enclose the base portion of the LAA during an intermediate capture state, and assume a final implanted state in which the inherent spring-biasing force of the biasing member 408 biases one or both of the elongated portions 406 of the biasing member 408 towards the other to create a secure grip on the LAA. It is noted that FIGS. 32 to 41 depict the exclusion clip 400 just in its freestanding (or resting) state in which no external counter-force to the inherent spring-biasing force is being applied to the clip 400. FIG. 42 depicts the exclusion clip 400 engaged by an exemplary embodiment of a clip-application head 480 of a non-illustrated clip delivery device, wherein the exclusion clip 400 is not yet expanded and remains in this resting state.

In addition, in comparison to other prior art exclusion or occlusion devices of this type, it is believed that the shape and structure of the biasing member 408 of the presently-described embodiment advantageously requires a slower, or more gradual, rise in the amount of counter-force necessary to place the exclusion clip 400 into its expanded state while still ensuring that, once applied, the exclusion clip 400 provides the sufficient amount of gripping force needed to close off the fluid pathway of the LAA and to permanently secure the exclusion clip 400 in place.

Figure 37:
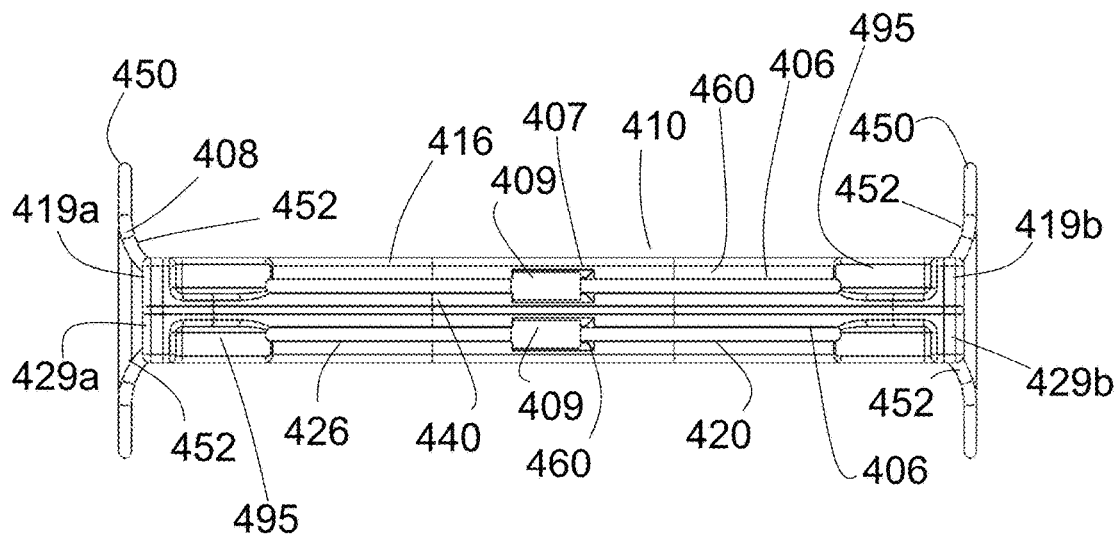
FIG. 37 is a bottom plan view of the clip of FIG. 32.
Figure 38:
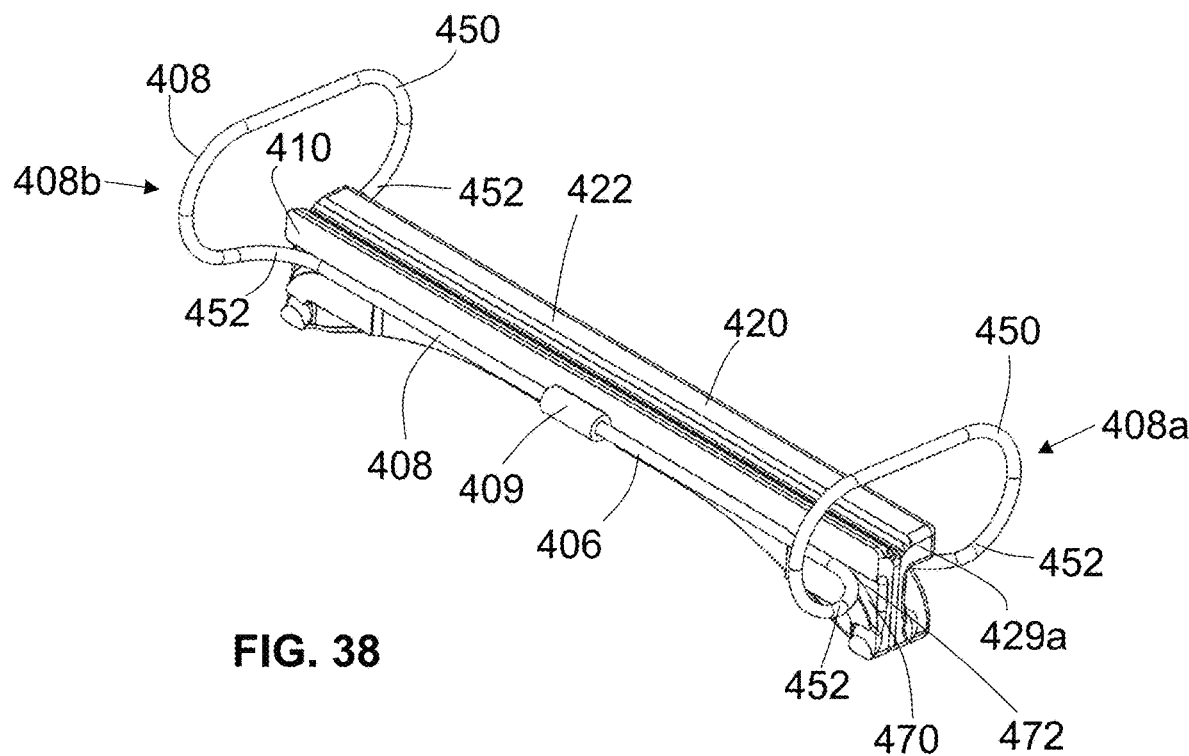
FIG. 38 is a perspective and partially longitudinal cross-sectional view of the clip of FIG. 32.
Figure 39:
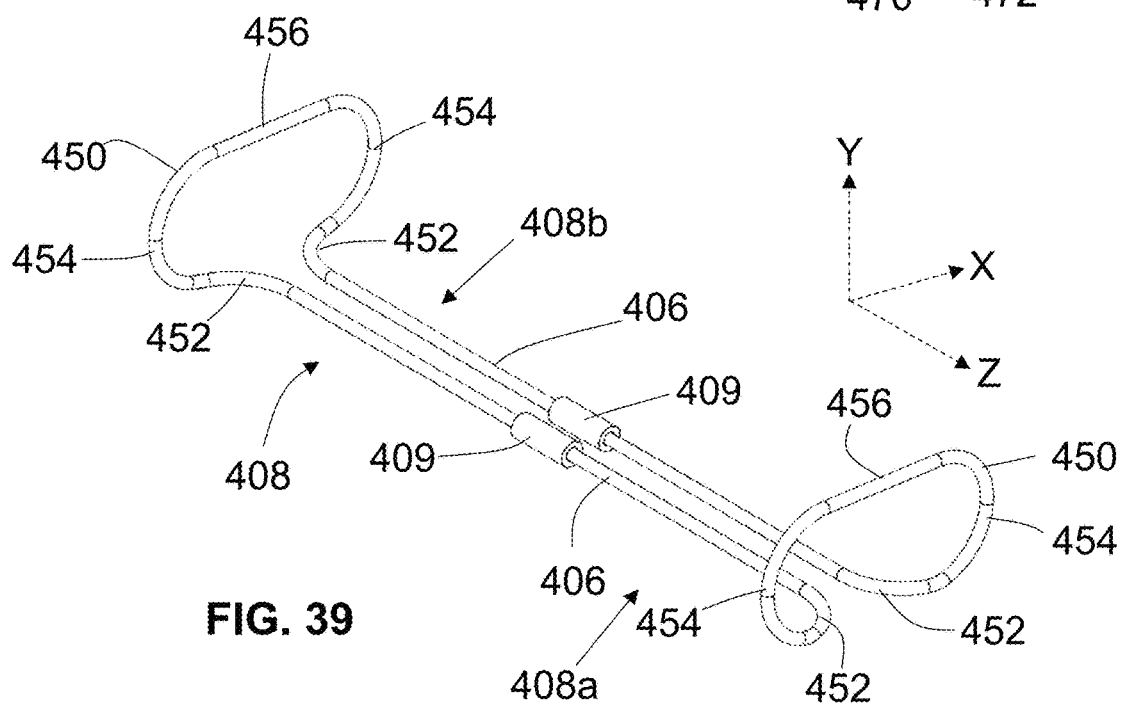
FIG. 39 is a perspective view of a biasing member of the clip of FIG. 32.

Referring now to the clipping assembly 402 of the exclusion clip 400, the body of the first and second clip struts 410, 420 is comprised of any of one or more suitable biocompatible materials, such as titanium, stainless steel, chromium-cobalt alloy, nickel-titanium alloy, ceramic, polyetheretherketone, liquid-crystal polymer, polymethylmethacrylate, and epoxy. Furthermore, as in the case of the exclusion clip embodiments described above, the body of the clip strut 410, 420 is formed to not present or have any sharp edges or corners that could potentially cause damage to tissue within the patient's body. Each edge and corner of the clip strut body is rounded, curved, and/or beveled to create smooth or blunted surfaces. With respect to the configuration and contours of the first and second clip struts 410, 420, each clip strut 410, 420 is a mirror image of the other. Further, each clip strut 410, 420 can generally be described as a six-sided rectangular column. However, each clip strut 410, 420 has several significant shape and structural features. In broad terms, each of the clip struts 410, 420 comprises a first side 412, 422, a second side 414, 424, a third side 416, 426, a fourth side 418, 428, and two opposing ends 419a-b, 429a-b. To connect the clip struts 410, 420 to the biasing member 408 to form the complete exclusion clip 400, each clip strut 410, 420 is configured to have a longitudinal, cylindrical throughbore or channel 460 running through a central region of the clip strut body, wherein each of the two elongated portions 406 of the biasing member 408 traverse the throughbore or channel 460 such that each clip strut 410, 420 is freely rotatably mounted about a respective one of the elongated portions 406 of the biasing member 408. The throughbore or channel 460 is most clearly shown in FIG. 37, which illustrates the underside of the exclusion clip 400 when the clip 400 is in its resting state (see also the cross-section of FIG. 38). As shown, recessed areas of the third sides 416, 426 of the clip struts 410, 420 partially expose portion(s) of the throughbore or channel 460 such that area(s) of the elongated portions 406 of the biasing member 408 are visible. Further, FIGS. 38, 40, and 41 depict the exclusion clip 400 in which, for purposes of clarity and illustration, a longitudinal section of the first clip strut 410 is omitted such that a cross-section of the first clip strut 410 can be observed. From this cross-sectional view, the throughbore or channel 460 can be seen with its respective elongated portion 406 of the biasing member 408 running therethrough. Accordingly, to accommodate the elongated portions 406 of the biasing member 408, the diameter of the throughbore or channel 460 is greater than the diameter of the elongated portions 406. To retain in place and stabilize the clip struts 410, 420 with respect to the biasing member 408 such that the clip struts 410, 420 are not permitted to slide longitudinally upon the elongated portions 406 along the z-axis, each elongated member 406 comprises a fixing band 409 (for example, at any intermediate longitudinal point or at the longitudinal midpoint of the clip struts 410, 420). In an exemplary embodiment, the fixing band 409 is a crimp sleeve. Where the fixing band 409 is at the longitudinal midpoint of the clip struts 410, 420, the two parts 408a, 408b of the biasing member 408 can be made identically, as depicted in FIGS. 48 to 51. The exemplary embodiment of the fixing band 409 has a diameter that is larger than the diameter of the throughbore or channel 460 and is captured inside a widening notch 407 correspondingly located at the intermediate point of the throughbore or channel 460 where the ends of the opposing parts 408a, 408b are located so that the fixing band 409 can secure the two spring member parts 408a, 408b to the clip struts 410, 420. The clip struts 410, 420 are restricted in their longitudinal movement by either longitudinal movement of the fixing band 409 within the notch 407 (if there is play therein) or between the turn sections 450 of the biasing member 408 (where the play in the notch 407 is larger than the bend of the turn sections 450). Accordingly, with each clip strut 410, 420 mounted about a respective one of the elongated portions 406 of the biasing member 408, where the distance between the two parallel elongated portions 406 is less than the distance between the throughbore or channel 460 and the third sides 416, 426, the clip struts 410, 420 are also biased towards the other clip strut 410, 420 due to the inherent spring-biasing force of the biasing member 408.

Figure 36:
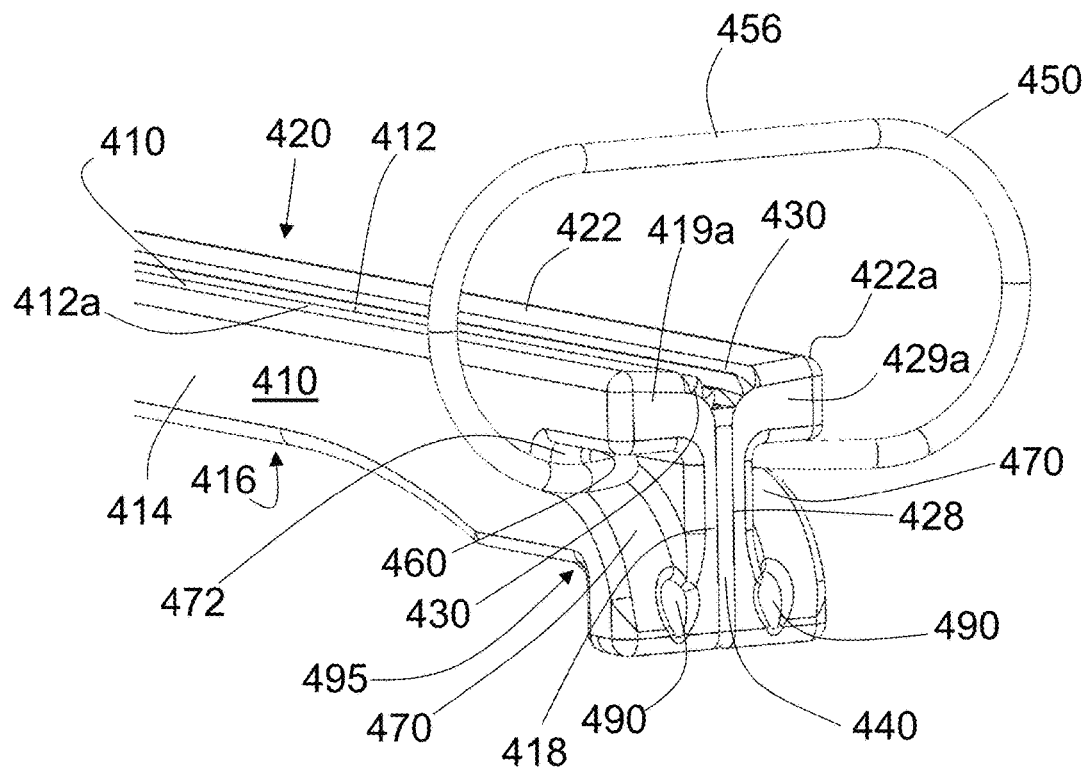
FIG. 36 is a fragmentary, enlarged, perspective view of a distal end of the clip of FIG. 32.

As mentioned above, each clip strut 410, 420 is mounted about a respective one of the elongated portions 406 such that the clip strut 410, 420 can freely rotate with respect to the elongated portion in response to an external force placed upon the clip strut 410, 420 without requiring the separation of the clip struts 410, 420 by placing the exclusion clip in its expanded state. On account of the throughbores or channels 460 of the clip strut bodies, this rotational freedom is made possible despite the pre-loaded spring-biasing force generated by the biasing member 408. As described above in connection with the previously-disclosed exemplary embodiments of an exclusion clip and clip delivery device, and the corresponding methods of implantation, rotation of the clip struts during the final implantation stage of the exclusion clip assists in manipulating the LAA further into the clip interior and enhances the gripping force exerted by the exclusion clip when it is applied to the LAA. A description of an exemplary embodiment of the entire implantation procedure of the exclusion clip 400 is set forth in the following explanation. In a beginning step, a clip delivery device compatible for use with the exclusion clip 400 is configured to temporarily engage and retain the clip 400. Depicted in FIG. 42 is an exemplary embodiment of a clip-application head 480 of a suitable clip delivery device for temporarily engaging the exclusion clip 400, where the clip-application head 480 is located at the distal end of a non-illustrated elongated shaft that interconnects the clip-application head 480 to a non-illustrated control handle of the clip delivery device. In this embodiment, the clip-application head 480 is in the form of a C-shape that comprises two oppositely-situated arms 486a, 486b interconnected by a bridge 488, where each of the clip struts 410, 420 is secured to an adjacent one of the clip-application arms 486a and 486b, respectively, by one or more cords 482, 484 (e.g., sutures) that are looped or threaded through an eye 490 that is formed in a lower portion of each of the clip strut ends 419a-b, 429a-b. Significant about the position of the eye 490 is that the cords 482, 484 is isolated from any tissue disposed between the clip struts 410, 420 and does not get pinched or contacted by the LAA or by the clip struts 410, 420. FIGS. 32, 33, 36, and 41 most clearly illustrate the eye(s) 490, wherein each eye 490 comprises an aperture that is passable by the one or more cord(s) 482, 484. Further, the circumference at the entrance into and exit out of each eye 490 is sloped or rounded in order to avoid any sharp or dramatic edges that could damage (e.g., break) the cord(s) 482, 484 or cause any undue strain or tension on the cord(s) when operated to control the movement of the clip struts 410, 420. In addition, to allow for the existence of the eye(s) 490 and to provide adequate clearance for the cord(s) 482, 484, a triangular cut-out 495 is formed at the two far ends of each of the third sides 416, 426 of the clip struts 410, 420, in proximity to the eye 490 (as best shown in FIGS. 34, 36, and 37). Referring back now to FIG. 42, one or more cords 482 are looped around a respective eye 490 of each of the two clip strut ends 419a, 419b of the first clip strut 410 and pulled taut such that the first clip strut 410 is securely retained against the adjacent clip-application arm 486a. To maintain the tautness of the cord(s) 482, the two ends of each cord 482 are attached or connected to the clip-application arm 486a at attachment points 485 by, for example, a suture crimp mechanism, which fixes the cords 482 respectively at the attachment points 485. Accordingly, the cord(s) 482 may be beneficially characterized as "retaining" cords. Conversely, with respect to the second clip strut 420, one or more cord(s) 484 are similarly threaded or looped around a respective eye 490 of each of the two clip strut ends 429a, 429b of the second clip strut 420, but are left with a degree of slack in order that the cord(s) 484 may be selectively tensioned and released by the operator of the clip delivery device, when placing the exclusion clip 400 in its expanded state, to pull the second clip strut 420 away from the stationary first clip strut 410 in a direction towards the clip-application arm 486b with a force that counters the inherent spring-biasing force of the clip 400, and, when placing the exclusion clip 400 in its intermediate capture and final implantation states, controllably release the applied counter-force to permit the spring-biasing force of the exclusion clip 400 to cause the second clip strut 420 to assume its biased position bringing it in close proximity to the stationary first clip strut 410. Accordingly, as is depicted in FIG. 42, each of the cord(s) 484 is channeled through the clip-application arm 486b and exits the clip-application arm 486b to extend through the clip delivery device in a proximal direction and be operatively connected to the control handle (not shown) of the clip delivery device such that the surgeon can selectively tension and release the cord(s) 484 at the control handle. As such, the cord(s) 484 may be beneficially characterized as "tensioning" cords, thereby distinguishing the cord(s) 484 from the "retaining" function provided by the cord(s) 482. With respect to this cord-tensioning mechanism, it is noted that the placement of the eye(s) 490 relative to the clip-application arms 486*a-b* advantageously puts the counter-force (or tensioning force) from the cords 482, 484 in line with the inherent spring-biasing force of the exclusion clip 400, which improves the efficiency of the counter-force mechanism and prevents the cords 482, 484 from obstructing or interfering with the rotational freedom of the clip struts 410, 420 and potentially getting caught up in the interaction between the exclusion clip 400 and the LAA tissue.

Accordingly, after the exclusion clip 400 has been removably engaged with the clip-application head 480, the clip 400 is readied for its application to the LAA by controllably transitioning the clip 400 into an expanded state to widen the interior opening of the clip 400 by displacing one or both of the clip struts 110, 120 in a direction that is opposite from the other of the clip struts 110, 120. In the example above of the cord-tensioning mechanism of the clip-application head 480, this expanded state may be achieved by tensioning the tensioning cord(s) 484 to pull the second clip strut 420 in the direction of the adjacent clip-application arm 486*b*. Depending upon the type of configuration of the clip delivery device, the expansion of the exclusion clip 400 may be performed before or after the surgeon has advanced the clip delivery device into the patient's thoracic cavity by any of the surgical methods previously described. In this regard, it is noted that an elongated shaft of the control device extends upwards in the orientation shown in FIG. 42, which direction is 90 degrees from the longitudinal extent of the arms 486*a*, 486*b*. In an alternative embodiment that is not illustrated, the elongated shaft can extend parallel to the clip-application arms 486*a*, 486*b* from the bridge 488 in the direction opposite the direction in which the arms 486*a*, 486*b* extend. This parallel orientation creates a delivery device that is narrower than when the extents are at the 90-degree orientation shown in FIG. 42.

Figure 33:
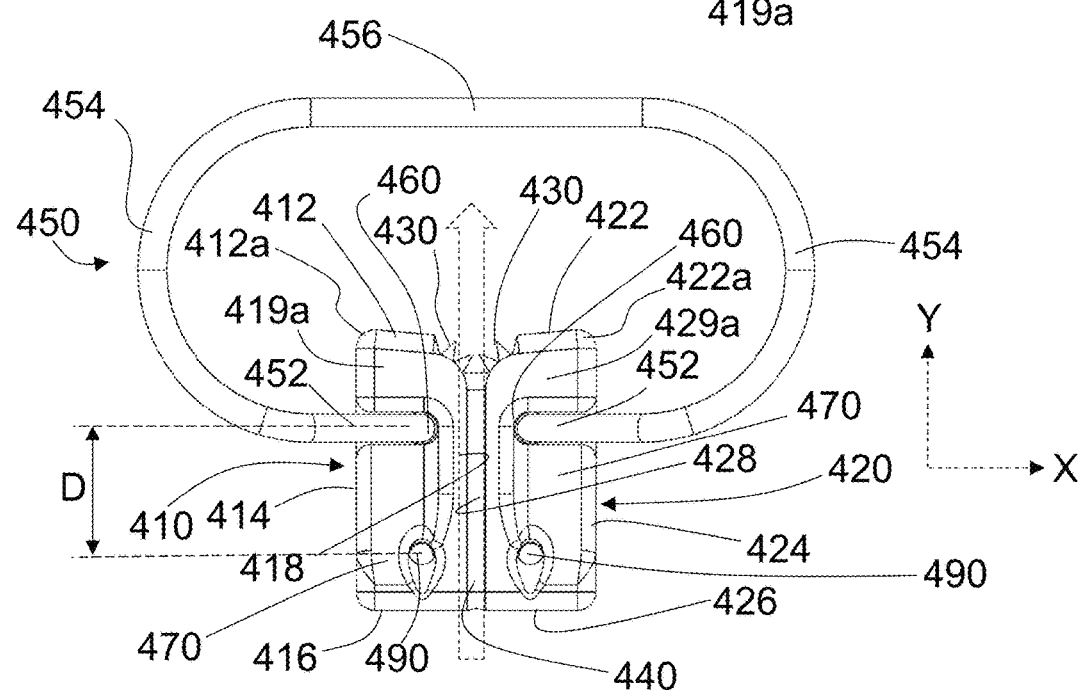
FIG. 33 is an enlarged, elevational view of a distal end of the clip of FIG. 32.
Figure 34:
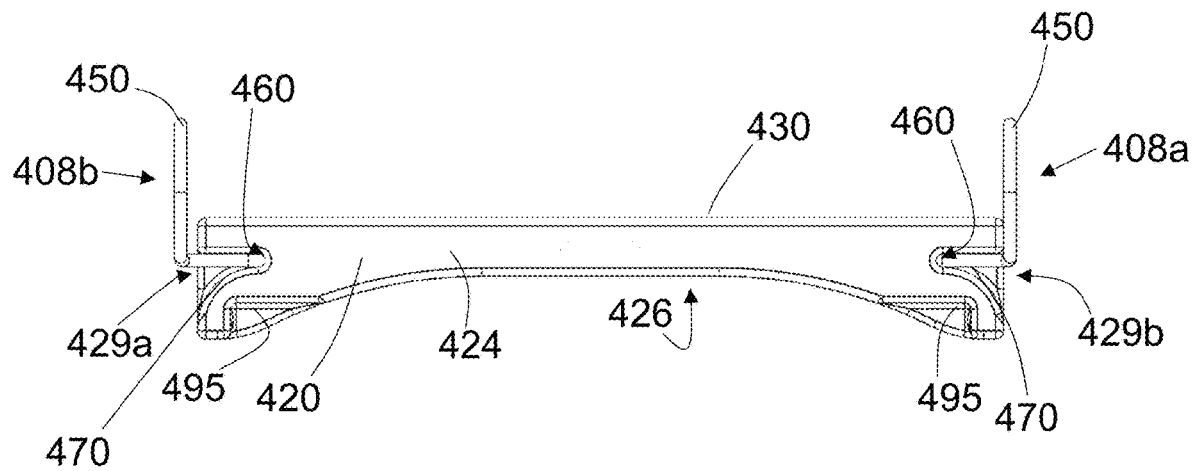
FIG. 34 is a side elevational view of the clip of FIG. 32.
Figure 35:
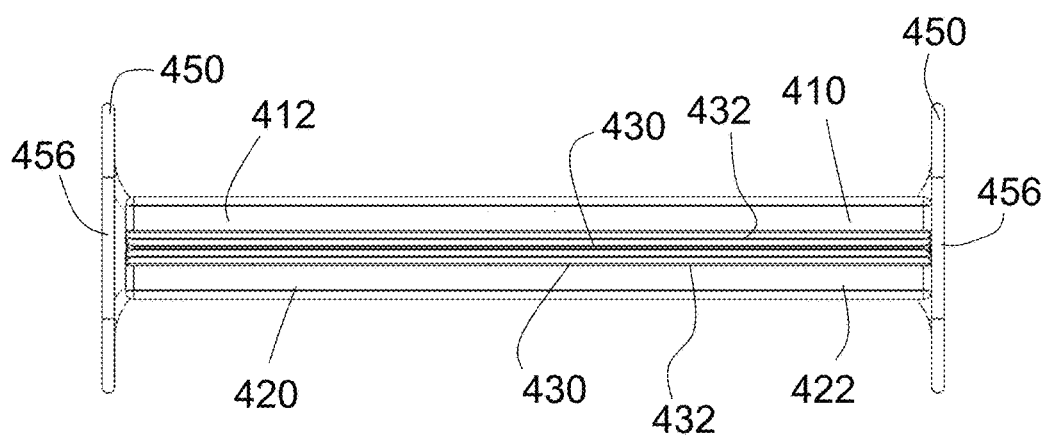
FIG. 35 is a top plan view of the clip of FIG. 32.

Although not shown in the figures, when the exclusion clip 400 is in its expanded state, each of the four sides 412, 422, 414, 424, 416, 426, 418, and 428 of the clip 400 is rotated substantially 90 degrees from the position shown in FIG. 33. Specifically, the first side 412, 422 of each of the clip struts 410, 420 faces inward (along the x-axis) towards the interior of the clip 400 such that the two first sides 412, 422 are situated face-to-face and substantially directly opposite one another. The second side 414, 424 of each clip strut 410, 420 is situated at a substantially 90-degree angle with respect to the first side 412, 422 of a respective one of the clip struts 410, 420, and faces in the upward direction along the y-axis. Further, the fourth side 418, 428 of each clip strut 410, 420 is also positioned at a substantially 90-degree angle with respect to the first side 412, 422 of a respective one of the clip struts 410, 420, but faces in the opposite direction of the first side 412, 422, namely, in the downward direction along the y-axis. In addition, the third side 416, 426 of each clip strut 410, 420 forms a common edge with a respective second side 414, 424, forms a common edge with a respective fourth side 418, 428, and is situated opposite from the respective first side 412, 422 such that it faces along the x-axis in a direction that points outward away from the interior of the exclusion clip 400 (i.e., towards the clip-application arms 486*a*, 486*b* when installed in the clip-application head 480). Similarly to the exemplary embodiment of FIGS. 1 to 12, the third sides 416, 426 each exhibit a bend or curve that arches in the inward direction (i.e., towards the interior of clip 400) along the x-axis to form a concave surface Lastly, each pair of clip strut ends 419*a-b*, 429*a-b* of each clip strut 410, 420 comprises the two opposing ends of the clip 400, wherein each end 419*a-b*, 429*a-b* faces in a direction that is perpendicular to both the x and y axes (i.e., along a z-axis).

It is noted that, while the configuration of the biasing assembly 404 and the clipping assembly 402 is such that each clip strut 410, 420 is capable of freely rotating with respect to the biasing member 408, in order to control and effectively apply the exclusion clip 400 to the LAA, the operating range or degree of rotation should necessarily be restricted to, for example, substantially 90 degrees. As such, in the exemplary embodiment of exclusion clip 400, there is formed in a middle portion of each clip strut end 419*a-b*, 429*a-b* a shoulder 470 that recesses into a pocket 472 (as best seen in FIG. 36). The back of the recessed pocket 472 leads into the throughbore or channel 460. Accordingly, the curved section 452 of each turn section 450 of the biasing member 408 is inset into the pocket 472 and enters the throughbore or channel 460 such that each turn section 450 is beneficially placed substantially flush with the respective clip strut ends 419*a-b*, 429*a-b*. When the exclusion clip 400 is placed in its expanded configuration such that the second side 414, 424 of each clip strut 410, 420 faces in the upward direction at a substantially 90-degree angle with respect to the y-axis, the geometry of the shoulder 470 not only accommodates the respective curved section 452 of the turn section 450, but also comes into abutting contact with the curved section 452 such that the clip strut 410, 420 is not permitted to rotate past this point (i.e., the second side 414, 424 of each clip strut 410, 420 is not permitted to form a $\theta > 0°$ with respect to the x-axis).

Turning now to the next step of the implantation method, once the surgeon delivers the exclusion clip 400 (in its expanded state) into the thoracic cavity and to the location of the LAA, the surgeon carefully advances the LAA into the central opening (not shown) of the expanded exclusion clip 400 (in the direction of the dashed arrow indicated in FIG. 33), such that the base portion of the LAA is situated between the first sides 412, 422 of the first and second clip struts 410, 420, and the fourth sides 418, 428 of the first and second clip struts 410, 420 have come to rest, as best as possible, in surface-to-surface contact with the topography of the heart's outer surface on either side of the LAA. At this stage, the initial capture of the LAA is complete.

Thereafter, the surgeon actuates the clip delivery device to controllably close the exclusion clip 400 about the base portion of the LAA to such a degree that the clamping force exerted by the first sides 412, 422 of the clip struts 410, 420 against the LAA is sufficient to effectively suppress the blood flow entering and exiting the interior of the LAA. In the exemplary embodiment described above of the cord-tensioning mechanism of the clip-application head 480, this intermediate capture state is achieved by releasing the tensioning cord(s) 484 to relieve or ease the amount of counter-force being exerted by the clip delivery device in opposition to the inherent spring-biasing force of the biasing member 408. Relieving the counter-force permits one or both clip struts 410, 420 to passively return to its (or their) inherent spring-biased condition, thus allowing one or both clip struts 410, 420 to move towards the opposing clip strut 410, 420 in the inward direction. At this stage in the implantation process, the surgeon may now assess the position of the exclusion clip 400 to determine if the current, intermediate position is optimal and effective, or if the clip 400 should be repositioned by repeating these initial steps.

When the surgeon has determined that the exclusion clip 400 is in a desirable LAA-exclusion position, the surgeon actuates the clip delivery device to place the exclusion clip 400 into a final implanted state, which state is generally represented in FIGS. 32 to 41. As closely depicted in FIG. 33, this final implanted state of the exclusion clip 400 is characterized by a substantially 90-degree rotation of each of the first and second clip struts 410, 420 with respect to each of the turn sections 450 of the biasing member 408. As shown in FIGS. 32 to 41, this transformation places the first sides 412, 422 of each clip strut 410, 420 facing in the upward direction along the y-axis, the second sides 414, 424 of each clip strut 410, 420 facing in the outward direction along the x-axis, the third sides 416, 426 facing in the downward direction along the y-axis such that each of the third sides 416, 426 now comprise the clip surface that is resting against the heart topography surrounding the base portion of the LAA, and the fourth sides 418, 428 facing one another in the inward direction along the x-axis such that each of the fourth sides 418, 428 is pressed into surface-to-surface contact with the outside surface of the LAA. (It is noted that the surfaces of the fourth sides 418, 428 shown in FIGS. 32 to 41 are depicted as touching one another. This orientation, however, does not apply when tissue, such as the LAA is disposed therebetween. In that situation, there is a distance between the two surfaces as described and shown herein.)

As mentioned above, to produce the 90-degree rotation of the clip struts 410, 420 with respect to the turn sections 450, a torque force must be applied to each of the clip struts 410, 420 to cause the angular displacement. With respect to the instant exemplary embodiment, this torque force is created by the surgeon's actuation of a portion of the control handle to start the release of the counter-force being applied by the cords 484 of the clip delivery device. As the force imposed on the cords 484 is released, the clip struts 410, 420 approach one another. A first geometric structure of the first side 412, 422 causes the clip struts 410, 420 to rotate as desired from the flat orientation to the vertical orientation. This first geometric structure is depicted well in FIGS. 33 and 36. In particular, the first sides 412, 422 are not coplanar as the third sides 416, 426. Instead, the first sides 412, 422 are angled from horizontal, each surface respectively angled inwards/downward as the surface extends from the corners 412a, 422a towards the self-motivators 430 (or towards the fourth sides 418, 428 when self-motivators are not present). Although the clip struts 410, 420 are not depicted in the horizontal orientation, when the clip struts 410, 420 finally touch one another in the approach, the two edges 412a, 422a are the first locations of the clip struts 412, 420 to contact. Because the first sides 412, 422 are angled, the geometry of these surfaces causes the first clip strut 410 to rotate counterclockwise and the second clip strut 420 to rotate clockwise in the desired directions that start the final LAA implantation movement. A second geometric feature assists this rotational movement of the clip struts 410, 420. In particular, the geometry of the eyes 490 with respect to the elongated portion 406 residing in the throughbore allows the clip struts 410 to move from the flat orientation (e.g., shown in FIGS. 29 and 30) and rotate to the installed orientation depicted in FIGS. 34 to 37, for example. More specifically, the centerpoint of the eye 490 is below the centerpoint of the elongated portion 406 as shown by the distance D in FIG. 33. When the tensioning cords 484 pull on the clip strut 410, the clip strut 410 pivots about the centerpoint of the elongated portion 406 to move the clip strut 410 through a 90-degree angle. The cords 482 are fixed in the arm 486a and pass through the eyes 490 of the clip strut 420. Accordingly, the pulling force imparted by the cords 484 on the clip strut 410 also causes a corresponding 90-degree rotation of the clip strut 420, which has the same two centerpoints for the eyes 490 and the elongated portion 406 running through the clip strut 420. Closing of the clip 400 causes the reverse motion to occur. Specifically, as the surgeon causes the clip 400 to close by allowing the clip struts 410, 420 to come closer together, first contact with LAA tissue disposed therebetween is by the first side 412, 422 of each of the clip struts 410, 420. As the force on the cords 484 continues to reduce, the clip struts 410, 420 have no other way to rotate than to pivot about the elongated portion 406 because the moment arm of the force being imparted about the axis of the elongated portion arises at the eyes 490. Accordingly, the clip struts 410, 420 rotate ninety degrees towards one another (counterclockwise for clip strut 410 and clockwise for clip strut 420) and, at the same time, the self-motivator grips 430 the LAA tissue and causes the LAA to enter the intervening space between the clip struts 410, 420 in the direction of the dashed arrow in FIG. 33.

The biasing assembly 404 also assists with rotating the clip struts 410, 420 about and upon the LAA tissue and does so by including a dip or valley 458 within the intermediate portion 456 of the turn section 450 as shown in FIGS. 43 to 47. When the biasing member 408 is installed in the clip-application head 480 and the two clip struts 410, 420 are pulled apart, the intermediate portion 456 is stretched so that the valley 458 straightens (which is ideally depicted in FIGS. 32 to 42 but, practically, the valley 458 does not completely straighten in use of the clip 400). As the valley 458 straightens and becomes shallower, the bends of the valley 458 impart a force to each of the respective opposite turn sections, which force is clockwise for clip strut 420 and counterclockwise for clip strut 410, the exact force that is needed to move the clip struts 410, 420 from the horizontal installation position to the vertical installed position. These rotational forces supplement and augment the natural motion of the clip struts 410, 420 caused by the geometry of the eyes 490 and the pivot axes of the elongated portions 406 and are especially effective the further the fourth sides 418, 428 are apart from one another as the LAA tissue is clamped therebetween. Further, the lowered curve projecting into the center opening of the turn section 450 positions the material of the valley 458 in a location that boxes in the LAA tissue to further inhibit extrusion of the LAA tissue longitudinally through that center opening.

Figure 45:
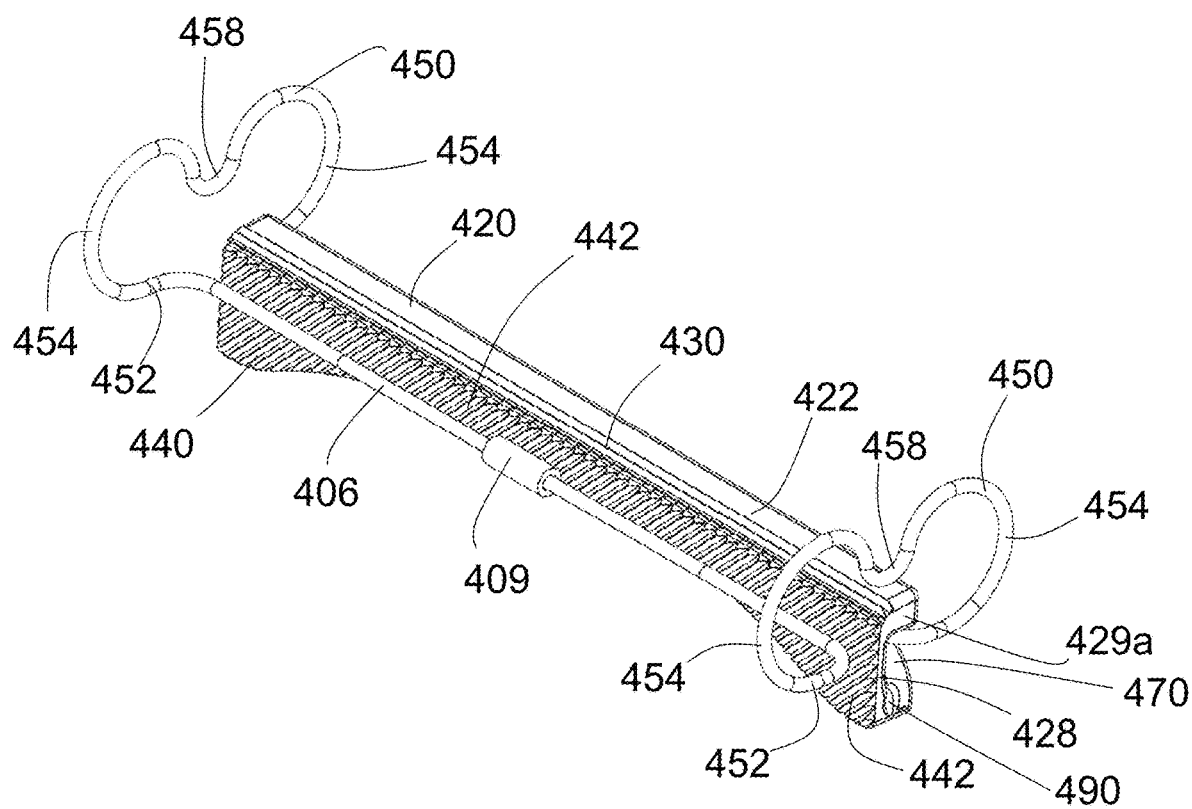
FIG. 45 is a perspective and partially longitudinal cross-sectional view of the clip of FIG. 43 having a tissue contacting with an exemplary embodiment of surface roughening.
Figure 46:
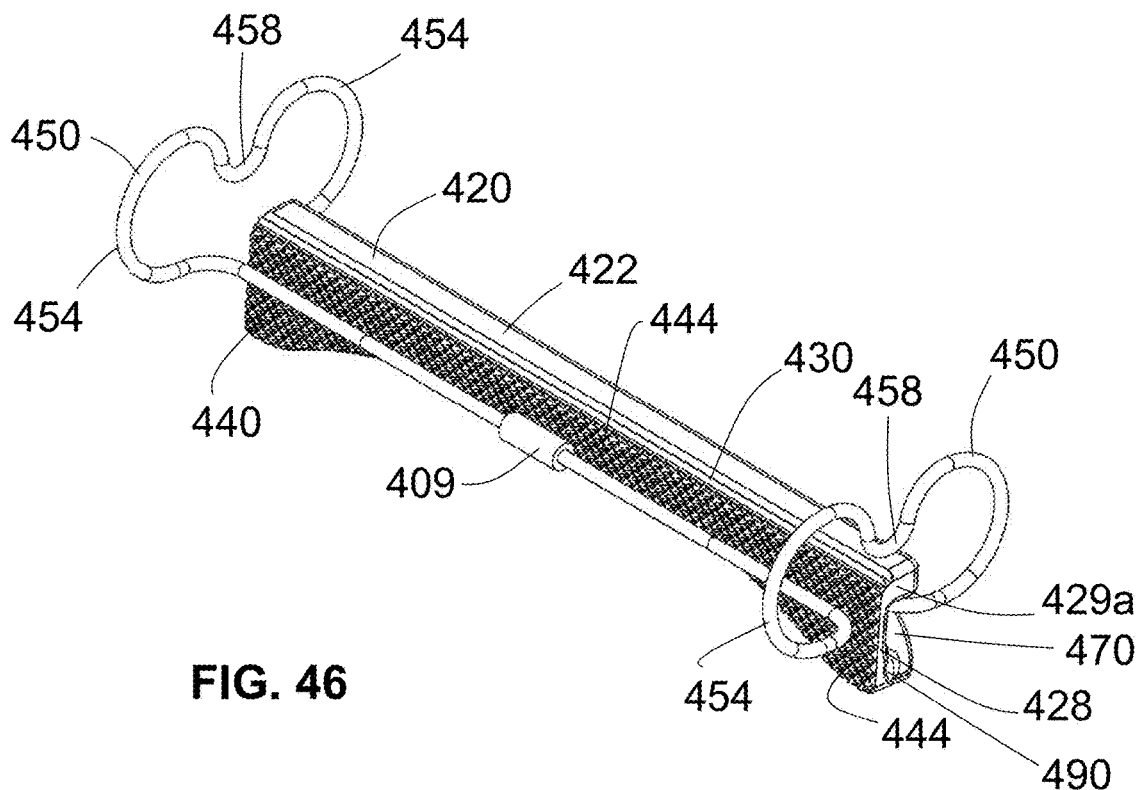
FIG. 46 is a perspective and partially longitudinal cross-sectional view of the clip of FIG. 43 having a tissue contacting with another exemplary embodiment of surface roughening.
Figure 47:
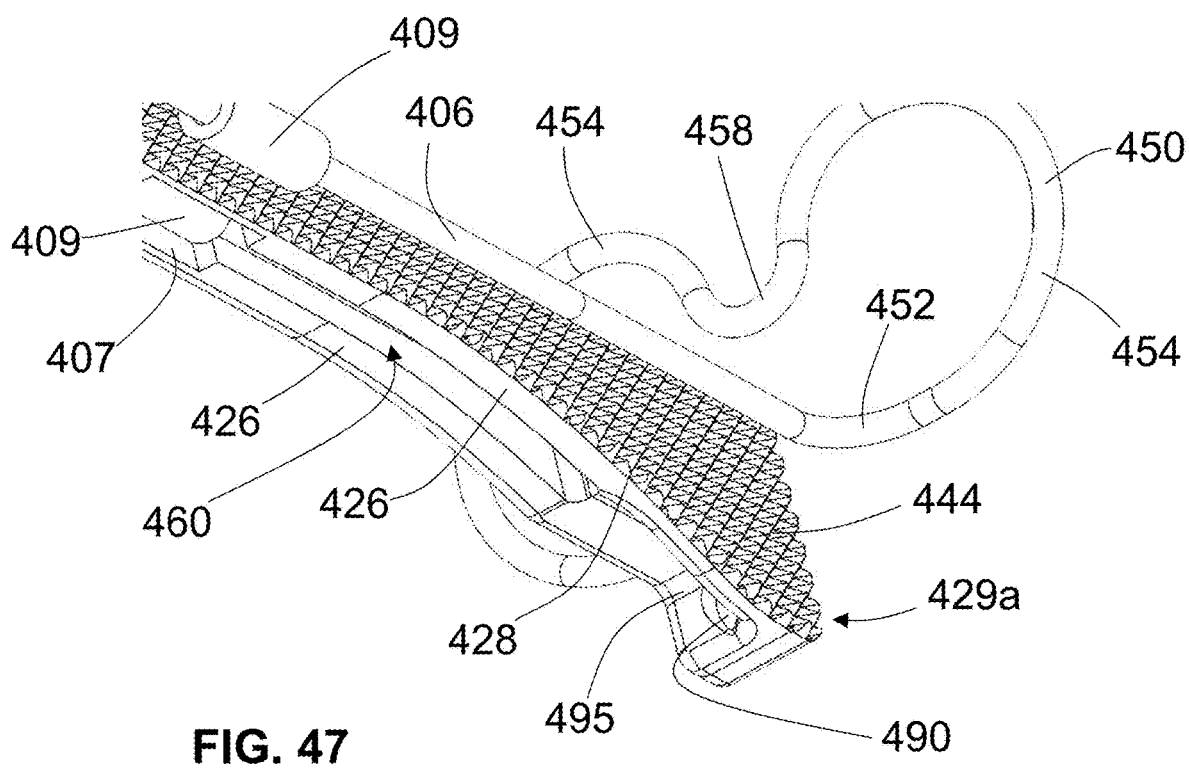
FIG. 47 is a fragmentary, enlarged, perspective view of a portion of the clip of FIG. 46.
Figure 48:
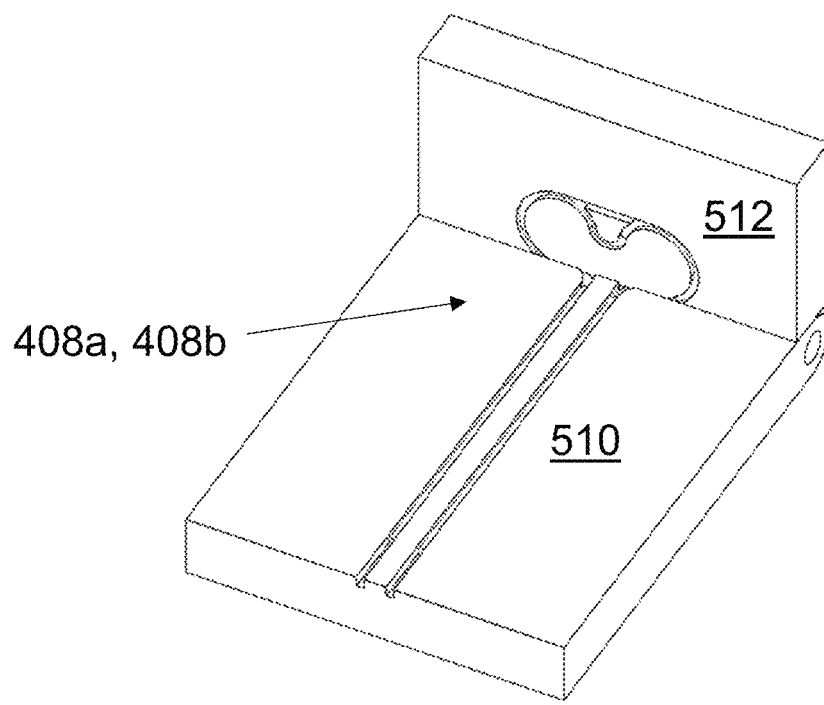
FIG. 48 is a fragmentary, perspective view of an exemplary embodiment of a two-part mold for manufacturing a spring member part of the biasing member of the clip of FIG. 43.
Figure 49:
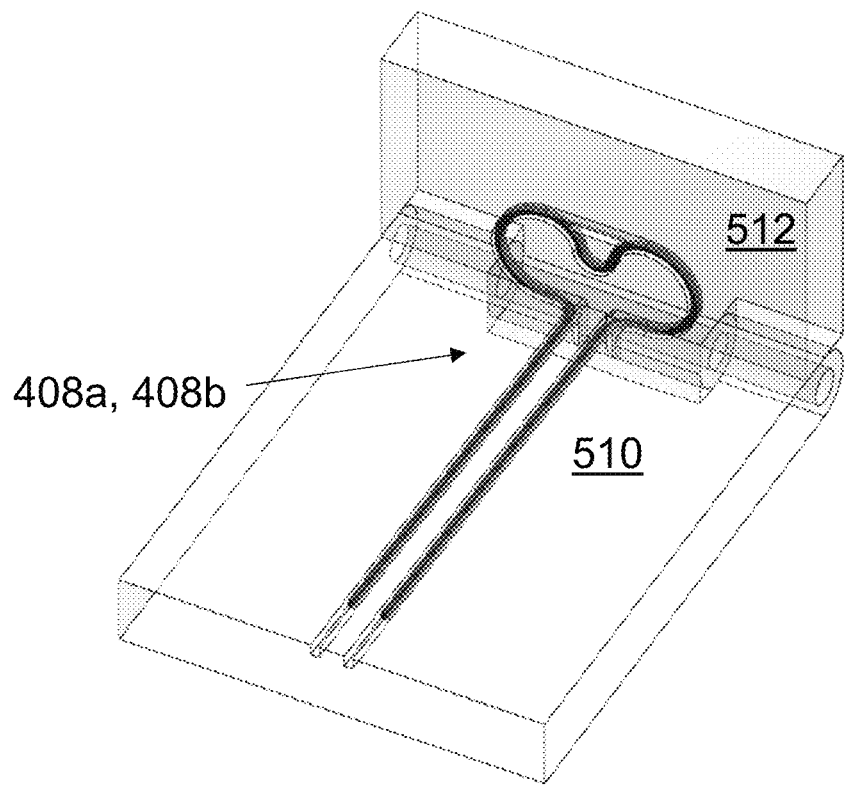
FIG. 49 is a fragmentary, hidden line, perspective view of the mold of FIG. 49.

In addition to the girding effect, a further benefit of the 90°-degree rotation of the clip struts 410, 420 is the ability to advantageously expose the LAA tissue surface to a succession of varying surface types of the clip struts 410, 420 as the exclusion clip 400 transitions through its expanded or initial capture, intermediate capture, and final implantation states during a single implantation procedure. More specifically, each of the surface areas of the clip struts 410, 420 that come into contact with the LAA may be cleverly constructed to have a specific surface type that is well-suited to the function of the surface-to-surface interaction, and the timing of that interaction, that occurs between the LAA and that particular surface area of the clip 400. For example, with respect to the above-described exemplary embodiment of the exclusion clip 400, the LAA-contacting surfaces thereof (namely the first side 412, 422, fourth side 418, 428, and common edge 432 therebetween) are constructed to each have a different type of surface texture such that, as the clip struts 410, 420 progress into the substantially 90°-degree rotation as the exclusion clip 400 advances into its final implanted state, the LAA experiences an increasing degree of frictional contact with the clip struts 410, 420 as the first side 412, 422, the rounded common edge 432, and the fourth side 418, 428 of each of the clip struts 410, 420 sequentially come into contact with the LAA. Thus, in combination with the rotational movement of the clip struts 410, 420, this increasing level of friction additionally assists in motivating and guiding the LAA into the interior of the clip 400 and, thereafter, forming a secure grip about the LAA. As the first side 412, 422 is the surface area of the clip struts 410, 420 that initially comes into surface contact with the LAA during the intermediate capture state of the clip 400 and as the rotation of the clip struts 410, 420 begins during the final implantation state, the first side 412, 422 may be molded or finished to be substantially flat and to have an ultra-low friction surface that gently engages the LAA and creates a substantially frictionless entry into the rotation of the clip struts 410, 420. As the rotation of each clip strut 410, 420 continues, the first side 412, 422 of the clip strut 410, 420 slides up and away from the lateral surface of the LAA such that the LAA next comes into contact with the rounded common edge 432 that lies between the first side 412, 422 and the fourth side 418, 428 of the clip strut 410, 420. Accordingly, as previously described, at this moment in the implantation process, the sweeping-like movement of the inward-advancing clip struts 410, 420 is intended to motivate the LAA further into the interior opening of the clip 400. As such, the frictional force may be increased by molding into, or finishing the rounded common edge 432 to have, a rougher surface texture or, as depicted in FIGS. 32 to 41, a "self-motivator" or traction element 430 may be beneficially applied to the common edge(s) 432 such that the LAA is exposed to the resulting higher-friction surface at the precise instant when the movement of the clip struts 410, 420 is motivating the LAA into the interior of the clip 400. The characteristics of such a "self-motivator" or traction element are described in detail above with respect to element 130 in the exemplary embodiment of FIGS. 1 to 12. Alternatively, the common edge 432 can also be substantially flattened to have an ultra-low friction surface. As previously described, as the rotation of the clip struts 410, 420 comes to completion, the LAA is securely gripped between the oppositely-situated fourth sides 418, 428 of the clip struts 410, 420 to place the clip 400 into its final implanted state. The fourth sides 418, 428 can have a substantially flattened, ultra-low friction surface. Alternatively, to bolster the gripping force of the clip 400 on the LAA, the frictional force created by the fourth sides 418, 428 of the clip struts 410, 420 may be further increased by applying a higher-friction surface to one or both of the fourth sides 418, 428. Alternatively, the surface(s) of one or both of the fourth sides 418, 428 of the clip struts 410, 420 may be molded or finished to have a higher-friction surface. FIG. 45 depicts one exemplary embodiment of a specific surface texture that can be applied to, or integrally formed with, one or both of the fourth sides 418, 428 of clip struts 410, 420. For purposes of clarity and illustration, the first clip strut 410 is omitted in order to better visualize the surface of the fourth side 428 of the second clip strut 420. In this embodiment, the surface texture is comprised of small striations or channel-like knurls 442 oriented at an angle that increases the friction between the LAA and the fourth sides 418, 428 of the clip struts 410, 420 and discourages any movement of the LAA back out from the clip 400. Further, FIG. 46 illustrates another exemplary embodiment of a specific surface texture that, when applied to or integrally formed with one or both of the fourth sides 418, 428, increases the frictional contact with the LAA. Again, the first clip strut 410 is omitted in this view to better visualize the surface of the fourth side 428. In this embodiment, the surface texture is comprised of pyramid-shaped knurls 444 that are oriented to increase the frictional force and discourage the backwards movement of the LAA. FIG. 47 illustrates the knurls 444 in larger detail. Therefore, by varying surface types amongst the LAA-contacting areas of the clip 400, it is possible to expose the LAA to different frictional surfaces at different and opportune times in a single implantation procedure that are advantageous to the function of the clip 400. For example, in the embodiment just described, the surface-to-surface interaction between the LAA and the clip 400 transitions from a "slippery" contact to a "grippy" contact through a single implantation procedure.

Despite this 90-degree rotation of the clip struts 410, 420 being the final implantation stage, the surgeon may continue to adjust the position of the exclusion clip 400 by reversing the closure of the clip 100, returning the clip 400 to its expanded state, and repeating the closure and rotation steps as many times as desired as described above. Once the surgeon is satisfied with placement of the clip 400, the clip-application head 480 of the clip delivery device is permanently disengaged from the exclusion clip 400. For example, in the exemplary embodiment described above with the cord-tensioning mechanism of the clip-application head 480 of FIG. 42, each clip-application arm 486*a-b* may be configured to have an internal cord-breaking mechanism 500 by which the surgeon may selectively sever the cord(s) 482, 484. In one example, each clip-application arm 486*a-b* may be configured to have a slide (not shown) in which one or more cut-outs are defined, the cut-outs having an edge (not shown) and, e.g., formed with a photo etching process. The cut-outs are positioned such that, when breakage of the cords 484, 482 is desired, the surgeon moves the slide to contact the edge of the cut-outs with the cords 482, 484.

Figure 50:
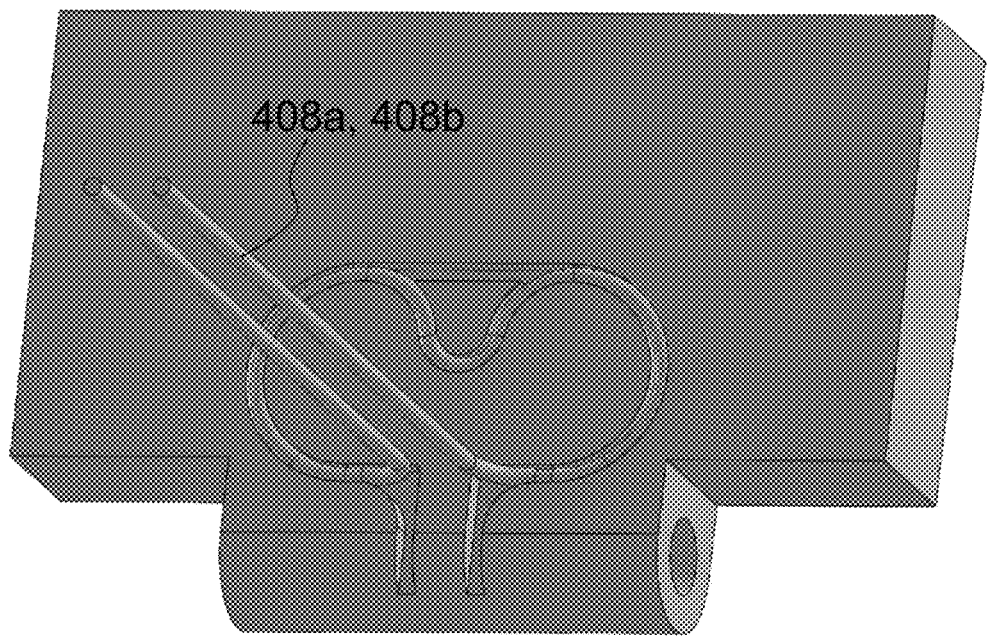
FIG. 50 is a fragmentary, perspective view of part of the mold and the spring member part of FIG. 48.
Figure 51:
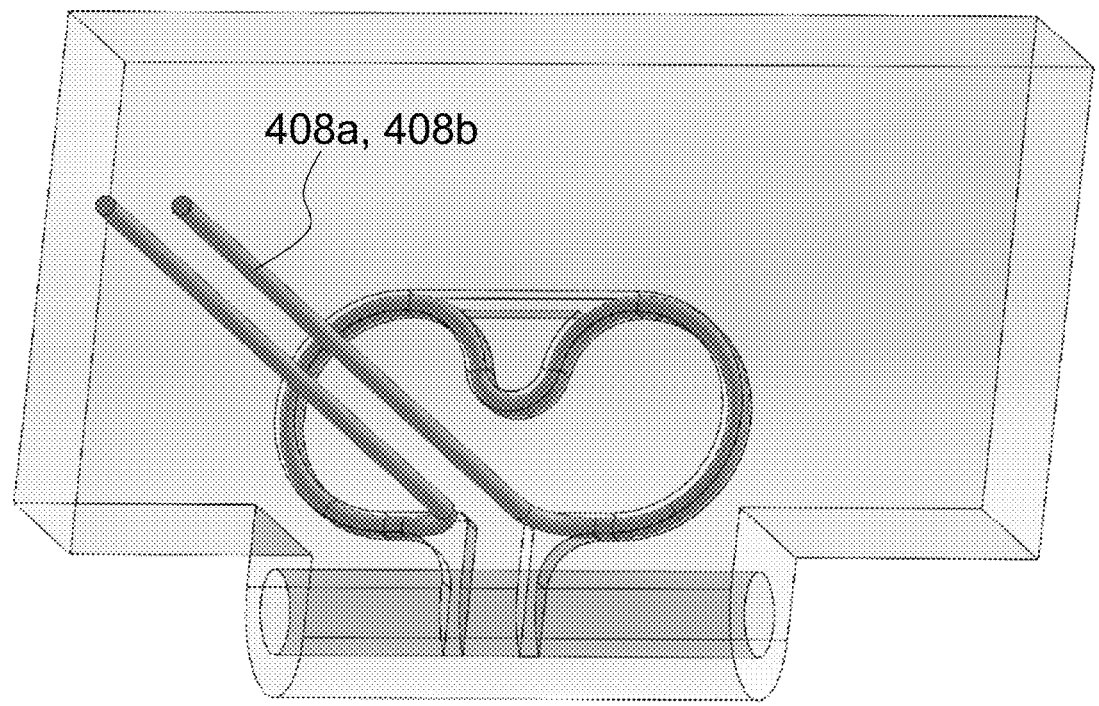
FIG. 51 is a fragmentary, hidden line, perspective view of the mold part and the spring member part of FIG. 50.

FIGS. 48 to 51 illustrate an exemplary embodiment for creating the two spring member parts 408*a*, 408*b*. The spring member parts 408*a*, 408*b* are formed with a two-part mold 510, 512. The two parts are hinged to one another. To fabricate the spring member part 408*a*, 408*b*, the mold parts are flattened and a length of wire forming the spring member parts 408*a*, 408*b* is laid down in the tracks of the mold. The first mold part 510 has the elongated portions 506 and a portion of the transition section 452. The second mold part 512 includes the remainder of the transition section 452, the turn section 450, and the intermediate portion 456 with the valley 458. The second mold part 512 is rotated to the position shown in FIGS. 48 and 49 and the assembly is heated to set the wire of the spring member part 408*a*, 408*b* into the shape shown in FIG. 44, for example. FIGS. 50 and 51 illustrate the spring member parts 408*a*, 408*b* and the second mold part 512 without the first mold part 510.

Figure 52:
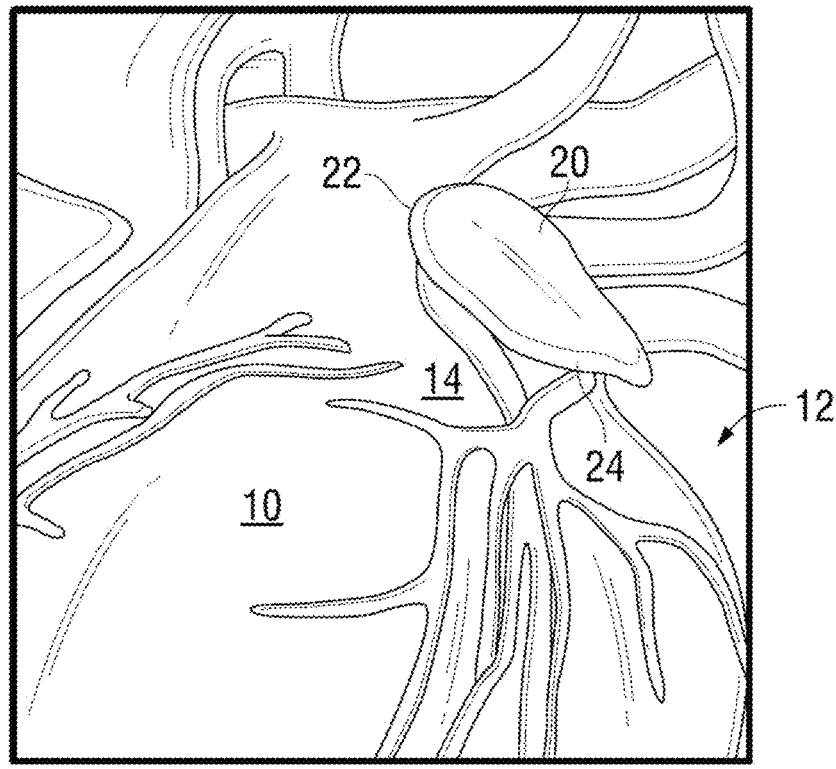
FIG. 52 is a fragmentary, diagrammatical illustration of a human heart with a left atrial appendage.
Figure 77:
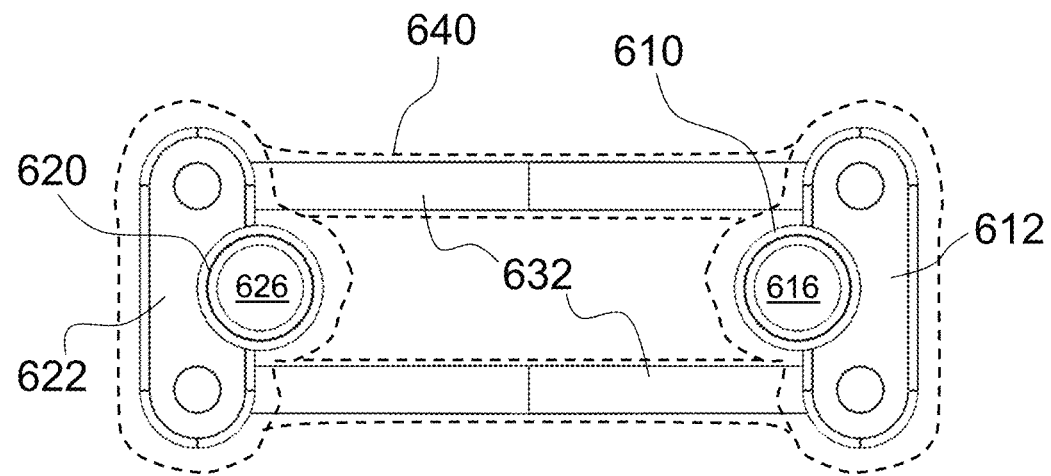
FIG. 77 is an enlarged, open end elevational view of the clip of FIG. 60 with an diagrammatical representation of an exemplary embodiment of clip cover.
Figure 65:
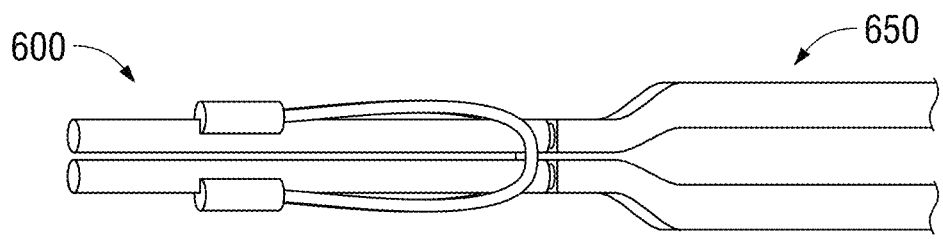
FIG. 65 is a top or bottom plan view of the clip of FIG. 53 installed on a fragment of an exemplary embodiment of clip delivery device with the clip and the delivery device in a closed orientation.
Figure 66:
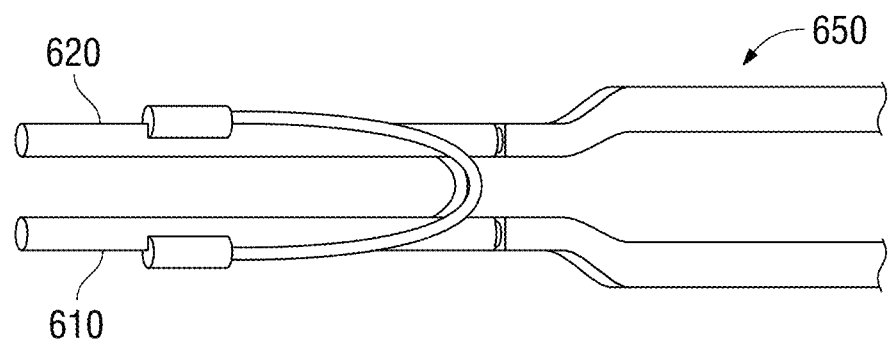
FIG. 66 is a top or bottom plan view of the clip and the clip delivery device of FIG. 65 in a first expanded orientation.
Figure 67:
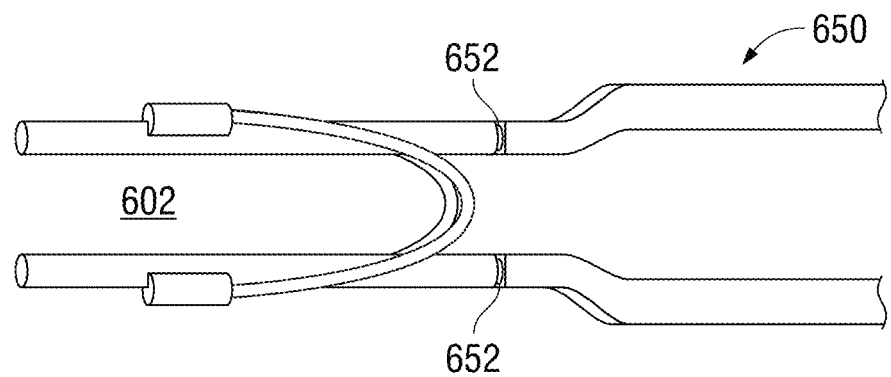
FIG. 67 is a top or bottom plan view of the clip and the clip delivery device of FIG. 65 in a second expanded orientation.
Figure 68:
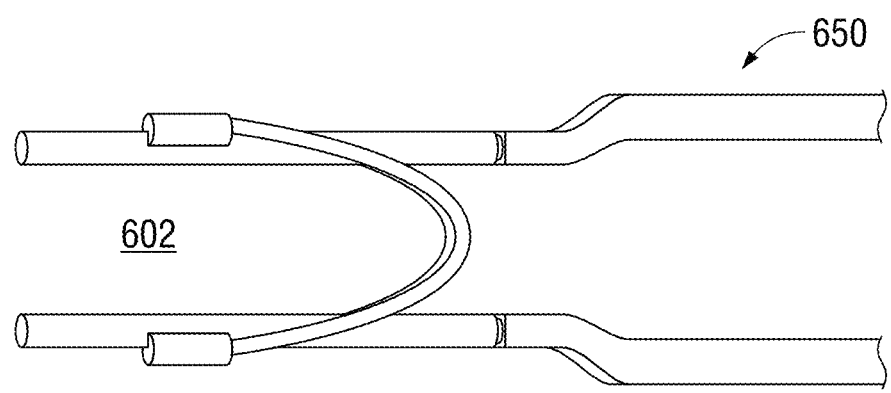
FIG. 68 is a top or bottom plan view of the clip and the clip delivery device of FIG. 65 in a third expanded orientation.
Figure 69:
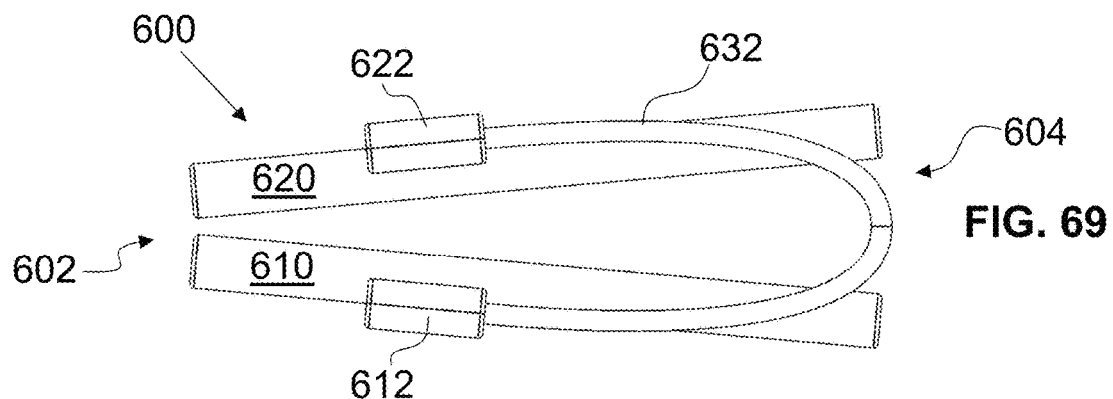
FIG. 69 is a top or bottom plan view of an exemplary embodiment of the clip of FIG. 53 in a proximal-side-open orientation.
Figure 70:
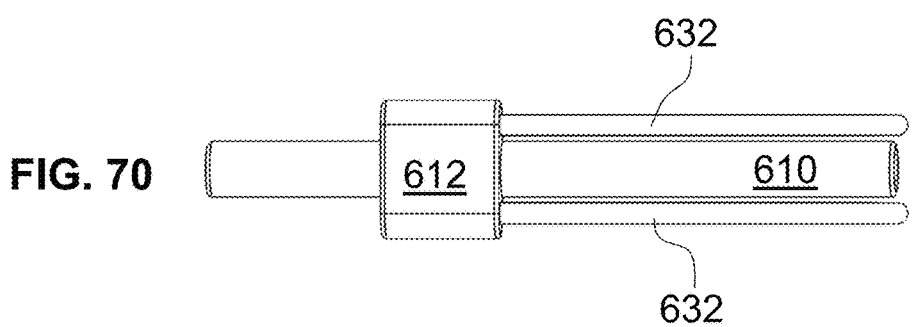
FIG. 70 is a side elevational view of the clip of FIG. 69.
Figure 71:
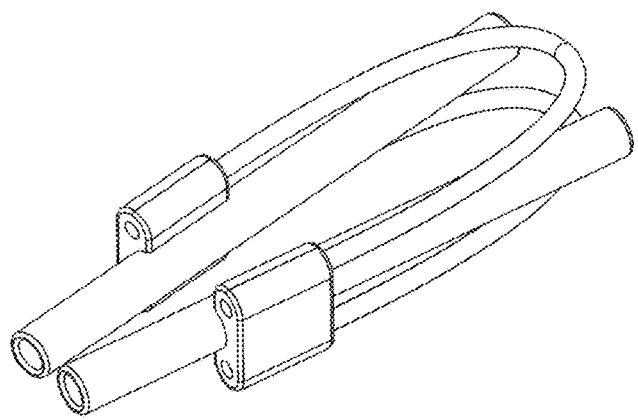
FIG. 71 is a perspective view of the clip of FIG. 69.
Figure 72:
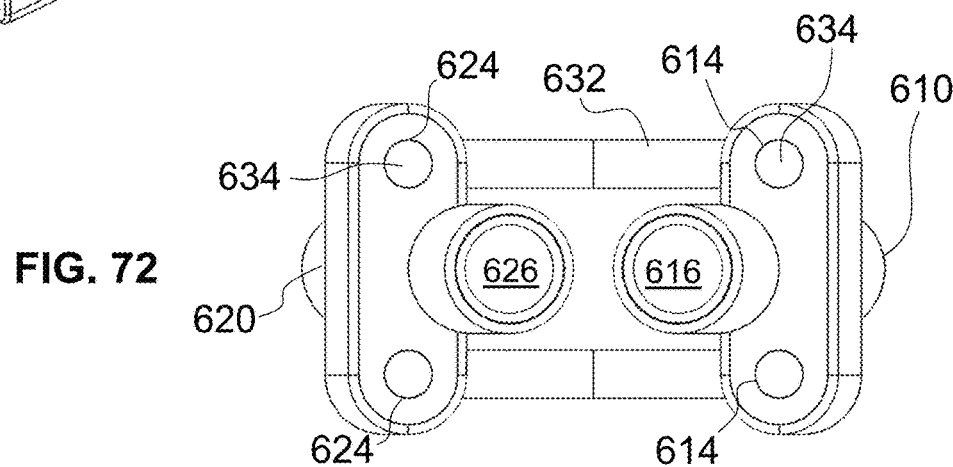
FIG. 72 is an enlarged, open end elevational view of the clip of FIG. 69.
Figure 73:
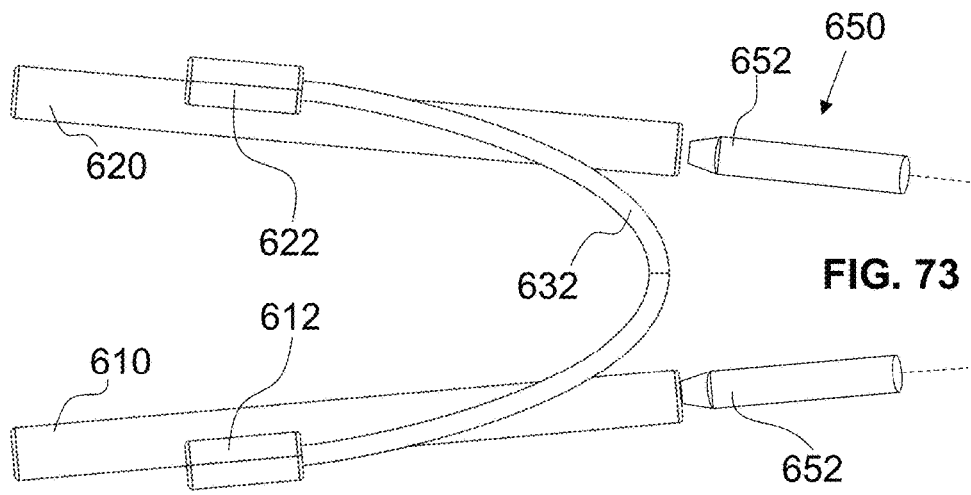
FIG. 73 is a top or bottom plan view of the clip of FIG. 53 in a distal-side-open, intermediate expanded orientation with an exploded, fragmentary, diagrammatical illustration of clip-contacting ends of the clip delivery device of FIG. 57 in a distal-side-open, intermediate expanded orientation.
Figure 74:
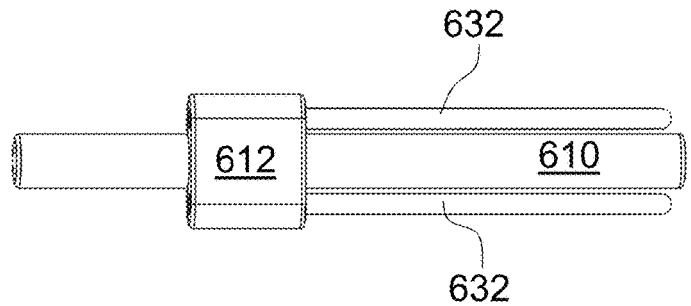
FIG. 74 is a side elevational view of the clip of FIG. 73.
Figure 75:
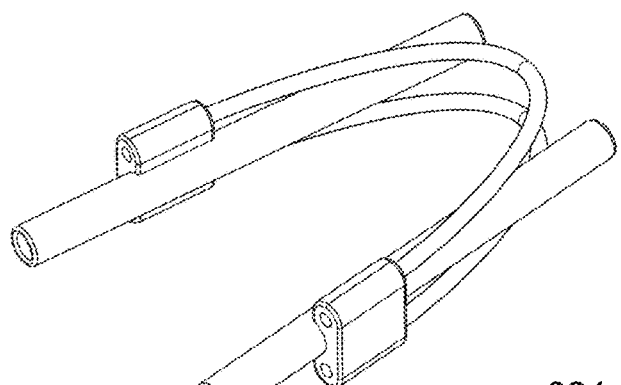
FIG. 75 is a perspective view of the clip of FIG. 73.
Figure 76:
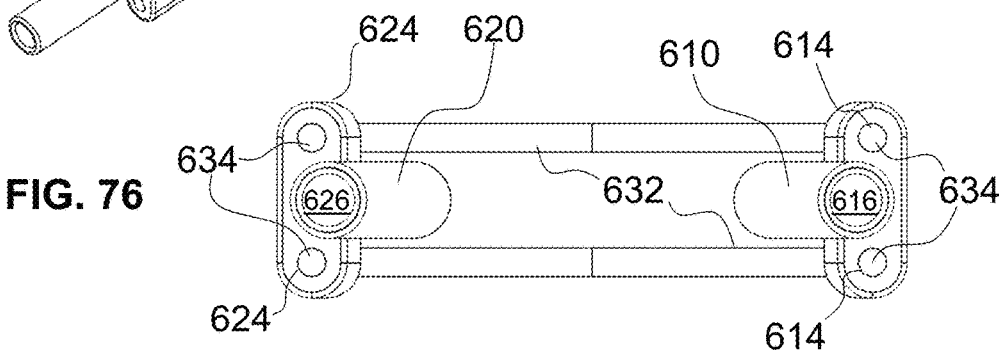
FIG. 76 is an enlarged, open end elevational view of the clip of FIG. 73.

The anterior view of the heart 10 in FIG. 52 illustrates how the LAA 20 projects away from and rests against the exterior surface 14 of the left atrium 12 to form a flap. In most instances, this flap formed by the LAA 20 against the exterior surface 14 is loose and the surgeon is able to manipulate the LAA 20 with a blunt Kittner dissector to stand the LAA upright. In such a position, the interior (e.g., 172, 272) of the exclusion clip (for example, clips 100, 200, 400) is placed over the outermost point of the LAA 20 and the exclusion clip is slid down and around all sides of the LAA 20 so that the surgeon positions the excluding sides (e.g., 110, 120) of the clip against the two opposing sides of the LAA at the base 22 of the LAA. In some instances, however, the LAA 20 can have adhesions, which hold portions of a side 24 of the LAA facing the left atrium 12 to the exterior surface 14 of the left atrium 12. In such an instance, the flap of the LAA 20 is fixed in one or more areas and, therefore, cannot be manipulated by the surgeon to stand the LAA 20 away from the exterior surface 14 of the left atrium 12. More particularly, the right base of the LAA (to the left of FIG. 52) is open and available to the surgeon but the opposite side, the left base (to the right of FIG. 52), is covered over by the left side of the LAA (if the LAA has grown in the other direction, then the opposite exists). Where adhesions exist, it is possible that the LAA 20 still can be manipulated sufficiently to allow a rod-shaped device to be inserted between the LAA 20 and the exterior surface 14 of the left atrium 12 and passed under the LAA (from anterior to posterior) along the left of the base 22 of the LAA 20 and through to the other side of the LAA 20 (adjacent the pulmonary artery). This means that, if an exclusion clip has a closed loop at distal end of the clip (such as clips 100, 200, 400), the surgeon would be required to physically separate the left side of the LAA from the surface of the heart to use that particular clip. This separation is problematic for many reasons, one of which is that it can cause left atrial tearing, which can have fatal consequences. In such a situation, therefore, it is desirable to approach the LAA 20 with an exclusion clip having an open distal end. An open-ended exclusion clip allows the surgeon to tunnel one strut of the clip between the left side of the LAA 20 and the left atrium 12 without being required to peel an adhesioned section of the LAA 20 from the exterior surface 14 of the left atrium 12.

FIGS. 53 to 82 illustrate an LAA exclusion clip 600 having an open distal end. FIGS. 53 to 56 show the exclusion clip 600 in a rest or steady state, FIGS. 57 to 60 show the exclusion clip 600 in an intermediate expanded or stretched state, and FIGS. 61 to 64 show the exclusion clip 600 in a fully expanded or stretched state.

The exclusion clip 600 comprises first and second clip struts 610, 620 that, together, define a central longitudinal axis 601 (see FIG. 61). In the exemplary embodiment, the clip struts 610, 620 are hollow tubes (although the configuration of the clip struts 610, 620 can be shaped differently). A length of the tubes is between approximately 15 mm and approximately 70 mm, more specifically between approximately 25 mm and approximately 60 mm, and, in particular, between approximately 35 mm and approximately 50 mm. In the exemplary embodiment depicted, the outer surface is smooth and cylindrical although the outer surface can take other shapes and have other surface structures and/or treatments and/or textures as detailed herein. The tubes can be covered with plastic (e.g., polyether ether ketone (PEEK)) covers or they can be made entirely of PEEK and integrate all of the features of the tubes 610, 620 and the blocks 612, 622. In a desirable embodiment, a connection between the biasing device 632 and the PEEK is rotationally grounded for stability of the exclusion clip 600. This can be done with crimping or welding or through a biasing member geometry that engages features in the tubes 610, 620 such as a bent section (e.g., a 90-degree L or a full 180-degree hook). The biasing members can be attached to each other by crimping or welding through an intermediate member or the two biasing members can be made from a single piece of material using a more complex forming process. In an exemplary embodiment, first and second bias anchors or bias device connectors 612, 622 are attached respectively to each of the clip struts 610, 620. Each bias anchor 612, 622 can be fixed to the respective clip strut 610, 620 (for example, by welding, brazing, soldering, or with an adhesive, or mechanically with pins or rivets) or the bias anchor 612, 622 can be integral with the respective clip strut 610, 620. In the exemplary embodiment depicted, each bias anchor 612, 622 is welded to the clip strut 610, 620 and has a raceway cross-sectional shape with a cutout having an interior shape corresponding substantially to an exterior shape of the clip strut 610, 620—this is true at least for the shape that exists at the location where the two parts are connected together. In alternative embodiments, at locations where the bias anchors 612, 622 are not connected to the clip strut 610, 620, the clip struts 610, 620 can have an exterior surface shape or shapes that are different along the length of the clip struts 610, 620. For example, the exterior shape of the clip strut 610, 620 at/under the bias anchor 612, 622 can be circular or ovular and the exterior shape of the clip strut 610, 620 away from the bias anchor 612, 622 can be hexagonal or octagonal.

The two clip struts 610, 620 are connected to one another through a bias device 630. The bias device 630 is anchored to the first clip strut 610 at the first bias anchor 612 and is anchored to the second clip strut 620 at the second bias anchor 622. Although the bias device 630 is shown and explained as connected to the clip struts 610, 620 indirectly through the bias anchors 612, 622, in alternative embodiments, the bias device 630 can be connected directly to the clip struts 610, 620 or can be integral with the clip struts 610, 620. In operation, the bias device 630 applies a force (e.g., a bias) to move the clip struts 610, 620 towards one another. In the exemplary embodiment depicted, the bias device 630 provides a force sufficient to touch the two clip struts 610, 620 together and press them together with a positive force. Further a rigid connection of the bias member to the anchors (as in the exemplary embodiment shown) allows each strut to resist being at an angle other than parallel. Thus, a given force (e.g., 0.75 pounds/3.34 Newtons) is required to start separating the clip struts 610, 620 from one another. Further, even to start separating only one end of the struts requires force. The force to spread a single end of the struts may be greater than simply a calculatable force based on the strut lengths and the point of force application of the force by the bias member. For example, if the bias members are acting on the center of the strut length and only one end of the struts was to be opened the force to open only that end would be half of the bias member force. However, the rigid connection of the bias member to the strut means that, to open one end, the bias member not only is moved linearly away from the central axis in a normal direction, it also goes through an angular change and, therefore, requires more force to deform, which makes the force to spread a single end greater than the simple calculated amount. In another exemplary embodiment, the bias device 630 has a steady state that keeps the two clip struts 610, 620 adjacent one another but applies no force to the two clip struts 610, 620 when they are next to one another or touch one another. Similarly, a force (e.g., 0.75 pounds/3.34 Newtons) is required to move the clip struts 610, 620 apart from the orientation where the clip struts 610, 620 are adjacent or touch one another. In a further exemplary embodiment, the bias device 630 has a steady state where the clip struts 610, 620 are separated from one another by a given distance (e.g., 1 mm). Thus, no force is imparted to the two clip struts 610, 620 when in the steady state but a force (e.g., 0.75 pounds/3.34 Newtons) is required to move them apart from this steady-state separated orientation. In this state, a force (e.g., 0.75 pounds/3.34 Newtons)

is required to move the clip struts 610, 620 towards one another and touch the two clip struts 610, 620 together.

The bias device 630 can take any shape that causes a counterforce to be applied to the clip struts 610, 620 in a direction towards the central longitudinal axis 601 when the clip struts 610, 620 are caused to move apart from one another. In the exemplary embodiment depicted in FIGS. 53 to 64, the bias device 630 is a set of two U-shaped spring clips 632. Alternatively, the bias device 630 can be a single spring. The single spring can be one of the spring clips 632 positioned above the clip struts 610, 620, one of the spring clips 632 positioned below the clip struts 610, 620, or one of the spring clips 632 positioned in the same plane as the clip struts 610, 620. It is noted that, when the bias device 630 is in the same plane as the clip struts 610, 620, such a configuration limits the movement of the clip struts 610, 620. This limit is not present when the bias device 630 is above or below or both above and below the clip struts 610, 620. When the bias device 630 is above and/or below, the proximal end of the clip struts 610, 620 can be angled and not prevented from movement by the bias device 630. This is significant because it provides the user with the advantageous ability to maneuver the clip struts 610, 620 individually or together in any way. For example, the proximal ends of the clip struts 610, 620 can be moved apart from one another (which places the distal ends closer to one another) or can be moved closer together (which places the distal ends further apart) or one of the clip struts 610, 620 can be angled while the other clip strut 620, 610 remains in line, thereby allowing one distal end of one clip strut 610, 620 to be closer to or further away from the other distal end of the other clip strut 620, 610. It can be said, therefore, that the bias device 630 does not interfere with any desirable movement of the clip struts 610, 620. In this regard, a maximum width for displacement of the clip struts 610, 620 with respect to one another at the proximal closed ends thereof is not going to be limited or interfered with by the bias device 630.

Each of the bias anchors 612, 622 has a set of blind holes or throughbores 614, 624 in which are secured respective ends 634 of the spring clips 632. The spring clips 632 are pre-set (e.g., heat set if made of Nitinol) in a steady state shape. In an embodiment where the two clip struts 610, 620 are pressed together with a force in the steady state, the spring clips 632 (when separated from the clip struts 610, 620) have a shape different from the one shown in FIGS. 53, 55, and 56. More particularly, the respective pairs of ends 634 of the spring clips 632 are preset to be closer together than the shape depicted, for example, in FIG. 53. In comparison, for the exemplary embodiment where the clip struts 610, 620 are touching one another in the steady state but are not pressed against one another with a force, the pre-set shape of the spring clips 632 is approximately the shape shown in FIG. 53.

With the bias device 630 connecting the clip struts 610, 620 together, the exclusion clip 600 defines an open end 602 and a closed end 604. The open end 602 is referred to as open because the area between the distal ends of the clip struts 610, 620 is open for entry of the LAA (see, e.g., arrow A in FIG. 59) between the two clip struts 610, 620 and the closed end 604 is referred to as closed because the area between the proximal ends of the clip struts 610, 620 is prevented from being entered from an end (see, e.g., arrow A' in FIG. 59) because the spring clips 632 traverse a distance from one of the clip struts 610 to the other of the clip struts 620 when separated from one another. The view of FIGS. 56, 60, and 64 looks down the open end 602 of the clip 600 in various states of expansion of the clip 600.

The clip 600 has a size that is beneficial for use in a thoracoscopic procedure because the cross-sectional area is very small. The largest feature of the clip 600 that defines this cross-section is a width of the bias device 630. In the steady-state orientation shown in FIG. 53, for example, the largest cross-sectional diameter that defines smallest port size in which the clip 600 may fit is the width W of the spring clip 632 when in the collapsed state of the clip 600. In particular, for a clip 600 long enough to occlude a typical LAA, the smallest cross-sectional width W of the spring clip 632 is between approximately 8 mm and approximately 9.9 mm. Thus, the clip 600 is able to fit within a 10 mm thoracoscopic port (30 French) for delivery to the LAA during a clip-implantation procedure.

To retain this minimal cross-section throughout a LAA clip-implantation procedure, a delivery device 650 for the clip 630 is configured to grasp the clip struts 610, 620 from respective interior hollows 616, 626. Distal clip-contacting ends 652 of the delivery device 650 are diagrammatically indicated in FIG. 57, in which the delivery device 650 has opened the clip 600 into an intermediate expanded position. FIGS. 57 to 60 are various views of the clip 600 in this intermediate expanded position. These ends 652 insert into the clip struts 610, 620 to temporarily secure and control movement and delivery of the clip 600. An exemplary embodiment of the delivery device 650 is shown in FIGS. 65 to 68. Various exemplary embodiments of mechanisms that open and close the clip contacting ends 652 of the delivery device 650 are explained below.

To cooperate with the clip-contacting ends 652 of the delivery device 650, the clip struts 610, 620 are either entirely hollow, as shown in FIG. 56, for example, or the clip struts 610, 620 have non-illustrated blind holes starting from the closed end 604 of each of the clip struts 610, 620 and passing within the clip struts 610, 620 to an interior distance sufficient to allow controlled separation between the two clip struts 610, 620 and control of yaw of the clip struts 610, 620 with respect to one another, which is described in further detail below. With the delivery device 650 accessing and controlling the clip 600 from an interior of the clip 600 and not from an exterior of the clip 600, the delivery device 650 is sized to be smaller in cross-sectional area than the largest cross-sectional diameter of the clip 600. This means that, in use of the clip 600, the width of the port is minimized to the largest cross-sectional diameter of the clip 600 and not the diameter of the delivery device. It is noted that each of the arms proximal of and/or connected to a respective one of the clip-contacting ends 652 in the exemplary embodiment of FIGS. 65 to 68 are illustrated as being thicker than a width of each respective clip strut 610, 620. For use in a thoracoscopic procedure where the port size is approximately 30 French, these arms can vary in size, they can be slightly larger than the outer diameter of the clip struts 610, 620 (e.g., but still having a total outer diameter less than 30 French), they can be the same diameter as each of the clip struts 610, 620 (e.g., to have a total outer diameter of less than 30 French), and/or they can be narrower than each of the clip struts 610, 620 (e.g., to have a total outer diameter of much less than 30 French).

As shown in the progression of FIGS. 65 to 68, the clip 600 starts in a smallest compressed state and is enlarged by the delivery device 650 to a size where the open end 602 is large enough to straddle the LAA and slide the clip struts 610, 620 along the base of opposing sides of the LAA. To carry out an implantation procedure of the clip 600, the clip-contacting ends 652 of the delivery device 650 are inserted into the holes/throughbores 614, 624 at the proximal ends of the clip struts 610, 620, and the delivery device 600 is made ready to open the clip 600 from its smallest, port-installation orientation position in which the width W is minimized. A non-illustrated thoracoscopic port is installed in a patient to provide access to the heart and the LAA of the patient. Under visualization (e.g., through another thoracoscopic port in which an appropriately sized camera rests), the surgeon inserts the clip 600 through the thoracoscopic port and up to and adjacent the LAA 20. With use of a Kittner dissector (or another grasping/movement tool), the LAA is lifted (if there are no adhesions preventing such lifting) or a path under the LAA 20 is opened (if adhesion(s) permit entry of one of the clip struts 610, 620 under the LAA). Either before, during, or after, the two clip struts 610, 620 are separated from one another to a distance sufficient to encompass the base of the LAA 20. The surgeon extends the delivery device 650 to move the clip 600 along the base of the LAA 20 by positioning the first clip strut 610 on one side of the base and the second clip strut 620 on the other side of the base. The surgeon manipulates the clip 600 to place the clip struts 610, 620 as low as possible about the LAA. When a desirable implantation position of the clip 600 is obtained, the surgeon causes the delivery device 650 to have the clip 600 spring back towards its steady-state orientation to, as completely as possible, close off the interior of the LAA 20 from the interior of the left atrium 12. In this state, the base of the LAA exists between the clip struts 610, 620 with the clip struts 610, 620 compressing the LAA therebetween using the force imparted by the outwardly stretched bias device 630. The surgeon determines if the clip 600 is in a successful implantation position (e.g., by visualizing blood flow through the left atrium 12 with transesophageal echocardiography (TEE) and/or by examining cardiac rhythm). If the position is not desirable, the surgeon uses the delivery device 650 to re-expand the clip 600 and the surgeon repositions the clip 600 about the LAA 20. When a desirable implantation state of the clip 600 exists, the delivery device 650 is separated from the closed end 604 of the clip 600 and is retracted out from the thoracoscopic port.

Connection between the clip-contacting ends 652 of the delivery device 650 and the clip struts 610, 620 can take various forms. In an exemplary embodiment, the delivery device 650 is separated from the closed end 604 of the clip 600 by a release pin or wire engaging at least one clip strut 610, 620 and at least one clip-contacting end 652 (e.g., similar to the form of a grenade pin). When disengaged, the clip-contacting ends 652 are free to be removed from the clip struts 610, 620 and the delivery device 650 can be removed from the patient. Other exemplary embodiments of such release mechanisms include catch hooks, pawls, lassos, retaining fingers, ball detents, expanding features on the clip-contacting end 652 within the inner hollow 616, 626 of the clip strut 610, 620, barbs, electronic ablation or cutting of a connecting feature between the clip strut(s) 610, 620 and clip-contacting end(s) 652, mechanical ablation or cutting of a connecting feature between the clip strut(s) 610, 620 and clip-contacting end(s) 652, to name a few.

In an exemplary embodiment, with respect to the surfaces of the clip struts 610, 620 that face one another and are in contact with the LAA when the clip 600 is implanted, one or both of these surfaces have self-motivator or traction elements that, as described herein, retain the clip struts on the LAA. Texturing features can be present on one or more outer surfaces of the clip struts 610, 620. For example, the texturing can be surface finish or knurling or similar. Preferentially the texture can be longitudinal grooves and/or grooves that are at an angle to the longitudinal extent of the clip struts 610, 620. Such texturing features assist with sliding the clip 600 onto the LAA from a side of the LAA while simultaneously resisting movement of the LAA out from between the opposing clip struts 610, 620 when the LAA is clamped between the clip struts 610, 620 during or after implantation.

In the embodiments of the clip 600 shown in the figures, motion of the clip struts 610, 620 is substantially parallel, in other words, the clip struts 610, 620 are parallel when close together and are parallel when apart and remain parallel when moved therebetween. The delivery device 650 can be configured to move the clip struts 610, 620 in a non-parallel manner at any time during the implantation procedure. For example, as shown in FIGS. 69 to 72, anytime during movement from the parallel resting position shown in FIGS. 53 to 56, to a parallel expanded position shown in FIGS. 61 to 64, one of the clip struts 610, 620 can be angled with respect to the other. FIGS. 69 to 72 illustrate the ends of the clip struts 610, 620 at the open end 602 of the clip 600 closer together than the ends of the clip struts 610, 620 at the closed end 604 of the clip 600. In contrast, FIGS. 73 to 76 illustrate the ends of the clip struts 610, 620 at the closed end 604 of the clip 600 closer together than the ends of the clip struts 610, 620 at the open end 602 of the clip 600. These figure sets depict the clip struts 610, 620 disposed in substantially similar angles with respect to a central longitudinal axis. However, each of the first and second clip struts 610, 620 can be moved in the yaw direction independently as desired. The delivery device 650 controls each of the clip struts 610, 620 individually and each distal and proximal end individually to position the clip struts 610, 620 in any combination of angles during opening and during closing of the clip 600. For example, if one side needs to be angled in order to circumvent an adhesion, that clip strut 610, 620 can be angled with the other clip strut 620, 610 remaining in a parallel orientation. With such freedom of movement under control by the delivery device 650, the clip 600 can approach the LAA 20 at respective optimal angles on both sides of the LAA 20.

The bias anchors 612, 622 are illustrated herein as being located off of the center of the clip struts 610, 620. This exemplary orientation allows the distal legs of the spring clip 632 to be longer. It is noted that, where the legs of the spring clip 632 are longer, there is less foreshortening of the useable clip length that occurs when the clip 600 is fully opened. Also, a longer length assists to reduce strain in the spring clip 632 and allows the use of a larger/stiffer spring clip 632.

In an exemplary embodiment, the clip struts 610, 620 are of PEEK. The clip struts 610, 620 can also be of stainless steel, aluminum, titanium, nickel-titanium (Ni—Ti) alloy (e.g., nitinol), polycarbonate, for example.

In an exemplary embodiment, the bias anchors 612, 622 are of any of stainless steel, aluminum, titanium, nickel-titanium (Ni—Ti) alloy (e.g., nitinol), polycarbonate, for example.

In an exemplary embodiment, the bias device 630 is of any of stainless steel, aluminum, titanium, nickel-titanium (Ni—Ti) alloy (e.g., nitinol), polycarbonate, for example.

In an exemplary embodiment, parts or all of the clip 600 can be covered with a softened material (e.g., silicone or polyurethane) for atraumatic contact between the clip 600 and structures of the heart and adjacent anatomy, as well as to reduce pinching between surfaces of the clip 600. In an exemplary embodiment depicted in FIG. 77, a protective cover 640 (diagrammatically shown with dashed lines) shields any one or all of the clip struts 610, 620, the bias anchors 612, 622, and spring clips 632 of the bias device 630. The cover 640 is open at least at the proximal ends of the clip struts 610, 620 for manipulation of the clip 600 by the delivery device 650. It is noted that portions of the spring clips 632 adjacent the clip struts 610, 620 move with respect to the exterior surface of the clip struts 610, 620. This movement can be seen in the progression of the spring clip 632 in FIGS. 53, 57, and 61. When structures such as these move, a pinching or scissor region exists between the spring clip 632 and the clip struts 610, 620. Accordingly, placing the cover 640 at this region reduces or removes any pinch or scissor hazard between spring clip 632 and the clip struts 610, 620. In an exemplary embodiment, the cover 640 can be a multi-lumen extrusion. The multi-lumen extrusion can cover the clip 600 or just the spring clips 632 and the proximal ends of the clip struts 610, 620.

FIGS. 78 to 82 illustrate another exemplary embodiment of the cover 640. In this embodiment, the cover 640 has an interior 642 that surrounds the clip struts 610, 620 at least on an interior/central surface, an upper surface, and a lower surface of the clip struts 610, 620 (upper and lower referring to the orientation of the clip 600 in FIG. 81). The cover 640 has an intermediate cutout 644 that surrounds the bias anchors 612, 622 (when present) such that the exterior surfaces of the cover 640 next to a respective bias anchor 612, 622 form a substantially smooth transition with the outer surface 613 of the bias anchors 612, 622. For example, the exterior surfaces of the cover 640 next to the bias anchors 612, 622 are substantially flush with the outer surface 613, 623 of the bias anchors 612, 622. As set forth above, when the bias device 630 is in the form of spring clips 632 located above (and/or below) the clip struts 610, 620, a pinching area is formed at a distal portion of each spring clip 632 adjacent a respective bias anchor 612, 622. To minimize this pinching area, the cover 640 comprises a protective mesa 646 that is shown enlarged in FIG. 82. This mesa 646 has a top surface that extends distally towards the bias anchors 612, 622 where the spring clips 632 are grounded. In the exemplary embodiment shown, this top surface is substantially the same as the upper surface of the cover 640 from the mesa 646 to the distal end of the cover 640 (at the open end 602). The mesa 646 also comprises a vertical wall respectively next to each spring clip 632, the wall defining a shape to match a portion of the spring clip 632 that is adjacent the wall and the bias anchors 612, 622. This shape substantially corresponds to a shape of an interior/central surface of the spring clip 632 at a time when the spring clip 632 is stretched to a substantially open state of the clip 600, such as that state shown in FIG. 61, for example. The shape of the wall can be, in an exemplary embodiment, a limit stop for opening the clip 600. As a limit stop, the wall prevents the spring clips 632 from bending inwards towards the longitudinal axis 601 past a certain point. Because the spring clips 632 project out from the bias anchors 612, 622, if the spring clips 632 are bent too far, the spring clips 632 might break at the clip-anchor junction. Providing the wall as a limit stop prevents further bending of the spring clips 632 at the clip-anchor junction and, with continued bending, causes the spring clips 632 to bend/flex at an intermediate point located at or adjacent the proximal end of the wall. As in other exemplary embodiments, various surfaces of the cover 640 can have textured or self-motivating features, e.g., on the inner opposing faces, to engage the LAA.

As the surgeon approaches the LAA 20 with the clip 600 and the clip struts 610, 620 pass along the opposing sides of the LAA 20, it may not be possible for the surgeon to visualize the far side of the LAA 20. Therefore, it is possible that the surgeon places the clip 600 on the LAA 20 in an orientation where the distal ends of the clip struts 610, 620 (at the open end 620) are not completely past the far side of the LAA 20. In order to confirm that the distal ends of the clip struts 610, 620 have passed the far end of the LAA, a visual flag 660 is associated with at least one of the clip 600 and the delivery system 650. In general, the flag 660 is a structure that is located at the distal end of the clip 600 (at the open end 602) and is able to pivot (or otherwise articulate, bend, fold) from one of the clip struts 610, 620 to or towards the other of the clip struts 620, 610 and, with this pivoting motion, the surgeon will be able to see the end of the flag 660 to indicate that the clip 660 has its distal open end 602 at or past the far side of the LAA 20. If the flag 660 is actuated and is not able to be viewed by the surgeon on the other side of the LAA 20, then the surgeon can conclude that the distal ends of the clip struts 610, 620 are not secured at or past the far side of the LAA 20, which means that the surgeon needs to re-position the clip 600 on the LAA 20. This flag 660 can be part of the delivery device 650 or it can be part of the clip 600 (for example, a part of one of the clip struts 610, 620) or it can be an entirely separate device from the clip 600 and the delivery device 650.

Figure 83:
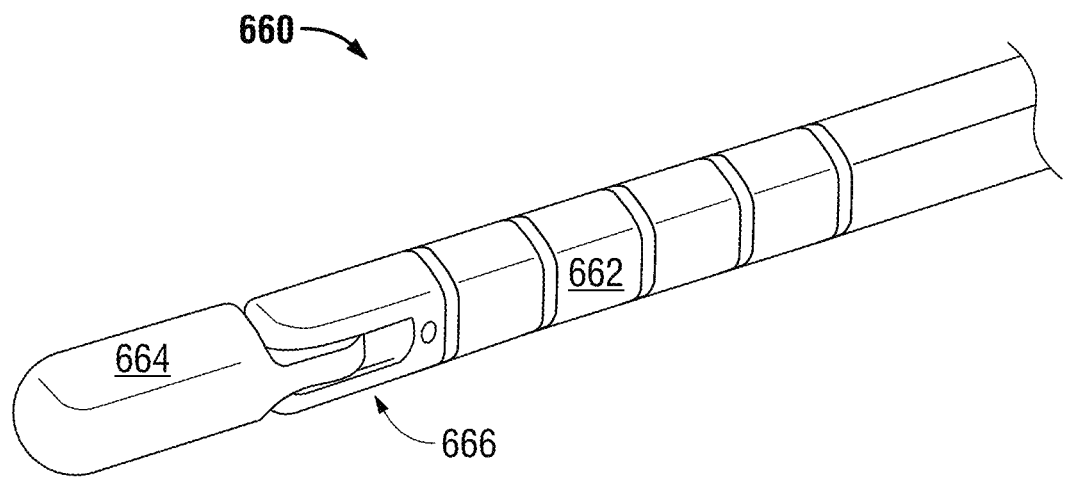
FIG. 83 is a fragmentary, perspective view of a distal end of an exemplary embodiment of a visual flag in an extended orientation.
Figure 84:
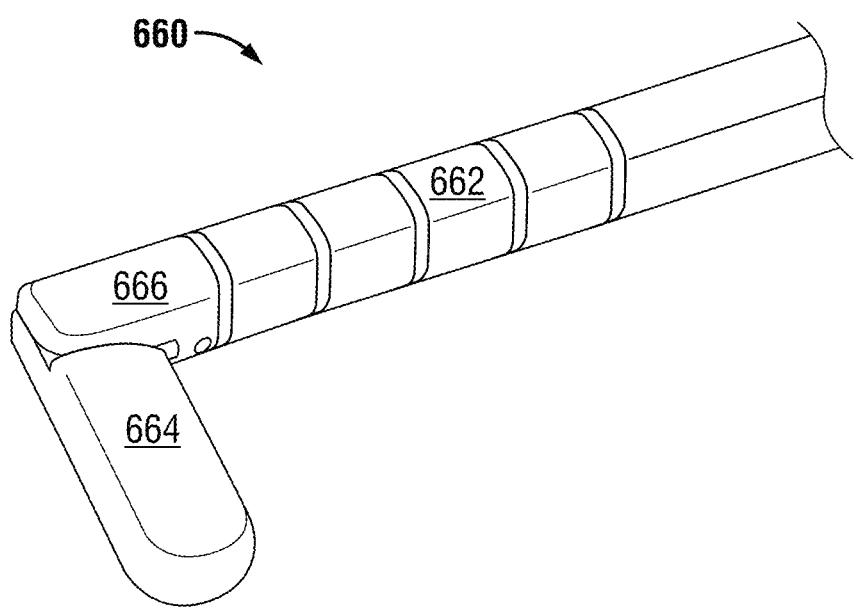
FIG. 84 is a perspective view of the flag of FIG. 84 in an articulated orientation.

An exemplary embodiment of the flag 660 is shown in FIGS. 83 and 84. At the end of a shaft 662 is a finger 664 connected to the shaft 662 by a pivot connection 666. A non-illustrated finger controller is attached to the finger 664 through the shaft 662 and selectively moves the finger 664 between an aligned position shown in FIG. 83 and a pivoted position shown in FIG. 84. In an exemplary embodiment where the flag 660 is part of the clip 600, one of the clip struts 610, 620 is the shaft 662 and the pivot connection is located at the distal end of the clip strut 610, 620. When clip struts 610, 620 are disposed on either side of the LAA during a clip-implantation procedure, the surgeon actuates the finger controller and determines whether or not the finger 664 can be viewed from the side of the LAA opposite from where the finger 664 originates. If the finger 664 is visible, then adequate implantation distance on the LAA 20 is confirmed.

Figure 85:
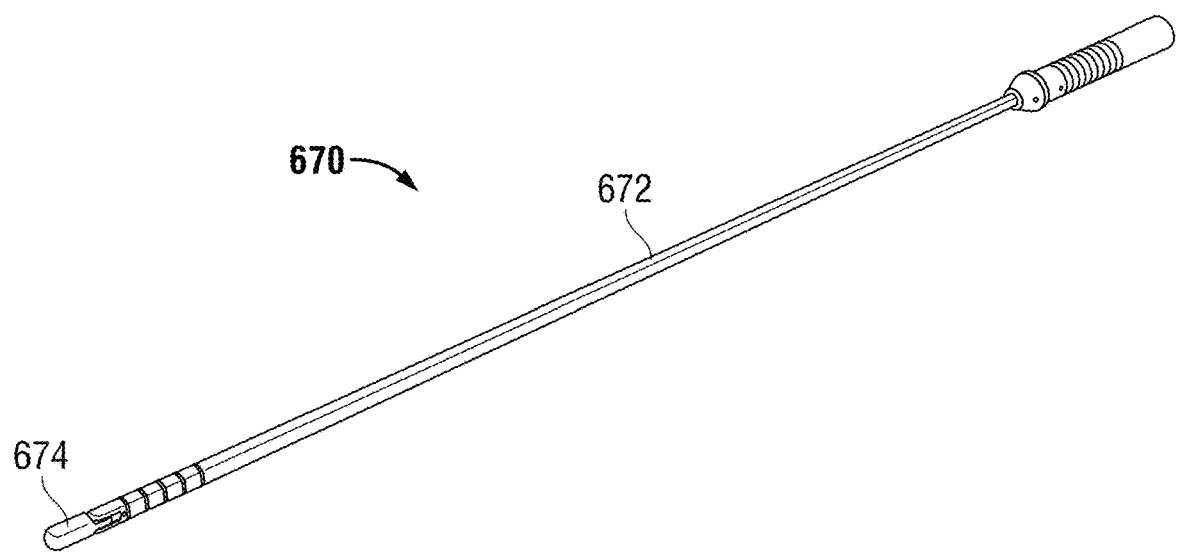
FIG. 85 is a perspective view of an exemplary embodiment of a visual flag device.

Other exemplary embodiments include the flag 660 being part of the delivery device 650. As indicated herein, at least one of the clip struts 610, 620 can be hollow from a proximal end to a distal end. The shaft 662 and the finger 664 can be sized to fit within the lumen of the clip struts 610, 620. When the clip 600 is secured on the LAA 20 with the clip struts 610, 620 disposed on either side of the LAA, the shaft 662 can be inserted through the lumen to extend the finger 664 out from the distal end of the clip strut 610, 620. The surgeon actuates the finger controller and determines whether or not the finger 664 can be viewed from the side of the LAA 20 opposite from where the finger 664 originates. If the finger 664 is visible, then adequate implantation distance on the LAA 20 is confirmed. If the finger 664 is not visible, then the implantation distance on the LAA 20 is inadequate and the clip 600 needs to be re-positioned further on the LAA 20. This exemplary embodiment with the finger 664 separate from the clip 600 can take a number of variations. First, the shaft 662 can be one of the clip-contacting ends 652 of the delivery device 650 itself and the finger 664 can reside at the end of this clip-contacting end 652. The finger 664 is extended by moving the delivery device 650 further into the clip struts 610, 620. Alternatively, the shaft 662 can be its own instrument, separate from the delivery device 650, such as the flag device 670 shown in FIG. 85. When the clip 600 is secured on the LAA 20 with the clip struts 610, 620 disposed on either side of the LAA, the delivery device 650 is removed and the shaft 672 of the flag device 670 can be inserted through the lumen of one of the clip struts 610, 620 to extend the finger 674 out from the distal end of the clip strut 610, 620. As above, the surgeon actuates the finger controller and determines whether or not the finger 674 can be viewed from the side of the LAA 20 opposite from where the finger 674 originates. If the finger 674 is visible, then adequate implantation distance on the LAA 20 is confirmed. If the finger 674 is not visible, then the implantation distance on the LAA 20 is inadequate and the clip 600 needs to be re-positioned further on the LAA 20 by re-connecting the delivery device 650 and moving the clip 600. Alternatively, the shaft 662 can be one of the clip-contacting ends 652 of the delivery device 650 itself and the finger 664 can be separate from the shaft 662 and reside within the inner hollow 616, 626 of the clip strut 610, 620. To actuate the finger 664, the shaft 662 advances distally inside the clip strut 610, 620 until the finger 664 exits the distal end 602 of the clip strut 610, 620, at which point the finger 664 is free to rotate or otherwise articulate. Alternatively, the finger can be made of a soft material (such as silicone or polyurethane) and be disposed on or about the clip strut and actuated through or around the clip strut 610, 620. This soft finger is atraumatic and can stay on the clip strut 610, 620 after implantation or can stay attached to the delivery device 650 and be removed after the delivery device 650 is separated from the clip 600.

Figure 87:
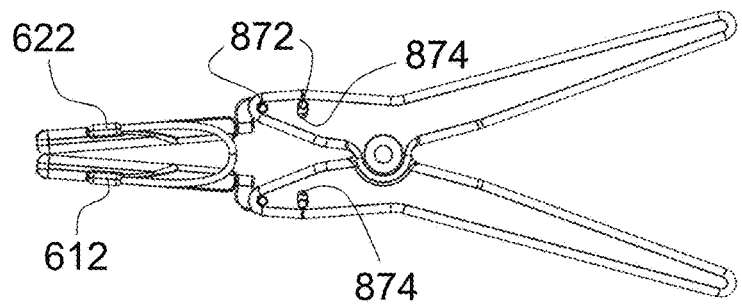
FIG. 87 is a side elevational view of the delivery device of FIG. 86 in a clip-distal end-closed orientation.

An exemplary embodiment of a mechanism to open and close the clip-contacting ends 652 of the delivery device 650 is shown in FIGS. 86 to 89. The progression from FIG. 86 to FIG. 89 illustrates stages in the opening of the clip 600. The clip 600 is advanced to the LAA in the closed configuration shown in FIG. 86. When next to the LAA, the surgeon squeezes the handles 860, which are attached pivotally at a fulcrum 862. The clip-contacting ends 652 are respectively attached to a distal end of each of the handles 860 with a multi-axis pivoting assembly 870. In this exemplary embodiment of the multi-axis pivoting assembly 870, each of the handles 860 has two connecting rods 872. Each distal connecting rod 872 is inserted in a hole at the distal end of the each handle 860. The distal rod 872 and the hole form a pivot. Each proximal connecting rod 872, in contrast, is inserted in a slot 864 at the distal end of the handle 860 and proximal of the hole. Each slot 864 extends over a distance that is orthogonal (up-and-down with respect to FIG. 86) to the longitudinal extent of the clip-contacting end 652 (left-and-right with respect to FIG. 86). Each connecting rod 872 in the exemplary embodiment extends orthogonally through a respective distal hole or proximal slot 874. The length of the slot 874 is longer than the diameter of the connecting rod 872. Thus, the proximal connecting rod 872 slides along and within the slot 874 over a distance. The two connecting rods 872 of each of the multi-axis pivoting assemblies 870 are fixed to a plate 876. The distal end of the plate 876 is fixed to the proximal end of the clip-connecting end 652. Thus, the clip 600 and the multi-axis pivoting assembly 870 are able to pivot about the distal connecting rod 872 in the distal hole over a pivot angle. This pivot angle then forms and defines the rear opening angle that the clip 600 is able to open to at the proximal side of the clip 600, which is shown in the view of FIG. 87.

Figure 88:
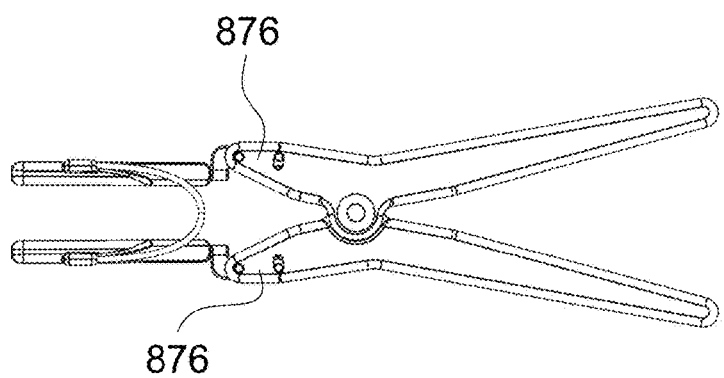
FIG. 88 is a side elevational view of the delivery device of FIG. 86 in an intermediate clip-open parallel orientation.
Figure 89:
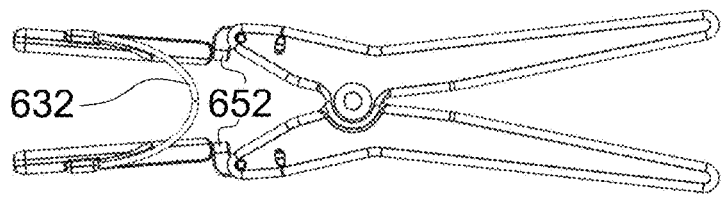
FIG. 89 is a side elevational view of the delivery device of FIG. 86 in a clip-open distal end-extended orientation.

In the orientation of FIGS. 86 to 89, the distal holes are completely hidden behind the plate 876 and the proximal slots 874 are slightly visible in FIGS. 87 to 89. The configuration of handles 860 and the multi-axis pivoting assembly 870 allows the struts 610, 620 to open in a particular manner as shown in the progression from FIGS. 86 to 89. Specifically, as the handles 860 start moving towards one another, forces automatically cause the proximal connecting rod 872 to slide outwardly to the outer end of the proximal slot 874. This means that the proximal side of the clip 600 opens before the distal side of the clip 600 opens, which orientation is shown in FIG. 87. As the handles 860 are moved even closer together, the struts 610, 620 are moved further apart and forces automatically cause the proximal connecting rods 872 to slide within the proximal slots 874. Thus, the struts 610, 620 move into a parallel orientation in an intermediate closing state of the two handles 860, which state is shown in FIG. 88. Finally, as the handles 860 are moved even closer together to a fully open position of the clip 600, the struts 610, 620 are moved further apart and forces automatically cause the proximal connecting rods 872 remain at the outer end of the proximal slot 874, at which point the struts 610, 620 move into an angled orientation where the distal ends of the struts 610, 620 are further apart than the proximal ends of the struts 610, 620; this latter orientation is shown in FIG. 89. During the opposite movement of the handles 860, this progression is reversed with the clip moving into the parallel orientation and then into an orientation where the distal ends of the struts 610, 620 close and touch one another before the opposite, proximal end of the struts 610, 620 touch one another in the clip-installed orientation.

The progression is desirable because the distal ends of struts 610, 620 touch one another first as the clip 600 is closed upon the LAA. Such an orientation has benefits, one of which is that the LAA is closed off from a distal side towards a proximal side as the surgeon installs the clip 600. This closing direction ensures that the LAA is fully captured within the jaws before the jaws start applying clamping pressure. The operator can visually confirm the full surrounding of the appendage because there is sufficient space for it to reside within the jaws while they are forming this intermediate step of a closed loop shown in FIG. 87. This further helps to keep the closing pressure from forcing the tissue out the open end, which is referred to as "watermelon seeding." This closing direction ensures that the LAA is completely closed off even if the surgeon cannot view the entire span of the LAA during clip implantation. As will be described in further detail below, the clip 600 can be formed with structures to inform the surgeon (or ensure to the surgeon) that the distal ends are closed past the distal side of the LAA, in which state a complete closure of the LAA is guaranteed.

Figure 90:
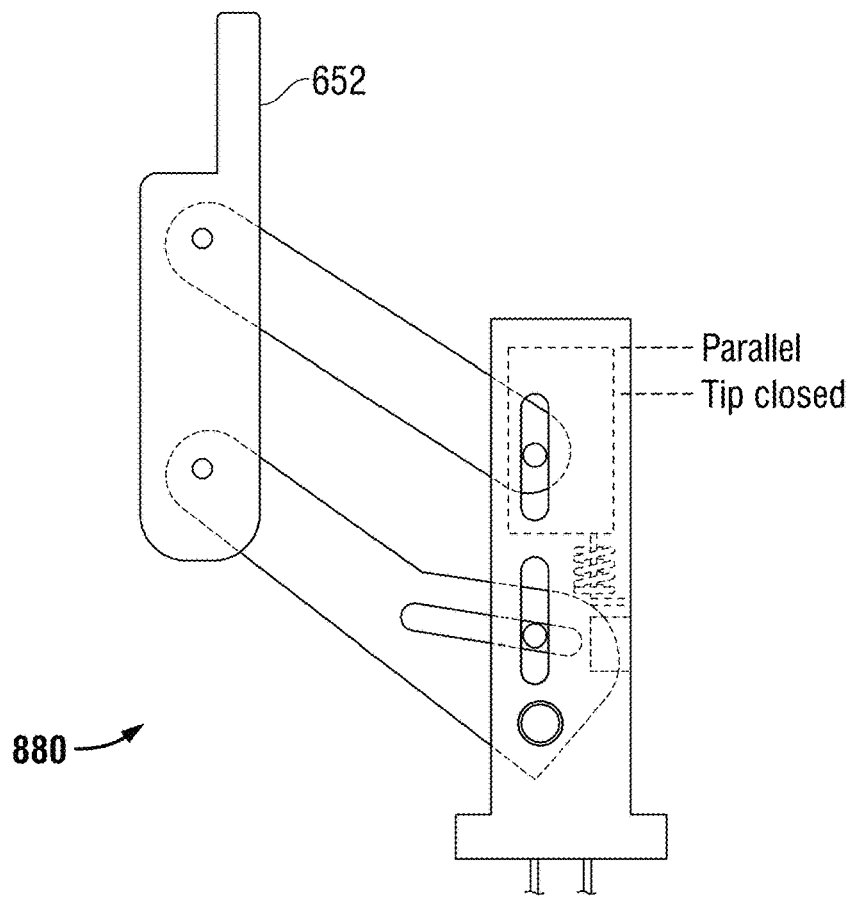
FIG. 90 is a diagrammatical illustration of a mechanism to open and close clip-contacting ends of an exemplary embodiment of a delivery device.
Figure 86:
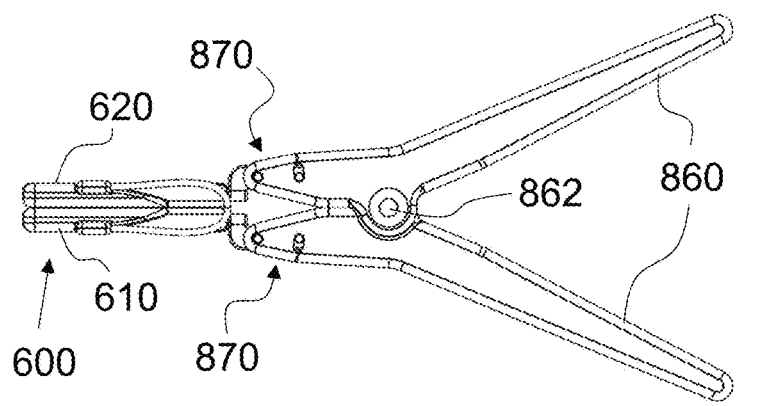
FIG. 86 is a side elevational view of an exemplary embodiment of a delivery device that opens and closes clip-contacting ends removably attached to a left atrial appendage surgical implant clip in a clip-fully-closed orientation.

FIG. 90 shows another exemplary embodiment of a multi-axis pivoting assembly 880. In this view, only one side of the clip-opening structure or assembly is depicted. The other side is not depicted for reasons of clarity. When the clip-connecting end 652 is inserted in the clip 600, this multi-axis pivoting assembly 880 allows the clip 600 to open in the progression illustrated in FIGS. 86 to 90.

The configuration of the handles 860 of the delivery device 650 shown in FIGS. 86 to 89 is one that can be used in an open surgical procedure. In such a procedure, the pericardial sac is open to the surgeon and, therefore, the handles 860 can be close to the fulcrum and can be spaced far apart from one another (e.g., in the form of a pliers) because the surgeon has a relatively large area in which to maneuver the delivery device 650. FIGS. 91 to 103, in contrast, illustrate a delivery device 900 that is scaled down and can be configured to be used in the lesser invasive surgical approaches (e.g., thoracotomy or thoracoscopy). The delivery device 900 has an end effector 910 configured to open and close the left atrial appendage exclusion clip 600 in a size that can be use laparoscopically, but the exemplary configuration of the end effector 910 illustrated in FIGS. 91 to 103, has a fixed clevis 912 comprising a neck 914 and side flanges 916. Therefore, this end effector is used in an open chest procedure. To convert this end effector 910 into one used in a laparoscopic procedure, the fixed bend of the clevis 912 is replaced with a non-illustrated articulation device or joint (which can be passive or active). The articulation device, like the shaft 902, has a diameter sufficient to be used in a laparoscopic port. Accordingly, the shaft 902 of the delivery device 900 (and the articulation device) has an outer diameter no greater than approximately 10 mm (30 French). Both the fixed clevis and articulation variants are described with the exemplary embodiment of the fixed end effector 910 shown in FIGS. 91 to 103. FIGS. 91 to 103 also depict another exemplary embodiment of a left atrial appendage exclusion clip 1000 having some features different from the clip 600. Nonetheless, all features of the clip 600 can be used with the clip 1000 and all features of the clip 1000 can be used with the clip 600.

Figure 91:
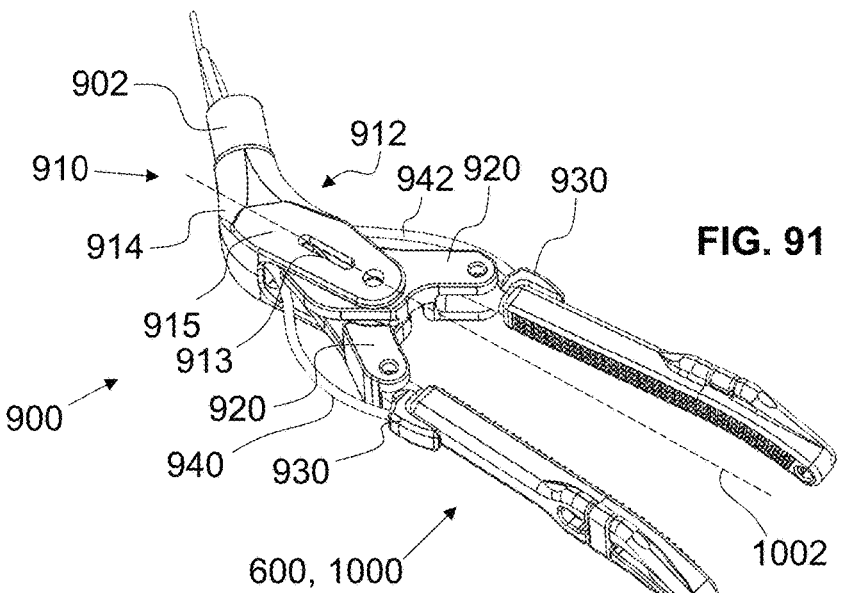
FIG. 91 is a fragmentary, perspective view of an exemplary embodiment of a distal end of a delivery device that opens and closes clip-contacting ends removably attached to a left atrial appendage surgical implant clip in a clip-fully-open orientation with a portion of the shaft removed, with pivot pins removed, and with the bias device of the clip removed.
Figure 92:
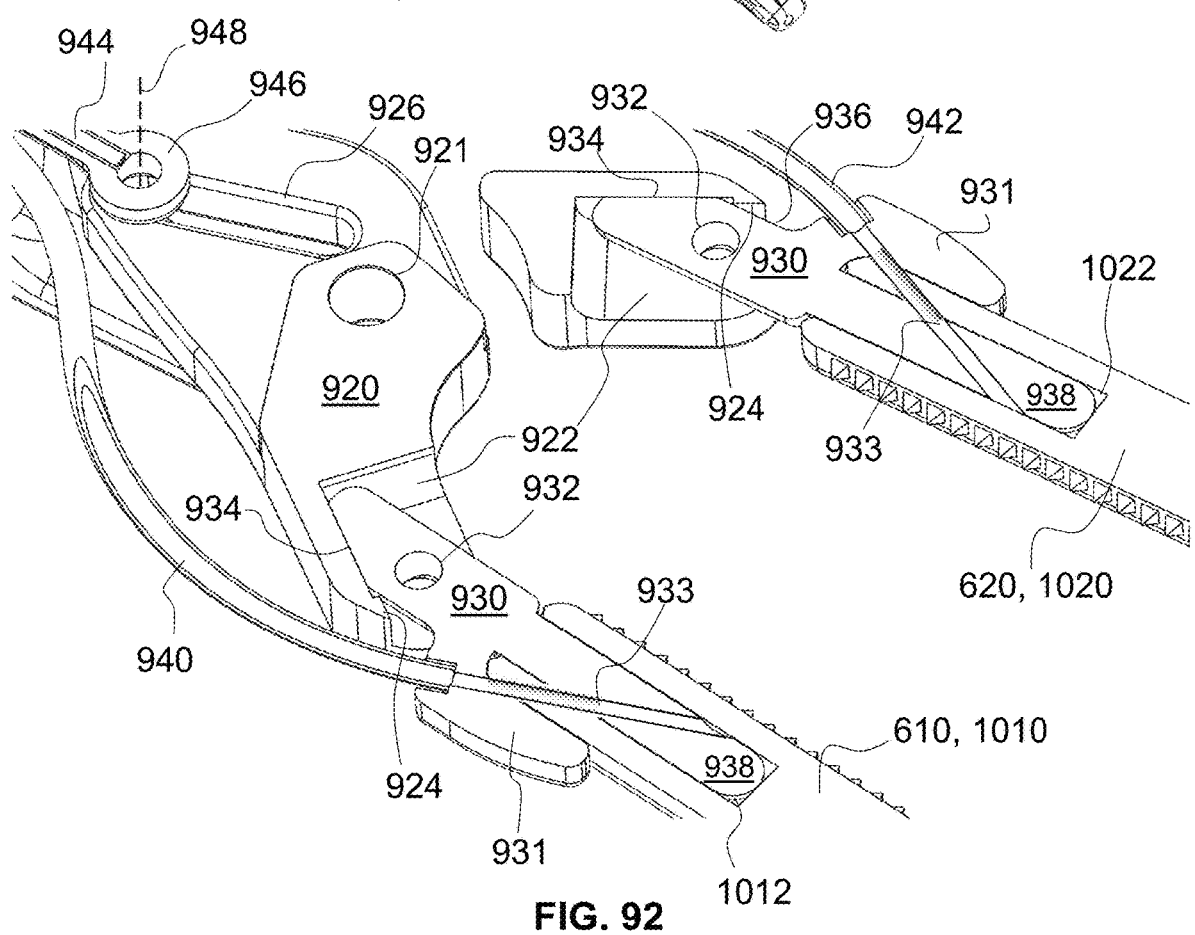
FIG. 92 is a fragmentary, enlarged, perspective and horizontally cross-sectional view of a clevis portion of the delivery device and clip of FIG. 91 with locking wires removed.

A pair of jaws 920 are pivotally connected to the distal end of the clevis 912. Each jaw 920 has a pivot hole that surrounds a jaw pivot axle that is not illustrated in the figures for clarity. The jaw pivot axle is fixed to each of the side flanges 916 of the clevis 912. Accordingly, the jaws 920 can pivot about the jaw pivot axle with respect to the clevis 912. Each of the jaws 920 have a distal end connected to a respective one of the clip-contacting ends 652. In the embodiment shown in FIGS. 91 to 103, the clip-contacting ends 652 comprise pivotable strut pins 930. In contrast to the multi-axis pivoting assemblies above, the strut pins 930 provide a multi-axis movement with a single pin pivot 932. The free "wiggling" movement of the strut pin 930 to allow the struts 610, 620, 1010, 1020 to angle with respect to one another is accomplished by having one edge 934 of the strut pin 930 that is disposed within a slot 922 of the jaw 920 be angled with respect to the longitudinal extent of the strut pin 930 (which longitudinal extent is parallel to or collinear with the longitudinal extent of each strut 610, 620, 1010, 1020). As such, when the strut pins 930 are connected to the jaws 920 at the respective pivots 932, instead of just moving slightly within the slots 922 of the jaws 920, the strut pins 930 can move at a substantial angle with respect to the distal end of the jaws 920, which angle is shown in the enlarged view of FIG. 92. In this cross-section, each of the strut pins 930 are disposed at the greatest angle with respect to the slot 922, a position where the edge 934 rests against and lies along the side wall of the slot 922 opposite the edge 934. In the view of FIG. 92, therefore, the strut pin 930 at the top of the figure cannot rotate about the pivot 932 in a direction further clockwise but can be rotated counterclockwise, at least until a sidewall 936 of the upper strut pin 930 hits the inner wall 924 of the slot 922. Similarly, the strut pin 930 at the bottom of FIG. 92 cannot rotate about the pivot 932 in a direction further counterclockwise but can be rotated clockwise, at least until the sidewall 936 of the lower strut pin 930 in FIG. 92 hits the inner wall 924 of the slot 922. This free rotation ability of the strut pins 930 allows the clip 1000 to assume each of the orientations shown in FIGS. 86 to 89.

The struts 1010, 1020 of the clip 1000 are provided with blind holes 1012, 1022 that extend inwards from the proximal end of the struts 1010, 1020 (the blind holes, can, instead, extend all the way to the distal ends of the struts 1010, 1020 in another exemplary embodiment). The distal ends 938 of the strut pins 930 project into the holes 1012, 1022 to anchor the struts 1010, 1020 respectively thereto (temporarily until the clip is ready to release for implantation). In the exemplary embodiment, the distal ends 938 and the holes 1012, 1022 are cylindrical. In an alternative exemplary embodiment, the holes 1012, 1022 and the outer surfaces of the distal ends 938 have a polygonal cross-sectional shape, which shape prevents the struts 1012, 1022 from spinning about the distal ends 938.

To secure the struts 1012, 1022 to the distal ends 938 of the strut pins 930 (both rotationally and longitudinally), the strut pins 930 have lateral guides 931. The lateral guides 931 define an entry or start point of a locking lumen 933 that tunnels at an angle from an outer edge of the lateral guide 931, through a proximal first sidewall of the strut 1012, 1022, and through part or all of the distal ends 938 of the strut pins 930. In an alternative exemplary configuration, the locking lumen 933 can continue the tunnel through all or a portion of a second sidewall opposite the first sidewall (which continuation is not illustrated). First and second strut locking tubes 940, 942 extend from a non-illustrated proximal control end of the delivery device 900, through the shaft 902, through the clevis 912, and along the jaws 920 to enter and secure in the side opening of the lateral guides 931 that defines the start point of the locking lumen 933. These strut locking tubes 940, 942 acts as guides for non-illustrated locking wires that, when in a locked orientation, extend through the strut locking tubes 940, 942, through the locking lumen 933 of the lateral guide 931, and into and through the locking lumen 933 of the distal ends 938. In such a configuration, the locking wire prevents the struts 1012, 1022 from moving rotationally or longitudinally with respect to the strut pins 930. To unlock the struts 1012, 1022 from the strut pins 930, and thereby unlock the clip 1000 from the entire delivery device 900, a non-illustrated actuator at the proximal handle of the delivery device 900 is actuated to retract the locking wires so that the distal end of the locking wires moves proximally out from the locking lumen 933 at least to an extent where the distal end of the locking wires are out of the portions of the locking lumen 933 in the distal end 938 and in the struts 1012, 1022. Accordingly, when the distal end of the locking wires is at least in the portion of the locking lumen 933 within the lateral guide 931, proximal movement of the delivery device 900 will allow the clip 1000 that is attached to the LAA to slide easily and smoothly off of the distal ends 938 to be implanted on the LAA.

In another exemplary embodiment, the locking wires that secure the struts 1012, 1022 to the delivery device 900 can be heat crimped to, mechanically crimped to, or otherwise deformed within the clip strut 1012, 1022 to provide resistance to the removal of the locking wires, allowing the locking wires to retain the clip strut 1012, 1022 onto the strut pin 930. Pulling the locking wires beyond the yield force of mechanical resistance between the clip strut 1012, 1022 and the locking wires releases the clip strut 1012, 1022 from the strut pin 930, allowing the clip to freely release from the delivery device 900.

Figure 93:
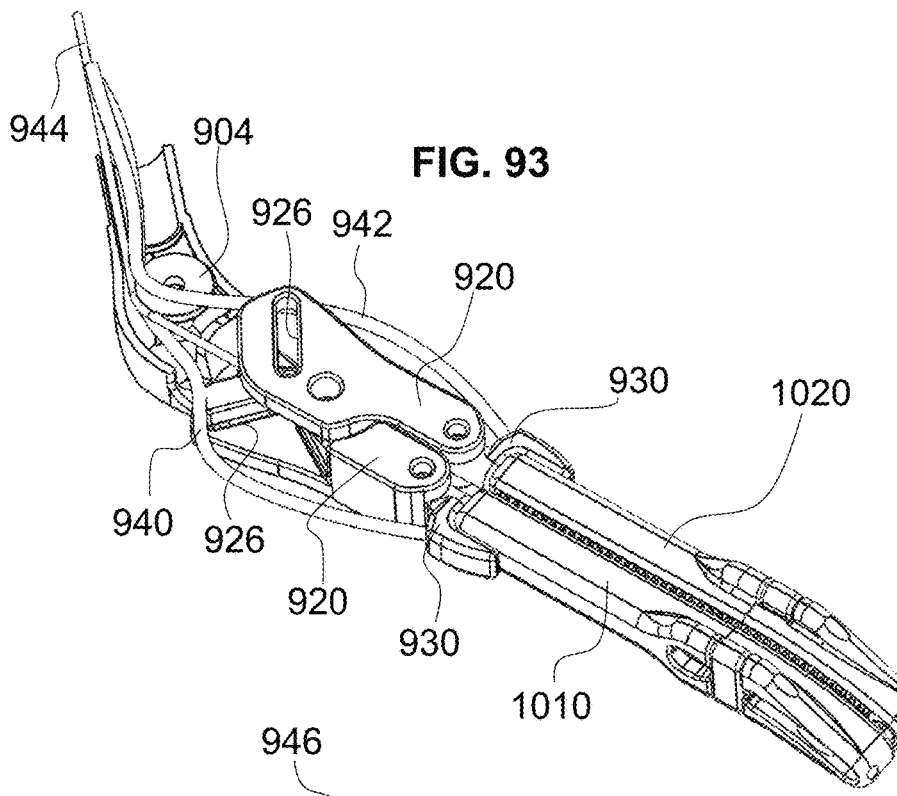
FIG. 93 is a fragmentary, perspective view of the delivery device and clip of FIG. 91 with a top half of the clevis and shaft removed in a clip-fully-closed orientation.
Figure 94:
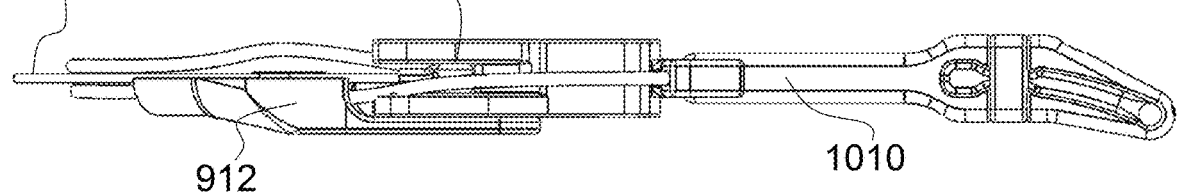
FIG. 94 is a fragmentary, side elevational view of the delivery device and clip of FIG. 93.
Figure 95:
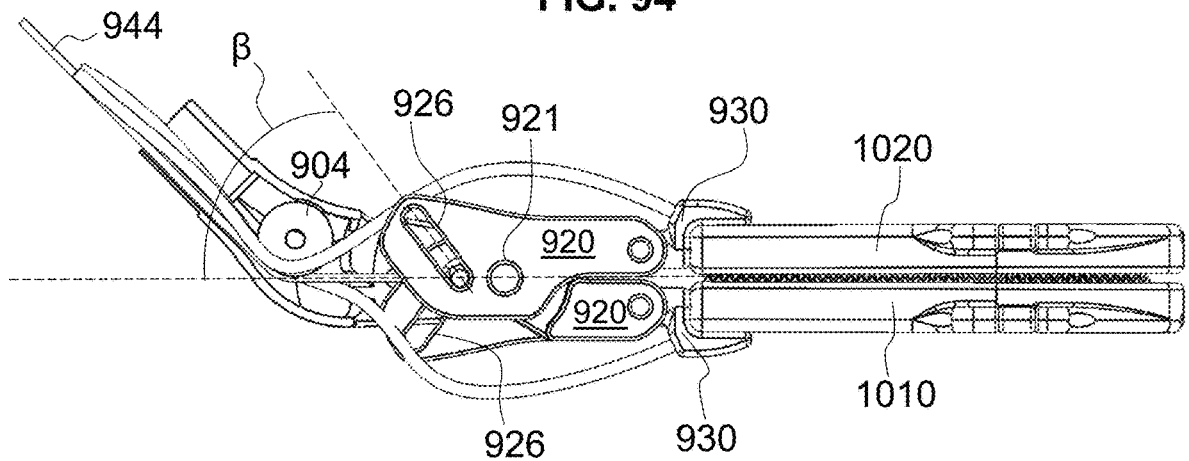
FIG. 95 is a fragmentary, top plan view of the delivery device and clip of FIG. 93.
Figure 97:
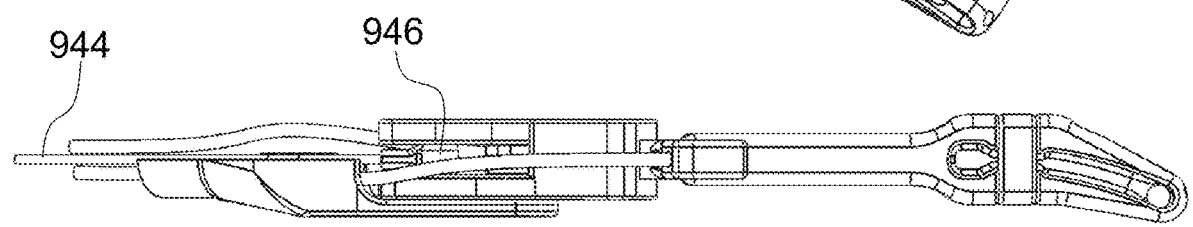
FIG. 97 is a fragmentary, side elevational view of the delivery device and clip of FIG. 96.
Figure 98:
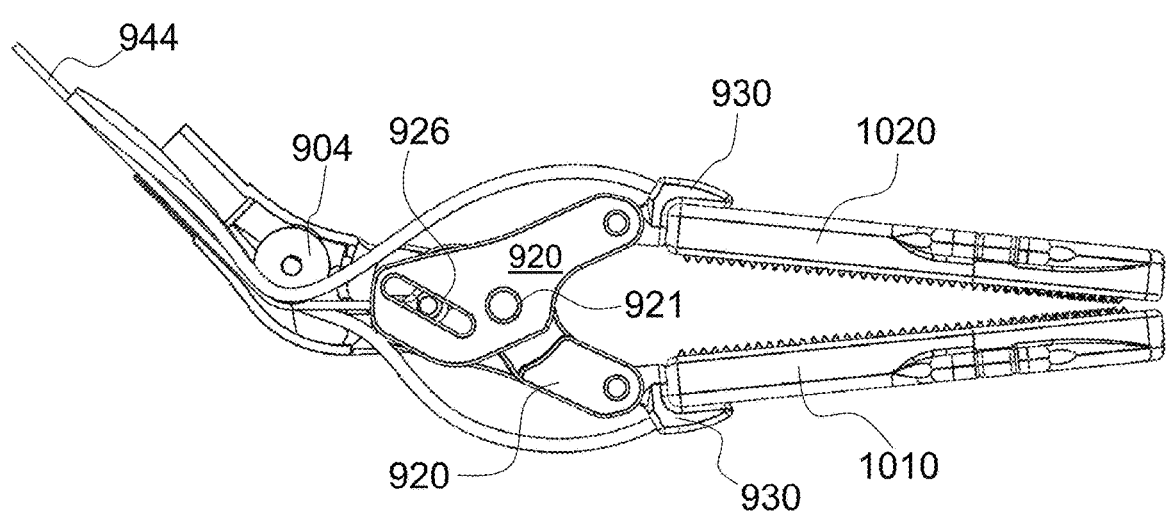
FIG. 98 is a fragmentary, top plan view of the delivery device and clip of FIG. 96.
Figure 99:
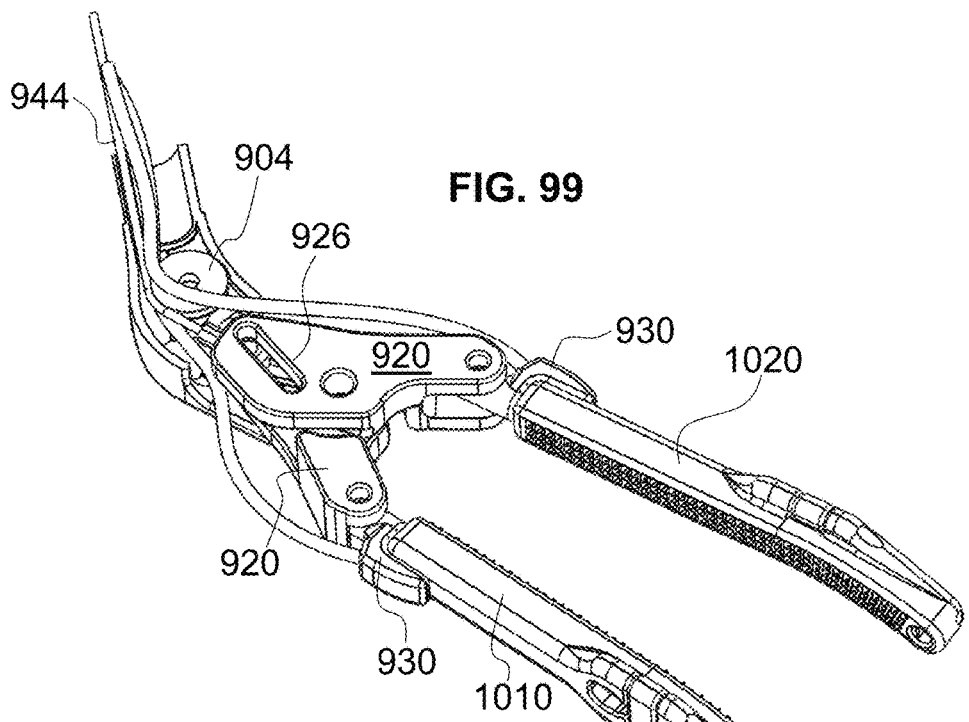
FIG. 99 is a fragmentary, perspective view of the delivery device and clip of FIG. 91 with a top half of the clevis and shaft removed in a clip-fully-opened orientation.
Figure 100:
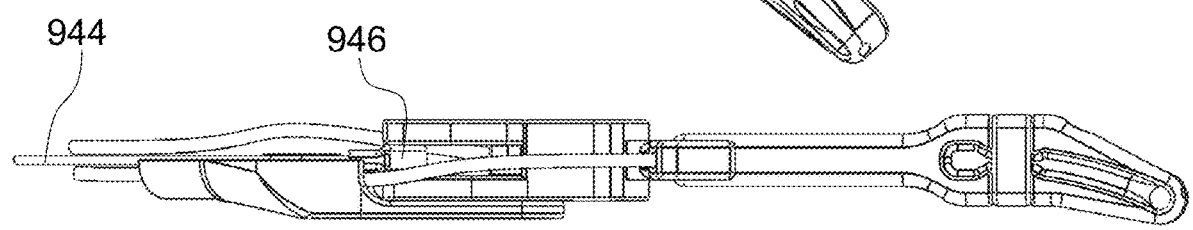
FIG. 100 is a fragmentary, side elevational view of the delivery device and clip of FIG. 99.
Figure 101:
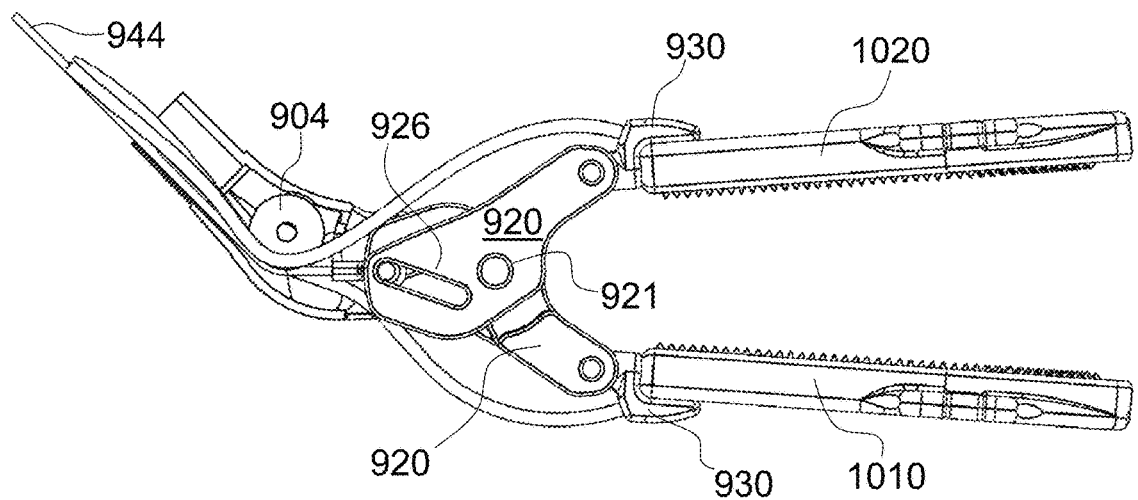
FIG. 101 is a fragmentary, top plan view of the delivery device and clip of FIG. 99.
Figure 102:
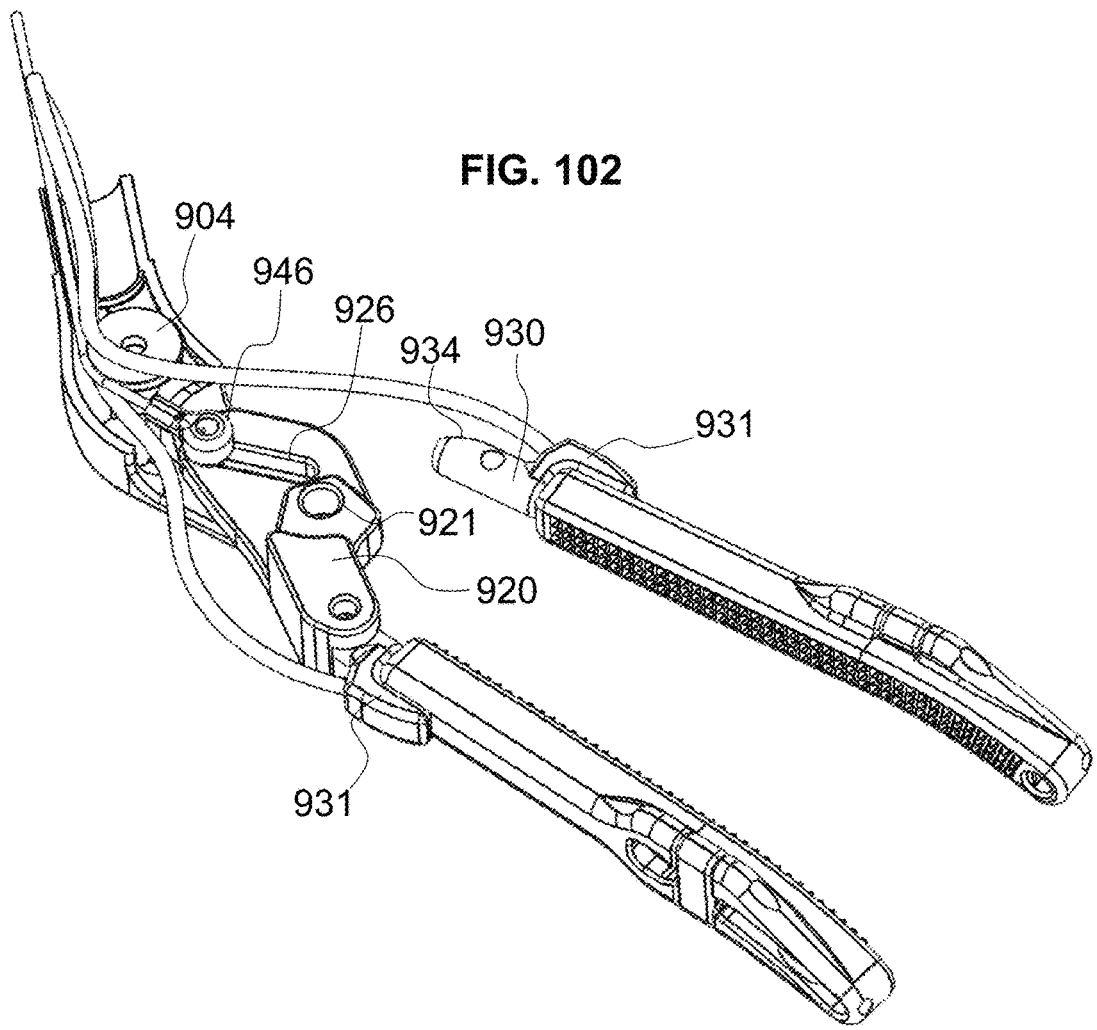
FIG. 102 is a fragmentary, perspective view of the delivery device and clip of FIG. 99 with an upper jaw removed in the clip-fully-opened orientation.
Figure 103:
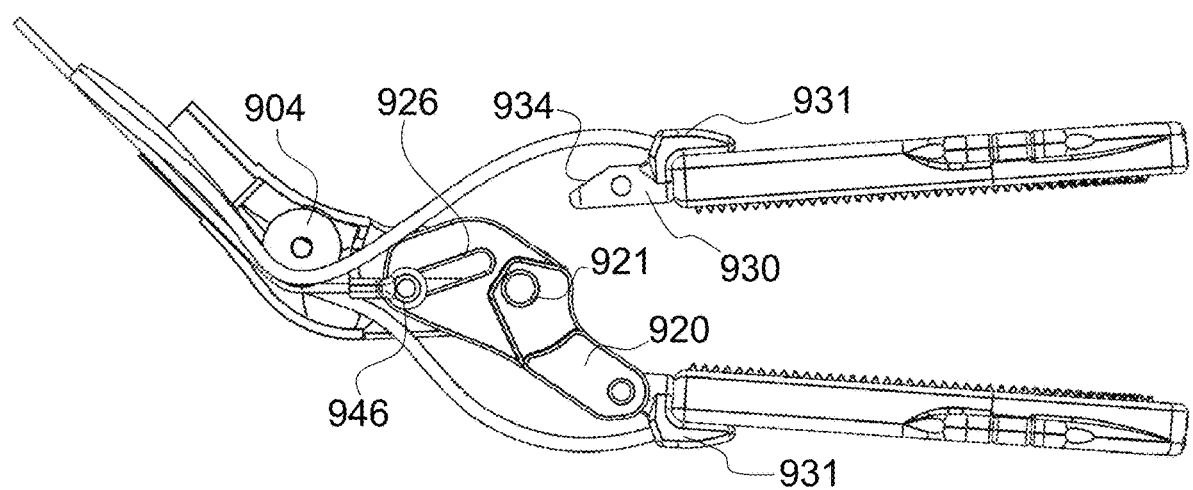
FIG. 103 is a fragmentary, top plan view of the delivery device and clip of FIG. 102.
Figure 104:
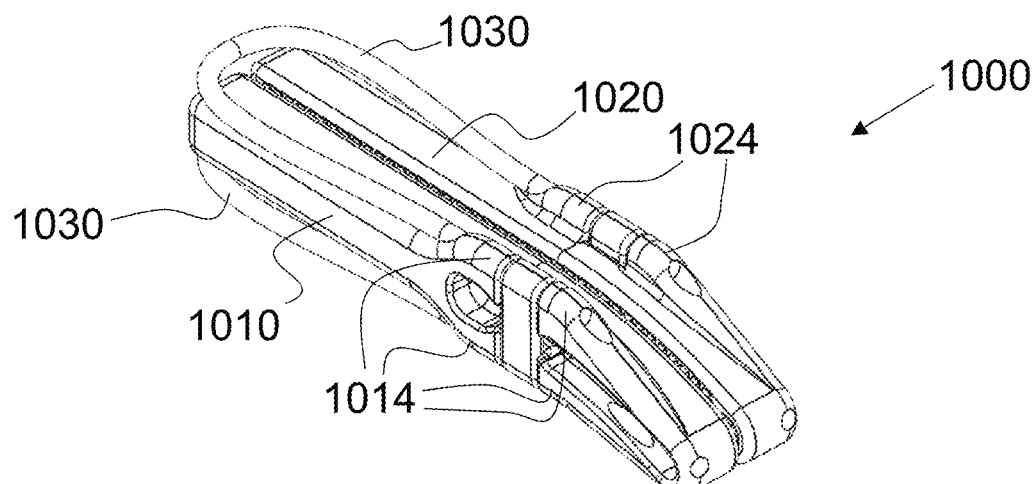
FIG. 104 is a perspective view of the clip of FIG. 91 in a clip-fully-closed orientation.
Figure 105:
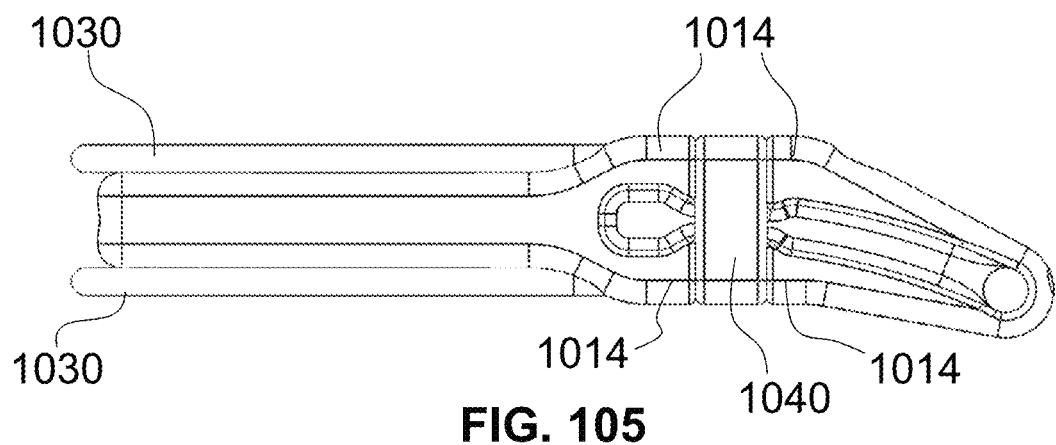
FIG. 105 is a side elevational view of the clip of FIG. 104.

Opening and closing of the jaws 920 and, therefore, opening and closing of the clip 1000, is explained with regard to a progression from FIG. 93 to FIG. 101. A jaw control wire 944 extends from the proximal handle of the delivery device 900 through the shaft 902, around a pulley 904, and is fixed at a distal wire end to a jaw control collar 946. The pulley 904 is connected to the clevis 912 through a pulley axle, which is not illustrated, and rotates about the pulley axle to allow the jaw control wire 944 to move around the pulley 904. The collar 946 at the end of the jaw control wire 944 surrounds a jaw control pin 948, illustrated only diagrammatically in FIG. 92 with a dashed line, and is fixed to the jaw control pin 948, for example, by press-fit, welding, soldering, brazing. The jaw control pin 948 is sized and shaped to slide within a pivot control slot 926 of each of the jaws 920. The jaw control pin 948 is also sized and shaped to slide with a pin guide slot 913 present on each side of the clevis 912 within the side flanges 916, as shown in FIG. 91 (the pin guide slot 913 is not shown in FIGS. 93 to 101 as the upper half of the clevis 912 is removed in these figures for clarity). The pin guide slot 913 is oriented parallel to the central longitudinal axis 1002 of the clip 1000 and, in this exemplary embodiment, is collinear as shown in FIG. 91. The opposite ends of the jaw control pin 948 respectively slide within the pin guide slots 913 of the side flanges 916 and, in the exemplary embodiment, do not extend out from the pin guide slot 913 past the outer sides of the flanges 916 to keep the size of the clevis 912 as small as possible. Accordingly, movement of the jaw control wire 944 in the proximal or distal directions causes the jaw control pin 948 to move along the central longitudinal axis 1002 proximally or distally, respectively. This movement, which corresponds to movement of the jaw control collar 946, can be seen by the placement of the jaw control collar 946 in FIGS. 94, 97, and 100. In contrast to the pin guide slot 913 in the clevis 912, the pivot control slots 926 of the jaws 920 are oriented at an angle β to the central longitudinal axis 1002, as shown in FIG. 95. Thus, with the clevis 912 fixed to the shaft 902 and the jaws 920 pivotally connected to the clevis 912 through the jaw pivot axle, when the jaw control pin 948 is located at the distal end of the pin guide slot 913, as shown in FIGS. 93 to 95, the clip 1000 is in a fully closed orientation. In comparison, when the jaw control pin 948 is located at the proximal end of the pin guide slot 913, as shown in FIGS. 99 to 101, the clip 1000 is in a fully open orientation. Movement of the jaw control pin 948 from the distal end of the pin guide slot 913 towards the proximal end of the pint guide slot 913 will cause the clip 1000 to open in a selective manner from fully closed, to partially closed (proximal end open but distal end closed), to partially open (struts separated and possible parallel to one another), to fully open (struts separated and at an angle to one another with the distal end of the clip 1000 open further than the proximal end).

With this exemplary configuration, an exemplary procedure for implanting the clip 1000 on an LAA in an open chest procedure can be carried out. In describing the procedure, the terms related to the LAA will be simplified. The LAA has a medial long axis that is against the heart and is referred to as a juxta-cardia side. This side of the LAA will be simplified and referred to herein as the inside. The lateral axis of the LAA is referred to as the free axis and that side is the free wall. This side of the LAA will be simplified and referred to herein as the outside.

Figure 96:
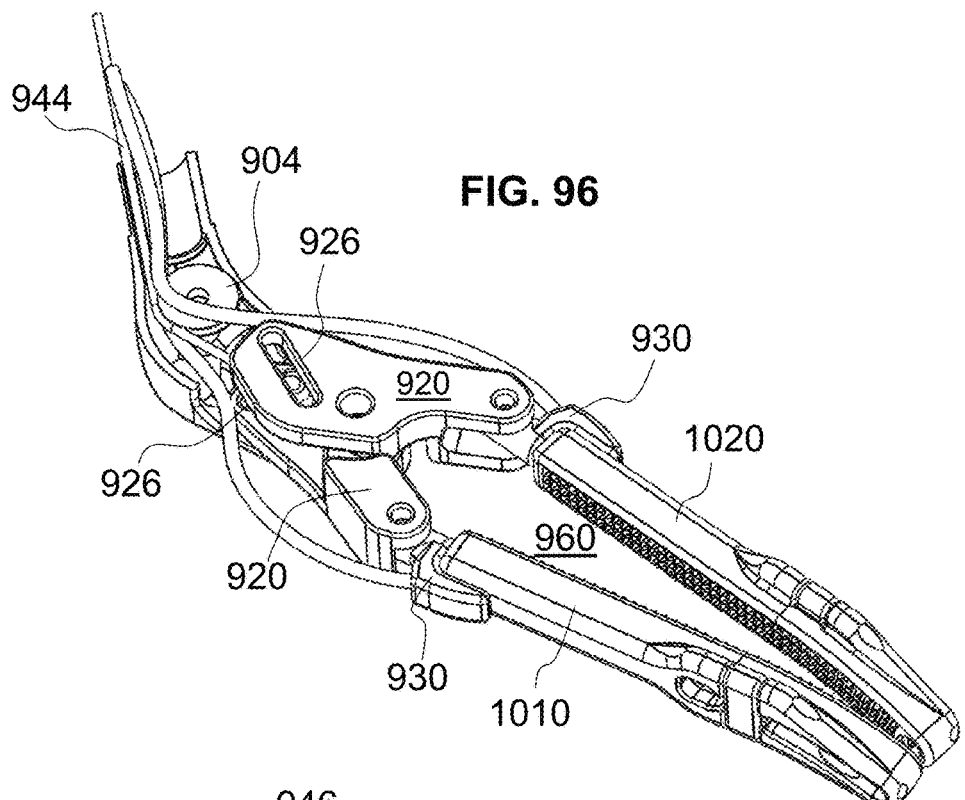
FIG. 96 is a fragmentary, perspective view of the delivery device and clip of FIG. 91 with a top half of the clevis and shaft removed in a clip-distal end-closed orientation.

The end effector 910 is maneuvered to the LAA. The surgeon can move the end effector 910 to the LAA in the closed orientation of FIGS. 93 to 95 or in a fully opened orientation shown in FIGS. 99 to 101. In the latter orientation, the surgeon does not need to open the clip 1000 before maneuvering the clip 1000 around the LAA. In the former orientation, the surgeon opens the clip 1000 (e.g., to the orientation shown in FIGS. 99 to 101) by actuating the jaw opening assembly at the handle of the delivery device 900, which pulls on the jaw control wire 944 to open the jaws 920 and, therefore, to move the struts 1010, 1020 away from one another. If the inside of the LAA is able to be maneuvered away from the left atrium, the surgeon uses a manipulator to lift the LAA and place the strut 1010 on the inside of the LAA and place the strut 1020 on the outside of the LAA. In instances where one or more adhesions prevent movement of the LAA, then the surgeon slides one of the struts 1010, 1020 (e.g., strut 1010) under the inside of the LAA so that the strut 1010 can be placed at the base of the LAA on the inside with the strut 1020 placed at the base of the LAA on the outside of the LAA. When the struts 1010, 1020 are placed at the base of the LAA, the surgeon actuates a closing of the clip 1000, which moves the jaw control wire 944 distally and, in turn, moves the jaw control pin 948 distally. Movement of the jaw control pin 948 causes the jaws 930 to close as shown in FIGS. 96 to 98. Because the strut pins 930 are pivoted to the outermost open orientation pivot (as shown in FIG. 92), this closing of the jaws 920 causes the distal ends of the struts 1010, 1010 to approach one another and touch first (which state shown in FIGS. 96 to 98. Ideally, when closing, the distal ends of the struts 1010, 1020 are located past the distal extent of the base of the LAA and, therefore, the clip 1000 completely spans the base of the LAA and is enclosed within the interior space 960 of the clip 1000. The surgeon causes the further closing of the clip 1000 by continuing to actuate the delivery device 900, which actuation moves the jaw control pin 948 to the distal end of the pin guide slot 913. This state is depicted in FIGS. 93 to 95. At this stage, the surgeon has closed the clip 1000 upon the base of the LAA and can determine if implantation of the clip 1000 is satisfactory, for example, with TEE. If the implantation is not satisfactory, then the surgeon opens the clip 1000 and repositions the clip 1000 on the base of the LAA. If implantation is satisfactory, then the surgeon actuates the clip release assembly of the delivery device 900, which causes the locking wires to retract from the locking lumen 933 as explained herein. When the locking wires have retracted out from the struts 1010, 1020, slight movement of the delivery device 900 will allow the clip 1000 to slip off of the strut pins 930 and, thereby, off of the end effector 910.

Figure 106:
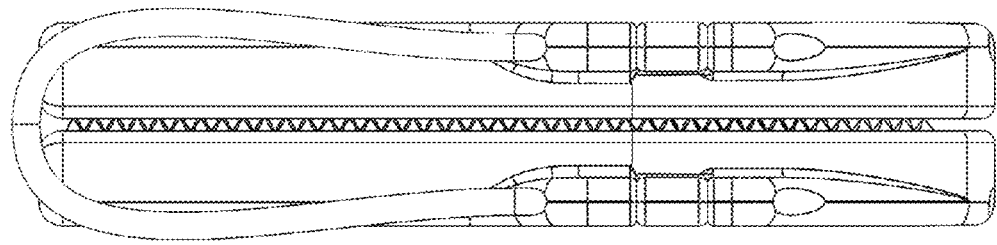
FIG. 106 is a top plan view of the clip of FIG. 104.
Figure 107:
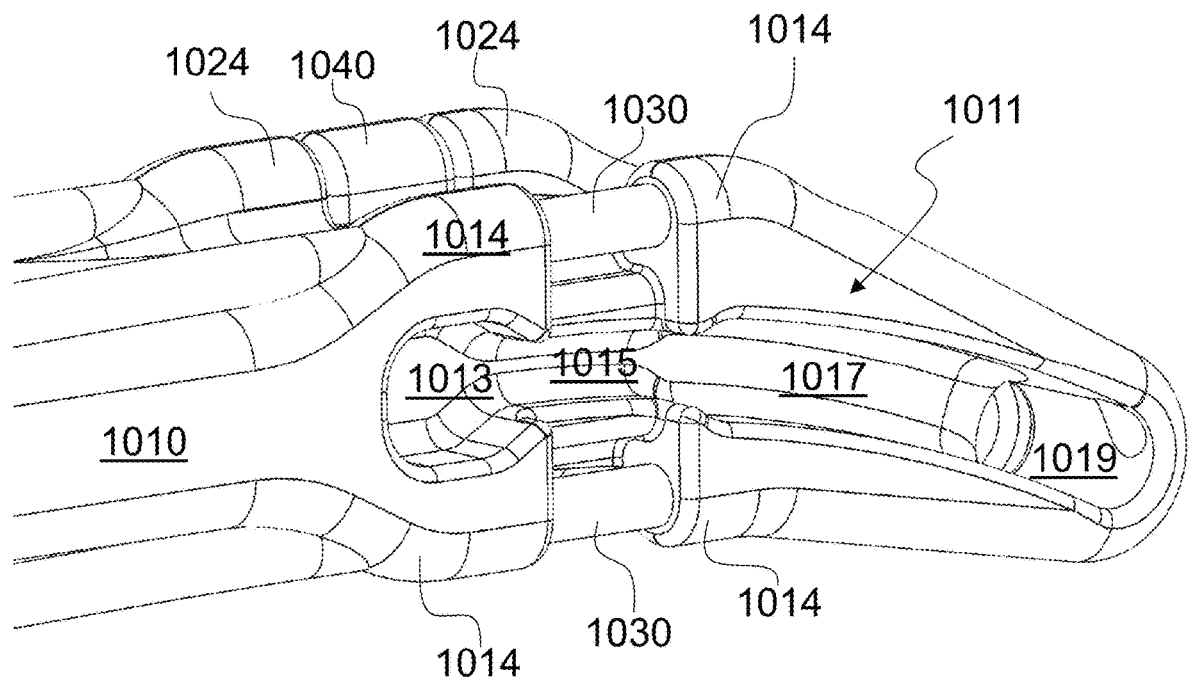
FIG. 107 is a fragmentary, enlarged, perspective view of the clip of FIG. 104.
Figure 108:
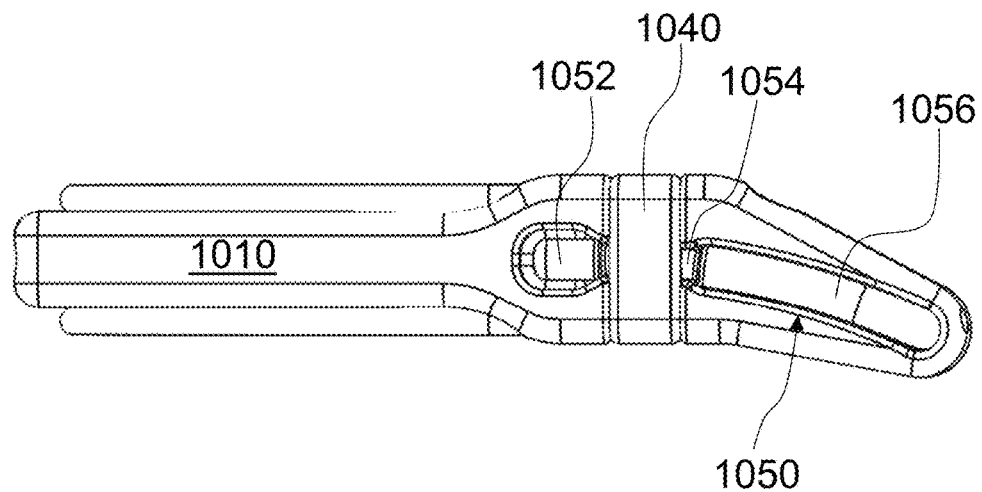
FIG. 108 is a side elevational view of the clip of FIG. 104 with an exemplary embodiment of a convertible band.
Figure 112:
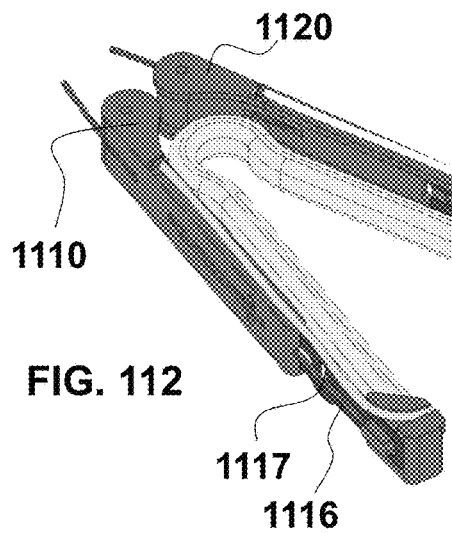
FIG. 112 is a perspective distal side view of an exemplary embodiment of end effector jaws with a closed-end sensor for installing a tissue-occlusion clip with the jaws in an open orientation, with the sensor in a jaw-open sensing state, with the clip in an open orientation loaded within the jaws, and with the clevis, shaft, and handle not illustrated.
Figure 113:
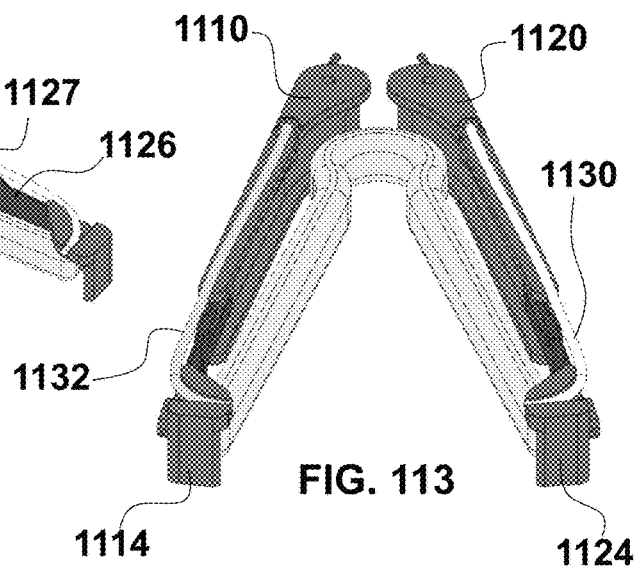
FIG. 113 is a perspective view of the end effector jaws and clip of FIG. 112 viewed from a distal end thereof.
Figure 114:
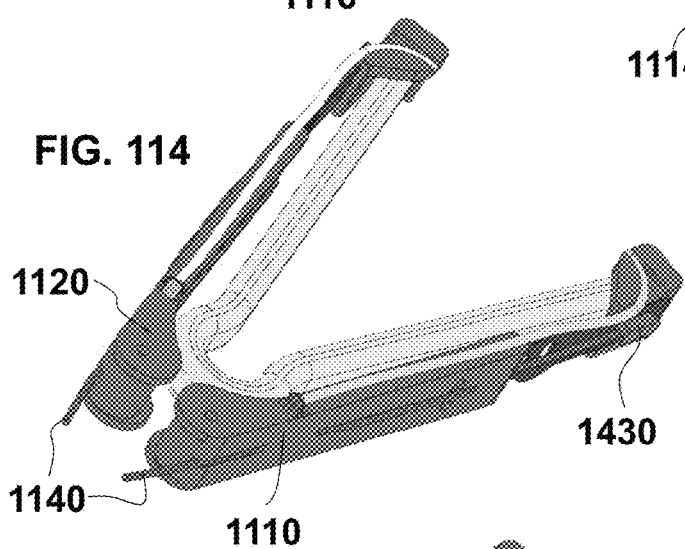
FIG. 114 is a perspective view of the end effector jaws and clip of FIG. 112 viewed from a side of a proximal end thereof.
Figure 115:
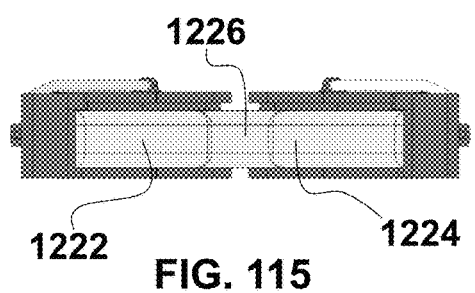
FIG. 115 is a distal elevational view of the end effector jaws and clip of FIG. 112.
Figure 118:
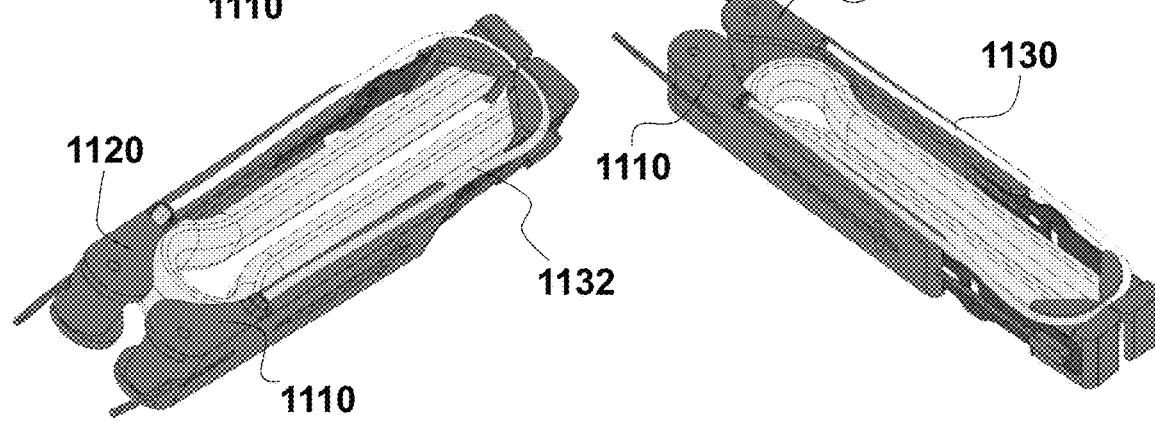
FIG. 118 is a perspective view of the end effector jaws and clip of FIG. 112 viewed from a side of a proximal end thereof with the jaws in a closed orientation, with the clip in a tissue-occluding state, and with the sensor in a jaw-closed sensing state.
Figure 119:
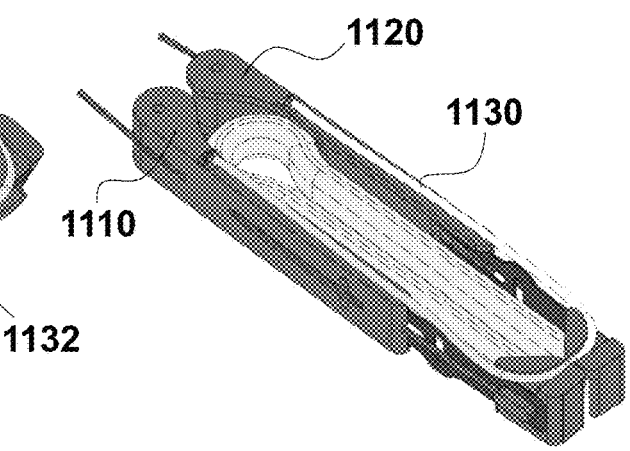
Figure 116:
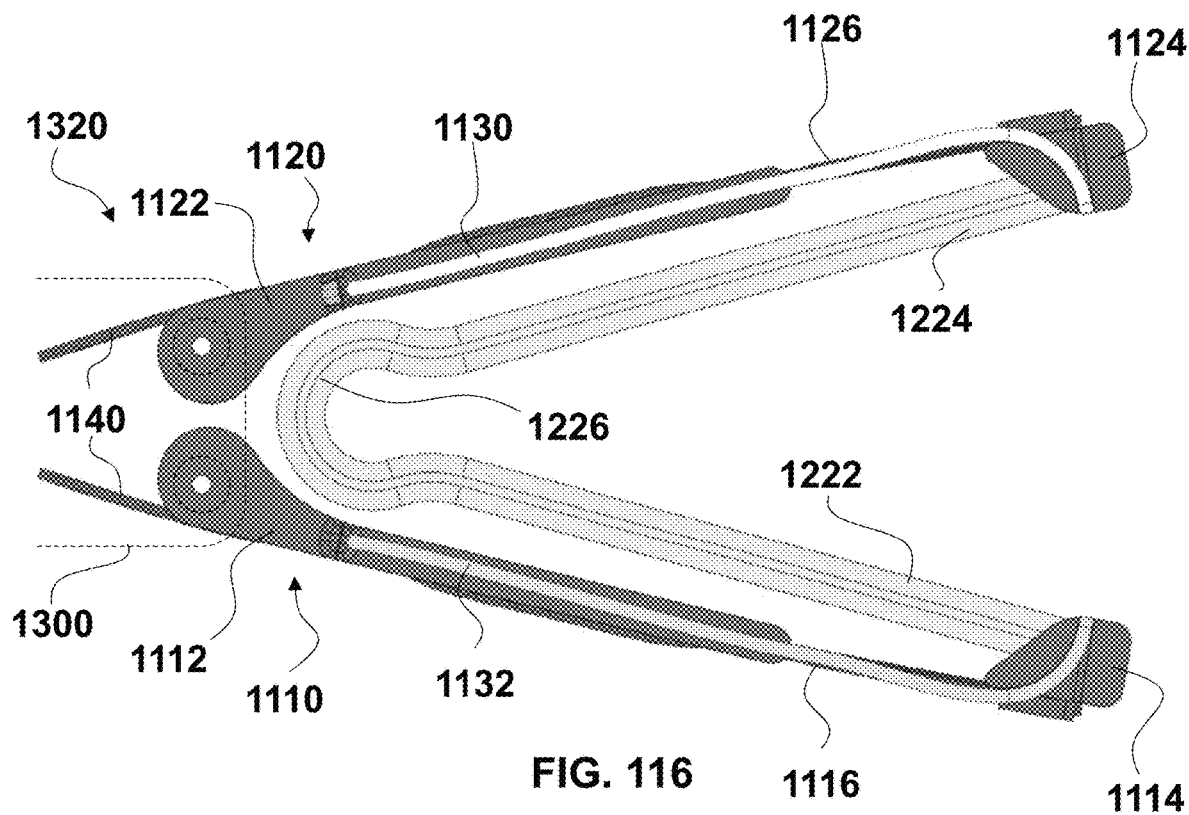
FIG. 116 is a top plan view of the end effector jaws and clip of FIG. 112.
Figure 117:
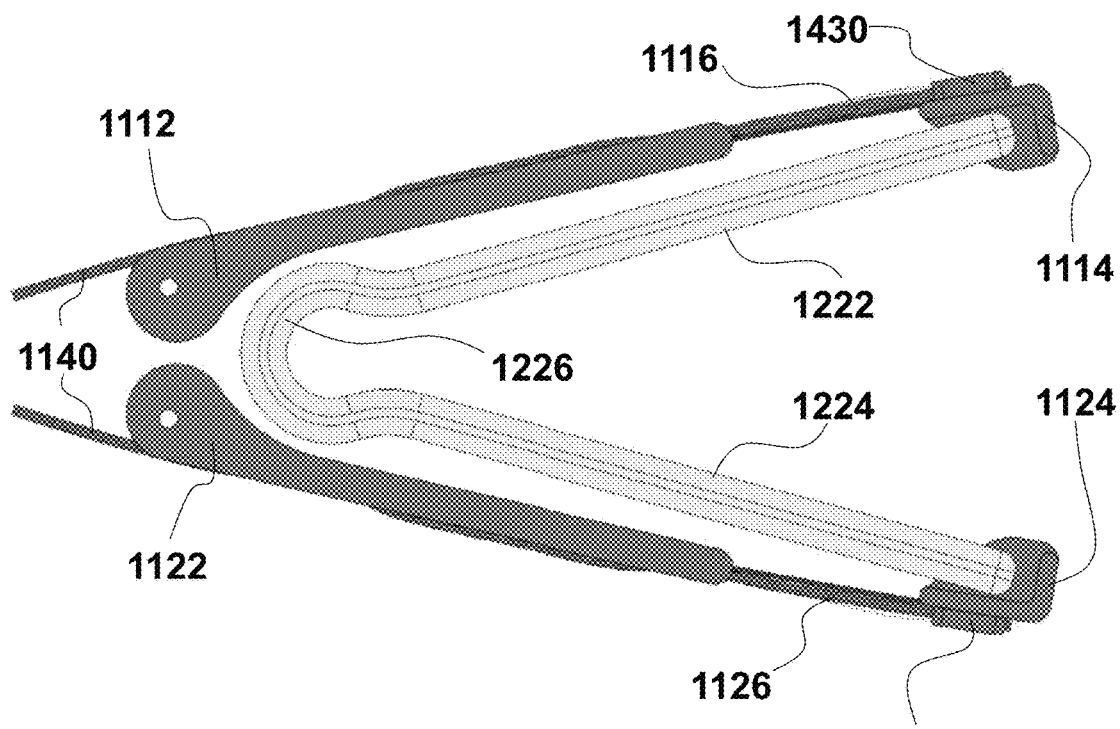
FIG. 117 is a bottom plan view of the end effector jaws and clip of FIG. 112.

FIGS. 104 to 108 illustrate the clip 1000 with the bias device 1030 on both the top and bottom of the struts 1010, 1020. The first and second bias anchors or bias device connectors 1014, 1024 are integral to the struts 1010, 1020 in this exemplary embodiment. The bias device 1030 is fixed to the struts 1010, 1020 by the first and second bias anchors 1014, 1024. In the exemplary embodiment, ends of the upper and lower bias devices 1030 are press-fit or attached to the bias anchors 1014, 1024, which are in the form of ports facing the proximal ends of the struts 1010, 1020. The bias anchors 1014, 1024 are, as shown in FIG. 107, formed from a front part and a back part with the bias devices 1030 extending through the front part, between and across the front and back parts, and into the back part. The bias devices 1030 can be fixed to the struts 1010, 1020 in either or both of the front and back parts. The span between the front and back parts of the bias anchors 1014, 1024 defines a connection space in which a band anchor 1040 is attached, in this example, to the portions of the upper and lower bias devices 1030 that span the front and back parts. In this configuration, therefore, the band anchor 1040 can be in the form of a C-shaped clip that can be connected to the portions of the upper and lower bias device 1030 temporarily or permanently. A band capture passage 1011 is formed in the outside surfaces of the struts 1010, 1020. The band capture passage 1011 has a proximal band anchor well 1013, an intermediate band locking passage 1015, a distal band passage 1017, and a terminal band passage 1019. The proximal band anchor well 1013 transitions into the intermediate band locking passage 1015 and has a width that is larger than the intermediate band locking passage 1015. The distal band passage 1017 continues the band capture passage 1011 from the intermediate band locking passage 1015 and, in the exemplary embodiment, has approximately the same width as the proximal band anchor well 1013. Thus, the intermediate band locking passage 1015 is narrower than the portions of the band capture passage 1011 immediately proximal and distal thereof. The distal band passage 1017 continues into the terminal band passage 1019, which is at an angle to the distal band passage 1017, in particular, approximately orthogonal thereto, to form an approximately 90-degree bend inwards from the outside surface and extending completely to the inside surface of the struts 1010, 1020.

In another exemplary embodiment of the bias device 1030 increases the inwards (clip-closing) force applied to the clip struts. In such an embodiment, the profile of the spring(s) 1030 is/are modified such that the end legs cross one another, creating a partial "figure-8" shape. Such a configuration provides a preload force between the clip struts that is proportional to an extent to which the end legs are crossed. To maintain a torque balance between the upper and lower springs 1030 in such a configuration, one spring has a left-over-right leg cross and the other spring has a right-over-left leg cross. Placing the springs in this mirror image cancels out any torque induced on the clip struts that would otherwise cause the clip struts to twist. To move a force balance point to a center of the longitudinal axis of the clip strut, the legs of the spring 1030 can be angled further relative to the U-portion, providing a biasing force to one end or the other of the clip strut.

Extending through the band capture passage 1011 is a convertible band 1050, depicted in FIGS. 108 to 111. The band 1050 is referred to as convertible because it is used to convert the clip 1000 from a closed-end clip (in which both the proximal and distal ends are closed to form a loop) to an open-end band (in which only the proximal end is closed and forms approximately a U-shape) as described in further detail below. From one end to the other, the band 1050 has a first enlarged band end 1052, a first reduced band locking portion 1054, an intermediate band portion 1056, a second reduced band locking portion 1054, and a second enlarged band end 1052. The proximal band anchor well 1013 is configured and shaped to hold the first enlarged distal band end 1052. The first reduced band locking portion 1054 is configured and shaped to hold the first reduced band locking portion 1054. The distal band passage 1017 and the terminal band passage 1019 are configured and shaped to hold the intermediate band portion 1056 to bend the band 1050 around the corner formed by the junction of the distal band passage 1017 and the terminal band passage 1019. The band capture passage 1021 is a mirror image of the band capture passage 1011 and, therefore, is not further described. The band capture passage 1021 holds the second reduced band locking portion 1054 and the second enlarged band end 1052 in the same way that the band capture passage 1011 holds the first reduced band locking portion 1054 and the first enlarged band end 1052. Alternatively, the band anchor 1040 can have protrusions such as barbs and teeth, that extend toward the band 1050 and pierce or pinch the band as it is installed. This has the benefit that the band 1050 can all be of a uniform diameter for easier fabrication and installation.

The band 1050 is made of a material that is at least partially elastic. Therefore, when the delivery device 900 expands the clip 100, at least the intermediate band portion 1056 stretches to accommodate the enlarged span between the distal ends of the clip 1000. When present, the clip 1000 is closed on both ends, as shown in FIG. 109, for example. The band 1050 is able to impart an inwards bias to the distal ends of the struts 1010, 1020 when implanted on the LAA. In this orientation, the clip 1000 forms a complete ring around the LAA. If the LAA is not able to be inserted in this closed state, the band 1050 can be cut between the two struts 1010, 1020 and, if stretched, the two cut ends of the band 1050 will spring into the distal and terminal band passages 1017, 1019.

The clips described herein provide a clipping assembly (e.g., 610-620, 1010-1020) and a bias assembly (e.g., 632, 1030). The clipping assembly comprises first and second opposing clip struts (e.g., 610-620, 1010-1020). Each of the clip struts has a tissue-contacting surface, which in an exemplary embodiment is the side facing the LAA. Each of the clip struts has first and second bias surfaces. The bias assembly connects the first clip strut to the second clip strut to align the first and second clip struts in a strut plane, which passes through the tissue-contacting surfaces. The bias assembly comprises one or more first bias springs (e.g., 632, 1030) connected on one side to the first bias surface of the first clip strut and on the other side to the first bias surface of the second clip strut. The bias assembly also comprises one or more second bias springs (e.g., 632, 1030) connected on one side to the second bias surface of the first clip strut and on the other side to the second bias surface of the second clip strut. In this manner, the first and second bias springs allow the first and second clip struts to move in the strut plane, for example, in a yaw motion that is shown, for example in the progression of FIGS. 86 to 89 and from FIGS. 91, 93, 96, and 99. Another way of describing this is that the bias assembly is configured to permit yaw movement of the first and second clip struts in the strut plane. The yaw movement of the first clip strut in the strut plane can be independent of yaw movement of the second clip strut in the strut plane.

Due to the positions of the bias assembly, the first and second bias springs balance forces such that the first and second clip struts undergo substantially no rotation about respective longitudinal axes when the first and second struts move in the strut plane. The first and second bias springs balance forces such that the first and second clip struts have substantially no torque when the first and second struts move in the strut plane.

The first clip strut has a first proximal end and a first distal end and the second clip strut has a second proximal end and a second distal end. In an exemplary embodiment, the first bias spring is connected to an intermediate position at the first bias surface of the first clip strut between the first proximal end and the first distal end and to an intermediate position at the first bias surface of the second clip strut between the second proximal end and the second distal end. Similarly, the second bias spring is connected to an intermediate position at the second bias surface of the first clip strut between the first proximal end and the first distal end and to an intermediate position at the second bias surface of the second clip strut between the second proximal end and the second distal end.

The first bias surface of the first clip strut can be a first upper side, the second bias surface of the first clip strut can be a first lower side, the first bias surface of the second clip strut can be a second upper side, and the second bias surface of the second clip strut can be a second lower side. The tissue-contacting surface of the first clip strut can be a first LAA contacting surface having a first longitudinal centerline and the tissue-contacting surface of the second clip strut can be a second LAA contacting surface having a second longitudinal centerline and the strut plan passes through the first and second longitudinal centerlines.

The clips described herein are, for example, sized to fit into a laparoscopic port having an interior diameter. In this regard, the clipping assembly and the bias assembly together have a maximum outer width that is no greater than the interior diameter of that port.

The first and second clip struts have a maximum longitudinal length and the first and second bias springs have a longitudinal length shorter than the maximum longitudinal length, for example, shown in FIGS. 88 and 106. As shown in these figures (e.g., FIGS. 86 to 89), the first upper side and the second upper side of the struts together define an outer upper boundary with the first bias spring remaining substantially within the outer upper boundary. Likewise, the first lower side and the second lower side together define an outer lower boundary with the second bias spring remains substantially within the outer lower boundary. As shown in FIGS. 86 to 89, for example, the delivery device (860, 862, 870) removably connects to first and second proximal ends of the struts and moves the first and second clip struts in the strut plane. The first and second clip struts move independently in the strut plane. As shown in FIGS. 86 to 89 and FIG. 92, the delivery device is removably connected to the proximal ends through first and second proximal openings. In an exemplary embodiment, the delivery device is removably connected only to the first and second proximal ends through the first and second proximal openings.

FIGS. 112 to 128 illustrate an exemplary embodiment of a surgical instrument having an end effector with various aspects of tissue-crossing sensors for jaw-based surgical instruments that give the surgeon greater precision and control over placement of a distal end of a jaw when that distal end is obscured or blocked by the surgical environment (e.g., angle of view and/or tissue) and with embodiments of jaws to hold and deploy a tissue-occlusion clip (e.g., an LAA exclusion clip). The sensors are particularly beneficial for LAA exclusion clips having a closed proximal end and an open distal end. This is because the sensors provide information to a surgeon that the LAA exclusion clip completely traverses the length of the LAA and, when closed, there is no tissue ejected out from the far (distal) end of the LAA exclusion clip that would fail to be incorporated within the clip when the clip is finally implanted (tissue ejection is a condition similar to the action of a toothpaste tube where at least a portion of the LAA is squeezed out from the distal end of the clip during closure).

FIGS. 112 to 124 illustrate a surgical end effector (e.g., an applicator head) in the exemplary embodiment of a jaw 1100 having an exemplary embodiment of an LAA exclusion clip 1200 loaded therein. FIGS. 112 to 116 illustrate the jaw 1100 and the clip 1200 in an open orientation and FIGS. 117 to 124 illustrated the jaw 1100 and the clip 1200 in a closed orientation. A distal end of an exclusion clip applicator 1300 is illustrated diagrammatically in FIG. 116 with dashed lines and is connected to the proximal ends of the jaws at a pivot assembly 1310. The pivot assembly 1310 includes a clevis 1312 pivotably attached to the jaw 1100 and attached (either fixedly or with articulation) to the distal end of a shaft 1314. Other proximal components of the applicator 1300 include a non-illustrated handle. As can be seen, the opposing first and second jaws 1110, 1120 are connected individually to the pivot assembly 1310, permitting them to pivot relative to each other. The pivot assembly 1310 is actuated by a non-illustrated control on the handle.

Each jaw 1110, 1120 comprises a proximal jaw base 1112, 1122, a distal cup member 1114, 1124, and a flexible, intermediate jaw member, 1116, 1126 respectively connecting the proximal jaw base 1112, 1122 to the cup member 1114, 1124. Attached to each of the jaws 1110, 1120 is one part of a fiber optic assembly, comprising a first fiber optic 1130 on one jaw 1110 and a second fiber optic 1132 on the other jaw 1120 (the fiber optics are equally referred to as cables, wires, tubes, and/or lines, for example). In an exemplary passive embodiment of the fiber optic assembly, the first fiber optic 1130 is a collector-type fiber optic and the second fiber optic 1132 is a transmission-type fiber optic, each respectively attached to a top surface of the first jaw 1110 and the second jaw 1120. In alternative exemplary embodiments, the fiber optics 1130, 1132 can be routed through channels in the jaws 1110, 1120 or attached to any surface of the jaws 1110, 1120. In one particular exemplary embodiment, the collector-type wire is coiled around the first jaw 1120 to maximize a length that is exposed to ambient light and, thus, increase the amount of light output by the wire.

Distal or terminal ends of the collector-type 1130 and transmission-type 1132 wires are received respectively by the cup members 1114, 1124 and are disposed so that they are in close proximity to each other when the jaws 1110, 1120 are closed. In a particularly beneficial embodiment, the distal ends of the fiber optics 1130, 1132 have distal surfaces that are parallel to one another, are co-axially aligned with one another, and are very close to one another or touch one another when the jaws are closed. This optimal opposing state is best shown in FIGS. 121 and 123, which respectively illustrate top plan and front perspective views of the end effector in the closed position or state. It is noted that the cup members 1114, 1124 and the distal ends of the fiber optics 1130, 1132 need not be in direct contact for light to be transmitted from one side of the jaw to the other. Depending on the type of wire used for the fiber optic 1130, 1132, light is still transmitted even where there is a gap between the distal ends, which gap can be between approximately 1 mm and approximately 3 mm, or even greater. In the illustrated embodiments, the fiber optics 1130, 1132 are routed and terminated along the respective top surfaces of the cup members 1114, 1124 and the distal ends of the fiber optics 1130, 1132 terminate at opposing symmetric locations on interior faces of the two cup members 1114, 1124. In alternative embodiments, the fiber optics 1130, 1132 are routed through orifices in the middle of the cup members 1114, 1124 or along a bottom surface of the cup members 1114, 1124. In further exemplary embodiments, multiple sets of separately routed fiber optic wires (e.g., through both the top and bottom surfaces of the jaws or in any combination of routes) could be used.

The proximal jaw base 1112, 1122 contains control paths 1113, 1123 that respectively guide clip-release control wires 1140 from the handle to the intermediate jaw member 1116, 1126 (and, thereafter, ending at the distal cup member 1114, 1124). The proximal jaw base 1112, 1122 also contains clip-securing orifices 1111, 1121. The clamping members 1222, 1224 of the clip 1200 are secured removably to a respective one of the proximal jaw bases 1112, 1122 with a proximal clip release device 1410. In the exemplary embodiment, the proximal clip release device 1410 for the jaw base 1112, 1122 is a suture that is wrapped around the clamping member 1222, 1224, passes through an upper portion of the clip-securing orifices 1111, 1121, passes around and outside the clip-release wire 1400 (which passes along and perpendicular to the orifice 1111, 1121), and passes back through a lower portion of the clip-securing orifice 1111, 1121 to be secured to another end of the suture 1410 by, for example, tying one or more knots. This suture 1410 is illustrated, for example, in FIGS. 125 to 128. Thus, when the clip-release control wire 1400 is pulled distally such that the distal end of the clip-release control wire 1400 is retracted proximally past the clip-securing orifice 1111, 1121, the proximal clip release device 1410 no longer holds the clamping member 1222, 1224 to the proximal jaw base 1112, 1122. As shown in FIGS. 112 to 128, the clip-release control wire 1400 of each side of the jaw 1110, 1120 terminates in a wire end block 1430 that is attached, respectively, to each of the cup members 1114, 1124. This wire end block 1430 retains the terminal end of the clip-release control wire until deployment of the clip 1200 is desired. Retention of the clip-release control wire 1400 at the wire end block 1430 can occur in a variety of ways, for example, through a press-fit or with friction fittings.

In contrast to the proximal jaw base 1112, 1122, which is relatively stiff, the intermediate jaw member 1116, 1126 is relatively flexible, which flexibility allows the respective cup member 1114, 1124 to move inwards and outwards with respect to the proximal jaw base 1112, 1122 as the jaw 1100 is moved between its opened and closed positions. Like the proximal jaw base 1112, 1122, the intermediate jaw members 1116, 1126 each have a clip-securing orifice 1117, 1127. The clamping members 1222, 1224 of the clip 1200 are secured removably to a respective one of the intermediate jaw members 1116, 1126 with a distal clip release device 1440. In the exemplary embodiment, the distal clip release device 1440 is a suture that is wrapped around the clamping member 1222, 1224, passes through an upper portion of the clip-securing orifices 1117, 1127, passes around and outside the clip-release wire 1400 (which passes along and perpendicular to the orifice 1117, 1127), and passes back through a lower portion of the clip-securing orifice 1117, 1127 to be secured to another end of the suture 1440 by, for example, tying one or more knots. This distal suture 1440 is illustrated, for example, in FIGS. 125 to 128. Thus, when the clip-release control wire 1400 is pulled distally such that the distal end is retracted proximally past the clip-securing orifice 1117, 1127, the clip release device 1440 no longer holds the clamping member 1222, 1224 to the intermediate jaw member 1116, 1126.

The distal cup member 1114, 1124, as shown enlarged in FIG. 124, has a ceiling 1115, 1125, a distal wall 1118, 1128 substantially perpendicular to the ceiling 1115, 1125 at the distal end of the cup member 1114, 1124, and a side wall 1119, 1129 substantially perpendicular to the both ceiling 1115, 1125 and the distal wall 1118, 1128. These three walls of each of the cup members 1114, 1124 form a respective cup in which the distal end of the clamping members 1222, 1224 of the clip 1200 reside while attached to the jaw 1100.

FIGS. 125 to 128 illustrate the attachment of the LAA exclusion clip 1200 to the applicator head by, for example, wrapping sutures 1410, 1440 around the clip-release control wires 1400. To detach the clip 1200 from the jaw 1100, the clip-release control wires 1400 are pulled proximally through, for example, a pull tab in the handle and are, thereby dislodged from the wire end blocks 1430. The clip-release control wires 1400 are then removed from most or all the jaw 1100 to free the sutures 1410, 1440 and detach the clip 1200 from the jaw 1100.

In an exemplary embodiment, the terminal ends of the fiber optics 1130, 1132 are placed slightly proximally or distally of the respective terminal ends of the parallel clamping members 1222, 1224 of the exclusion clip 1200. The position of the fiber relative to the tip of the clamping member determines how much overlap between the end of the clip and the detected tissue is desired. It may be desirable, for example, that a length of the clip extend distally past the fiber optic so that a greater safety margin of overlap is created. In an exemplary embodiment, the fiber optics 1130, 1132 extend inwards past respective inner surfaces of the clamping members 1222, 1224 of the clip 1200 to accommodate for the distance between the clamping members 122, 1224 when tissue is disposed therebetween. The thickness is, generally approximately 3 mm+/−1 mm but the distance can accommodate 4 mm to 6 mm), which is typical for the thickness of a LAA after clamping. With such an inward extension, the two ends of the fiber optics 1130, 1132 are substantially orthogonal.

In an exemplary embodiment of the applicator for the exclusion clip with the distal tip sensor, the applicator comprises a handle housing one or more controls, an applicator head, an elongated shaft having a proximal end and a distal end, the proximal end being coupled to the handle and the distal end being coupled to the applicator head. The applicator head comprises first and second elongated jaw members each having a proximal end and a distal end, the proximal ends of the first and second elongated jaw members are pivotally connected. The pivot connection can be to one another or to the clevis separately. The first and second elongated jaw members each comprise cup members at distal ends thereof. Flexible members connect the distal ends of the jaw members to the proximal ends of the cup members. In an exemplary passive optical embodiment, a first fiber optic wire is disposed on the first elongated jaw member, the first fiber optic wire having two ends and a length, and collects light along its length and outputs the collected light through its ends. At least one of the ends of the first fiber optic wire is disposed at or in the cup member of the first elongated jaw member. A second fiber optic wire is disposed on the second elongated jaw member, the second fiber optic wire having two ends and being adapted to collect light at one of the ends and output the collected light at the other end. The collecting end of the second fiber optic wire is disposed at or in the cup member of the second elongated jaw member. The output end of the second fiber optic wire is disposed proximally from the cup member of the second elongated jaw member in a position that is either visible by the operator of the applicator or is forwarded to a light sensor either in the clevis, the shaft, or the handle to detect light automatically and indicate to the user that the jaws and/or the cup members are aligned and unobstructed. The first and second elongated jaw members are operably pivoted between a closed position and an open position through actuation of a control on the handle. Upon pivoting of the first and second elongated jaw members into a closed position, the at least one end of the first fiber optic wire and the collecting end of the second fiber optic wire are placed in close proximity. Upon pivoting of the first and second elongated jaw members into a closed position, the light collected by the first fiber optic wire is transmitted to the second fiber optic wire and is output at the output end of the second fiber optic wire. In an exemplary configuration, the collecting fiber optic is green in color and, therefore, the light that is incident along an external surface of the fiber passes into the fiber and is directed along its axis. Because of the material's color, green light would be what is collected and transmitted. The transmitting fiber, in comparison, is clear and, therefore, when the two fiber optics are brought together, the green light exits the end of the green fiber and passes into the clear fiber when the ends are aligned and not blocked by tissue. This light is transmitted through the clear fiber and shines out from the proximal end of the fiber optic so that it that can be visualized by an operator/surgeon. If the operator sees green color light coming out of the clear fiber, there is surety that nothing is blocking the opposing transmission ends of the fibers and, therefore, the fastener has extended completely past the tissue that is to be clamped. Alternatively, both fiber optics could be clear and extend along the delivery device or possibly even all the way to the handle of the delivery device. A light of any given frequency can be input into the transmitting fiber, which can be steady or pulsed in a particular pattern. When the fiber optics are sufficiently aligned at the distal end of the end effector, the receiving fiber bring the transmitted light back to the shaft/handle where a detector is placed. The detector sees the light and determines if the light is the known transmitted signal. When a positive determination of the transmitted light is confirmed, this signals that the fastener is implanted adequately across the tissue and a user interface, e.g., LED and/or sound and/or haptic feedback alerts the user thereof.

As indicated in exemplary embodiments herein, the clip struts 110, 120, 210, 220, 410, 420 of FIGS. 1 to 51 are substantially rectangular in cross-section. These are only exemplary embodiments. The clip struts 110, 120, 210, 220, 410, 420 can also be circular, ovular, or polygonal in cross-section. Accordingly, the use of first, second, third, and fourth as descriptors of four sides is merely exemplary and is not to be taken as limiting. In an embodiment where the cross-section is circular or ovular, the enumerated sections could be first, second, third, and fourth quadrants, portions, or sides.

Herein, the LAA-contacting pad is described as being of various materials. In an alternative exemplary embodiment, the clip struts 210, 220 can be completely enclosed with a woven sleeve that provides a non-slip surface and promotes tissue in-growth, e.g., it can be made from braided Dacron®. Another alternative to a pad of fabric is a smooth or textured surface or a surface covered with an elastomeric (e.g., polyurethane or polydimethylsiloxane) smooth or textured pad, possibly fitted with self-motivator materials as described above or with features that otherwise enhance traction against the LAA.

Herein, the word "cord" is used with respect to, for example, the control cords 252, 262. This word is meant to be broad and not limited to a particular material or cross-section. The cord refers to any longitudinally extending material that can comprise the structure and function described herein. As defined herein, the term cord is not limited to a single cord; a cord can be a plurality of cords as well. Therefore, cord and cords are used interchangeably. Cords also are not limited to a particular type of material. The material can be made of natural fibers, man-made or synthetic fibers, plastics, and/or metals, to name a few. Cords also are not limited to a particular structure. The material can be made of twisted strands, twisted strands with a central core, or a single strand or wire, to name a few. One exemplary embodiment described herein is a surgical suture. The embodiments described herein, however, are not limited to surgical sutures, even though the example of surgical sutures is referred to or is used herein.

In various instances herein, a hole is referred to as a "blind" hole. Where so indicated, in exemplary alternative embodiments, some of the holes can be through-holes.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the systems, apparatuses, and methods. However, the systems, apparatuses, and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems, apparatuses, and methods as defined by the following claims.

What is claimed is:

1. An external left atrial appendage (LAA) exclusion clip, comprising:
    a clipping assembly comprising first and second opposing clip struts each of the clip struts having:
        a tissue-contacting surface; and
        first and second bias surfaces, the first clip strut having a first proximal end and the second clip strut having a second proximal end;
    a bias assembly connecting the first clip strut to the second clip strut to align the first and second clip struts in a strut plane passing through the tissue-contacting surface, the bias assembly comprising:
        at least one first bias spring connected to the first bias surface of the first clip strut and to the first bias surface of the second clip strut; and
        at least one second bias spring connected to the second bias surface of the first clip strut and the second bias surface of the second clip strut;
    the at least one first bias spring and the at least one second bias spring being configured to permit movement of the first and second clip struts in the strut plane; and
    a delivery device removably connected to the first and second proximal ends and configured to move the first and second clip struts independently in the strut plane.

2. The clip according to claim 1, wherein:
    the first clip strut has a first distal end;
    the second clip strut has a second distal end;
    the at least one first bias spring is connected to:
        an intermediate position at the first bias surface of the first clip strut between the first proximal end and the first distal end; and
        an intermediate position at the first bias surface of the second clip strut between the second proximal end and the second distal end; and the at least one second bias spring is connected to:
  an intermediate position at the second bias surface of the first clip strut between the first proximal end and the first distal end; and
  an intermediate position at the second bias surface of the second clip strut between the second proximal end and the second distal end.

3. The clip according to claim 1, wherein:
the first bias surface of the first clip strut is a first upper side;
the second bias surface of the first clip strut is a first lower side;
the first bias surface of the second clip strut is a second upper side;
the second bias surface of the second clip strut is a second lower side;
the tissue-contacting surface of the first clip strut comprises a first LAA contacting surface having a first longitudinal centerline;
the tissue-contacting surface of the second clip strut comprises a second LAA contacting surface having a second longitudinal centerline; and
the strut plane passes through the first and second longitudinal centerlines.

4. The clip according to claim 1, wherein:
the clip is sized to fit into a laparoscopic port having an interior diameter; and
the clipping assembly and the bias assembly together have a maximum outer width that is no greater than the interior diameter of the port.

5. The clip according to claim 1, wherein:
the first and second clip struts have a maximum longitudinal length;
the at least one first bias spring has a longitudinal length shorter than the maximum longitudinal length; and
the at least one second bias spring has a longitudinal length shorter than the maximum longitudinal length.

6. The clip according to claim 1, wherein:
the clip is sized to fit into a laparoscopic port having an interior diameter;
the clipping assembly and the bias assembly together have a maximum outer width that is no greater than the interior diameter of the port;
the first and second clip struts have a maximum longitudinal length;
the at least one first bias spring has a longitudinal length shorter than the maximum longitudinal length; and
the at least one second bias spring has a longitudinal length shorter than the maximum longitudinal length.

7. The clip according to claim 1, wherein the bias assembly is configured to permit yaw movement of the first and second clip struts in the strut plane.

8. The clip according to claim 1, wherein the bias assembly is configured to permit yaw movement of the first clip strut in the strut plane independent of yaw movement of the second clip strut in the strut plane.

9. The clip according to claim 1, wherein:
the first bias surface of the first clip strut is a first upper side;
the first bias surface of the second clip strut is a second upper side;
the first upper side and the second upper side together define an outer upper boundary; and
the first bias spring remains within the outer upper boundary.

10. The clip according to claim 1, wherein:
the second bias surface of the first clip strut is a first lower side;
the second bias surface of the second clip strut is a second lower side;
the first lower side and the second lower side together define an outer lower boundary; and
the second bias spring remains within the outer lower boundary.

11. The clip according to claim 1, wherein:
the first clip strut has a first longitudinal axis;
the second clip strut has a second longitudinal axis; and
the at least one first bias spring and the at least one second bias spring balance forces such that the first and second clip struts undergo substantially no rotation about the respective first and second longitudinal axes when the first and second struts move in the strut plane.

12. The clip according to claim 1, wherein:
the first clip strut has a first longitudinal axis;
the second clip strut has a second longitudinal axis; and
the at least one first bias spring and the at least one second bias spring balance forces such that the first and second clip struts have substantially no torque when the first and second struts move in the strut plane.

13. The clip according to claim 1, wherein the first clip strut has a first proximal end and the second clip strut has a second proximal end, and which further comprises a delivery device removably connected to the first and second proximal ends and configured to move the first and second clip struts in the strut plane.

14. An external left atrial appendage (LAA) exclusion clip, comprising:
a clipping assembly comprising first and second opposing clip struts each of the clip struts having:
  a tissue-contacting surface; and
  first and second bias surfaces;
a bias assembly connecting the first clip strut to the second clip strut to align the first and second clip struts in a strut plane passing through the tissue-contacting surface, the bias assembly comprising:
  at least one first bias spring connected to the first bias surface of the first clip strut and to the first bias surface of the second clip strut; and
  at least one second bias spring connected to the second bias surface of the first clip strut and the second bias surface of the second clip strut; and
a delivery device removably connected to the first and second struts and configured to move the first and second clip struts independently in the strut plane.

15. The clip according to claim 14, wherein:
the first clip strut has a first proximal end and a first distal end;
the second clip strut has a second proximal end and a second distal end;
the at least one first bias spring is connected to:
  an intermediate position at the first bias surface of the first clip strut between the first proximal end and the first distal end; and
  an intermediate position at the first bias surface of the second clip strut between the second proximal end and the second distal end; and
the at least one second bias spring is connected to:
  an intermediate position at the second bias surface of the first clip strut between the first proximal end and the first distal end; and
  an intermediate position at the second bias surface of the second clip strut between the second proximal end and the second distal end.

16. The clip according to claim 14, wherein:
the first bias surface of the first clip strut is a first upper side;
the second bias surface of the first clip strut is a first lower side;
the first bias surface of the second clip strut is a second upper side;
the second bias surface of the second clip strut is a second lower side;
the tissue-contacting surface of the first clip strut comprises a first LAA contacting surface having a first longitudinal centerline;
the tissue-contacting surface of the second clip strut comprises a second LAA contacting surface having a second longitudinal centerline; and
the strut plane passes through the first and second longitudinal centerlines.

17. The clip according to claim 14, wherein:
the clip is sized to fit into a laparoscopic port having an interior diameter; and
the clipping assembly and the bias assembly together have a maximum outer width that is no greater than the interior diameter of the laparoscopic port.

18. The clip according to claim 14, wherein:
the first and second clip struts have a maximum longitudinal length;
the at least one first bias spring has a longitudinal length shorter than the maximum longitudinal length; and
the at least one second bias spring has a longitudinal length shorter than the maximum longitudinal length.

19. The clip according to claim 14, wherein:
the clip is sized to fit into a laparoscopic port having an interior diameter;
the clipping assembly and the bias assembly together have a maximum outer width that is no greater than the interior diameter of the laparoscopic port;
the first and second clip struts have a maximum longitudinal length;
the at least one first bias spring has a longitudinal length shorter than the maximum longitudinal length; and
the at least one second bias spring has a longitudinal length shorter than the maximum longitudinal length.

20. The clip according to claim 14, wherein the bias assembly is configured to permit yaw movement of the first and second clip struts in the strut plane.

21. The clip according to claim 14, wherein the bias assembly is configured to permit yaw movement of the first clip strut in the strut plane independent of yaw movement of the second clip strut in the strut plane.

22. The clip according to claim 14, wherein:
the first bias surface of the first clip strut is a first upper side;
the first bias surface of the second clip strut is a second upper side;
the first upper side and the second upper side together define an outer upper boundary; and
the first bias spring remains within the outer upper boundary.

23. The clip according to claim 14, wherein:
the second bias surface of the first clip strut is a first lower side;
the second bias surface of the second clip strut is a second lower side;
the first lower side and the second lower side together define an outer lower boundary; and
the second bias spring remains within the outer lower boundary.

24. The clip according to claim 14, wherein:
the first clip strut has a first longitudinal axis;
the second clip strut has a second longitudinal axis; and
the at least one first bias spring and the at least one second bias spring balance forces such that the first and second clip struts undergo substantially no rotation about the respective first and second longitudinal axes when the first and second struts move in the strut plane.

25. The clip according to claim 14, wherein:
the first clip strut has a first longitudinal axis;
the second clip strut has a second longitudinal axis; and
the at least one first bias spring and the at least one second bias spring balance forces such that the first and second clip struts have substantially no torque when the first and second struts move in the strut plane.

26. An external left atrial appendage (LAA) exclusion clip, comprising:
a clipping assembly comprising first and second opposing clip struts each of the clip struts having:
a tissue-contacting surface; and
first and second bias surfaces;
a bias assembly connecting the first clip strut to the second clip strut to align the first and second clip struts in a strut plane passing through the tissue-contacting surface, the bias assembly comprising:
at least one first bias spring connected to the first bias surface of the first clip strut and to the first bias surface of the second clip strut; and
at least one second bias spring connected to the second bias surface of the first clip strut and the second bias surface of the second clip strut; and
the at least one first bias spring and the at least one second bias spring being configured to permit movement of the first and second clip struts in the strut plane;
the first clip strut having a first proximal end with a first proximal opening;
the second clip strut having a second proximal end with a second proximal opening; and
a delivery device removably connected to the first and second proximal ends through the first and second proximal openings, the delivery device configured to move the first and second clip struts in the strut plane.

27. The clip according to claim 26, wherein:
the first clip strut has a first distal end;
the second clip strut has a second distal end;
the at least one first bias spring is connected to:
an intermediate position at the first bias surface of the first clip strut between the first proximal end and the first distal end; and
an intermediate position at the first bias surface of the second clip strut between the second proximal end and the second distal end; and
the at least one second bias spring is connected to:
an intermediate position at the second bias surface of the first clip strut between the first proximal end and the first distal end; and
an intermediate position at the second bias surface of the second clip strut between the second proximal end and the second distal end.

28. The clip according to claim 26, wherein:
the first bias surface of the first clip strut is a first upper side;
the second bias surface of the first clip strut is a first lower side;
the first bias surface of the second clip strut is a second upper side;

the second bias surface of the second clip strut is a second lower side;
the tissue-contacting surface of the first clip strut comprises a first LAA contacting surface having a first longitudinal centerline;
the tissue-contacting surface of the second clip strut comprises a second LAA contacting surface having a second longitudinal centerline; and
the strut plane passes through the first and second longitudinal centerlines.

29. The clip according to claim 26, wherein:
the clip is sized to fit into a laparoscopic port having an interior diameter; and
the clipping assembly and the bias assembly together have a maximum outer width that is no greater than the interior diameter of the port.

30. The clip according to claim 26, wherein:
the first and second clip struts have a maximum longitudinal length;
the at least one first bias spring has a longitudinal length shorter than the maximum longitudinal length; and
the at least one second bias spring has a longitudinal length shorter than the maximum longitudinal length.

31. The clip according to claim 26, wherein:
the clip is sized to fit into a laparoscopic port having an interior diameter;
the clipping assembly and the bias assembly together have a maximum outer width that is no greater than the interior diameter of the port;
the first and second clip struts have a maximum longitudinal length;
the at least one first bias spring has a longitudinal length shorter than the maximum longitudinal length; and
the at least one second bias spring has a longitudinal length shorter than the maximum longitudinal length.

32. The clip according to claim 26, wherein the bias assembly is configured to permit yaw movement of the first and second clip struts in the strut plane.

33. The clip according to claim 26, wherein the bias assembly is configured to permit yaw movement of the first clip strut in the strut plane independent of yaw movement of the second clip strut in the strut plane.

34. The clip according to claim 26, wherein:
the first bias surface of the first clip strut is a first upper side;
the first bias surface of the second clip strut is a second upper side;
the first upper side and the second upper side together define an outer upper boundary; and
the first bias spring remains within the outer upper boundary.

35. The clip according to claim 26, wherein:
the second bias surface of the first clip strut is a first lower side;
the second bias surface of the second clip strut is a second lower side;
the first lower side and the second lower side together define an outer lower boundary; and
the second bias spring remains within the outer lower boundary.

36. The clip according to claim 26, wherein:
the first clip strut has a first longitudinal axis;
the second clip strut has a second longitudinal axis; and
the at least one first bias spring and the at least one second bias spring balance forces such that the first and second clip struts undergo substantially no rotation about the respective first and second longitudinal axes when the first and second struts move in the strut plane.

37. The clip according to claim 26, wherein:
the first clip strut has a first longitudinal axis;
the second clip strut has a second longitudinal axis; and
the at least one first bias spring and the at least one second bias spring balance forces such that the first and second clip struts have substantially no torque when the first and second struts move in the strut plane.

38. The clip according to claim 26, wherein the first clip strut has a first proximal end and the second clip strut has a second proximal end, and which further comprises a delivery device removably connected to the first and second proximal ends and configured to move the first and second clip struts in the strut plane.

39. An external left atrial appendage (LAA) exclusion clip, comprising:
a clipping assembly comprising first and second opposing clip struts each of the clip struts having:
a tissue-contacting surface; and
first and second bias surfaces;
a bias assembly connecting the first clip strut to the second clip strut to align the first and second clip struts in a strut plane passing through the tissue-contacting surface, the bias assembly comprising:
at least one first bias spring connected to the first bias surface of the first clip strut and to the first bias surface of the second clip strut; and
at least one second bias spring connected to the second bias surface of the first clip strut and the second bias surface of the second clip strut; and
the at least one first bias spring and the at least one second bias spring being configured to permit movement of the first and second clip struts in the strut plane;
the first clip strut having a first proximal end with a first proximal opening;
the second clip strut having a second proximal end with a second proximal opening; and
a delivery device removably connected only to the first and second proximal ends through the first and second proximal openings, the delivery device configured to move the first and second clip struts in the strut plane.

40. The clip according to claim 39, wherein:
the first clip strut has a first distal end;
the second clip strut has a second distal end;
the at least one first bias spring is coimected to:
an intermediate position at the first bias surface of the first clip strut between the first proximal end and the first distal end; and
an intermediate position at the first bias surface of the second clip strut between the second proximal end and the second distal end; and
the at least one second bias spring is connected to:
an intermediate position at the second bias surface of the first clip strut between the first proximal end and the first distal end; and
an intermediate position at the second bias surface of the second clip strut between the second proximal end and the second distal end.

41. The clip according to claim 39, wherein:
the first bias surface of the first clip strut is a first upper side;
the second bias surface of the first clip strut is a first lower side;
the first bias surface of the second clip stint is a second upper side;

the second bias surface of the second clip strut is a second lower side;

the tissue-contacting surface of the first clip strut comprises a first LAA contacting surface having a first longitudinal centerline;

the tissue-contacting surface of the second clip strut comprises a second LAA contacting surface having a second longitudinal centerline; and the strut plane passes through the first and second longitudinal centerlines.

42. The clip according to claim 39, wherein:

the clip is sized to fit into a laparoscopic port having an interior diameter; and the clipping assembly and the bias assembly together have a maximum outer width that is no greater than the interior diameter of the laparoscopic port.

43. The clip according to claim 39, wherein:

the first and second clip struts have a maximum longitudinal length;

the at least one first bias spring has a longitudinal length shorter than the maximum longitudinal length; and the at least one second bias spring has a longitudinal length shorter than the maximum longitudinal length.

44. The clip according to claim 39, wherein:

the clip is sized to fit into a laparoscopic port having an interior diameter;

the clipping assembly and the bias assembly together have a maximum outer width that is no greater than the interior diameter of the laparoscopic port;

the first and second clip struts have a maximum longitudinal length;

the at least one first bias spring has a longitudinal length shorter than the maximum longitudinal length; and the at least one second bias spring has a longitudinal length shorter than the maximum longitudinal length.

45. The clip according to claim 39, wherein the bias assembly is configured to permit yaw movement of the first and second clip struts in the strut plane.

46. The clip according to claim 16, wherein the bias assembly is configured to permit yaw movement of the first clip strut in the strut plane independent of yaw movement of the second clip strut in the strut plane.

47. The clip according to claim 39, wherein:

the first bias surface of the first clip strut is a first upper side;

the first bias surface of the second clip strut is a second upper side;

the first upper side and the second upper side together define an outer upper boundary; and the first bias spring remains within the outer upper boundary.

48. The clip according to claim 39, wherein:

the second bias surface of the first clip strut is a first lower side;

the second bias surface of the second clip strut is a second lower side;

the first lower side and the second lower side together define an outer lower boundary; and the second bias spring remains within the outer lower boundary.

49. The clip according to claim 39, wherein:

the first clip strut has a first longitudinal axis;

the second clip strut has a second longitudinal axis; and the at least one first bias spring and the at least one second bias spring balance forces such that the first and second clip struts undergo substantially no rotation about the respective first and second longitudinal axes when the first and second struts move in the strut plane.

50. The clip according to claim 39, wherein:

the first clip strut has a first longitudinal axis;

the second clip strut has a second longitudinal axis; and the at least one first bias spring and the at least one second bias spring balance forces such that the first and second clip struts have substantially no torque when the first and second struts move in the strut plane.

* * * * *